US010704061B2

(12) United States Patent
Alton et al.

(10) Patent No.: US 10,704,061 B2
(45) Date of Patent: Jul. 7, 2020

(54) LENTIVIRAL VECTORS

(71) Applicants: IP2IPO INNOVATIONS LIMITED, London (GB); ID Pharma Co., Ltd., Tsukuba-shi (JP)

(72) Inventors: Eric Walter Frederick Wolfgang Alton, London (GB); Uta Griesenbach, London (GB); Kamila Malgorzata Pytel, London (GB); Michael Christian Paul-Smith, London (GB); Ian Andrew Pringle, Oxford (GB); Stephen Charles Hyde, Oxford (GB); Deborah Rebecca Gill, Oxford (GB); Lee Adrian Davies, Oxfordshire (GB); Alan Christopher Boyd, Edinburgh (GB); Gerard McLachlan, West Linton (GB); Makoto Inoue, Tsukuba (JP)

(73) Assignees: IP2IPO INNOVATIONS LIMITED, London (GB); ID PHARMA CO., LTD., Ibaraki (JP)

( * ) Notice: Subject to any disclaimer, the term of this patent is extended or adjusted under 35 U.S.C. 154(b) by 0 days.

(21) Appl. No.: 15/312,026

(22) PCT Filed: Apr. 23, 2015

(86) PCT No.: PCT/GB2015/051201
§ 371 (c)(1),
(2) Date: Nov. 17, 2016

(87) PCT Pub. No.: WO2015/177501
PCT Pub. Date: Nov. 26, 2015

(65) Prior Publication Data
US 2017/0096684 A1    Apr. 6, 2017

(30) Foreign Application Priority Data

May 21, 2014 (GB) .................................. 1409089.8

(51) Int. Cl.
| C12N 15/86 | (2006.01) |
| A61K 38/37 | (2006.01) |
| A61K 48/00 | (2006.01) |
| C12N 7/00 | (2006.01) |
| C07K 14/47 | (2006.01) |
| C07K 14/755 | (2006.01) |

(52) U.S. Cl.
CPC .............. *C12N 15/86* (2013.01); *A61K 38/37* (2013.01); *A61K 48/0066* (2013.01); *C07K 14/4712* (2013.01); *C12N 7/00* (2013.01); *C07K 14/755* (2013.01); *C07K 2319/03* (2013.01); *C07K 2319/33* (2013.01); *C12N 2740/15032* (2013.01); *C12N 2740/15043* (2013.01); *C12N 2740/15045* (2013.01); *C12N 2740/15051* (2013.01); *C12N 2760/18845* (2013.01); *C12N 2810/6072* (2013.01); *C12N 2830/15* (2013.01)

(58) Field of Classification Search
None
See application file for complete search history.

(56) References Cited

U.S. PATENT DOCUMENTS

2009/0162320 A1    6/2009 Mitomo et al.

FOREIGN PATENT DOCUMENTS

| EP | 1 291 419 A1 | 3/2003 |
| EP | 1 950 307 A1 | 7/2008 |
| EP | 1950303 A1 | 7/2008 |
| WO | 00/39302 A2 | 7/2000 |
| WO | 03/029274 A2 | 4/2003 |
| WO | 2003/029412 A2 | 4/2003 |
| WO | 2007/110628 A2 | 10/2007 |
| WO | 2008/124724 A1 | 10/2008 |

OTHER PUBLICATIONS

Zou et al., Blood. 2011;117(21):5561-5572 (Year: 2011).*
Hyde, Nat Biotechnol. May 2008;26(5):549-51 (Year: 2008).*
Chuah et al., "Gene therapy for hemophilia," *The Journal of Gene Medicine* 3:3-20 (2001).
Cronin et al., "Altering the Tropism of Lentiviral Vectors through Pseudotyping," *Curr Gene Ther.* 5(4):387-398 (Aug. 2005).
Engelhardt, "The lung as a metabolic factory for gene therapy," *J. Clin. Invest.* 110:429-432 (2002).
Mitomo et al., "Toward Gene Therapy for Cystic Fibrosis Using a Lentivirus Pseudotyped With Sendai Virus Envelopes," *Molecular Therapy* 18(6):1173-1182 (Jun. 2010).
Nakajima et al., "Development of Novel Simian Immunodeficiency Virus Vectors Carrying a Dual Gene Expression System," *Human Gene Therapy* 11:1863-1874 (Sep. 1, 2000).
Witting et al., "Efficient Large Volume Lentiviral Vector Production Using Flow Electroporation," *Human Gene Therapy* 23:243-249 (Feb. 2012).
Zychlinski et al., "Physiological Promoters Reduce the Genotoxic Risk of Integrating Gene Vectors," www.moleculartherapy.org 16(4):718-725 (Apr. 2008).
Japanese Office Action, dated Mar. 28, 2019, for Japanese Application No. 2016-567082, 9 pages (with English machine translation).
Tolmachov et al., "Designing Lentiviral Gene Vectors," *Viral Gene Therapy*, 24 pages, 2011.
Bartholomae et al.: Lentiviral vector integration profiles differ in rodent postmitotic tissues. Mol Ther. 19(4): 703-710 (2011).
Borthwick et al.: Evidence for stem-cell niches in the tracheal epithelium. Am J Respir Cell Mol Biol. 24(6): 662-670 (2001).

(Continued)

*Primary Examiner* — James D Schultz
(74) *Attorney, Agent, or Firm* — Wilson Sonsini Goodrich & Rosati

(57) ABSTRACT

This invention relates to lentiviral gene transfer vectors pseudotyped with hemagglutinin-neuraminidase (HN) and fusion (F) proteins from a respiratory paramyxovirus, comprising a promoter and a transgene; and methods of making the same. The present invention also relates to the use of said vectors in gene therapy, particularly for the treatment of respiratory tract diseases such as Cystic Fibrosis (CF).

13 Claims, 39 Drawing Sheets
Specification includes a Sequence Listing.

(56) References Cited

OTHER PUBLICATIONS

Dekkers et al.: Afunctional CFTR assay using primary cystic fibrosis intestinal organoids. Nat Med. 19(7): 939-945 (2013).
Derand et al.: Comparative pharmacology of the activity of wild-type and G551D mutated CFTR chloride channel: effect of the benzimidazolone derivative NS004. J Membr Biol. 194(2): 109-117 (2003).
Griesenbach et al.: Assessment of CFTR function after gene transfer in vitro and in vivo. Methods Mol Biol. 433: 229-242 (2008).
Kobayashi et al.: Pseudotyped lentivirus vectors derived from simian immunodeficiency virus SIVagm with envelope glycoproteins from paramyxovirus. J Virol. 77(4): 2607-2614 (2003).
Limberis et al.: Recovery of airway cystic fibrosis transmembrane conductance regulator function in mice with cystic fibrosis after single-dose lentivirus-mediated gene transfer. Hum Gene Ther. 13(16): 1961-1970 (2002).
McIntosh et al., Therapeutic levels of FVIII following a single peripheral vein administration of rAAV vector encoding a novel human factor VIII variant, Blood, 121(17): 3335-3344 (2013).
Moreno et al.: Pharmacology of airways and vessels in lung slices in situ: role of endogenous dilator hormones. Respir Res. 7: 111 (2006).
Pringle et al.: Rapid identification of novel functional promoters for gene therapy. J Mol Med (Berl). 90(12): 1487-1496 (2012).
Rennard et al.: Estimation of vol. of epithelial lining fluid recovered by lavage using urea as marker of dilution. J Appl Physiol (1985). 1986 Feb; 60(2): 532-538.
Ukrainian Patent Application No. a 2016 12986 Office Action dated Aug. 6, 2019 with English Translation.
Xenariou et al.: Use of ultrasound to enhance nonviral lung gene transfer in vivo. Gene Ther. 14(9): 768-774 (2007).

\* cited by examiner

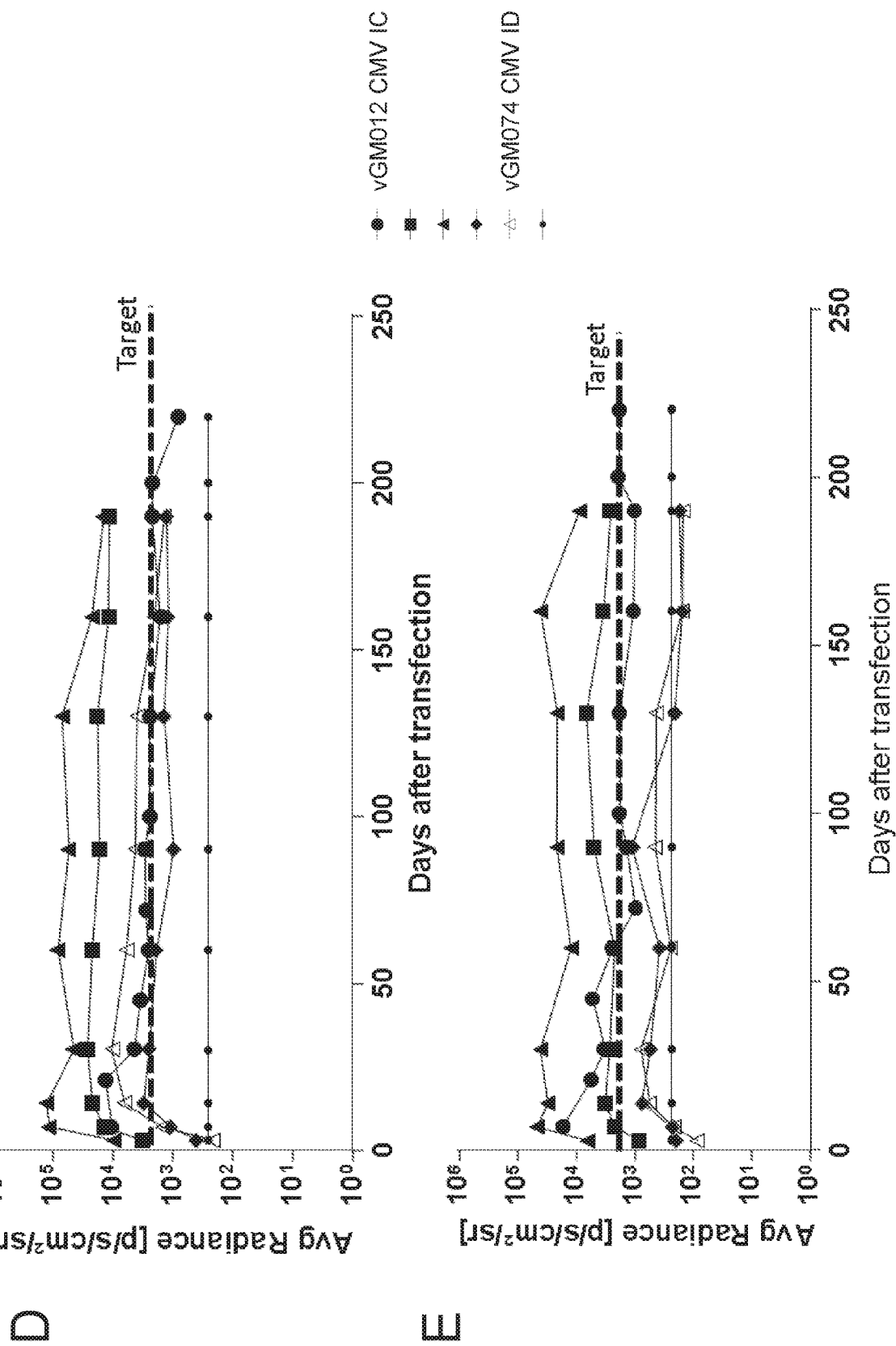

A

B

C

D

E

SEQUENCE LISTING

<160> NUMBER OF SEQ ID NOS: 35

<210> SEQ ID NO 1
<211> LENGTH: 10535
<212> TYPE: DNA
<213> ORGANISM: Artificial Sequence
<220> FEATURE:
<223> OTHER INFORMATION: pGM326 plasmid

<400> SEQUENCE: 1
ggtacctcaa tattggccat tagccatatt attcattggt tatatagcat aaatcaatat    60
tggctattgg ccattgcata cgttgtatct atatcataat atgtacattt atattggctc   120
atgtccaata tgaccgccat gttggcattg attattgact agtattaat agtaatcaat   180

```
tacggggtca ttagttcata gcccatatat ggagttccgc gttacataac ttacggtaaa    240
tggcccgcct ggctgaccgc ccaacgaccc ccgcccattg acgtcaataa tgacgtatgt    300
tcccatagta acgccaatag ggactttcca ttgacgtcaa tgggtggagt atttacggta    360
aactgcccac ttggcagtac atcaagtgta tcatatgcca agtccgcccc ctattgacgt    420
caatgacggt aaatggcccg cctggcatta tgcccagtac atgaccttac gggactttcc    480
tacttggcag tacatctacg tattagtcat cgctattacc atggtgatgc ggttttggca    540
gtacaccaat gggcgtggat agcggtttga ctcacgggga tttccaagtc tccaccccat    600
tgacgtcaat gggagtttgt tttggcacca aaatcaacgg gactttccaa aatgtcgtaa    660
caactgcgat cgcccgcccc gttgacgcaa atgggcggta ggcgtgtacg gtgggaggtc    720
tatataagca gagctcgctg gcttgtaact cagtctctta ctaggagacc agcttgagcc    780
tgggtgttcg ctggttagcc taacctggtt ggccaccagg ggtaaggact ccttggctta    840
gaaagctaat aaacttgcct gcattagagc ttatctgagt caagtgtcct cattgacgcc    900
tcactctctt gaacgggaat cttccttact gggttctctc tctgacccag gcgagagaaa    960
ctccagcagt ggcgcccgaa cagggacttg agtgagagtg taggcacgta cagctgagaa   1020
ggcgtcggac gcgaaggaag cgcggggtgc gacgcgacca agaaggagac ttggtgagta   1080
ggcttctcga gtgccgggaa aaagctcgag cctagttaga ggactaggag aggccgtagc   1140
cgtaactact cttgggcaag tagggcaggc ggtgggtacg caatggggc ggctacctca    1200 gcactaaata ggagacaatt agaccaattt gagaaaatac gacttcgccc gaacggaaag   1260 aaaagtacc aaattaaaca tttaatatgg gcaggcaagg agatggagcg cttcggcctc    1320
catgagaggt tgttggagac agaggagggg tgtaaaagaa tcatagaagt cctctacccc   1380
ctagaaccaa caggatcgga gggcttaaaa agtctgttca atcttgtgtg cgtgctatat   1440
tgcttgcaca aggaacagaa agtgaaagac acagaggaag cagtagcaac agtaagacaa   1500
cactgccatc tagtggaaaa agaaaaaagt gcaacagaga catctagtgg acaaaagaaa   1560
aatgacaagg gaatagcagc gccacctggt ggcagtcaga attttccagc gcaacaacaa   1620
ggaaatgcct gggtacatgt acccttgtca ccgcgcacct aaatgcgtg ggtaaaagca    1680 gtagaggaga aaaatttgg agcagaaata gtacccattt ttttgtttca gccctatcg     1740 aattcccgtt tgtgctaggg ttcttaggct tcttgggggc tgctgaact gcaatgggag    1800 cagcggcgac agccctgacg gtccagtctc agcatttgct tgctgggata ctgcagcagc   1860
agaagaatct gctggcggct gtggaggctc aacagcagat gttgaagctg accatttggg   1920
gtgttaaaaa cctcaatgcc cgcgtcacag cccttgagaa gtacctagag gatcaggcac   1980
gactaaactc ctgggggtgc gcatggaaac aagtatgtca taccacagtg gagtggccct   2040
ggacaaatcg gactccggat tggcaaaata tgacttggtt ggagtgggaa agacaaatag   2100
ctgatttgga aagcaacatt acgagacaat tagtgaaggc tagagaacaa gaggaaaaga   2160
atctagatgc ctatcagaag ttaactagtt ggtcagattt ctggtcttgg ttcgatttct   2220
caaaatggct taacatttta aaatgggat ttttagtaat agtaggaata atagggttaa     2280
gattacttta cacagtatat ggatgtatag tgagggttag gcaggatat gttcctctat     2340 ctccacagat ccatatccgc ggcaatttta aagaaaggg aggaataggg ggacagactt     2400
cagcagagag actaattaat ataataacaa cacaattaga aatacaacat ttacaaacca   2460
aaattcaaaa aattttaaat tttagagccg cggagatctg ttcataact tatggtaaat    2520
```

```
ggcctgcctg gctgactgcc caatgacccc tgcccaatga tgtcaataat gatgtatgtt    2580
cccatgtaat gccaataggg actttccatt gatgtcaatg ggtggagtat ttatggtaac    2640
tgcccacttg gcagtacatc aagtgtatca tatgccaagt atgcccccta ttgatgtcaa    2700
tgatggtaaa tggcctgcct ggcattatgc ccagtacatg accttatggg actttcctac    2760
ttggcagtac atctatgtat tagtcattgc tattaccatg gaattcact agtggagaag    2820 agcatgcttg agggctgagt gcccctcagt gggcagagag cacatggccc acagtccctg    2880
agaagttggg gggaggggtg ggcaattgaa ctggtgccta gagaaggtgg ggcttgggta    2940
aactgggaaa gtgatgtggt gtactggctc cacctttttc cccagggtgg gggagaacca    3000
tatataagtg cagtagtctc tgtgaacatt caagcttctg ccttctccct cctgtgagtt    3060
tgctagccac catgcagaga agccctctgg agaaggcctc tgtggtgagc aagctgttct    3120
tcagctggac caggcccatc ctgaggaagg gctacaggca gagactggag ctgtctgaca    3180
tctaccagat cccctctgtg gactctgctg acaacctgtc tgagaagctg gagagggagt    3240
gggatagaga gctggccagc aagaagaacc ccaagctgat caatgccctg aggagatgct    3300
tcttctggag attcatgttc tatggcatct tcctgtacct gggggaagtg accaaggctg    3360
tgcagcctct gctgctgggc agaatcattg ccagctatga ccctgacaac aaggaggaga    3420
ggagcattgc catctacctg ggcattggcc tgtgcctgct gttcattgtg aggaccctgc    3480
tgctgcaccc tgccatcttt ggcctgcacc acattggcat gcagatgagg attgccatgt    3540
tcagcctgat ctacaagaaa accctgaagc tgtccagcag agtgctggac aagatcagca    3600
ttggccagct ggtgagcctg ctgagcaaca acctgaacaa gtttgatgag ggcctggccc    3660
tggcccactt tgtgtggatt gcccctctgc aggtggccct gctgatgggc ctgatttggg    3720
agctgctgca ggcctctgcc ttttgtggcc tgggcttcct gattgtgctg gccctgtttc    3780
aggctggcct gggcaggatg atgatgaagt acagggacca gagggcaggc aagatcagtg    3840
agaggctggt gatcacctct gagatgattg agaacatcca gtctgtgaag gcctactgtt    3900
gggaggaagc tatggagaag atgattgaaa acctgaggca gacagagctg aagctgacca    3960
ggaaggctgc ctatgtgaga tacttcaaca gctctgcctt cttcttctct ggcttctttg    4020
tggtgttcct gtctgtgctg ccctatgccc tgatcaaggg gatcatcctg agaaagattt    4080
tcaccaccat cagcttctgc attgtgctga ggatggctgt gaccagacag ttccctggg    4140 ctgtgcagac ctggtatgac agcctggggg ccatcaacaa gatccaggac ttcctgcaga    4200
agcaggagta caagaccctg gagtacaacc tgaccaccac agaagtggtg atggagaatg    4260
tgacagcctt ctgggaggag ggctttgggg agctgtttga aaggccaag cagaacaaca    4320 acaacagaaa gaccagcaat ggggatgact ccctgttctt ctccaacttc tccctgctgg    4380
gcacacctgt gctgaaggac atcaacttca agattgagag gggcagctg ctggctgtgg    4440 ctggatctac aggggctggc aagaccagcc tgctgatgat gatcatgggg gagctggagc    4500
cttctgaggg caagatcaag cactctggca ggatcagctt ttgcagccag ttcagctgga    4560
tcatgcctgg caccatcaag agaacatca tctttggagt gagctatgat gagtacagat    4620
acaggagtgt gatcaaggcc tgccagctgg aggaggacat cagcaagttt gctgagaagg    4680
acaacattgt gctgggggag ggaggcatta cactgtctgg gggccagaga gccagaatca    4740
gcctggccag ggctgtgtac aaggatgctg acctgtacct gctggactcc cctttggct    4800 acctggatgt gctgacagag aaggagattt tgagagctg tgtgtgcaag ctgatggcca    4860
acaagaccag aatcctggtg accagcaaga tggagcacct gaagaaggct gacaagatcc    4920
```

```
tgatcctgca tgagggcagc agctacttct atgggacctt ctctgagctg cagaacctgc   4980
agcctgactt cagctctaag ctgatgggct gtgacagctt tgaccagttc tctgctgaga   5040
ggaggaacag catcctgaca gagaccctgc acagattcag cctggaggga gatgcccctg   5100
tgagctggac agagaccaag aagcagagct caagcagac aggggagttt ggggagaaga    5160
ggaagaactc catcctgaac cccatcaaca gcatcaggaa gttcagcatt gtgcagaaaa   5220 ccccctgca gatgaatggc attgaggaag attctgatga gcccctggag aggagactga    5280
gcctggtgcc tgattctgag cagggagagg ccatcctgcc taggatctct gtgatcagca   5340
cagggcctac actgcaggcc agaaggaggc agtctgtgct gaacctgatg acccactctg   5400
tgaaccaggg ccagaacatc cacaggaaaa ccacagcctc caccaggaaa gtgagcctgg   5460
cccctcaggc caatctgaca gagctggaca tctacagcag gaggctgtct caggagacag   5520
gcctggagat ttctgaggag atcaatgagg aggacctgaa agagtgcttc tttgatgaca   5580
tggagagcat ccctgctgtg accacctgga cacctacct gagatacatc acagtgcaca   5640
agagcctgat ctttgtgctg atctggtgcc tggtgatctt cctggctgaa gtggctgcct   5700
ctctggtggt gctgtggctg ctgggaaaca ccccactgca ggacaagggc aacagcaccc   5760
acagcaggaa caacagctat gctgtgatca tcacctccac ctccagctac tatgtgttct   5820
acatctatgt gggagtggct gataccctgc tggctatggg cttctttaga ggcctgcccc   5880
tggtgcacac actgatcaca gtgagcaaga tcctccacca caagatgctg cactctgtgc   5940
tgcaggctcc tatgagcacc ctgaataccc tgaaggctgg gggcatcctg aacagattct   6000
ccaaggatat tgccatcctg gatgacctgc tgcctctcac catctttgac ttcatccagc   6060
tgctgctgat tgtgattggg gccattgctg tggtggcagt gctgcagccc tacatctttg   6120
tggccacagt gcctgtgatt gtggccttca tcatgctgag ggcctacttt ctgcagacct   6180
cccagcagct gaagcagctg gagtctgagg gcagaagccc catcttcacc cacctggtga   6240
caagcctgaa gggcctgtgg accctgagag cctttggcag gcagccctac tttgagaccc   6300
tgttccacaa ggccctgaac ctgcacacag ccaactggtt cctctacctg tccaccctga   6360
gatggttcca gatgagaatt gagatgatct ttgtcatctt cttcattgct gtgaccttca   6420
tcagcattct gaccacagga gagggagagg gcagagtggg cattatcctg accctggcca   6480
tgaacatcat gagcacactg cagtgggcag tgaacagcag cattgatgtg gacagcctga   6540
tgaggagtgt gagcagagtg ttcaagttca ttgatatgcc cacagagggc aagcctacca   6600
agagcaccaa gcctacaag aatggccagc tgagcaaagt gatgatcatt gagaacagcc    6660
atgtgaagaa ggatgatatc tggcccagtg gaggccagat gacagtgaag gacctgacag   6720
ccaagtacac agagggggc aatgctatcc tggagaacat ctccttcagc atctcccctg    6780
gccagagagt gggactgctg ggaagaacag gctctggcaa gtctaccctg ctgtctgcct   6840
tcctgaggct gctgaacaca gagggagaga tccagattga tggagtgtcc tgggacagca   6900
tcacactgca gcagtggagg aaggcctttg gtgtgatccc ccagaaagtg ttcatcttca   6960
gtggcacctt caggaagaac ctggaccccct atgagcagtg gtctgaccag gagatttgga   7020
aagtggctga tgaagtgggc ctgagaagtg tgattgagca gttccctggc aagctggact   7080
ttgtcctggt ggatgggggc tgtgtgctga gccatggcca caagcagctg atgtgcctgg   7140
ccagatcagt gctgagcaag gccaagatcc tgctgctgga tgagccttct gcccacctgg   7200
atcctgtgac ctaccagatc atcaggagga ccctcaagca ggccttttgct gactgcacag   7260
```

```
tcatcctgtg tgagcacagg attgaggcca tgctggagtg ccagcagttc ctggtgattg    7320
aggagaacaa agtgaggcag tatgacagca tccagaagct gctgaatgag aggagcctgt    7380
tcaggcaggc catcagcccc tctgatagag tgaagctgtt cccccacagg aacagctcca    7440
agtgcaagag caagcccag attgctgccc tgaaggagga gacagaggag gaagtgcagg     7500
acaccaggct gtgagggccc aatcaacctc tggattacaa aatttgtgaa agattgactg    7560
gtattcttaa ctatgttgct ccttttacgc tatgtggata cgctgcttta atgcctttgt    7620
atcatgctat tgcttcccgt atggctttca ttttctcctc cttgtataaa tcctggttgc    7680
tgtctcttta tgaggagttg tggcccgttg tcaggcaacg tggcgtggtg tgcactgtgt    7740
ttgctgacgc aaccccact ggttggggca ttgccaccac ctgtcagctc ctttccggga    7800 cttcgcttt cccctccct attgccacg cggaactcat cgccgcctgc cttgcccgct    7860
gctggacagg ggctcggctg ttgggcactg acaattccgt ggtgttgtcg gggaaatcat    7920 cgtccttcc ttggctgctc gcctgtgttg ccacctggat tctgcgcggg acgtccttct    7980
gctacgtccc ttcggccctc aatccagcgg accttccttc ccgcgccctg ctgccggctc    8040
tgcggcctct tccgcgtctt cgccttcgcc ctcagacgag tcggatctcc ctttgggccg    8100
cctccccgca agcttcgcac tttttaaaag aaaaggagg actggatggg atttattact    8160
ccgataggac gctggcttgt aactcagtct cttactagga gaccagcttg agcctgggtg    8220
ttcgctggtt agcctaacct ggttggccac caggggtaag gactccttgg cttagaaagc    8280
taataaactt gcctgcatta gagctcttac gcgtcccggg ctcgagatcc gcatctcaat    8340
tagtcagcaa ccatagtccc gcccctaact ccgcccatcc cgcccctaac tccgcccagt    8400
tccgcccatt ctccgcccca tggctgacta atttttttta tttatgcaga ggccgaggcc    8460
gcctcggcct ctgagctatt ccagaagtag tgaggaggct ttttggagg cctaggcttt    8520 tgcaaaagc taacttgttt attgcagctt ataatggtta caaataaagc aatagcatca    8580
caaatttcac aaataaagca ttttttttcac tgcattctag ttgtggtttg tccaaactca    8640
tcaatgtatc ttatcatgtc tgtccgcttc ctcgctcact gactcgctgc gctcggtcgt    8700
tcggctgcgg cgagcggtat cagctcactc aaaggcggta atacggttat ccacagaatc    8760 agggggataac gcaggaaaga acatgtgagc aaaaggccag caaaaggcca ggaaccgtaa    8820
aaaggccgcg ttgctggcgt ttttccatag gctccgcccc cctgacgagc atcacaaaaa    8880
tcgacgctca agtcagaggt ggcgaaaccc gacaggacta taaagatacc aggcgtttcc    8940
ccctggaagc tccctcgtgc gctctcctgt tccgaccctg ccgcttaccg gatacctgtc    9000
cgcctttctc ccttcgggaa gcgtggcgct ttctcatagc tcacgctgta ggtatctcag    9060
ttcggtgtag tcgttcgct ccaagctggg ctgtgtgcac gaaccccccg ttcagcccga    9120
ccgctgcgcc ttatccggta actatcgtct tgagtccaac ccggtaagac acgacttatc    9180
gccactggca gcagccactg gtaacaggat tagcagagcg aggtatgtag gcggtgctac    9240
agagttcttg aagtggtggc ctaactacgg ctacactaga agaacagtat ttggtatctg    9300
cgctctgctg aagccagtta ccttcggaaa aagagttggt agctcttgat ccggcaaaca    9360
aaccaccgct ggtagcggtg gtttttttgt ttgcaagcag cagattacgc gcagaaaaaa    9420
aggatctcaa gaagatcctt tgatcttttc tacggggtct gacgctcagt ggaacgaaaa    9480
ctcacgttaa gggattttgg tcatgagatt atcaaaaagg atcttcacct agatcctttt    9540
aaattaaaaa tgaagtttta aatcaatcta agtatatat gagtaaactt ggtctgacag    9600
ttagaaaaac tcatcgagca tcaaatgaaa ctgcaattta ttcatatcag gattatcaat    9660
```

```
accatatttt tgaaaaagcc gtttctgtaa tgaaggagaa aactcaccga ggcagttcca    9720
taggatggca agatcctggt atcggtctgc gattccgact cgtccaacat caatacaacc    9780
tattaatttc ccctcgtcaa aaataaggtt atcaagtgag aaatcaccat gagtgacgac    9840
tgaatccggt gagaatggca acagcttatg catttctttc cagacttgtt caacaggcca    9900
gccattacgc tcgtcatcaa aatcactcgc atcaaccaaa ccgttattca ttcgtgattg    9960
cgcctgagcg agacgaaata cgcgatcgct gttaaaagga caattacaaa caggaatcga   10020
atgcaaccgg cgcaggaaca ctgccagcgc atcaacaata ttttcacctg aatcaggata   10080
ttcttctaat acctggaatg ctgttttttcc ggggatcgca gtggtgagta accatgcatc   10140
atcaggagta cggataaaat gcttgatggt cggaagaggc ataaattccg tcagccagtt   10200
tagtctgacc atctcatctg taacatcatt ggcaacgcta cctttgccat gtttcagaaa   10260
caactctggc gcatcgggct tcccatacaa tcgatagatt gtcgcacctg attgcccgac   10320
attatcgcga gcccatttat acccatataa atcagcatcc atgttggaat ttaatcgcgg   10380
cctagagcaa gacgtttccc gttgaatatg gctcataaca ccccttgtat tactgtttat   10440
gtaagcagac agttttattg ttcatgatga tatattttta tcttgtgcaa tgtaacatca   10500
gagattttga gacacaacaa ttggtcgacg gatcc                              10535

<210> SEQ ID NO 2
<211> LENGTH: 9885
<212> TYPE: DNA
<213> ORGANISM: Artificial Sequence
<220> FEATURE:
<223> OTHER INFORMATION: pGM297 plasmid

<400> SEQUENCE: 2
gctcgagact agtgacttgg tgagtaggct tcgagcctag ttagaggact aggagaggcc      60
gtagccgtaa ctactctggg caagtagggc aggcggtggg tacgcaatgg gggcggctac     120
ctcagcacta aataggagac aattagacca atttgagaaa atacgacttc gcccgaacgg     180
aaagaaaaag taccaaatta aacatttaat atgggcaggc aaggagatgg agcgcttcgg     240
cctccatgag aggttgttgg agacagagga ggggtgtaaa agaatcatag aagtcctcta     300 cccctagaa ccaacaggat cggagggctt aaaaagtctg ttcaatcttg tgtgcgtact     360
atattgcttg cacaaggaac agaaagtgaa agacacagag gaagcagtag caacagtaag     420
acaacactgc catctagtgg aaaagaaaa aagtgcaaca gagacatcta gtggacaaaa     480
gaaaaatgac aagggaatag cagcgccacc tggtggcagt cagaattttc cagcgcaaca     540
acaaggaaat gcctgggtac atgtacccct gtcaccgcgc accttaaatg cgtgggtaaa     600
agcagtagag gagaaaaaat ttggagcaga aatagtaccc atgtttcaag ccctatcaga     660
aggctgcaca ccctatgaca ttaatcagat gcttaatgtg ctaggagatc atcaagggc     720 attacaaata gtgaaagaga tcattaatga agaagcagcc cagtgggatg taacacaccc     780
actacccgca ggaccctac cagcaggaca gctcagggac cctcgcggct cagatatagc     840
agggaccacc agctcagtac aagaacagtt agaatggatc tatactgcta acccccgggt     900
agatgtaggt gccatctacc ggagatggat tattctagga cttcaaaagt gtgtcaaaat     960
gtacaaccca gtatcagtcc tagacattag gcagggacct aaagagccct tcaaggatta    1020
tgtggacaga ttttacaagg caattagagc agaacaagcc tcagggaag tgaacaatg    1080 gatgacagaa tcattactca ttcaaaatgc taatccagat tgtaaggtca tcctgaaggg    1140
```

```
cctaggaatg cacccccaccc ttgaagaaat gttaacggct tgtcaggggg taggaggccc    1200
aagctacaaa gcaaaagtaa tggcagaaat gatgcagacc atgcaaaatc aaaacatggt    1260
gcagcaggga ggtccaaaaa gacaaagacc cccactaaga tgttataatt gtggaaaatt    1320
tggccatatg caaagacaat gtccggaacc aaggaaaaca aaatgtctaa agtgtggaaa    1380
attgggacac ctagcaaaag actgcagggg acaggtgaat ttttaggggt atggacggtg    1440 gatggggca aaaccgagaa attttcccgc cgctactctt ggagcggaac cgagtgcgcc    1500
tcctccaccg agcggcacca ccccatacga cccagcaaag aagctcctgc agcaatatgc    1560
agagaaaggg aaacaactga gggagcaaaa gaggaatcca ccggcaatga atccggattg    1620
gaccgaggga tattctttga actccctctt tggagaagac caataaagac agtgtatata    1680
gaaggggtcc ccattaaggc actgctagac acagggcag atgacaccat aattaaagaa    1740
aatgatttac aattatcagg tccatggaga cccaaaatta taggggcat aggaggaggc    1800 cttaatgtaa aagaatataa cgacaggaa gtaaaaatag aagataaat tttgagagga    1860 acaatattgt taggagcaac tcccattaat ataataggta gaaatttgct ggccccggca    1920
ggtgcccggt tagtaatggg acaattatca gaaaaaattc ctgtcacacc tgtcaaattg    1980
aaggaagggg ctcggggacc ctgtgtaaga caatggcctc tctctaaaga gaagattgaa    2040
gctttacagg aaatatgttc ccaattagag caggaaggaa aaatcagtag agtaggagga    2100
gaaaatgcat acaataccc aatattttgc ataaagaaga aggacaaatc ccagtggagg    2160
atgctagtag actttagaga gttaaataag gcaacccaag atttctttga agtgcaatta    2220 gggataccc acccagcagg attaagaag atgagacaga taacagtttt agatgtagga    2280
gacgcctatt attccatacc attggatcca aattttagga aatatactgc ttttactatt    2340
cccacagtga ataatcaggg acccgggatt aggtatcaat tcaactgtct cccgcaaggg    2400
tggaaaggat ctcctacaat cttccaaaat acagcagcat ccattttgga ggagataaaa    2460
agaaacttgc cagcactaac cattgtacaa tacatggatg atttatgggt aggttctcaa    2520
gaaaatgaac acacccatga caaattagta gaacagttaa gaacaaaatt acaagcctgg    2580
ggcttagaaa cccagaaaa gaaggtgcaa aagaaccac cttatgagtg gatgggatac    2640
aaactttggc ctcacaaatg ggaactaagc agaatacaac tggaggaaaa agatgaatgg    2700
actgtcaatg acatccagaa gttagttggg aaactaaatt gggcagcaca attgtatcca    2760
ggtcttagga ccaagaatat atgcaagtta attagaggaa agaaaaatct gttagagcta    2820
gtgacttgga caccctgaggc agaagctgaa tatgcagaaa atgcagagat tcttaaaaca    2880
gaacaggaag gaacctatta caaaccagga atacctatta gggcagcagt acagaaattg    2940
gaaggaggac agtggagtta ccaattcaaa caagaaggac aagtcttgaa agtaggaaaa    3000
tacaccaagc aaaagaacac ccatacaaat gaacttcgca cattagctgg tttagtgcag    3060
aagatttgca aagaagctct agttatttgg gggatattac cagttctaga actcccgata    3120
gaaagagagg tatgggaaca atggtgggcg gattactggc aggtaagctg gattcccgaa    3180
tgggattttg tcagcacccc accttttgctc aaactatggt acacattaac aaaagaaccc    3240
atacccaagg aggacgttta ctatgtgat ggagcatgca cagaaattc aaaagaagga    3300 aaagcaggat acatctcaca atacggaaaa cagagagtag aaacattaga aaacactacc    3360
aatcagcaag cagaattaac agctataaaa atggctttgg aagacagtgg gcctaatgtg    3420
aacatagtaa cagactctca atatgcaatg ggaattttga cagcacaacc cacacaaagt    3480
gattcaccat tagtagagca aattatagcc ttaatgatac aaaagcaaca aatatatttg    3540
```

```
cagtgggtac cagcacataa aggaatagga ggaaatgagg agatagataa attagtgagt    3600
aaaggcatta gaagagtttt attcttagaa aaaatagaaa aagctcaaga agagcatgaa    3660
agatatcata ataattggaa aaacctagca gatacatatg gcttccaca aatagtagca     3720 aaagagatag tggccatgtg tccaaaatgt cagataaagg gagaaccagt gcatggacaa    3780
gtggatgcct cacctggaac atggcagatg gattgtactc atctagaagg aaaagtagtc    3840
atagttgcgg tccatgtagc cagtggattc atagaagcag aagtcatacc tagggaaaca    3900
ggaaaagaaa cggcaaagtt tctattaaaa atactgagta gatggcctat aacacagtta    3960
cacacagaca atgggcctaa ctttacctcc caagaagtgg cagcaatatg ttggtgggga    4020
aaaattgaac atacaacagg tataccatat aaccccccaat ctcaaggatc aatagaaagc    4080
atgaacaaac aattaaaaga gataattggg aaaataagag atgattgcca atatacagag    4140
acagcagtac tgatggcttg ccatattcac aattttaaaa gaaagggagg aataggggga    4200
cagacttcag cagagagact aattaatata ataacaacac aattagaaat acaacattta    4260
caaaccaaaa ttcaaaaaat tttaaatttt agagtctact acagagaagg gagagaccct    4320
gtgtggaaag gaccagcaca attaatctgg aaaggggaag gagcagtggt cctcaaggac    4380
ggaagtgacc taaaggttgt accaagaagg aaagctaaaa ttattaagga ttatgaaccc    4440
aaacaaagag tgggtaatga gggtgacgtg aaggtacca ggggatctga taactaaatg     4500
gcagggaata gtcagatatt ggatgagaca agaaatttg aaatggaact attatatgca     4560
tcagctggcg gccgcgaatt cactagtgat tcccgtttgt gctagggttc ttaggcttct    4620
tgggggctgc tggaactgca atgggagcag cggcgacagc cctgacggtc cagtctcagc    4680
atttgcttgc tgggatactg cagcagcaga gaatctgct ggcggctgtg gaggctcaac     4740
agcagatgtt gaagctgacc atttggggtg ttaaaaacct caatgcccgc gtcacagccc    4800
ttgagaagta cctagaggat caggcacgac taaactcctg ggggtgcgca tggaaacaag    4860
tatgtcatac cacagtggag tggccctgga caaatcggac tccggattgg caaaatatga    4920
cttggttgga gtgggaaaga caaatagctg atttggaaag caacattacg agacaattag    4980
tgaaggctag agaacaagag gaaaagaatc tagatgccta tcagaagtta actagttggt    5040
cagatttctg gtcttggttc gatttctcaa aatggcttaa catttttaaaa atgggatttt    5100 tagtaatagt aggaataata gggttaagat tactttacac agtatatgga tgtatagtga    5160
gggttaggca gggatatgtt cctctatctc cacagatcca tatccaatcg aattcccgcg    5220
gccgcaattc actcctcagg tgcaggctgc ctatcagaag gtggtggctg tgtgtggccaa    5280 tgccctggct cacaaatacc actgagatct ttttcccctct gccaaaaatt atggggacat    5340
catgaagccc cttgagcatc tgacttctgg ctaataaagg aaatttattt tcattgcaat    5400
agtgtgttgg aattttttgt gtctctcact cggaaggaca tatgggaggg caaatcattt    5460
aaaacatcag aatgagtatt tggtttagag tttggcaaca tatgcccata tgctggctgc    5520
catgaacaaa ggttggctat aaagaggtca tcagtatatg aaacagcccc ctgctgtcca    5580
ttccttattc catagaaaag ccttgacttg aggttagatt tttttatat tttgttttgt      5640 gttatttttt tctttaacat ccctaaaatt ttccttacat gttttactag ccagattttt    5700
cctcctctcc tgactactcc cagtcatagc tgtccctctt ctcttatgga gatccctcga    5760
cctgcagccc aagcttggcg taatcatggt catagctgtt tcctgtgtga aattgttatc    5820
cgctcacaat tccacacaac atacgagccg gaagcataaa gtgtaaagcc tggggtgcct    5880
```

```
aatgagtgag ctaactcaca ttaattgcgt tgcgctcact gcccgctttc cagtcgggaa      5940
acctgtcgtg ccagcggatc cgcatctcaa ttagtcagca accatagtcc cgcccctaac      6000
tccgcccatc ccgcccctaa ctccgcccag ttccgcccat tctccgcccc atggctgact      6060 aattttttt atttatgcag aggccgaggc cgcctcggcc tctgagctat tccagaagta      6120
gtgaggaggc ttttttggag gcctaggctt ttgcaaaaag ctaacttgtt tattgcagct      6180
tataatggtt acaaataaag caatagcatc acaaatttca caaataaagc attttttca      6240 ctgcattcta gttgtggttt gtccaaactc atcaatgtat cttatcatgt ctgtccgctt      6300
cctcgctcac tgactcgctg cgctcggtcg ttcggctgcg gcgagcggta tcagctcact      6360
caaaggcggt aatacggtta ccacagaat caggggataa cgcaggaaag aacatgtgag      6420
caaaaggcca gcaaaaggcc aggaaccgta aaaaggccgc gttgctggcg ttttccata      6480 ggctccgccc ccctgacgag catcacaaaa atcgacgctc aagtcagagg tggcgaaacc      6540
cgacaggact ataaagatac caggcgtttc ccctggaag ctccctcgtg cgctctcctg      6600
ttccgaccct gccgcttacc ggatacctgt ccgcctttct cccttcggga agcgtggcgc      6660
tttctcatag ctcacgctgt aggtatctca gttcggtgta ggtcgttcgc tccaagctgg      6720
gctgtgtgca cgaaccccc gttcagcccg accgctgcgc cttatccggt aactatcgtc      6780
ttgagtccaa cccggtaaga cacgacttat cgccactggc agcagccact ggtaacagga      6840
ttagcagagc gaggtatgta ggcggtgcta cagagttctt gaagtggtgg cctaactacg      6900
gctacactag aagaacagta tttggtatct gcgctctgct gaagccagtt accttcggaa      6960
aaagagttgg tagctcttga tccggcaaac aaaccaccgc tggtagcggt ggtttttttg      7020
tttgcaagca gcagattacg cgcagaaaaa aaggatctca agaagatcct ttgatcttt     7080 ctacggggtc tgacgctcag tggaacgaaa actcacgtta agggattttg gtcatgagat      7140
tatcaaaaag gatcttcacc tagatccttt taaattaaaa atgaagtttt aaatcaatct      7200
aaagtatata tgagtaaact tggtctgaca gttagaaaaa ctcatcgagc atcaaatgaa      7260
actgcaattt attcatatca ggattatcaa taccatattt ttgaaaaagc cgtttctgta      7320
atgaaggaga aaactcaccg aggcagttcc ataggatggc aagatcctgg tatcggtctg      7380
cgattccgac tcgtccaaca tcaatacaac ctattaatt cccctcgtca aaataaggt      7440 tatcaagtga aaatcacca tgagtgacga ctgaatccgg tgagaatggc aacagcttat      7500
gcatttcttt ccagacttgt tcaacaggcc agccattacg ctcgtcatca aaatcactcg      7560
catcaaccaa accgttattc attcgtgatt gcgcctgagc gagacgaaat acgcgatcgc      7620
tgttaaaagg acaattacaa acaggaatcg aatgcaaccg gcgcaggaac actgccagcg      7680
catcaacaat attttcacct gaatcaggat attcttctaa tacctggaat gctgtttttc      7740
cggggatcgc agtggtgagt aaccatgcat catcaggagt acggataaaa tgcttgatgg      7800
tcggaagagg cataaattcc gtcagccagt ttagtctgac catctcatct gtaacatcat      7860
tggcaacgct acctttgcca tgtttcagaa acaactctgg cgcatcgggc ttcccataca      7920
atcgatagat tgtcgcacct gattgcccga cattatcgcg agcccattta tacccatata      7980
aatcagcatc catgttggaa tttaatcgcg gcctagagca agacgtttcc cgttgaatat      8040
ggctcataac accccttgta ttactgttta tgtaagcaga cagttttatt gttcatgatg      8100
atatattttt atcttgtgca atgtaacatc agagattttg agacacaaca attgtcgaca      8160
ttgattattg actagttatt aatagtaatc aattacgggg tcattagttc atagcccata      8220
tatggagttc cgcgttacat aacttacggt aaatggcccg cctggctgac cgcccaacga      8280
```

```
cccccgccca ttgacgtcaa taatgacgta tgttcccata gtaacgccaa tagggacttt    8340
ccattgacgt caatgggtgg agtatttacg gtaaactgcc cacttggcag tacatcaagt    8400
gtatcatatg ccaagtacgc ccc ctattga cgtcaatgac ggtaaatggc ccgcctggca    8460
ttatgcccag tacatgacct tatgggactt tcctacttgg cagtacatct acgtattagt    8520
catcgctatt accatggtcg aggtgagccc cacgttctgc ttcactctcc ccatctcccc    8580
ccctccccca cccccaattt tgtatttatt tattttttaa ttattttgtg cagcgatggg    8640
ggcggggggg gggggggggc gcgcgccagg cggggcgggg cggggcgagg ggcggggcgg    8700
ggcgaggcgc agaggtgcgg cggcagccaa tcagagcggc gcgctccgaa agtttccttt    8760
tatggcgagg cggcggcggc ggcggcccta taaaaagcga agcgcgcggc gggcgggagt    8820
cgctgcgcgc tgccttcgcc ccgtgccccg ctccgccgcc gcctcgcgcc gcccgccccg    8880
gctctgactg accgcgttac tcccacaggt gagcgggcgg gacggccctt ctcctccggg    8940
ctgtaattag cgcttggttt aatgacggct tgtttctttt ctgtggctgc gtgaaagcct    9000
tgaggggctc cggggagggcc ctttgtgcgg ggggagcggg tcgggggtg cgtgcgtgtg    9060 tgtgtgcgtg gggagcgccg cgtgcggctc cgcgctgccc ggcggctgtg agcgctgcgg    9120
gcgcggcgcg gggctttgtg cgctccgcag tgtgcgcgag gggagcgcgg ccgggggcgg    9180
tgccccgcgg tgcggggggg gctgcgaggg gaacaaaggc tgcgtgcggg gtgtgtgcgt    9240
gggggggtga gcaggggtg tgggcgcgtc ggtcggcctg caacccccc tgcacccccc    9300 tcccccgagtt gctgagcacg gcccggcttc gggtgcgggg ctccgtacgg ggcgtggcgc    9360
ggggctcgcc gtgccgggcg ggggtggcg gcaggtgggg gtgccgggcg gggcggggcc    9420
gcctcgggcc ggggagggct cggggagggg gcgcggcggc ccccggagcg ccggcggctg    9480
tcgaggcgcg gcgagccgca gccattgcct tttatggtaa tcgtgcgaga gggcgcaggg    9540
acttcctttg tcccaaatct gtgcggagcc gaaatctggg aggcgccgcc gcacccccctc    9600 tagcgggcgc ggggcgaagc ggtgcggcgc cggcaggaag gaaatgggcg gggagggcct    9660
tcgtgcgtcg ccgcgccgcc gtcccccttct ccctctccag cctcggggct gtccgcgggg    9720
ggacggctgc cttcgggggg gacggggcag ggcgggggttc ggcttctggc gtgtgaccgg    9780
cggctctaga gcctctgcta accatgttca tgccttcttc ttttttcctac agctcctggg    9840 caacgtgctg gttattgtgc tgtctcatca ttttggcaaa gaatt                    9885
```

<210> SEQ ID NO 3
<211> LENGTH: 3384
<212> TYPE: DNA
<213> ORGANISM: Artificial Sequence
<220> FEATURE:
<223> OTHER INFORMATION: pGM299 plasmid

<400> SEQUENCE: 3

```
tcaatattgg ccattagcca tattattcat tggttatata gcataaatca atattggcta     60
ttggccattg catacgttgt atctatatca taatatgtac atttatattg gctcatgtcc    120
aatatgaccg ccatgttggc attgattatt gactagttat taatagtaat caattacggg    180
gtcattagtt catagcccat atatggagtt ccgcgttaca taacttacgg taaatggccc    240
gcctggctga ccgcccaacg acccccgccc attgacgtca ataatgacgt atgttcccat    300
agtaacgcca atagggactt tccattgacg tcaatgggtg gagtatttac ggtaaactgc    360
ccacttggca gtacatcaag tgtatcatat gccaagtccg cccctattg acgtcaatga    420
```

```
cggtaaatgg cccgcctggc attatgccca gtacatgacc ttacgggact ttcctacttg    480
gcagtacatc tacgtattag tcatcgctat taccatggtg atgcggtttt ggcagtacac    540
caatgggcgt ggatagcggt ttgactcacg gggatttcca agtctccacc ccattgacgt    600
caatgggagt ttgttttggc accaaaatca acgggacttt ccaaaatgtc gtaataaccc    660
cgccccgttg acgcaaatgg gcggtaggcg tgtacggtgg gaggtctata taagcagagc    720
tcgtttagtg aaccgtcaga tcactagaag ctttattgcg gtagtttatc acagttaaat    780
tgctaacgca gtcagtgctt ctgacacaac agtctcgaac ttaagctgca gaagttggtc    840
gtgaggcact gggcaggtaa gtatcaaggt tacaagacag gtttaaggag accaatagaa    900
actgggcttg tcgagacaga gaagactctt gcgtttctga taggcaccta ttggtcttac    960
tgacatccac tttgcctttc tctccacagg tgtccactcc cagttcaatt acagctctta   1020
aggctagagt acttaatacg actcactata ggctagcctc gagaattcga ttatgcccct   1080
aggaccagaa gaaagaagat tgcttcgctt gatttggctc ctttacagca ccaatccata   1140
tccaccaagt ggggaaggga cggccagaca acgccgacga gccaggagaa ggtggagaca   1200
acagcaggat caaattagag tcttggtaga aagactccaa gagcaggtgt atgcagttga   1260
ccgcctggct gacgaggctc aacacttggc tatacaacag ttgcctgacc ctcctcattc   1320
agcttagaat cactagtgaa ttcacgcgtg gtacctctag agtcgacccg gcggccgct    1380 tcgagcagac atgataagat acattgatga gtttggacaa accacaacta gaatgcagtg   1440
aaaaaaatgc tttatttgtg aaatttgtga tgctattgct ttatttgtaa ccattataag   1500
ctgcaataaa caagttaaca acaacaattg cattcatttt atgtttcagg ttcaggggga   1560
gatgtgggag gttttttaaa gcaagtaaaa cctctacaaa tgtggtaaaa tcgataagga   1620
tccgtcgacc aattgttgtg tctcaaaatc tctgatgtta cattgcacaa gataaaaata   1680
tatcatcatg aacaataaaa ctgtctgctt acataaacag taatacaagg ggtgttatga   1740
gccatattca acgggaaacg tcttgctcta ggccgcgatt aaattccaac atggatgctg   1800
atttatatgg gtataaatgg gctcgcgata atgtcgggca atcaggtgcg acaatctatc   1860
gattgtatgg gaagcccgat gcgccagagt tgtttctgaa acatggcaaa ggtagcgttg   1920
ccaatgatgt tacagatgag atggtcagac taaactggct gacggaattt atgcctcttc   1980
cgaccatcaa gcattttatc cgtactcctg atgatgcatg gttactcacc actgcgatcc   2040
ccggaaaaac agcattccag gtattagaag aatatcctga ttcaggtgaa aatattgttg   2100
atgcgctggc agtgttcctg cgccggttgc attcgattcc tgtttgtaat tgtccttta   2160 acagcgatcg cgtatttcgt ctcgctcagg cgcaatcacg aatgaataac ggtttggttg   2220
atgcgagtga ttttgatgac gagcgtaatg gctggcctgt tgaacaagtc tggaaagaaa   2280
tgcataagct gttgccattc tcaccggatt cagtcgtcac tcatggtgat ttctcacttg   2340
ataaccttat ttttgacgag gggaaattaa taggttgtat tgatgttgga cgagtcggaa   2400
tcgcagaccg ataccaggat cttgccatcc tatggaactg cctcggtgag ttttctcctt   2460
cattacagaa acggcttttt caaaaatatg gtattgataa tcctgatatg aataaattgc   2520
agtttcattt gatgctcgat gagttttct aactgtcaga ccaagtttac tcatatatac   2580
tttagattga tttaaaactt catttttaat ttaaaaggat ctaggtgaag atcctttttg   2640
ataatctcat gaccaaaatc ccttaacgtg agttttcgtt ccactgagcg tcagaccccg   2700
tagaaaagat caaaggatct tcttgagatc ctttttttct gcgcgtaatc tgctgcttgc   2760
aaacaaaaaa accaccgcta ccagcggtgg tttgtttgcc ggatcaagag ctaccaactc   2820
```

| | |
|---|---:|
| tttttccgaa ggtaactggc ttcagcagag cgcagatacc aaatactgtt cttctagtgt | 2880 |
| agccgtagtt aggccaccac ttcaagaact ctgtagcacc gcctacatac ctcgctctgc | 2940 |
| taatcctgtt accagtggct gctgccagtg gcgataagtc gtgtcttacc gggttggact | 3000 |
| caagacgata gttaccggat aaggcgcagc ggtcgggctg aacggggggt tcgtgcacac | 3060 |
| agcccagctt ggagcgaacg acctacaccg aactgagata cctacagcgt gagctatgag | 3120 |
| aaagcgccac gcttcccgaa gggagaaagg cggacaggta tccggtaagc ggcagggtcg | 3180 |
| gaacaggaga gcgcacgagg gagcttccag ggggaaacgc ctggtatctt tatagtcctg | 3240 |
| tcgggtttcg ccacctctga cttgagcgtc gattttgtg atgctcgtca ggggggcgga | 3300 |
| gcctatggaa aaacgccagc aacgcggcct ttttacggtt cctggccttt tgctggcctt | 3360 |
| ttgctcacat ggctcgacag atct | 3384 |

<210> SEQ ID NO 4
<211> LENGTH: 6264
<212> TYPE: DNA
<213> ORGANISM: Artificial Sequence
<220> FEATURE:
<223> OTHER INFORMATION: pGM301 plasmid

<400> SEQUENCE: 4

| | |
|---|---:|
| attgattatt gactagttat taatagtaat caattacggg gtcattagtt catagcccat | 60 |
| atatggagtt ccgcgttaca taacttacgg taaatggccc gcctggctga ccgcccaacg | 120 |
| acccccgccc attgacgtca ataatgacgt atgttcccat agtaacgcca atagggactt | 180 |
| tccattgacg tcaatgggtg gagtatttac ggtaaactgc ccacttggca gtacatcaag | 240 |
| tgtatcatat gccaagtacg ccccctattg acgtcaatga cggtaaatgg cccgcctggc | 300 |
| attatgccca gtacatgacc ttatgggact ttcctacttg gcagtacatc tacgtattag | 360 |
| tcatcgctat taccatggtc gaggtgagcc cacgttctg cttcactctc cccatctccc | 420 |
| cccctcccc accccaatt tgtatttat ttattttta attattttgt gcagcgatgg | 480 |
| gggcgggggg ggggggggg cgcgcgccag gcggggcggg gcgggcaag gggcggggcg | 540 |
| gggcgaggcg gaaaggtgcg gcggcagcca atcaaagcgg cgcgctccga aagtttcctt | 600 |
| ttatggcgag gcggcggcgg cggcggccct ataaaaagcg aagcgcgcgg cgggcgggag | 660 |
| tcgctgcgcg ctgccttcgc cccgtgcccc gctccgccgc cgcctcgcgc cgcccgcccc | 720 |
| ggctctgact gaccgcgtta ctcccacagg tgagcgggcg gacggcccct tctcctccgg | 780 |
| gctgtaatta gcgcttggtt taatgacggc ttgtttcttt tctgtggctg cgtgaaagcc | 840 |
| ttgaggggct ccgggagggc cctttgtgcg ggggagcgg ctcgggggt gcgtgcgtgt | 900 |
| gtgtgtgcgt ggggagcgcc gcgtgcggct ccgcgctgcc cggcggctgt gagcgctgcg | 960 |
| ggcgcggcgc ggggctttgt gcgctccgca gtgtgcgcga ggggagcgcg gccggggcg | 1020 |
| gtgccccgcg gtgcgggggg ggctgcgagg ggaacaaagg ctgcgtgcgg ggtgtgtgcg | 1080 |
| tggggggtg agcaggggt gtgggcgcgt cggtcgggct gcaacccccc ctgcacccc | 1140 |
| ctccccgagt tgctgagcac ggcccggctt cgggtgcggg gctccgtacg gggcgtggcg | 1200 |
| cggggctcgc cgtgccgggc gggggtggc ggcaggtggg ggtgccgggc ggggcgggc | 1260 |
| cgcctcgggc cggggagggc tcggggagg ggcgcggcgg ccccggagc gccggcggct | 1320 |
| gtcgaggcgc ggcgagccgc agccattgcc ttttatggta atcgtgcgag agggcgcagg | 1380 |
| gacttccttt gtcccaaatc tgtgcggagc cgaaatctgg gaggcgccgc cgcacccct | 1440 |

```
ctagcgggcg cggggcgaag cggtgcggcg ccggcaggaa ggaaatgggc ggggagggcc    1500
ttcgtgcgtc gccgcgccgc cgtcccctto tccctctcca gcctcgggc tgtccgcggg    1560 gggacggctg ccttcggggg ggacggggca gggcggggtt cggcttctgg cgtgtgaccg    1620
gcggctctag agcctctgct aaccatgttc atgccttctt cttttttccta cagctcctgg   1680 gcaacgtgct ggttattgtg ctgtctcatc attttggcaa agaattcgat tgccatggca    1740
acatatatcc agagagtaca gtgcatctca acatcactac tggttgttct caccacattg    1800
gtctcgtgtc agattcccag ggataggctc tctaacatag gggtcatagt cgatgaaggg    1860
aaatcactga agatagctgg atcccacgaa tcgaggtaca tagtactgag tctagttccg    1920
ggggtagact ttgagaatgg gtgcggaaca gcccaggtta tccagtacaa gagcctactg    1980
aacaggctgt taatcccatt gagggatgcc ttagatcttc aggaggctct gataactgtc    2040
accaatgata cgacacaaaa tgccggtgct ccccagtcga gattcttcgg tgctgtgatt    2100
ggtactatcg cacttggagt ggcgacatca gcacaaatca ccgcagggat tgcactagcc    2160
gaagcgaggg aggccaaaag agacatagcg ctcatcaaag aatcgatgac aaaaacacac    2220
aagtctatag aactgctgca aaacgctgtg ggggaacaaa ttcttgctct aaagacactc    2280
caggatttcg tgaatgatga gatcaaaccc gcaataagcg aattaggctg tgagactgct    2340
gccttaagac tgggtataaa attgacacag cattactccg agctgttaac tgcgttcggc    2400
tcgaatttcg gaaccatcgg agagaagagc ctcacgctgc aggcgctgtc ttcactttac    2460
tctgctaaca ttactgagat tatgaccaca atcaggacag ggcagtctaa catctatgat    2520
gtcatttata cagaacagat caaaggaacg gtgatagatg tggatctaga gagatacatg    2580
gtcaccctgt ctgtgaagat ccctattctt tctgaagtcc caggtgtgct catacacaag    2640
gcatcatcta tttcttacaa catagacggg gaggaatggt atgtgactgt ccccagccat    2700
atactcagtc gtgcttcttt cttaggggt gcagacataa ccgattgtgt tgagtccaga    2760
ttgacctata tatgccccag ggatcccgca caactgatac ctgacagcca gcaaaagtgt    2820
atcctggggg acacaacaag gtgtcctgtc acaaaagttg tggacagcct tatccccaag    2880
tttgcttttg tgaatggggg cgttgttgct aactgcatag catccacatg tacctgcggg    2940
acaggccgaa gaccaatcag tcaggatcgc tctaaaggtg tagtattcct aacccatgac    3000
aactgtggtc ttataggtgt caatggggta gaattgtatg ctaaccggag agggcacgat    3060
gccacttggg gggtccagaa cttgacagtc ggtcctgcaa ttgctatcag acccgttgat    3120
atttctctca accttgctga tgctacgaat ttcttgcaag actctaaggc tgagcttgag    3180
aaagcacgga aaatcctctc ggaggtaggt agatggtaca actcaagaga gactgtgatt    3240
acgatcatag tagttatggt cgtaatattg gtggtcatta tagtgatcat catcgtgctt    3300
tatagactca gaaggtgaaa tcactagtga attcactcct caggtgcagg ctgcctatca    3360
gaaggtggtg gctggtgtgg ccaatgccct ggctcacaaa taccactgag atcttttttcc    3420 ctctgccaaa aattatgggg acatcatgaa gccccttgag catctgactt ctggctaata    3480
aaggaaattt attttcattg caatagtgtg ttggaatttt ttgtgtctct cactcggaag    3540
gacatatggg agggcaaatc atttaaaaca tcagaatgag tatttggttt agagtttggc    3600
aacatatgcc catatgctgg ctgccatgaa caaaggttgg ctataaagag gtcatcagta    3660
tatgaaacag cccctgctg tccattcctt attccataga aaagccttga cttgaggtta    3720 gattttttttt atattttgtt ttgtgttatt ttttcttta acatccctaa aatttttcctt    3780 acatgttttta ctagccagat ttttcctcct ctcctgacta ctcccagtca tagctgtccc    3840
```

```
tcttctctta tggagatccc tcgacctgca gcccaagctt ggcgtaatca tggtcatagc    3900
tgtttcctgt gtgaaattgt tatccgctca caattccaca caacatacga gccggaagca    3960
taaagtgtaa agcctggggt gcctaatgag tgagctaact cacattaatt gcgttgcgct    4020
cactgcccgc tttccagtcg ggaaacctgt cgtgccagcg gatccgcatc tcaattagtc    4080
agcaaccata gtcccgcccc taactccgcc catcccgccc ctaactccgc ccagttccgc    4140
ccattctccg ccccatggct gactaatttt ttttatttat gcagaggccg aggccgcctc    4200
ggcctctgag ctattccaga agtagtgagg aggcttttt ggaggcctag gcttttgcaa    4260
aaagctaact tgtttattgc agcttataat ggttacaaat aaagcaatag catcacaaat    4320
ttcacaaata aagcattttt ttcactgcat tctagttgtg gtttgtccaa actcatcaat    4380
gtatcttatc atgtctgtcc gcttcctcgc tcactgactc gctgcgctcg tcgttcggc    4440 tgcggcgagc ggtatcagct cactcaaagg cggtaatacg gttatccaca gaatcagggg    4500
ataacgcagg aaagaacatg tgagcaaaag gccagcaaaa ggccaggaac cgtaaaaagg    4560
ccgcgttgct ggcgtttttc cataggctcc gcccccctga cgagcatcac aaaaatcgac    4620
gctcaagtca gaggtggcga aacccgacag gactataaag ataccaggcg tttccccctg    4680
gaagctccct cgtgcgctct cctgttccga ccctgccgct taccggatac ctgtccgcct    4740
ttctcccttc gggaagcgtg gcgctttctc atagctcacg ctgtaggtat ctcagttcgg    4800
tgtaggtcgt tcgctccaag ctgggctgtg tgcacgaacc ccccgttcag cccgaccgct    4860
gcgccttatc cggtaactat cgtcttgagt ccaacccggt aagacacgac ttatcgccac    4920
tggcagcagc cactggtaac aggattagca gagcgaggta tgtaggcggt gctacagagt    4980
tcttgaagtg gtggcctaac tacggctaca ctagaagaac agtatttggt atctgcgctc    5040
tgctgaagcc agttaccttc ggaaaaagag ttggtagctc ttgatccggc aaacaaacca    5100
ccgctggtag cggtggtttt tttgtttgca agcagcagat tacgcgcaga aaaaaaggat    5160
ctcaagaaga tcctttgatc ttttctacgg ggtctgacgc tcagtggaac gaaaactcac    5220
gttaagggat tttggtcatg agattatcaa aaaggatctt cacctagatc cttttaaatt    5280
aaaaatgaag ttttaaatca atctaaagta tatatgagta aacttggtct gacagttaga    5340
aaaactcatc gagcatcaaa tgaaactgca atttattcat atcaggatta tcaataccat    5400 attttttgaaa aagccgtttc tgtaatgaag gagaaaactc accgaggcag ttccatagga    5460
tggcaagatc ctggtatcgg tctgcgattc cgactcgtcc aacatcaata caacctatta    5520
atttcccctc gtcaaaaata aggttatcaa gtgagaaatc accatgagtg acgactgaat    5580
ccggtgagaa tggcaacagc ttatgcattt cttccagac ttgttcaaca ggccagccat    5640
tacgctcgta tcaaaatca ctcgcatcaa ccaaaccgtt attcattcgt gattgcgcct    5700
gagcgagacg aaatacgcga tcgctgttaa aaggacaatt acaaacagga tcgaatgca    5760 accggcgcag gaacactgcc agcgcatcaa caatattttc acctgaatca ggatattctt    5820 ctaataccctg gaatgctgtt tttccgggga tcgcagtggt gagtaaccat gcatcatcag    5880
gagtacggat aaaatgcttg atggtcggaa gaggcataaa ttccgtcagc cagtttagtc    5940
tgaccatctc atctgtaaca tcattggcaa cgctacctt gccatgttc agaaacaact    6000 ctggcgcatc gggcttccca tacaatcgat agattgtcgc acctgattgc ccgacattat    6060
cgcgagccca tttatcccca tataaatcag catccatgtt ggaatttaat cgcggcctag    6120
agcaagacgt ttcccgttga atatggctca taacacccct tgtattactg tttatgtaag    6180
```
cagacagttt tattgttcat gatgatatat ttttatcttg tgcaatgtaa catcagagat    6240
tttgagacac aacaattggt cgac    6264

<210> SEQ ID NO 5
<211> LENGTH: 6522
<212> TYPE: DNA
<213> ORGANISM: Artificial Sequence
<220> FEATURE:
<223> OTHER INFORMATION: pGM303 plasmid

<400> SEQUENCE: 5
attgattatt gactagttat taatagtaat caattacggg gtcattagtt catagcccat      60
atatggagtt ccgcgttaca taacttacgg taaatggccc gcctggctga ccgcccaacg     120 accccgccc attgacgtca ataatgacgt atgttcccat agtaacgcca atagggactt      180
tccattgacg tcaatgggtg gagtatttac ggtaaactgc ccacttggca gtacatcaag     240
tgtatcatat gccaagtacg ccccctattg acgtcaatga cggtaaatgg cccgcctggc     300
attatgccca gtacatgacc ttatgggact ttcctacttg gcagtacatc tacgtattag     360
tcatcgctat taccatggtc gaggtgagcc ccacgttctg cttcactctc cccatctccc     420
cccccctccc accccccaatt ttgtatttat ttattttttta attattttgt gcagcgatgg     480 gggcggggg ggggggggg cgcgcgccag gcggggcggg gcggggcgag ggggcggggcg     540 gggcgaggcg gaaaggtgcg gcggcagcca atcaaagcgg cgcgctccga aagtttcctt     600
ttatggcgag gcggcggcgg cggcggccct ataaaaagcg aagcgcgcgg cgggcgggag     660
tcgctgcgcg ctgccttcgc cccgtgcccc gctccgccgc cgcctcgcgc cgcccgcccc     720
ggctctgact gaccgcgtta ctcccacagg tgagcgggcg ggacggccct tctcctccgg     780
gctgtaatta gcgcttggtt taatgacggc ttgtttcttt tctgtggctg cgtgaaagcc     840 ttgagggct ccgggagggc cctttgtgcg ggggagcgg ctcgggggt gcgtgcgtgt       900 gtgtgtgcgt ggggagcgcc gcgtgcggct ccgcgctgcc cggcggctgt gagcgctgcg     960
ggcgcggcgc ggggctttgt gcgctccgca gtgtgcgcga ggggagcgcg gccggggggcg    1020 gtgccccgcg gtgcgggggg ggctgcgagg ggaacaaagg ctgcgtgcgg ggtgtgtgcg    1080
tgggggggtg agcaggggggt gtgggcgcgt cggtcgggct gcaaccccccc ctgcaccccc    1140 ctccccgagt tgctgagcac ggcccggctt cgggtgcggg gctccgtacg gggcgtggcg    1200
cggggctcgc cgtgccgggc ggggggtggc ggcaggtggg ggtgccgggc ggggcggggc    1260
cgcctcgggc cggggagggc tcggggagg ggcgcggcgg ccccggagc gccggcggct     1320 gtcgaggcgc ggcgagccgc agccattgcc ttttatggta atcgtgcgag agggcgcagg    1380
gacttccttt gtcccaaatc tgtgcggagc cgaaatctgg gaggcgccgc cgcaccccct    1440
ctagcgggcg cggggcgaag cggtgcggcg ccggcaggaa ggaaatgggc ggggagggcc    1500
ttcgtgcgtc gccgcgccgc cgtcccctcc tccctctcca gcctcggggc tgtccgcggg    1560
gggacggggc agggcggggt tcggcttctg gcgtgtgacc ggcggctcta gagcctctgc    1620
taaccatgtt catgccttct tctttttcct acagctcctg ggcaacgtgc tggttattgt    1680
gctgtctcat cattttggca aagaattcct cgagcatgtg gtctgagtta aaaatcagga    1740
gcaacgacgg aggtgaagga ccagaggacg ccaacgaccc ccggggaaag ggggtgcaac    1800
acatccatat ccagccatct ctacctgttt atggacagag ggttagggat ggtgataggg    1860
gcaaacgtga ctcgtactgg tctacttctc ctagtggtag caccacaaaa ccagcatcag    1920
gttgggagag gtcaagtaaa gccgacacat ggttgctgat tctctcattc acccagtggg    1980

```
ctttgtcaat tgccacagtg atcatctgta tcataatttc tgctagacaa gggtatagta   2040
tgaaagagta ctcaatgact gtagaggcat tgaacatgag cagcagggag gtgaaagagt   2100
cacttaccag tctaataagg caagaggtta tagcaagggc tgtcaacatt cagagctctg   2160
tgcaaaccgg aatcccagtc ttgttgaaca aaaacagcag ggatgtcatc cagatgattg   2220
ataagtcgtg cagcagacaa gagctcactc agcactgtga gagtacgatc gcagtccacc   2280
atgccgatgg aattgcccca cttgagccac atagtttctg gagatgccct gtcggagaac   2340
cgtatcttag ctcagatcct gaaatctcat tgctgcctgg tccgagcttg ttatctggtt   2400
ctacaacgat ctctggatgt gttaggctcc cttcactctc aattggcgag gcaatctatg   2460
cctattcatc aaatctcatt acacaaggtt gtgctgacat agggaaatca tatcaggtcc   2520
tgcagctagg gtacatatca ctcaattcag atatgttccc tgatcttaac cccgtagtgt   2580
cccacactta tgacatcaac gacaatcgga atcatgctc tgtggtggca accgggacta   2640
ggggttatca gctttgctcc atgccgactg tagacgaaag aaccgactac tctagtgatg   2700
gtattgagga tctggtcctt gatgtcctgg atctcaaagg gagaactaag tctcaccggt   2760
atcgcaacag cgaggtagat cttgatcacc cgttctctgc actataccc agtgtaggca   2820 acggcattgc aacagaaggc tcattgatat ttcttgggta tggtggacta accacccctc   2880
tgcagggtga tacaaaatgt aggacccaag atgccaaca ggtgtcgcaa gacacatgca   2940
atgaggctct gaaaattaca tggctaggag ggaaacaggt ggtcagcgtg atcatccagg   3000
tcaatgacta tctctcagag aggccaaaga taagagtcac aaccattcca atcactcaaa   3060
actatctcgg ggcggaaggt agattattaa aattgggtga tcgggtgtac atctatacaa   3120
gatcatcagg ctggcactct caactgcaga taggagtact tgatgtcagc caccctttga   3180
ctatcaactg gacacctcat gaagccttgt ctagaccagg aaataaagag tgcaattggt   3240
acaataagtg tccgaaggaa tgcatatcag gcgtatacac tgatgcttat ccattgtccc   3300
ctgatgcagc taacgtcgct accgtcacgc tatatgccaa tacatcgcgt gtcaacccaa   3360
caatcatgta ttctaacact actaacatta taaatatgtt aaggataaag gatgttcaat   3420
tagaggctgc atataccacg acatcgtgta tcacgcattt tggtaaaggc tactgctttc   3480
acatcatcga gatcaatcag aagagcctga ataccttaca gccgatgctc tttaagacta   3540
gcatccctaa attatgcaag gccgagtctt aagcggccgc gcatgcgaat tcactcctca   3600
ggtgcaggct gcctatcaga aggtggtggc tggtgtggcc aatgccctgg ctcacaaata   3660
ccactgagat cttttttccct ctgccaaaaa ttatgggac atcatgaagc cccttgagca   3720
tctgacttct ggctaataaa ggaaatttat tttcattgca atagtgtgtt ggaatttttt   3780
gtgtctctca ctcggaagga catatgggag ggcaaatcat ttaaaacatc agaatgagta   3840
tttggtttag agtttggcaa catatgccca tatgctggct gccatgaaca aaggttggct   3900
ataaagaggt catcagtata tgaaacagcc cctgctgtc tattccttat tccatagaaa   3960
agccttgact tgaggttaga ttttttttat attttgtttt gtgttatttt tttctttaac   4020
atccctaaaa ttttccttac atgttttact agccagattt ttcctcctct cctgactact   4080
cccagtcata gctgtccctc ttctcttatg gagatccctc gacctgcagc caagcttgg   4140 cgtaatcatg gtcatagctg tttcctgtgt gaaattgtta tccgctcaca attccacaca   4200
acatacgagc cggaagcata aagtgtaaag cctggggtgc ctaatgagtg agctaactca   4260
cattaattgc gttgcgctca ctgcccgctt tccagtcggg aaacctgtcg tgccagcgga   4320
```

```
tccgcatctc aattagtcag caaccatagt cccgccccta actccgccca tcccgcccct    4380
aactccgccc agttccgccc attctccgcc ccatggctga ctaattttt ttatttatgc    4440 agaggccgag gccgcctcgg cctctgagct attccagaag tagtgaggag gcttttttgg    4500
aggcctaggc ttttgcaaaa agctaacttg tttattgcag cttataatgg ttacaaataa    4560
agcaatagca tcacaaattt cacaaataaa gcattttttt cactgcattc tagttgtggt    4620
ttgtccaaac tcatcaatgt atcttatcat gtctgtccgc ttcctcgctc actgactcgc    4680
tgcgctcggt cgttcggctg cggcgagcgg tatcagctca ctcaaaggcg gtaatacggt    4740
tatccacaga atcaggggat aacgcaggaa agaacatgtg agcaaaaggc cagcaaaagg    4800
ccaggaaccg taaaaaggcc gcgttgctgg cgtttttcca taggctccgc cccctgacg    4860 agcatcacaa aaatcgacgc tcaagtcaga ggtggcgaaa cccgacagga ctataaagat    4920
accaggcgtt tcccctgga agctccctcg tgcgctctcc tgttccgacc ctgccgctta    4980
ccggatacct gtccgccttt ctcccttcgg aagcgtggc gctttctcat agctcacgct    5040
gtaggtatct cagttcggtg taggtcgttc gctccaagct gggctgtgtg cacgaacccc    5100
ccgttcagcc cgaccgctgc gccttatccg gtaactatcg tcttgagtcc aacccggtaa    5160
gacacgactt atcgccactg gcagcagcca ctggtaacag gattagcaga gcgaggtatg    5220
taggcggtgc tacagagttc ttgaagtggt ggcctaacta cggctacact agaagaacag    5280
tatttggtat ctgcgctctg ctgaagccag ttaccttcgg aaaaagagtt ggtagctctt    5340
gatccggcaa acaaaccacc gctggtagcg gtggttttt tgtttgcaag cagcagatta    5400
cgcgcagaaa aaaaggatct caagaagatc ctttgatctt ttctacgggg tctgacgctc    5460
agtggaacga aaactcacgt taagggattt tggtcatgag attatcaaaa aggatcttca    5520
cctagatcct tttaaattaa aaatgaagtt ttaaatcaat ctaaagtata tatgagtaaa    5580
cttggtctga cagttagaaa aactcatcga gcatcaaatg aaactgcaat ttattcatat    5640
caggattatc aataccatat ttttgaaaaa gccgtttctg taatgaagga gaaaactcac    5700
cgaggcagtt ccataggatg gcaagatcct ggtatcggtc tgcgattccg actcgtccaa    5760
catcaataca accttattaa tttcccctcgt caaaaataag gttatcaagt gagaaatcac    5820
catgagtgac gactgaatcc ggtgagaatg gcaacagctt atgcatttct ttccagactt    5880
gttcaacagg ccagccatta cgctcgtcat caaaatcact cgcatcaacc aaaccgttat    5940
tcattcgtga ttgcgcctga gcgagacgaa atacgcgatc gctgttaaaa ggacaattac    6000
aaacaggaat cgaatgcaac cggcgcagga acactgccag cgcatcaaca atattttcac    6060
ctgaatcagg atattcttct aatacctgga atgctgtttt tccggggatc gcagtggtga    6120
gtaaccatgc atcatcagga gtacggataa aatgcttgat ggtcggaaga ggcataaatt    6180
ccgtcagcca gtttagtctg accatctcat ctgtaacatc attggcaacg ctacctttgc    6240
catgtttcag aaacaactct ggcgcatcgg gcttcccata caatcgatag attgtcgcac    6300
ctgattgccc gacattatcg cgagcccatt tatacccata taaatcagca tccatgttgg    6360
aatttaatcg cggcctagag caagacgttt cccgttgaat atggctcata cacccttg    6420 tattactgtt tatgtaagca gacagtttta ttgttcatga tgatatattt ttatcttgtg    6480
caatgtaaca tcagagattt tgagacacaa caattggtcg ac                       6522
```

<210> SEQ ID NO 6
<211> LENGTH: 574
<212> TYPE: DNA
<213> ORGANISM: Artificial Sequence

```
<220> FEATURE:
<223> OTHER INFORMATION: hCEF promoter

<400> SEQUENCE: 6
agatctgtta cataacttat ggtaaatggc ctgcctggct gactgccaa tgaccctgc      60 ccaatgatgt caataatgat gtatgttccc atgtaatgcc aatagggact ttccattgat  120
gtcaatgggt ggagtattta tggtaactgc ccacttggca gtacatcaag tgtatcatat  180
gccaagtatg cccctattg atgtcaatga tggtaaatgg cctgcctggc attatgccca   240
gtacatgacc ttatgggact ttcctacttg gcagtacatc tatgtattag tcattgctat  300
taccatggga attcactagt ggagaagagc atgcttgagg gctgagtgcc cctcagtggg  360
cagagagcac atggcccaca gtccctgaga gttgggggg aggggtgggc aattgaactg   420
gtgcctagag aagtgggc ttgggtaaac tgggaaagtg atgtggtgta ctggctccac    480
ctttttcccc agggtggggg agaaccatat ataagtgcag tagtctctgt gaacattcaa  540
gcttctgcct ctccctcct gtgagtttgc tagc                               574

<210> SEQ ID NO 7
<211> LENGTH: 4459
<212> TYPE: DNA
<213> ORGANISM: Artificial Sequence
<220> FEATURE:
<223> OTHER INFORMATION: codon-optimised CpG depleted CFTR transgene

<400> SEQUENCE: 7
gctagccacc atgcagagaa gccctctgga aaggcctct gtggtgagca agctgttctt    60
cagctggacc aggcccatcc tgaggaaggg ctacaggcag agactggagc tgtctgacat  120
ctaccagatc ccctctgtgg actctgctga caacctgtct gagaagctgg agagggagtg  180
ggatagagag ctggccagca gaagaaccc caagctgatc aatgccctga ggagatgctt   240
cttctgagga ttcatgttct atggcatctt cctgtacctg ggggaagtga ccaaggctgt  300
gcagcctctg ctgctgggca gaatcattgc cagctatgac cctgacaaca ggaggagag   360 gagcattgcc atctacctgg gcattggcct gtgcctgctg ttcattgtga ggaccctgct  420
gctgcaccct gccatctttg gcctgcacca cattggcatg cagatgagga ttgccatgtt  480
cagcctgatc tacaagaaaa ccctgaagct gtccagcaga gtgctggaca gatcagcat   540 tggccagctg gtgagcctgc tgagcaacaa cctgaacaag tttgatgagg gcctggccct  600
ggcccacttt gtgtggattg ccctctgca ggtggccctg ctgatgggcc tgatttggga   660
gctgctgcag gcctctgcct tttgtggcct gggcttcctg attgtgctgg ccctgtttca  720
ggctggcctg ggcaggatga tgatgaagta cagggaccag agggcaggca gatcagtga   780 gaggctggtg atcacctctg agatgattga gaacatccga tctgtgaagg cctactgttg  840
ggaggaagct atggagaaga tgattgaaaa cctgaggcag acagagctga agctgaccag  900
gaaggctgcc tatgtgagat acttcaacag ctctgccttc ttcttctctg gcttctttgt  960
ggtgttcctg tctgtgctgc cctatgccct gatcaagggg atcatcctga aaagatttt  1020 caccaccatc agcttctgca ttgtgctgag gatggctgtg accagacagt tccctgggc  1080 tgtgcagacc tggtatgaca gcctgggggc catcaacaag atccaggact cctgcagaa   1140 gcaggagtac aagaccctgg agtacaacct gaccaccaca gaagtggtga tggagaatgt  1200
gacagccttc tgggaggagg gctttgggga gctgtttgag aaggccaagc agaacaacaa  1260
caacagaaag accagcaatg gggatgactc cctgttcttc tccaacttct ccctgctggg  1320
```

```
cacacctgtg ctgaaggaca tcaacttcaa gattgagagg gggcagctgc tggctgtggc    1380
tggatctaca ggggctggca agaccagcct gctgatgatg atcatggggg agctggagcc    1440
ttctgagggc aagatcaagc actctggcag gatcagcttt tgcagccagt tcagctggat    1500
catgcctggc accatcaagg agaacatcat ctttggagtg agctatgatg agtacagata    1560
caggagtgtg atcaaggcct gccagctgga ggaggacatc agcaagtttg ctgagaagga    1620
caacattgtg ctgggggagg gaggcattac actgtctggg ggccagagag ccagaatcag    1680
cctggccagg gctgtgtaca aggatgctga cctgtacctg ctggactccc cctttggcta    1740
cctggatgtg ctgacagaga aggagatttt tgagagctgt gtgtgcaagc tgatggccaa    1800
caagaccaga atcctggtga ccagcaagat ggagcacctg aagaaggctg acaagatcct    1860
gatcctgcat gagggcagca gctacttcta tgggaccttc tctgagctgc agaacctgca    1920
gcctgacttc agctctaagc tgatgggctg tgacagcttt gaccagttct ctgctgagag    1980
gaggaacagc atcctgacag agaccctgca cagattcagc ctggagggag atgcccctgt    2040
gagctggaca gagaccaaga agcagagctt caagcagaca ggggagtttg gggagaagag    2100
gaagaactcc atcctgaacc ccatcaacag catcaggaag ttcagcattg tgcagaaaac    2160 cccccctgcag atgaatggca ttgaggaaga ttctgatgag cccctggaga ggagactgag    2220
cctggtgcct gattctgagc agggagaggc catcctgcct aggatctctg tgatcagcac    2280
aggccctaca ctgcaggcca gaaggaggca gtctgtgctg aacctgatga cccactctgt    2340
gaaccagggc cagaacatcc acaggaaaac cacagcctcc accaggaaag tgagcctggc    2400
ccctcaggcc aatctgacag agctggacat ctacagcagg aggctgtctc aggagacagg    2460
cctggagatt tctgaggaga tcaatgagga ggacctgaaa gagtgcttct ttgatgacat    2520
ggagagcatc cctgctgtga ccacctggaa cacctacctg agatacatca cagtgcacaa    2580
gagcctgatc tttgtgctga tctggtgcct ggtgatcttc ctggctgaag tggctgcctc    2640
tctggtggtg ctgtggctgc tgggaaacac cccactgcag acaagggca acagcaccca    2700 cagcaggaac aacagctatg ctgtgatcat cacctccacc tccagctact atgtgttcta    2760
catctatgtg ggagtggctg ataccctgct ggctatgggc ttctttagag cctgccccct    2820
ggtgcacaca ctgatcacag tgagcaagat cctccaccac aagatgctgc actctgtgct    2880
gcaggctcct atgagcaccc tgaataccct gaaggctggg ggcatcctga acagattctc    2940
caaggatatt gccatcctgg atgacctgct gcctctcacc atctttgact tcatccagct    3000
gctgctgatt gtgattgggg ccattgctgt ggtggcagtg ctgcagccct acatctttgt    3060
ggccacagtg cctgtgattg tggccttcat catgctgagg gcctactttc tgcagacctc    3120
ccagcagctg aagcagctgg agtctgaggg cagaagcccc atcttcaccc acctggtgac    3180
aagcctgaag ggcctgtgga ccctgagagc ctttggcagg cagccctact tgagaccct    3240 gttccacaag gccctgaacc tgcacacagc caactggttc ctctacctgt ccaccctgag    3300
atggttccag atgagaattg agatgatctt tgtcatcttc ttcattgctg tgaccttcat    3360
cagcattctg accacaggag agggagaggg cagagtgggc attatcctga ccctggccat    3420
gaacatcatg agcacactgc agtgggcagt gaacagcagc attgatgtgg acagcctgat    3480
gaggagtgtg agcagagtgt tcaagttcat tgatatgccc acagagggca agcctaccaa    3540
gagcaccaag ccctacaaga atggccagct gagcaaagtg atgatcattg agaacagcca    3600
tgtgaagaag gatgatatct ggcccagtgg aggccagatg acagtgaagg acctgacagc    3660
caagtacaca gagggggggca atgctatcct ggagaacatc tccttcagca tctcccctgg    3720
```

```
ccagagagtg ggactgctgg gaagaacagg ctctggcaag tctaccctgc tgtctgcctt    3780
cctgaggctg ctgaacacag agggagagat ccagattgat ggagtgtcct gggacagcat    3840
cacactgcag cagtggagga aggccttttgg tgtgatcccc cagaaagtgt tcatcttcag   3900
tggcaccttc aggaagaacc tggacccta tgagcagtgg tctgaccagg agatttggaa     3960
agtggctgat gaagtgggcc tgagaagtgt gattgagcag ttccctggca agctggactt    4020
tgtcctggtg gatgggggct gtgtgctgag ccatggccac aagcagctga tgtgcctggc    4080
cagatcagtg ctgagcaagg ccaagatcct gctgctggat gagccttctg cccacctgga    4140
tcctgtgacc taccagatca tcaggaggac cctcaagcag gcctttgctg actgcacagt    4200
catcctgtgt gagcacagga ttgaggccat gctggagtgc cagcagttcc tggtgattga    4260
ggagaacaaa gtgaggcagt atgacagcat ccagaagctg ctgaatgaga ggagcctgtt    4320
caggcaggcc atcagcccct ctgatagagt gaagctgttc ccccacagga acagctccaa    4380
gtgcaagagc aagcccccaga ttgctgccct gaaggaggag acagaggagg aagtgcagga   4440
caccaggctg tgagggccc                                                 4459
```

<210> SEQ ID NO 8
<211> LENGTH: 600
<212> TYPE: DNA
<213> ORGANISM: Woodchuck hepatitis virus

<400> SEQUENCE: 8

```
gggcccaatc aacctctgga ttacaaaatt tgtgaaagat tgactggtat tcttaactat     60
gttgctcctt ttacgctatg tggatacgct gctttaatgc ctttgtatca tgctattgct    120
tcccgtatgg ctttcatttt ctcctccttg tataaatcct ggttgctgtc tctttatgag    180
gagttgtggc ccgttgtcag gcaacgtggc gtggtgtgca ctgtgtttgc tgacgcaacc    240
cccactggtt gggcattgc caccacctgt cagctccttt ccgggacttt cgctttcccc    300
ctccctattg ccacggcgga actcatcgcc gcctgccttg cccgctgctg gacagggget    360 cggctgttgg gcactgacaa ttccgtggtg ttgtcgggga atcatcgtc ctttccttgg    420 ctgctcgcct gtgttgccac ctggattctg cgcgggacgt ccttctgcta cgtcccttcg    480
gccctcaatc cagcggacct tccttcccgc ggcctgctgc cggctctgcg gcctcttccg    540
cgtcttcgcc ttcgccctca gacgagtcgg atctcccttt gggccgcctc cccgcaagct    600
```

<210> SEQ ID NO 9
<211> LENGTH: 7349
<212> TYPE: DNA
<213> ORGANISM: Artificial Sequence
<220> FEATURE:
<223> OTHER INFORMATION: pGM407 plasmid

<400> SEQUENCE: 9

```
ggtacctcaa tattggccat tagccatatt attcattggt tatatagcat aaatcaatat     60
tggctattgg ccattgcata cgttgtatct atatcataat atgtacattt atattggctc   120
atgtccaata tgaccgccat gttggcattg attattgact agttattaat agtaatcaat   180 tacgggtca ttagttcata gcccatatat ggagttccgc gttacataac ttacggtaaa   240
tggcccgcct ggctgaccgc ccaacgaccc ccgcccattg acgtcaataa tgacgtatgt   300
tcccatagta acgccaatag ggactttcca ttgacgtcaa tgggtggagt atttacggta   360
aactgcccac ttggcagtac atcaagtgta tcatatgcca agtccgcccc ctattgacgt   420
```

```
caatgacggt aaatggcccg cctggcatta tgcccagtac atgaccttac gggactttcc      480
tacttggcag tacatctacg tattagtcat cgctattacc atggtgatgc ggttttggca      540
gtacaccaat gggcgtggat agcggtttga ctcacgggga tttccaagtc tccaccccat      600
tgacgtcaat gggagtttgt tttggcacca aaatcaacgg gactttccaa aatgtcgtaa      660
caactgcgat cgcccgcccc gttgacgcaa atgggcggta ggcgtgtacg gtgggaggtc      720
tatataagca gagctcgctg gcttgtaact cagtctctta ctaggagacc agcttgagcc      780
tgggtgttcg ctggttagcc taacctggtt ggccaccagg ggtaaggact ccttggctta      840
gaaagctaat aaacttgcct gcattagagc ttatctgagt caagtgtcct cattgacgcc      900
tcactctctt gaacgggaat cttccttact gggttctctc tctgacccag gcgagagaaa      960
ctccagcagt ggcgcccgaa cagggacttg agtgagagtg taggcacgta cagctgagaa     1020
ggcgtcggac gcgaaggaag cgcggggtgc gacgcgacca agaaggagac ttggtgagta     1080
ggcttctcga gtgccgggaa aaagctcgag cctagttaga ggactaggag aggccgtagc     1140
cgtaactact cttgggcaag tagggcaggc ggtgggtacg caatgggggc ggctacctca     1200
gcactaaata ggagacaatt agaccaattt gagaaaatac gacttcgccc gaacggaaag     1260
aaaaagtacc aaattaaaca tttaatatgg gcaggcaagg agatggagcg cttcggcctc     1320
catgagaggt tgttggagac agaggagggg tgtaaaagaa tcatagaagt cctctacccc     1380
ctagaaccaa caggatcgga gggcttaaaa agtctgttca atcttgtgtg cgtgctatat     1440
tgcttgcaca aggaacagaa agtgaaagac acagaggaag cagtagcaac agtaagacaa     1500
cactgccatc tagtggaaaa agaaaaaagt gcaacagaga catctagtgg acaaaagaaa     1560
aatgacaagg gaatagcagc gccacctggt ggcagtcaga attttccagc gcaacaacaa     1620
ggaaatgcct gggtacatgt acccttgtca ccgcgcacct aaatgcgtg ggtaaaagca     1680 gtagaggaga aaaaatttgg agcagaaata gtacccattt ttttgtttca gccctatcg     1740 aattcccgtt tgtgctaggg ttcttaggct tcttgggggc tgctggaact gcaatgggag     1800
cagcggcgac agccctgacg gtccagtctc agcatttgct tgctgggata ctgcagcagc     1860
agaagaatct gctggcggct gtggaggctc aacagcagat gttgaagctg accatttggg     1920
gtgttaaaaa cctcaatgcc cgcgtcacag cccttgagaa gtacctagag gatcaggcac     1980
gactaaactc ctgggggtgc gcatggaaac aagtatgtca taccacagtg gagtggccct     2040
ggacaaatcg gactccggat tggcaaaata tgacttggtt ggagtgggaa agacaaatag     2100
ctgatttgga aagcaacatt acgagacaat tagtgaaggc tagagaacaa gaggaaaaga     2160
atctagatgc ctatcagaag ttaactagtt ggtcagattt ctggtcttgg ttcgatttct     2220
caaaatggct taacattta aaaatgggat ttttagtaat agtaggaata atagggttaa     2280
gattacttta cacagtatat ggatgtatag tgagggttag gcaggatat gttcctctat     2340 ctccacagat ccatatccgc ggcaattta aagaaaggg aggaataggg ggacagactt     2400
cagcagagag actaattaat ataataacaa cacaattaga aatacaacat ttacaaacca     2460
aaattcaaaa aattttaaat tttagagccg cggagatctg ttacataact tatggtaaat     2520
ggcctgcctg gctgactgcc caatgacccc tgcccaatga tgtcaataat gatgtatgtt     2580
cccatgtaat gccaataggg actttccatt gatgtcaatg ggtggagtat ttatggtaac     2640
tgcccacttg gcagtacatc aagtgtatca tatgccaagt atgcccccta ttgatgtcaa     2700
tgatggtaaa tggcctgcct ggcattatgc ccagtacatg acctatggg actttcctac     2760 ttggcagtac atctatgtat tagtcattgc tattaccatg gaattcact agtggagaag     2820
```

```
agcatgcttg agggctgagt gcccctcagt gggcagagag cacatggccc acagtccctg    2880
agaagttggg gggaggggtg ggcaattgaa ctggtgccta gagaaggtgg ggcttgggta    2940
aactgggaaa gtgatgtggt gtactggctc cacctttttc cccagggtgg gggagaacca    3000
tatataagtg cagtagtctc tgtgaacatt caagcttctg ccttctccct cctgtgagtt    3060
tgctagccac catgcccagc tctgtgtcct ggggcattct gctgctggct ggcctgtgct    3120
gtctggtgcc tgtgtccctg gctgaggacc ctcaggggga tgctgcccag aaaacagaca    3180
cctcccacca tgaccaggac caccccacct tcaacaagat caccccccaac ctggcagagt    3240 ttgccttcag cctgtacaga cagctggccc accagagcaa cagcaccaac atcttttca    3300 gccctgtgtc cattgccaca gcctttgcca tgctgagcct gggcaccaag gctgacaccc    3360
atgatgagat cctggaaggc ctgaacttca acctgacaga gatccctgag gcccagatcc    3420
atgagggctt ccaggaactg ctgagaaccc tgaaccagcc agacagccag ctgcagctga    3480
caacaggcaa tggctgtttc ctgtctgagg cctgaagct ggtggacaag tttctggaag    3540
atgtgaagaa gctgtaccac tctgaggcct tcacagtgaa ctttggggac acagaagagg    3600
ccaagaaaca gatcaatgac tatgtggaaa agggcaccca gggcaagatt gtggaccttg    3660
tgaaagagct ggacagggac actgtgtttg cccttgtgaa ctacatcttc ttcaagggca    3720
agtgggagag gcccttgaa gtgaaggaca ctgaggaaga ggacttccat gtggaccaag    3780
tgaccacagt gaaggtgcca atgatgaaga gactggggat gttcaatatc cagcactgca    3840
agaaactgag cagctgggtg ctgctgatga agtacctggg caatgctaca gccatattct    3900
ttctgcctga tgagggcaag ctgcagcacc tggaaaatga gctgacccat gacatcatca    3960
ccaaatttct ggaaaatgag gacagaagat ctgccagcct gcatctgccc aagctgagca    4020
tcacaggcac atatgacctg aagtctgtgc tgggacagct gggaatcacc aaggtgttca    4080 gcaatgggc agacctgagt ggagtgacag aggaagcccc tctgaagctg tccaaggctg    4140
tgcacaaggc agtgctgacc attgatgaga agggcacaga ggctgctggg ccatgtttc    4200 tggaagccat ccccatgtcc atcccccag aagtgaagtt caacaagccc tttgtgttcc    4260
tgatgattga gcagaacacc aagagccccc tgttcatggg caaggttgtg aaccccaccc    4320
agaaatgagg gcccaatcaa cctctggatt acaaaatttg tgaaagattg actggtattc    4380
ttaactatgt tgctcctttt acgctatgtg atacgctgc tttaatgcct ttgtatcatg    4440
ctattgcttc ccgtatggct ttcattttct cctccttgta taaatcctgg ttgctgtctc    4500
tttatgagga gttgtggccc gttgtcaggc aacgtggcgt ggtgtgcact gtgtttgctg    4560
acgcaacccc cactggttgg ggcattgcca ccacctgtca gctcctttcc gggactttcg    4620 ctttcccct ccctattgcc acggcggaac tcatcgccgc ctgccttgcc cgctgctgga    4680
caggggctcg gctgttgggc actgacaatt ccgtggtgtt gtcggggaaa tcatcgtcct    4740
ttccttggct gctcgcctgt gttgccacct ggattctgcg cggacgtcc ttctgctacg    4800 tcccttcggc cctcaatcca gcggaccttc cttcccgcgg cctgctgccg gctctgcggc    4860
ctcttccgcg tcttcgcctt cgccctcaga cgagtcggat ctccctttgg gccgcctccc    4920
cgcaagcttc gcactttta aagaaaagg gaggactgga tgggatttat tactccgata    4980
ggacgctggc ttgtaactca gtctcttact aggagaccag cttgagcctg ggtgttcgct    5040
ggttagccta acctggttgg ccaccagggg taaggactcc ttggcttaga aagctaataa    5100
acttgcctgc attagagctc ttacgcgtcc cgggctcgag atccgcatct caattagtca    5160
```

```
gcaaccatag tcccgcccct aactccgccc atcccgcccc taactccgcc cagttccgcc    5220
cattctccgc cccatggctg actaattttt tttatttatg cagaggccga ggccgcctcg    5280
gcctctgagc tattccagaa gtagtgagga ggcttttttg gaggcctagg cttttgcaaa    5340
aagctaactt gtttattgca gcttataatg gttacaaata aagcaatagc atcacaaatt    5400
tcacaaataa agcatttttt tcactgcatt ctagttgtgg tttgtccaaa ctcatcaatg    5460
tatcttatca tgtctgtccg cttcctcgct cactgactcg ctgcgctcgg tcgttcggct    5520
gcggcgagcg gtatcagctc actcaaaggc ggtaatacgg ttatccacag aatcagggga    5580
taacgcagga aagaacatgt gagcaaaagg ccagcaaaag gccaggaacc gtaaaaaggc    5640
cgcgttgctg gcgtttttcc ataggctccg ccccctgac gagcatcaca aaaatcgacg    5700
ctcaagtcag aggtggcgaa acccgacagg actataaaga taccaggcgt ttccccctgg    5760
aagctccctc gtgcgctctc ctgttccgac cctgccgctt accggatacc tgtccgcctt    5820
tctcccttcg ggaagcgtgg cgctttctca tagctcacgc tgtaggtatc tcagttcggt    5880
gtaggtcgtt cgctccaagc tgggctgtgt gcacgaaccc cccgttcagc ccgaccgctg    5940
cgccttatcc ggtaactatc gtcttgagtc caacccggta agacacgact tatcgccact    6000
ggcagcagcc actggtaaca ggattagcag agcgaggtat gtaggcggtg ctacagagtt    6060
cttgaagtgg tggcctaact acggctacac tagaagaaca gtatttggta tctgcgctct    6120
gctgaagcca gttaccttcg gaaaaagagt tggtagctct tgatccggca acaaaccac    6180 cgctggtagc ggtggttttt tgtttgcaa gcagcagatt acgcgcagaa aaaaggatc    6240 tcaagaagat cctttgatct tttctacggg gtctgacgct cagtggaacg aaaactcacg    6300
ttaagggatt ttggtcatga gattatcaaa aaggatcttc acctagatcc ttttaaatta    6360
aaaatgaagt tttaaatcaa tctaaagtat atatgagtaa acttggtctg acagttagaa    6420
aaactcatcg agcatcaaat gaaactgcaa tttattcata tcaggattat caataccata    6480
tttttgaaaa agccgtttct gtaatgaagg agaaaactca ccgaggcagt tccataggat    6540
ggcaagatcc tggtatcggt ctgcgattcc gactcgtcca acatcaatac aacctattaa    6600
tttcccctcg tcaaaaataa ggttatcaag tgagaaatca ccatgagtga cgactgaatc    6660
cggtgagaat ggcaacagct tatgcatttc tttccagact tgttcaacag gccagccatt    6720
acgctcgtca tcaaaatcac tcgcatcaac caaccgtta ttcattcgtg attgcgcctg    6780
agcgagacga atacgcgat cgctgttaaa aggacaatta caaacaggaa tcgaatgcaa    6840
ccggcgcagg aacactgcca gcgcatcaac aatattttca cctgaatcag gatattcttc    6900
taatacctgg aatgctgttt ttccggggat cgcagtggtg agtaaccatg catcatcagg    6960 agtacgata aatgcttga tggtcggaag aggcataaat tccgtcagcc agtttagtct    7020
gaccatctca tctgtaacat cattggcaac gctacctttg ccatgtttca gaaacaactc    7080
tggcgcatcg ggcttcccat acaatcgata gattgtcgca cctgattgcc cgacattatc    7140
gcgagcccat ttatacccat ataaatcagc atccatgttg gaatttaatc gcggcctaga    7200
gcaagacgtt tcccgttgaa tatggctcat aacacccctt gtattactgt ttatgtaagc    7260
agacagtttt attgttcatg atgatatatt tttatcttgt gcaatgtaac atcagagatt    7320
ttgagacaca acaattggtc gacggatcc                                     7349

<210> SEQ ID NO 10
<211> LENGTH: 6653
<212> TYPE: DNA
<213> ORGANISM: Artificial Sequence
```

<220> FEATURE:
<223> OTHER INFORMATION: pGM358 plasmid

<400> SEQUENCE: 10

| | | | | | |
|---|---|---|---|---|---|
| ggtacctcaa | tattggccat | tagccatatt | attcattggt | tatatagcat | aaatcaatat | 60 |
| tggctattgg | ccattgcata | cgttgtatct | atatcataat | atgtacattt | atattggctc | 120 |
| atgtccaata | tgaccgccat | gttggcattg | attattgact | agttattaat | agtaatcaat | 180 |
| tacggggtca | ttagttcata | gcccatatat | ggagttccgc | gttacataac | ttacggtaaa | 240 |
| tggcccgcct | ggctgaccgc | ccaacgaccc | ccgcccattg | acgtcaataa | tgacgtatgt | 300 |
| tcccatagta | acgccaatag | ggactttcca | ttgacgtcaa | tgggtggagt | atttacggta | 360 |
| aactgcccac | ttggcagtac | atcaagtgta | tcatatgcca | agtccgcccc | ctattgacgt | 420 |
| caatgacggt | aaatggcccg | cctggcatta | tgcccagtac | atgaccttac | gggactttcc | 480 |
| tacttggcag | tacatctacg | tattagtcat | cgctattacc | atggtgatgc | ggttttggca | 540 |
| gtacaccaat | gggcgtggat | agcggtttga | ctcacgggga | tttccaagtc | tccaccccat | 600 |
| tgacgtcaat | gggagtttgt | tttggcacca | aaatcaacgg | gactttccaa | aatgtcgtaa | 660 |
| caactgcgat | cgcccgcccc | gttgacgcaa | atgggcggta | ggcgtgtacg | gtgggaggtc | 720 |
| tatataagca | gagctcgctg | gcttgtaact | cagtctctta | ctaggagacc | agcttgagcc | 780 |
| tgggtgttcg | ctggttagcc | taacctggtt | ggccaccagg | ggtaaggact | ccttggctta | 840 |
| gaaagctaat | aaacttgcct | gcattagagc | ttatctgagt | caagtgtcct | cattgacgcc | 900 |
| tcactctctt | gaacgggaat | cttccttact | gggttctctc | tctgacccag | gcgagagaaa | 960 |
| ctccagcagt | ggcgcccgaa | cagggacttg | agtgagagtg | taggcacgta | cagctgagaa | 1020 |
| ggcgtcggac | gcgaaggaag | cgcggggtgc | gacgcgacca | agaaggagac | ttggtgagta | 1080 |
| ggcttctcga | gtgccgggaa | aaagctcgag | cctagttaga | ggactaggag | aggccgtagc | 1140 |
| cgtaactact | cttgggcaag | tagggcaggc | ggtgggtacg | caatggggc | ggctacctca | 1200 |
| gcactaaata | ggagacaatt | agaccaattt | gagaaaatac | gacttcgccc | gaacggaaag | 1260 |
| aaaaagtacc | aaattaaaca | tttaatatgg | gcaggcaagg | agatggagcg | cttcggcctc | 1320 |
| catgagaggt | tgttggagac | agaggagggg | tgtaaaagaa | tcatagaagt | cctctacccc | 1380 |
| ctagaaccaa | caggatcgga | gggcttaaaa | agtctgttca | atcttgtgtg | cgtgctatat | 1440 |
| tgcttgcaca | aggaacagaa | agtgaaagac | acagaggaag | cagtagcaac | agtaagacaa | 1500 |
| cactgccatc | tagtggaaaa | agaaaaaagt | gcaacagaga | catctagtgg | acaaagaaa | 1560 |
| aatgacaagg | gaatagcagc | gccacctggt | ggcagtcaga | attttccagc | gcaacaacaa | 1620 |
| ggaaatgcct | gggtacatgt | acccttgtca | ccgcgcacct | taaatgcgtg | gtaaaagca | 1680 |
| gtagaggaga | aaaatttggg | agcagaaata | gtacccattt | ttttgtttca | gccctatcg | 1740 |
| aattcccgtt | tgtgctaggg | ttcttaggct | tcttgggggc | tgctggaact | gcaatgggag | 1800 |
| cagcggcgac | agccctgacg | gtccagtctc | agcatttgct | tgctgggata | ctgcagcagc | 1860 |
| agaagaatct | gctggcggct | gtggaggctc | aacagcagat | gttgaagctg | accatttggg | 1920 |
| gtgttaaaaa | cctcaatgcc | cgcgtcacag | cccttgagaa | gtacctagag | gatcaggcac | 1980 |
| gactaaactc | ctggggtgc | gcatggaaac | aagtatgtca | taccacagtg | gagtggccct | 2040 |
| ggacaaatcg | gactccggat | tggcaaaata | tgacttggtt | ggagtgggaa | agacaaatag | 2100 |
| ctgatttgga | aagcaacatt | acgagacaat | tagtgaaggc | tagagaacaa | gaggaaaaga | 2160 |
| atctagatgc | ctatcagaag | ttaactagtt | ggtcagattt | ctggtcttgg | ttcgatttct | 2220 |

```
caaaatggct taacatttta aaaatgggat ttttagtaat agtaggaata atagggttaa    2280
gattacttta cacagtatat ggatgtatag tgagggttag gcagggatat gttcctctat    2340
ctccacagat ccatatccgc ggcaatttta aaagaaaggg aggaataggg ggacagactt    2400
cagcagagag actaattaat ataataacaa cacaattaga aatacaacat ttacaaacca    2460
aaattcaaaa aattttaaat tttagagccg cggagatctg ttacataact tatggtaaat    2520
ggcctgcctg gctgactgcc caatgacccc tgcccaatga tgtcaataat gatgtatgtt    2580
cccatgtaat gccaataggg actttccatt gatgtcaatg ggtggagtat ttatggtaac    2640
tgcccacttg gcagtacatc aagtgtatca tatgccaagt atgcccccta ttgatgtcaa    2700
tgatggtaaa tggcctgcct ggcattatgc ccagtacatg accttatggg actttcctac    2760
ttggcagtac atctatgtat tagtcattgc tattaccatg gaattcact agtggagaag     2820 agcatgcttg agggctgagt gcccctcagt gggcagagag cacatggccc acagtccctg    2880
agaagttggg gggaggggtg ggcaattgaa ctggtgccta gagaaggtgg ggcttgggta    2940
aactgggaaa gtgatgtggt gtactggctc cacctttttc cccagggtgg gggagaacca    3000
tatataagtg cagtagtctc tgtgaacatt caagcttctg ccttctccct cctgtgagtt    3060
tgctagccac catgggagtg aaggtgctgt ttgccctgat ctgcattgct gtggctgagg    3120
ccaagcccac agagaacaat gaggacttca acattgtggc tgtggccagc aactttgcca    3180
ccacagacct ggatgctgac aggggcaagc tgcctggcaa gaagctgccc ctggaagtcc    3240
tgaaagagat ggaagccaat gccaggaagg ctggctgcac aagaggctgt ctgatctgcc    3300
tgagccacat caagtgcacc cccaagatga agaagttcat ccctggcagg tgccacacct    3360
atgaagggga caaagagtct gcccaggggg gaattggaga ggccattgtg gacatccctg    3420
agatccctgg cttcaaggac ctggaaccca tggaacagtt cattgcccag gtggacctgt    3480
gtgtggactg cactacaggc tgtctcaagg gcctggccaa tgtgcagtgc tctgacctgc    3540
tgaagaagtg gctgccccag agatgtgcca ccttttgccag caagatccag ggccaggtgg    3600
acaagatcaa gggagctggg ggagattgat gagggcccaa tcaacctctg gattacaaaa    3660
tttgtgaaag attgactggt attcttaact atgttgctcc ttttacgcta tgtggatacg    3720
ctgctttaat gcctttgtat catgctattg cttcccgtat ggctttcatt ttctcctcct    3780
tgtataaatc ctggttgctg tctctttatg aggagttgtg gcccgttgtc aggcaacgtg    3840
gcgtggtgtg cactgtgttt gctgacgcaa ccccactgg ttggggcatt gccaccacct    3900
gtcagctcct ttccgggact ttcgctttcc cctccctat tgccacggcg gaactcatcg    3960
ccgcctgcct tgcccgctgc tggacagggg ctcggctgtt gggcactgac aattccgtgg    4020
tgttgtcggg gaaatcatcg tccttccctt ggctgctcgc ctgtgttgcc acctggattc    4080
tgcgcgggac gtccttctgc tacgtccctt cggccctcaa tccagcggac cttccttccc    4140
gcggcctgct gccggctctg cggcctcttc cgcgtcttcg ccttcgccct cagacgagtc    4200
ggatctccct ttgggccgcc tccccgcaag cttcgcactt tttaaagaa aagggaggac    4260 tggatgggat ttattactcc gataggacgc tggcttgtaa ctcagtctct tactaggaga    4320
ccagcttgag cctgggtgtt cgctggttag cctaacctgg ttggccacca ggggtaagga    4380
ctccttggct tagaaagcta ataaacttgc ctgcattaga gctcttacgc gtcccgggct    4440
cgagatccgc atctcaatta gtcagcaacc atagtcccgc ccctaactcc gcccatcccg    4500
cccctaactc cgcccagttc cgcccattct ccgccccatg gctgactaat ttttttatt    4560 tatgcagagg ccgaggccgc ctcggcctct gagctattcc agaagtagtg aggaggcttt    4620
```

```
tttggaggcc taggcttttg caaaaagcta acttgtttat tgcagcttat aatggttaca    4680
aataaagcaa tagcatcaca aatttcacaa ataaagcatt ttttcactg cattctagtt    4740 gtggtttgtc caaactcatc aatgtatctt atcatgtctg tccgcttcct cgctcactga    4800
ctcgctgcgc tcggtcgttc ggctgcggcg agcggtatca gctcactcaa aggcggtaat    4860
acggttatcc acagaatcag gggataacgc aggaaagaac atgtgagcaa aaggccagca    4920
aaaggccagg aaccgtaaaa aggccgcgtt gctggcgttt ttccataggc tccgcccccc    4980
tgacgagcat cacaaaaatc gacgctcaag tcagaggtgg cgaaacccga caggactata    5040
aagataccag gcgtttcccc ctggaagctc cctcgtgcgc tctcctgttc cgaccctgcc    5100
gcttaccgga tacctgtccg cctttctccc ttcgggaagc gtggcgcttt ctcatagctc    5160
acgctgtagg tatctcagtt cggtgtaggt cgttcgctcc aagctgggct gtgtgcacga    5220
accccccgtt cagcccgacc gctgcgcctt atccggtaac tatcgtcttg agtccaaccc    5280
ggtaagacac gacttatcgc cactggcagc agccactggt aacaggatta gcagagcgag    5340
gtatgtaggc ggtgctacag agttcttgaa gtggtggcct aactacggct acactagaag    5400
aacagtattt ggtatctgcg ctctgctgaa gccagttacc ttcggaaaaa gagttggtag    5460
ctcttgatcc ggcaaacaaa ccaccgctgg tagcggtggt ttttttgttt gcaagcagca    5520
gattacgcgc agaaaaaaag gatctcaaga agatcctttg atcttttcta cggggtctga    5580
cgctcagtgg aacgaaaact cacgttaagg gattttggtc atgagattat caaaaaggat    5640
cttcacctag atccttttaa attaaaaatg aagttttaaa tcaatctaaa gtatatatga    5700
gtaaacttgg tctgacagtt agaaaaactc atcgagcatc aaatgaaact gcaatttatt    5760
catatcagga ttatcaatac catattttg aaaaagccgt ttctgtaatg aaggagaaaa    5820
ctcaccgagg cagttccata ggatggcaag atcctggtat cggtctgcga ttccgactcg    5880
tccaacatca atacaaccta ttaatttccc ctcgtcaaaa ataaggttat caagtgagaa    5940
atcaccatga gtgacgactg aatccggtga gaatggcaac agcttatgca tttctttcca    6000
gacttgttca acaggccagc cattacgctc gtcatcaaaa tcactcgcat caaccaaacc    6060
gttattcatt cgtgattgcg cctgagcgag acgaaatacg cgatcgctgt taaaaggaca    6120
attacaaaca ggaatcgaat gcaaccggcg caggaacact gccagcgcat caacaatatt    6180
ttcacctgaa tcaggatatt cttctaatac ctggaatgct gttttccgg ggatcgcagt    6240 ggtgagtaac catgcatcat caggagtacg gataaaatgc ttgatggtcg aagaggcat    6300 aaattccgtc agccagttta gtctgaccat ctcatctgta acatcattgg caacgctacc    6360
tttgccatgt ttcagaaaca actctggcgc atcgggcttc ccatacaatc gatagattgt    6420
cgcacctgat tgcccgacat tatcgcgagc ccatttatac ccatataaat cagcatccat    6480
gttggaattt aatcgcggcc tagagcaaga cgtttcccgt tgaatatggc tcataacacc    6540
ccttgtatta ctgtttatgt aagcagacag ttttattgtt catgatgata tatttttatc    6600
ttgtgcaatg taacatcaga gatttgaga cacaacaatt ggtcgacgga tcc          6653
```

<210> SEQ ID NO 11
<211> LENGTH: 10812
<212> TYPE: DNA
<213> ORGANISM: Artificial Sequence
<220> FEATURE:
<223> OTHER INFORMATION: pGM411 plasmid

<400> SEQUENCE: 11

```
ggtacctcaa tattggccat tagccatatt attcattggt tatatagcat aaatcaatat        60
tggctattgg ccattgcata cgttgtatct atatcataat atgtacattt atattggctc       120
atgtccaata tgaccgccat gttggcattg attattgact agttattaat agtaatcaat       180 tacgggtca ttagttcata gcccatatat ggagttccgc gttacataac ttacggtaaa        240
tggcccgcct ggctgaccgc ccaacgaccc ccgcccattg acgtcaataa tgacgtatgt       300
tcccatagta acgccaatag ggactttcca ttgacgtcaa tgggtggagt atttacggta       360
aactgcccac ttggcagtac atcaagtgta tcatatgcca agtccgcccc ctattgacgt       420
caatgacggt aaatggcccg cctggcatta tgcccagtac atgaccttac ggactttcc       480 tacttggcag tacatctacg tattagtcat cgctattacc atggtgatgc ggttttggca       540
gtacaccaat gggcgtggat agcggtttga ctcacgggga tttccaagtc tccaccccat       600
tgacgtcaat gggagtttgt tttggcacca aaatcaacgg gactttccaa aatgtcgtaa       660
caactgcgat cgcccgcccc gttgacgcaa atgggcggta ggcgtgtacg gtgggaggtc       720
tatataagca gagctcgctg gcttgtaact cagtctctta ctaggagacc agcttgagcc       780
tgggtgttcg ctggttagcc taacctggtt ggccaccagg ggtaaggact ccttggctta       840
gaaagctaat aaacttgcct gcattagagc ttatctgagt caagtgtcct cattgacgcc       900
tcactctctt gaacgggaat cttccttact gggttctctc tctgacccag gcgagagaaa       960
ctccagcagt ggcgcccgaa cagggacttg agtgagagtg taggcacgta cagctgagaa      1020
ggcgtcggac gcgaaggaag cgcggggtgc gacgcgacca agaaggagac ttggtgagta      1080
ggcttctcga gtgccgggaa aaagctcgag cctagttaga ggactaggag aggccgtagc      1140
cgtaactact ctgggcaagt agggcaggcg gtgggtacgc aatgggggcg gctacctcag      1200
cactaaatag gagacaatta gaccaatttg agaaaatacg acttcgcccg aacggaaaga      1260
aaaagtacca aattaaacat ttaatatggg caggcaagga gatggagcgc ttcggcctcc      1320
atgagaggtt gttggagaca gaggaggggt gtaaagaaat catagaagtc ctctaccccc      1380
tagaaccaac aggatcggag ggcttaaaaa gtctgttcaa tcttgtgtgc gtgctatatt      1440
gcttgcacaa gaacagaaa gtgaaagaca cagaggaagc agtagcaaca gtaagacaac       1500
actgccatct agtggaaaaa gaaaaaagtg caacagagac atctagtgga caaagaaaa       1560 atgcaagggg aatagcagcg ccacctggtg gcagtcagaa ttttccagcg caacaacaag      1620
gaaatgcctg ggtacatgta cccttgtcac cgcgcacctt aaatgcgtgg gtaaaagcag      1680
tagaggagaa aaatttgga gcagaaatag tacccatgtt tcaagcccta tcgaattccc       1740
gtttgtgcta gggttcttag gcttcttggg ggctgctgga actgcaatgg gagcagcggc      1800
gacagccctg acggtccagt ctcagcattt gcttgctggg atactgcagc agcagaagaa      1860
tctgctggcg gctgtggagg ctcaacagca gatgttgaag ctgaccattt ggggtgttaa      1920
aaacctcaat gcccgcgtca cagcccttga aagtaccta gaggatcagg cacgactaaa       1980
ctcctggggg tgcgcatgga aacaagtatg tcataccaca gtggagtggc cctgacaaa       2040 tcggactccg gattggcaaa atatgacttg gttggagtgg aaagacaaa tagctgattt       2100 ggaaagcaac attacgagac aattagtgaa ggctagagaa caagaggaaa agaatctaga      2160
tgcctatcag aagttaacta gttggtcaga tttctggtct tggttcgatt tctcaaaatg      2220
gcttaacatt ttaaaaatgg gattttttagt aatagtagga ataataggt taagattact       2280 ttacacagta tatggatgta tagtgagggt taggcaggga tatgttcctc tatctccaca      2340
gatccatatc cgcggcaatt ttaaaagaaa gggaggaata gggggacaga cttcagcaga      2400
```

```
gagactaatt aatataataa caacacaatt agaaatacaa catttacaaa ccaaaattca    2460
aaaaatttta aattttagag ccgcggagat ctcaatattg gccattagcc atattattca    2520
ttggttatat agcataaatc aatattggct attggccatt gcatacgttg tatctatatc    2580
ataatatgta catttatatt ggctcatgtc caatatgacc gccatgttgg cattgattat    2640
tgactagtta ttaatagtaa tcaattacgg ggtcattagt tcatagccca tatatggagt    2700
tccgcgttac ataacttacg gtaaatggcc cgcctggctg accgcccaac gaccccccgcc    2760 cattgacgtc aataatgacg tatgttccca tagtaacgcc aatagggact ttccattgac    2820
gtcaatgggt ggagtattta cggtaaactg cccacttggc agtacatcaa gtgtatcata    2880
tgccaagtcc gccccctatt gacgtcaatg acggtaaatg gcccgcctgg cattatgccc    2940
agtacatgac cttacgggac tttcctactt ggcagtacat ctacgtatta gtcatcgcta    3000
ttaccatggt gatgcggttt tggcagtaca ccaatgggcg tggatagcgg tttgactcac    3060
ggggatttcc aagtctccac cccattgacg tcaatgggag tttgttttgg caccaaaatc    3120
aacgggactt tccaaaatgt cgtaataacc ccgccccgtt gacgcaaatg ggcggtaggc    3180
gtgtacggtg ggaggtctat ataagcagag ctcgtttagt gaaccgtcag atcactagaa    3240
gctttattgc ggtagtttat cacagttaaa ttgctaacgc agtcagtgct tctgacacaa    3300
cagtctcgaa cttaagctgc agaagttggt cgtgaggcac tgggcaggct agccaccaat    3360
gcagattgag ctgagcacct gcttcttcct gtgcctgctg aggttctgct tctctgccac    3420
caggagatac tacctgggg ctgtggagct gagctgggac tacatgcagt ctgacctggg    3480
ggagctgcct gtggatgcca ggttcccccc cagagtgccc aagagcttcc ccttcaacac    3540
ctctgtggtg tacaagaaga ccctgttttgt ggagttcact gaccacctgt tcaacattgc    3600
caagcccagg ccccccctgga tgggcctgct gggccccacc atccaggctg aggtgtatga    3660
cactgtggtg atcaccctga gaacatggc cagccaccct gtgagcctgc atgctgtggg    3720
ggtgagctac tggaaggcct ctgagggggc tgagtatgat gaccagacca gccagaggga    3780
gaaggaggat gacaaggtgt tccctggggg cagccacacc tatgtgtggc aggtgctgaa    3840
ggagaatggc cccatggcct ctgacccccct gtgcctgacc tacagctacc tgagccatgt    3900
ggacctggtg aaggacctga actctggcct gattggggcc ctgctggtgt gcagggaggg    3960
cagcctggcc aaggagaaga cccagaccct gcacaagttc atcctgctgt ttgctgtgtt    4020
tgatgagggc aagagctggc actctgaaac caagaacagc ctgatgcagg acagggatgc    4080
tgcctctgcc agggcctggc ccaagatgca cactgtgaat ggctatgtga acaggagcct    4140
gcctggcctg attggctgcc acaggaagtc tgtgtactgg catgtgattg catgggcac    4200 caccccctgag gtgcacagca tcttcctgga gggccacacc ttcctggtca ggaaccacag    4260
gcaggccagc ctggagatca gccccatcac cttcctgact gcccagaccc tgctgatgga    4320
cctgggccag ttcctgctgt tctgccacat cagcagccac cagcatgatg catggaggc    4380 ctatgtgaag gtggacagct gccctgagga gccccagctg aggatgaaga caatgagga    4440 ggctgaggac tatgatgatg acctgactga ctctgagatg gatgtggtga ggtttgatga    4500
tgacaacagc cccagcttca tccagatcag gtctgtggca aagaagcacc ccaagacctg    4560
ggtgcactac attgctgctg aggaggagga ctgggactat gccccctggg tgctggcccc    4620
tgatgacagg agctacaaga gccagtacct gaacaatggc ccccagagga ttggcaggaa    4680
gtacaagaag gtcaggttca tggcctacac tgatgaaacc ttcaagacca gggaggccat    4740
```

```
ccagcatgag tctggcatcc tgggccccct gctgtatggg gaggtggggg acaccctgct    4800
gatcatcttc aagaaccagg ccagcaggcc ctacaacatc taccccccatg gcatcactga   4860 tgtgaggccc ctgtacagca ggaggctgcc caagggggtg aagcacctga aggacttccc    4920
catcctgcct ggggagatct tcaagtacaa gtggactgtg actgtggagg atggccccac    4980
caagtctgac cccaggtgcc tgaccagata ctacagcagc tttgtgaaca tggagaggga    5040
cctggcctct ggcctgattg gcccctgct gatctgctac aaggagtctg tggaccagag    5100
gggcaaccag atcatgtctg acaagaggaa tgtgatcctg ttctctgtgt ttgatgagaa    5160
caggagctgg tacctgactg agaacatcca gaggttcctg cccaaccctg ctggggtgca    5220
gctggaggac cctgagttcc aggccagcaa catcatgcac agcatcaatg ctatgtgtt    5280 tgacagcctg cagctgtctg tgtgcctgca tgaggtggcc tactggtaca tcctgagcat    5340
tggggcccag actgacttcc tgtctgtgtt cttctctggc tacaccttca gcacaagat    5400 ggtgtatgag acaccctga ccctgttccc cttctctggg gagactgtgt tcatgagcat    5460
ggagaaccct ggcctgtgga ttctgggctg ccacaactct gacttcagga caggggcat    5520 gactgccctg ctgaaagtct ccagctgtga caagaacact ggggactact atgaggacag    5580
ctatgaggac atctctgcct acctgctgag caagaacaat gccattgagc ccaggagctt    5640
cagccagaat gccactaatg tgtctaacaa cagcaacacc agcaatgaca gcaatgtgtc    5700 tccccccagtg ctgaagaggc accagaggga gatcaccagg accaccctgc agtctgacca   5760
ggaggagatt gactatgatg acaccatctc tgtggagatg aagaaggagg actttgacat    5820
ctacgacgag gacgagaacc agagcccag gagcttccag aagaagacca ggcactactt    5880
cattgctgct gtggagaggc tgtgggacta tggcatgagc agcagccccc atgtgctgag    5940
gaacagggcc cagtctggct ctgtgcccca gttcaagaag gtggtgttcc aggagttcac    6000
tgatggcagc ttcacccagc ccctgtacag aggggagctg aatgagcacc tgggcctgct    6060
gggcccctac atcagggctg aggtggagga caacatcatg gtgaccttca ggaaccaggc    6120
cagcaggccc tacagcttct acagcagcct gatcagctat gaggaggacc agaggcaggg    6180
ggctgagccc aggaagaact tgtgaagcc caatgaaacc aagacctact ctggaaggt    6240 gcagcaccac atggccccca ccaaggatga gtttgactgc aaggcctggg cctacttctc    6300
tgatgtggac ctggagaagg atgtgcactc tggcctgatt ggccccctgc tggtgtgcca    6360
caccaacacc ctgaaccctg cccatggcag gcaggtgact gtgcaggagt ttgccctgtt    6420
cttcaccatc tttgatgaaa ccaagagctg gtacttcact gagaacatgg agaggaactg    6480 cagggcccc tgcaacatcc agatggagga ccccacctttc aaggagaact acaggttcca    6540
tgccatcaat ggctacatca tggacaccct gcctggcctg gtgatggccc aggaccagag    6600
gatcaggtgg tacctgctga gcatgggcag caatgagaac atccacagca tccacttctc    6660
tggccatgtg ttcactgtga ggaagaagga ggagtacaag atgggcctgt acaacctgta    6720 ccctgggggtg tttgagactg tggagatgct gcccagcaag gctggcatct ggaggggtgga   6780 gtgcctgatt ggggagcacc tgcatgctgg catgagcacc ctgttcctgg tgtacagcaa    6840
caagtgccag accccctgg gcatggcctc tggccacatc agggacttcc agatcactgc    6900
ctctggccag tatggccagt gggccccccaa gctggccagg ctgcactact ctggcagcat    6960
caatgcctgg agcaccaagg agcccttcag ctggatcaag gtggacctgc tggcccccat    7020
gatcatccat ggcatcaaga cccagggggc caggcagaag ttcagcagcc tgtacatcag    7080
ccagttcatc atcatgtaca gcctggatgg caagaagtgg cagacctaca ggggcaacag    7140
```

```
cactggcacc ctgatggtgt tctttggcaa tgtggacagc tctggcatca agcacaacat   7200
cttcaacccc cccatcattg ccagatacat caggctgcac cccacccact acagcatcag   7260
gagcaccctg aggatggagc tgatgggctg tgacctgaac agctgcagca tgccccctggg  7320 catggagagc aaggccatct ctgatgccca gatcactgcc agcagctact tcaccaacat   7380
gtttgccacc tggagcccca gcaaggccag gctgcacctg cagggcagga gcaatgcctg   7440
gaggccccag gtcaacaacc ccaaggagtg ctgcaggtg gacttccaga agaccatgaa   7500
ggtgactggg gtgaccaccc aggggtgaa gagcctgctg accagcatgt atgtgaagga   7560
gttcctgatc agcagcagcc aggatggcca ccagtggacc ctgttcttcc agaatggcaa   7620
ggtgaaggtg ttccagggca accaggacag cttcacccct gtggtgaaca gcctggaccc   7680 cccctgctg accagatacc tgaggattca ccccagagc tgggtgcacc agattgccct    7740
gaggatggag gtgctgggct gtgaggccca ggacctgtac tgagcggccg cgggcccaat   7800
caacctctgg attacaaaat tgtgaaaga ttgactggta ttcttaacta tgttgctcct   7860
tttacgctat gtggatacgc tgctttaatg cctttgtatc atgctattgc ttcccgtatg   7920
gctttcattt tctcctcctt gtataaatcc tggttgctgt ctctttatga ggagttgtgg   7980
cccgttgtca ggcaacgtgg cgtggtgtgc actgtgtttg ctgacgcaac ccccactggt   8040
tggggcattg ccaccacctg tcagctcctt tccgggactt tcgctttccc cctccctatt   8100
gccacggcgg aactcatcgc cgcctgcctt gcccgctgct ggacaggggc tcggctgttg   8160
ggcactgaca attccgtggt gttgtcgggg aaatcatcgt cctttccttg gctgctcgcc   8220
tgtgttgcca cctggattct gcgcgggacg tccttctgct acgtcccttc ggccctcaat   8280
ccagcggacc ttccttcccg cggcctgctg ccggctctgc ggcctcttcc gcgtcttcgc   8340
cttcgccctc agacgagtcg atctcccctt gggccgcct cccgcaagc ttcgcacttt    8400 ttaaagaaa agggaggact ggatgggatt tattactccg ataggacgct ggcttgtaac   8460
tcagtctctt actaggagac cagcttgagc ctgggtgttc gctggttagc ctaacctggt   8520
tggccaccag gggtaaggac tccttggctt agaaagctaa taaacttgcc tgcattagag   8580
ctcttacgcg tcccgggctc gagatccgca tctcaattag tcagcaacca tagtcccgcc   8640
cctaactccg cccatcccgc ccctaactcc gcccagttcc gcccattctc gccccatgg    8700 ctgactaatt tttttattt atgcagaggc cgaggccgcc tcggcctctg agctattcca   8760
gaagtagtga ggaggctttt ttggaggcct aggcttttgc aaaaagctaa cttgtttatt   8820
gcagcttata atggttacaa ataaagcaat agcatcacaa atttcacaaa taaagcattt   8880
ttttcactgc attctagttg tggtttgtcc aaactcatca atgtatctta tcatgtctgt   8940
ccgcttcctc gctcactgac tcgctgcgct cggtcgttcg gctgcggcga gcggtatcag   9000
ctcactcaaa ggcggtaata cggttatcca cagaatcagg gataacgca ggaaagaaca    9060 tgtgagcaaa aggccagcaa aaggccagga accgtaaaaa ggccgcgttg ctggcgtttt   9120
tccataggct ccgcccccct gacgagcatc acaaaaatcg acgctcaagt cagaggtggc   9180
gaaacccgac aggactataa agataccagg cgtttccccc tggaagctcc ctcgtgcgct   9240
ctcctgttcc gaccctgccg cttaccggat acctgtccgc ctttctccct tcgggaagcg   9300
tggcgctttc tcatagctca cgctgtaggt atctcagttc ggtgtaggtc gttcgctcca   9360
agctgggctg tgtgcacgaa ccccccgttc agcccgaccg ctgcgcctta tccggtaact   9420
atcgtcttga gtccaacccg gtaagacacg acttatcgcc actggcagca gccactggta   9480
```

```
acaggattag cagagcgagg tatgtaggcg gtgctacaga gttcttgaag tggtggccta      9540
actacggcta cactagaaga acagtatttg gtatctgcgc tctgctgaag ccagttacct      9600
tcggaaaaag agttggtagc tcttgatccg gcaaacaaac caccgctggt agcggtggtt      9660
ttttgtttg  caagcagcag attacgcgca gaaaaaagg  atctcaagaa gatcctttga      9720
tcttttctac ggggtctgac gctcagtgga acgaaaactc acgttaaggg attttggtca      9780
tgagattatc aaaaaggatc ttcacctaga tccttttaaa ttaaaaatga agttttaaat      9840
caatctaaag tatatatgag taaacttggt ctgacagtta gaaaaactca tcgagcatca      9900
aatgaaactg caatttattc atatcaggat tatcaatacc atattttga  aaaagccgtt      9960
tctgtaatga aggagaaaac tcaccgaggc agttccatag gatggcaaga tcctggtatc     10020
ggtctgcgat tccgactcgt ccaacatcaa tacaacctat taatttcccc tcgtcaaaaa     10080
taaggttatc aagtgagaaa tcaccatgag tgacgactga atccggtgag aatggcaaca     10140
gcttatgcat ttctttccag acttgttcaa caggccagcc attacgctcg tcatcaaaat     10200
cactcgcatc aaccaaaccg ttattcattc gtgattgcgc ctgagcgaga cgaaatacgc     10260
gatcgctgtt aaaaggacaa ttacaaacag gaatcgaatg caaccggcgc aggaacactg     10320
ccagcgcatc aacaatattt tcacctgaat caggatattc ttctaatacc tggaatgctg     10380
ttttccggg  gatcgcagtg gtgagtaacc atgcatcatc aggagtacgg ataaaatgct     10440
tgatggtcgg aagaggcata aattccgtca gccagtttag tctgaccatc tcatctgtaa     10500
catcattggc aacgctacct ttgccatgtt tcagaaacaa ctctggcgca tcgggcttcc     10560
catacaatcg atagattgtc gcacctgatt gcccgacatt atcgcgagcc catttatacc     10620
catataaatc agcatccatg ttggaattta atcgcggcct agagcaagac gtttcccgtt     10680
gaatatggct cataacaccc cttgtattac tgtttatgta agcagacagt tttattgttc     10740
atgatgatat attttatct  tgtgcaatgt aacatcagag attttgagac acaacaattg     10800
gtcgacggat cc                                                         10812

<210> SEQ ID NO 12
<211> LENGTH: 10519
<212> TYPE: DNA
<213> ORGANISM: Artificial Sequence
<220> FEATURE:
<223> OTHER INFORMATION: pGM413 plasmid

<400> SEQUENCE: 12
ggtacctcaa tattggccat tagccatatt attcattggt tatatagcat aaatcaatat        60
tggctattgg ccattgcata cgttgtatct atatcataat atgtacattt atattggctc       120
atgtccaata tgaccgccat gttggcattg attattgact agttattaat agtaatcaat       180
tacggggtca ttagttcata gcccatatat ggagttccgc gttacataac ttacggtaaa       240
tggcccgcct ggctgaccgc ccaacgaccc ccgcccattg acgtcaataa tgacgtatgt       300
tcccatagta acgccaatag ggactttcca ttgacgtcaa tgggtggagt atttacggta       360
aactgcccac ttggcagtac atcaagtgta tcatatgcca agtccgcccc ctattgacgt       420
caatgacggt aaatggcccg cctggcatta tgcccagtac atgaccttac gggactttcc       480
tacttggcag tacatctacg tattagtcat cgctattacc atggtgatgc ggttttggca       540
gtacaccaat gggcgtggat agcggtttga ctcacgggga tttccaagtc tccaccccat       600
tgacgtcaat gggagtttgt tttggcacca aaatcaacgg gactttccaa aatgtcgtaa       660
caactgcgat cgcccgcccc gttgacgcaa atgggcggta ggcgtgtacg gtgggaggtc       720
```

```
tatataagca gagctcgctg gcttgtaact cagtctctta ctaggagacc agcttgagcc    780
tgggtgttcg ctggttagcc taacctggtt ggccaccagg ggtaaggact ccttggctta    840
gaaagctaat aaacttgcct gcattagagc ttatctgagt caagtgtcct cattgacgcc    900
tcactctctt gaacgggaat cttccttact gggttctctc tctgacccag gcagagaaa     960
ctccagcagt ggcgcccgaa cagggacttg agtgagagtg taggcacgta cagctgagaa   1020
ggcgtcggac gcgaaggaag cgcggggtgc gacgcgacca agaaggagac ttggtgagta   1080
ggcttctcga gtgccgggaa aaagctcgag cctagttaga ggactaggag aggccgtagc   1140
cgtaactact ctgggcaagt agggcaggcg gtgggtacgc aatggggcg gctacctcag    1200
cactaaatag gagacaatta gaccaatttg agaaaatacg acttcgcccg aacggaaaga   1260
aaaagtacca aattaaacat ttaatatggg caggcaagga gatggagcgc ttcggcctcc   1320
atgagaggtt gttggagaca gaggaggggt gtaaagaat catagaagtc ctctaccccc    1380
tagaaccaac aggatcggag ggcttaaaaa gtctgttcaa tcttgtgtgc gtgctatatt   1440
gcttgcacaa ggaacagaaa gtgaaagaca cagaggaagc agtagcaaca gtaagacaac   1500
actgccatct agtggaaaaa gaaaaaagtg caacagagac atctagtgga caaaagaaaa   1560
atgacaaggg aatagcagcg ccacctggtg gcagtcagaa ttttccagcg caacaacaag   1620
gaaatgcctg ggtacatgta cccttgtcac cgcgcacctt aaatgcgtgg gtaaaagcag   1680
tagaggagaa aaaatttgga gcagaaatag tacccatgtt tcaagcccta tcgaattccc   1740
gtttgtgcta gggttcttag gcttcttggg ggctgctgga actgcaatgg gagcagcggc   1800
gacagccctg acggtccagt ctcagcattt gcttgctggg atactgcagc agcagaagaa   1860
tctgctggcg gctgtggagg ctcaacagca gatgttgaag ctgaccattt ggggtgttaa   1920
aaacctcaat gcccgcgtca cagcccttga gaagtaccta gaggatcagg cacgactaaa   1980
ctcctggggg tgcgcatgga acaagtatg tcataccaca gtggagtggc cctggacaaa    2040
tcggactccg gattggcaaa atatgacttg gttggagtgg gaaagacaaa tagctgattt   2100
ggaaagcaac attacgagac aattagtgaa ggctagagaa caagaggaaa agaatctaga   2160
tgcctatcag aagttaacta gttggtcaga tttctggtct tggttcgatt tctcaaaatg   2220
gcttaacatt ttaaaaatgg gatttttagt aatagtagga ataataggt taagattact    2280
ttacacagta tatggatgta tagtgagggt taggcaggga tatgttcctc tatctccaca   2340
gatccatatc cgcggcaatt ttaaaagaaa gggaggaata gggggacaga cttcagcaga   2400
gagactaatt aatataataa caacacaatt agaaatacaa catttacaaa ccaaaattca   2460
aaaaatttta aattttagag ccgcggagat ctgttacata acttatggta aatggcctgc   2520
ctggctgact gcccaatgac ccctgcccaa tgatgtcaat aatgatgtat gttcccatgt   2580
aatgccaata gggactttcc attgatgtca atgggtggag tatttatggt aactgcccac   2640
ttggcagtac atcaagtgta tcatatgcca agtatgcccc ctattgatgt caatgatggt   2700
aaatggcctg cctggcatta tgcccagtac atgaccttat gggactttcc tacttggcag   2760
tacatctatg tattagtcat tgctattacc atgggaattc actagtggag aagagcatgc   2820
ttgagggctg agtgccctc agtgggcaga gagcacatgg cccacagtcc ctgagaagtt    2880
gggggaggg gtgggcaatt gaactggtgc ctagagaagg tggggcttgg gtaaactggg    2940
aaagtgatgt ggtgtactgg ctccacccttt ttccccaggg tggggagaa ccatatataa    3000
gtgcagtagt ctctgtgaac attcaagctt ctgccttctc cctcctgtga gtttgctagc   3060
```

```
caccaatgca gattgagctg agcacctgct tcttcctgtg cctgctgagg ttctgcttct   3120
ctgccaccag gagatactac ctgggggctg tggagctgag ctgggactac atgcagtctg   3180
acctggggga gctgcctgtg gatgccaggt tccccccag agtgcccaag agcttcccct    3240
tcaacacctc tgtggtgtac aagaagaccc tgtttgtgga gttcactgac cacctgttca   3300
acattgccaa gcccaggccc ccctggatgg gcctgctggg ccccaccatc caggctgagg   3360
tgtatgacac tgtggtgatc accctgaaga acatggccag ccaccctgtg agcctgcatg   3420
ctgtggggt gagctactgg aaggcctctg agggggctga gtatgatgac cagaccagcc    3480
agagggagaa ggaggatgac aaggtgttcc ctgggggcag ccacacctat gtgtggcagg   3540
tgctgaagga gaatggcccc atggcctctg acccctgtg cctgacctac agctacctga    3600
gccatgtgga cctggtgaag gacctgaact ctggcctgat tggggccctg ctggtgtgca   3660
gggagggcag cctggccaag gagaagaccc agaccctgca caagttcatc ctgctgtttg   3720
ctgtgtttga tgagggcaag agctggcact ctgaaaccaa gaacagcctg atgcaggaca   3780
gggatgctgc ctctgccagg gcctggccca agatgcacac tgtgaatggc tatgtgaaca   3840
ggagcctgcc tggcctgatt ggctgccaca ggaagtctgt gtactggcat gtgattggca   3900
tgggcaccac ccctgaggtg cacagcatct tcctggaggg ccacaccttc ctggtcagga   3960
accacaggca ggccagcctg gagatcagcc ccatcacctt cctgactgcc cagaccctgc   4020
tgatggacct gggccagttc ctgctgttct gccacatcag cagccaccag catgatggca   4080
tggaggccta tgtgaaggtg gacagctgcc ctgaggagcc ccagctgagg atgaagaaca   4140
atgaggaggc tgaggactat gatgatgacc tgactgactc tgagatggat gtggtgaggt   4200
ttgatgatga caacagcccc agcttcatcc agatcaggtc tgtggccaag aagcacccca   4260
agacctgggt gcactacatt gctgctgagg aggaggactg ggactatgcc ccctggtgc    4320
tggcccctga tgacaggagc tacaagagcc agtacctgaa caatggcccc cagaggattg   4380
gcaggaagta caagaaggtc aggttcatgg cctacactga tgaaaccttc aagaccaggg   4440
aggccatcca gcatgagtct ggcatcctgg gcccctgct gtatgggag gtgggggaca   4500
ccctgctgat catcttcaag aaccaggcca gcaggcccta caacatctac ccccatggca   4560
tcactgatgt gaggcccctg tacagcagga ggctgcccaa gggggtgaag cacctgaagg   4620
acttccccat cctgcctggg gagatcttca agtacaagtg gactgtgact gtggaggatg   4680
gccccaccaa gtctgacccc aggtgcctga ccagatacta cagcagcttt gtgaacatgg   4740
agagggacct ggcctctggc ctgattggcc ccctgctgat ctgctacaag agtctgtgg    4800
accagagggg caaccagatc atgtctgaca agaggaatgt gatcctgttc tctgtgtttg   4860
atgagaacag gagctggtac ctgactgaga catccagag gttcctgccc aaccctgctg    4920
gggtgcagct ggaggaccct gagttccagg ccagcaacat catgcacagc atcaatggct   4980
atgtgtttga cagcctgcag ctgtctgtgt cctgcatga ggtggcctac tggtacatcc    5040
tgagcattgg ggcccagact gacttcctgt ctgtgttctt ctctggctac accttcaagc   5100
acaagatggt gtatgaggac acccctgacc tgttccccct tctctgggag actgtgttca   5160
tgagcatgga gaaccctggc ctgtggattc tgggctgcca caactctgac ttcaggaaca   5220
ggggcatgac tgccctgctg aaagtctcca gctgtgacaa gaacactggg gactactatg   5280
aggacagcta tgaggacatc tctgcctacc tgctgagcaa gaacaatgcc attgagccca   5340
ggagcttcag ccagaatgcc actaatgtgt ctaacaacag caacaccagc aatgacagca   5400
atgtgtctcc cccagtgctg aagaggcacc agagggagat caccaggacc accctgcagt   5460
```

```
ctgaccagga ggagattgac tatgatgaca ccatctctgt ggagatgaag aaggaggact    5520
ttgacatcta cgacgaggac gagaaccaga gccccaggag cttccagaag aagaccaggc    5580
actacttcat tgctgctgtg gagaggctgt gggactatgg catgagcagc agcccccatg    5640
tgctgaggaa cagggcccag tctggctctg tgccccagtt caagaaggtg gtgttccagg    5700
agttcactga tggcagcttc acccagcccc tgtacagagg ggagctgaat gagcacctgg    5760
gcctgctggg cccctacatc agggctgagg tggaggacaa catcatggtg accttcagga    5820
accaggccag caggccctac agcttctaca gcagcctgat cagctatgag gaggaccaga    5880
ggcagggggc tgagcccagg aagaactttg tgaagcccaa tgaaaccaag acctacttct    5940
ggaaggtgca gcaccacatg ccccccacca aggatgagtt tgactgcaag gcctgggcct    6000
acttctctga tgtggacctg gagaaggatg tgcactctgg cctgattggc ccctgctgg     6060 tgtgccacac caacaccctg aaccctgccc atggcaggca ggtgactgtg caggagtttg    6120
ccctgttctt caccatcttt gatgaaacca agagctggta cttcactgag aacatggaga    6180
ggaactgcag ggcccctgc aacatccaga tggaggaccc caccttcaag gagaactaca    6240
ggttccatgc catcaatggc tacatcatgg acaccctgcc tggcctggtg atggcccagg    6300
accagaggat caggtggtac ctgctgagca tgggcagcaa tgagaacatc cacagcatcc    6360
acttctctgg ccatgtgttc actgtgagga agaaggagga gtacaagatg ccctgtaca    6420 acctgtaccc tggggtgttt gagactgtgg agatgctgcc cagcaaggct ggcatctgga    6480
gggtggagtg cctgattggg gagcacctgc atgctggcat gagcacctg ttcctggtgt     6540 acagcaacaa gtgccagacc cccctgggca tggcctctgg ccacatcagg gacttccaga    6600
tcactgcctc tggccagtat ggccagtggg ccccaagct ggccaggctg cactactctg     6660
gcagcatcaa tgcctggagc accaaggagc ccttcagctg gatcaaggtg gacctgctgg    6720
cccccatgat catccatggc atcaagaccc aggggcccag gcagaagttc agcagcctgt    6780
acatcagcca gttcatcatc atgtacagcc tggatggcaa gaagtggcag acctacaggg    6840
gcaacagcac tggcacccctg atggtgttct ttggcaatgt ggacagctct ggcatcaagc    6900
acaacatctt caacccccc atcattgcca gatacatcag gctgcacccc cccactaca     6960 gcatcaggag caccctgagg atggagctga tgggctgtga cctgaacagc tgcagcatgc    7020
ccctgggcat ggagagcaag gccatctctg atgcccagat cactgccagc agctacttca    7080
ccaacatgtt tgccacctgg agccccagca aggccaggct gcacctgcag ggcaggagca    7140
atgcctggag gccccaggtc aacaacccca aggagtggct gcaggtggac ttccagaaga    7200
ccatgaaggt gactggggtg accacccagg gggtgaagag cctgctgacc agcatgtatg    7260
tgaaggagtt cctgatcagc agcagccagg atggccacca gtggacccctg ttcttccaga    7320 atggcaaggt gaaggtgttc caggcaacc aggacagctt caccccctgtg gtgaacagcc    7380 tggaccccc cctgctgacc agatacctga ggattcaccc ccagagctgg gtgcaccaga    7440
ttgccctgag gatggaggtg ctgggctgtg aggcccagga cctgtactga gcggccgcgg    7500
gcccaatcaa cctctggatt acaaaatttg tgaaagattg actggtattc ttaactatgt    7560
tgctcctttt acgctatgtg gatacgctgc tttaatgcct ttgtatcatg ctattgcttc    7620
ccgtatggct ttcattttct cctccttgta taaatcctgg ttgctgtctc tttatgagga    7680
gttgtggccc gttgtcaggc aacgtggcgt ggtgtgcact gtgtttgctg acgcaacccc    7740
cactggttgg ggcattgcca ccacctgtca gctccttttcc gggactttcg ctttccccct    7800
```

```
ccctattgcc acggcggaac tcatcgccgc ctgccttgcc cgctgctgga caggggctcg   7860
gctgttgggc actgacaatt ccgtggtgtt gtcggggaaa tcatcgtcct ttccttggct   7920
gctcgcctgt gttgccacct ggattctgcg cgggacgtcc ttctgctacg tcccttcggc   7980
cctcaatcca gcggaccttc cttcccgcgg cctgctgccg gctctgcggc ctcttccgcg   8040
tcttcgcctt cgccctcaga cgagtcggat ctcccttttgg gccgcctccc cgcaagcttc   8100
gcactttta aaagaaaagg gaggactgga tgggatttat tactccgata ggacgctggc   8160
ttgtaactca gtctcttact aggagaccag cttgagcctg ggtgttcgct ggttagccta   8220
acctggttgg ccaccagggg taaggactcc ttggcttaga aagctaataa acttgcctgc   8280
attagagctc ttacgcgtcc cgggctcgag atccgcatct caattagtca gcaaccatag   8340
tcccgcccct aactccgccc atcccgcccc taactccgcc cagttccgcc cattctccgc   8400
cccatggctg actaattttt tttatttatg cagaggccga ggccgcctcg gcctctgagc   8460
tattccagaa gtagtgagga ggcttttttg gaggcctagg cttttgcaaa aagctaactt   8520
gtttattgca gcttataatg gttacaaata aagcaatagc atcacaaatt tcacaaataa   8580
agcatttttt tcactgcatt ctagttgtgg tttgtccaaa ctcatcaatg tatcttatca   8640
tgtctgtccg cttcctcgct cactgactcg ctgcgctcgg tcgttcggct gcggcgagcg   8700
gtatcagctc actcaaaggc ggtaatacgg ttatccacag aatcagggga taacgcagga   8760
aagaacatgt gagcaaaagg ccagcaaaag gccaggaacc gtaaaaaggc cgcgttgctg   8820
gcgttttttcc ataggctccg ccccccctgac gagcatcaca aaaatcgacg ctcaagtcag   8880
aggtggcgaa acccgacagg actataaaga taccaggcgt ttccccctgg aagctccctc   8940
gtgcgctctc ctgttccgac cctgccgctt accggatacc tgtccgcctt tctcccttcg   9000
ggaagcgtgg cgctttctca tagctcacgc tgtaggtatc tcagttcggt gtaggtcgtt   9060
cgctccaagc tgggctgtgt gcacgaaccc cccgttcagc ccgaccgctg cgccttatcc   9120
ggtaactatc gtcttgagtc caacccggta agacacgact tatcgccact ggcagcagcc   9180
actggtaaca ggattagcag agcgaggtat gtaggcggtg ctacagagtt cttgaagtgg   9240
tggcctaact acggctacac tagaagaaca gtatttggta tctgcgctct gctgaagcca   9300
gttaccttcg gaaaaagagt tggtagctct tgatccggca acaaaccac cgctggtagc   9360
ggtggttttt ttgtttgcaa gcagcagatt acgcgcagaa aaaaaggatc tcaagaagat   9420
cctttgatct tttctacggg gtctgacgct cagtggaacg aaaactcacg ttaagggatt   9480
ttggtcatga gattatcaaa aaggatcttc acctagatcc ttttaaatta aaaatgaagt   9540
tttaaatcaa tctaaagtat atatgagtaa acttggtctg acagttagaa aaactcatcg   9600
agcatcaaat gaaactgcaa tttattcata tcaggattat caataccata ttttgaaaa   9660
agccgtttct gtaatgaagg agaaaactca ccgaggcagt tccataggat ggcaagatcc   9720
tggtatcggt ctgcgattcc gactcgtcca catcaatac aacctattaa tttcccctcg   9780
tcaaaaataa ggttatcaag tgagaaatca ccatgagtga cgactgaatc cggtgagaat   9840
ggcaacagct tatgcatttc tttccagact tgttcaacag gccagccatt acgctcgtca   9900
tcaaaatcac tcgcatcaac caaaccgtta ttcattcgtg attgcgcctg agcgagacga   9960
aatacgcgat cgctgttaaa aggacaatta caaacaggaa tcgaatgcaa ccggcgcagg  10020
aacactgcca gcgcatcaac aatatttttca cctgaatcag atattcttc taatacctgg  10080
aatgctgttt tcccggggat cgcagtggtg agtaaccatg catcatcagg agtacggata  10140
aaatgcttga tggtcggaag aggcataaat tccgtcagcc agtttagtct gaccatctca  10200
```

| | | |
|---|---|---|
| tctgtaacat | cattggcaac gctacctttg ccatgtttca gaaacaactc tggcgcatcg | 10260 |
| ggcttcccat | acaatcgata gattgtcgca cctgattgcc cgacattatc gcgagcccat | 10320 |
| ttatacccat | ataaatcagc atccatgttg gaatttaatc gcggcctaga gcaagacgtt | 10380 |
| tcccgttgaa | tatggctcat aacaccoctt gtattactgt ttatgtaagc agacagtttt | 10440 |
| attgttcatg | atgatatatt tttatcttgt gcaatgtaac atcagagatt ttgagacaca | 10500 |
| acaattggtc | gacggatcc | 10519 |

<210> SEQ ID NO 13
<211> LENGTH: 11400
<212> TYPE: DNA
<213> ORGANISM: Artificial Sequence
<220> FEATURE:
<223> OTHER INFORMATION: pGM412 plasmid

<400> SEQUENCE: 13

| | | |
|---|---|---|
| ggtacctcaa | tattggccat tagccatatt attcattggt tatatagcat aaatcaatat | 60 |
| tggctattgg | ccattgcata cgttgtatct atatcataat atgtacattt atattggctc | 120 |
| atgtccaata | tgaccgccat gttggcattg attattgact agttattaat agtaatcaat | 180 |
| tacggggtca | ttagttcata gcccatatat ggagttccgc gttacataac ttacggtaaa | 240 |
| tggcccgcct | ggctgaccgc ccaacgaccc ccgcccattg acgtcaataa tgacgtatgt | 300 |
| tcccatagta | acgccaatag ggactttcca ttgacgtcaa tgggtggagt atttacggta | 360 |
| aactgcccac | ttggcagtac atcaagtgta tcatatgcca gtccgcccc ctattgacgt | 420 |
| caatgacggt | aaatggcccg cctggcatta tgcccagtac atgaccttac gggactttcc | 480 |
| tacttggcag | tacatctacg tattagtcat cgctattacc atggtgatgc ggttttggca | 540 |
| gtacaccaat | gggcgtggat agcggtttga ctcacgggga tttccaagtc tccacccat | 600 |
| tgacgtcaat | gggagtttgt tttggcacca aaatcaacgg gactttccaa aatgtcgtaa | 660 |
| caactgcgat | cgcccgcccc gttgacgcaa atgggcggta ggcgtgtacg gtgggaggtc | 720 |
| tatataagca | gagctcgctg gcttgtaact cagtctctta ctaggagacc agcttgagcc | 780 |
| tgggtgttcg | ctggttagcc taacctggtt ggccaccagg ggtaaggact ccttggctta | 840 |
| gaaagctaat | aaacttgcct gcattagagc ttatctgagt caagtgtcct cattgacgcc | 900 |
| tcactctctt | gaacgggaat cttccttact gggttctctc tctgacccag gcgagagaaa | 960 |
| ctccagcagt | ggcgcccgaa cagggacttg agtgagagtg taggcacgta cagctgagaa | 1020 |
| ggcgtcggac | gcgaaggaag gcgggggtgc gacgcgacca agaaggagac ttggtgagta | 1080 |
| ggcttctcga | gtgccgggaa aaagctcgag cctagttaga ggactaggag aggccgtagc | 1140 |
| cgtaactact | ctgggcaagt agggcaggcg gtgggtacgc aatgggggcg gctacctcag | 1200 |
| cactaaatag | gagacaatta gaccaatttg agaaaatacg acttcgcccg aacggaaaga | 1260 |
| aaaagtacca | aattaaacat ttaatatggg caggcaagga gatggagcgc ttcggcctcc | 1320 |
| atgagaggtt | gttggagaca gaggagggt gtaaagaat catagaagtc ctctaccccc | 1380 |
| tagaaccaac | aggatcggag ggcttaaaaa gtctgttcaa tcttgtgtgc gtgctatatt | 1440 |
| gcttgcacaa | ggaacagaaa gtgaaagaca cagaggaagc agtagcaaca gtaagacaac | 1500 |
| actgccatct | agtggaaaaa gaaaaagtg caacagagac atcagtggaa caaagaaaa | 1560 |
| atgacaaggg | aatagcagcg ccacctggtg gcagtcagaa ttttccagcg caacaacaag | 1620 |
| gaaatgcctg | ggtacatgta cccttgtcac cgcgcacctt aaatgcgtgg gtaaaagcag | 1680 |

```
tagaggagaa aaaatttgga gcagaaatag tacccatgtt tcaagcccta tcgaattccc    1740
gtttgtgcta gggttcttag gcttcttggg ggctgctgga actgcaatgg gagcagcggc    1800
gacagccctg acggtccagt ctcagcattt gcttgctggg atactgcagc agcagaagaa    1860
tctgctggcg gctgtggagg ctcaacagca gatgttgaag ctgaccattt ggggtgttaa    1920
aaacctcaat gcccgcgtca cagcccttga aagtaccta gaggatcagg cacgactaaa     1980
ctcctggggg tgcgcatgga acaagtatg tcataccaca gtggagtggc cctgacaaa      2040
tcggactccg gattggcaaa atatgacttg gttggagtgg aaagacaaa tagctgattt     2100
ggaaagcaac attacgagac aattagtgaa ggctagagaa caagaggaaa agaatctaga    2160
tgcctatcag aagttaacta gttggtcaga tttctggtct tggttcgatt tctcaaaatg    2220
gcttaacatt ttaaaaatgg gattttagt aatagtagga ataataggt taagattact      2280
ttacacagta tatggatgta tagtgagggt taggcaggga tatgttcctc tatctccaca    2340
gatccatatc cgcggcaatt ttaaaagaaa gggaggaata gggggacaga cttcagcaga    2400
gagactaatt aatataataa caacacaatt agaaatacaa catttacaaa ccaaaattca    2460
aaaaatttta aattttagag ccgcggagat ctcaatattg gccattagcc atattattca    2520
ttggttatat agcataaatc aatattggct attggccatt gcatacgttg tatctatatc    2580
ataatatgta catttatatt ggctcatgtc caatatgacc gccatgttgg cattgattat    2640
tgactagtta ttaatagtaa tcaattacgg ggtcattagt tcatagccca tatatggagt    2700
tccgcgttac ataacttacg gtaaatggcc cgcctggctg accgcccaac gacccccgcc    2760
cattgacgtc aataatgacg tatgttccca tagtaacgcc aatagggact ttccattgac    2820
gtcaatgggt ggagtattta cggtaaactg cccacttggc agtacatcaa gtgtatcata    2880
tgccaagtcc gccccctatt gacgtcaatg acggtaaatg gcccgcctgg cattatgccc    2940
agtacatgac cttacgggac tttcctactt ggcagtacat ctacgtatta gtcatcgcta    3000
ttaccatggt gatgcggttt tggcagtaca ccaatgggcg tggatagcgg tttgactcac    3060
ggggatttcc aagtctccac cccattgacg tcaatgggag tttgttttgg caccaaaatc    3120
aacgggactt tccaaaatgt cgtaataacc ccgccccgtt gacgcaaatg ggcggtaggc    3180
gtgtacggtg ggaggtctat ataagcagag ctcgtttagt gaaccgtcag atcactagaa    3240
gctttattgc ggtagtttat cacagttaaa ttgctaacgc agtcagtgct tctgacacaa    3300
cagtctcgaa cttaagctgc agaagttggt cgtgaggcac tgggcaggct agccaccaat    3360
gcagattgag ctgagcacct gcttcttcct gtgcctgctg aggttctgct tctctgccac    3420
caggagatac tacctggggg ctgtggagct gagctgggac tacatgcagt ctgacctggg    3480
ggagctgcct gtggatgcca ggttcccccc cagagtgccc aagagcttcc ccttcaacac    3540
ctctgtggtg tacaagaaga ccctgttt gt ggagttcact gaccacctgt tcaacattgc    3600
caagcccagg ccccctgga tgggcctgct gggcccacc atccaggctg aggtgtatga      3660
cactgtggtg atcaccctga gaacatggc cagccaccct gtgagcctgc atgctgtggg    3720
ggtgagctac tggaaggcct ctgaggggc tgagtatgat accagacca gccagaggga     3780
gaaggaggat gacaaggtgt ccctgggggg cagccacacc tatgtgtggc aggtgctgaa    3840
ggagaatggc cccatggcct ctgacccct gtgcctgacc tacagctacc tgagccatgt    3900
ggacctggtg aaggacctga actctggcct gattggggcc ctgctggtgt gcagggaggg    3960
cagcctggcc aaggagaaga cccagaccct gcacaagttc atcctgctgt ttgctgtgtt    4020
tgatgagggc aagagctggc actctgaaac caagaacagc ctgatgcagg acaggatgc     4080
```

-continued

```
tgcctctgcc agggcctggc ccaagatgca cactgtgaat ggctatgtga acaggagcct    4140
gcctggcctg attggctgcc acaggaagtc tgtgtactgg catgtgattg catgggcac    4200 caccctgag gtgcacagca tcttcctgga gggccacacc ttcctggtca ggaaccacag    4260
gcaggccagc ctggagatca gccccatcac cttcctgact gcccagaccc tgctgatgga    4320
cctgggccag ttcctgctgt tctgccacat cagcagccac cagcatgatg catggaggc    4380 ctatgtgaag gtgacagct gccctgagga gccccagctg aggatgaaga caatgagga    4440 ggctgaggac tatgatgatg acctgactga ctctgagatg gatgtggtga ggtttgatga    4500
tgacaacagc cccagcttca tccagatcag gtctgtggcc aagaagcacc ccaagacctg    4560
ggtgcactac attgctgctg aggaggagga ctgggactat gcccccctgg tgctggcccc    4620
tgatgacagg agctacaaga gccagtacct gaacaatggc cccagagga ttggcaggaa    4680 gtacaagaag gtcaggttca tggcctacac tgatgaaacc ttcaagacca gggaggccat    4740
ccagcatgag tctggcatcc tgggcccccT gctgtatggg gaggtggggg acaccctgct    4800
gatcatcttc aagaaccagg ccagcaggcc ctacaacatc taccccatg gcatcactga    4860 tgtgaggccc ctgtacagca ggaggctgcc caaggggtg aagcacctga aggacttccc    4920
catcctgcct ggggagatct tcaagtacaa gtggactgtg actgtggagg atggccccac    4980
caagtctgac cccaggtgcc tgaccagata ctacagcagc tttgtgaaca tggagaggga    5040
cctggcctct ggcctgattg gcccctgct gatctgctac aaggagtctg tggaccagag    5100
gggcaaccag atcatgtctg acaagaggaa tgtgatcctg ttctctgtgt ttgatgagaa    5160
caggagctgg tacctgactg agaacatcca gaggttcctg cccaaccctg ctggggtgca    5220
gctggaggac cctgagttcc aggccagcaa catcatgcac agcatcaatg ctatgtgtt    5280 tgacagcctg cagctgtctg tgtgcctgca tgaggtggcc tactggtaca tcctgagcat    5340
tggggcccag actgacttcc tgtctgtgtt cttctctggc tacaccttca agcacaagat    5400
ggtgtatgag gacaccctga ccctgttccc cttctctggg gagactgtgt tcatgagcat    5460
ggagaaccct ggcctgtgga ttctgggctg ccacaactct gacttcagga caggggcat    5520 gactgccctg ctgaaagtct ccagctgtga caagaacact ggggactact atgaggacag    5580
ctatgaggac atctctgcct acctgctgag caagaacaat gccattgagc ccaggagctt    5640
cagccagaac agcaggcacc ccagcaccag gcagaagcag ttcaatgcca ccaccatccc    5700
tgagaatgac atagagaaga cagacccatg gtttgcccac cggaccccca tgcccaagat    5760
ccagaatgtg agcagctctg acctgctgat gctgctgagg cagagcccca cccccatgg    5820 cctgagcctg tctgacctgc aggaggccaa gtatgaaacc ttctctgatg acccccagcc    5880
tggggccatt gacagcaaca acagcctgtc tgagatgacc cacttcaggc cccagctgca    5940
ccactctggg gacatggtgt caccccctga gtctggcctg cagctgaggc tgaatgagaa    6000
gctgggcacc actgctgcca ctgagctgaa gaagctggac ttcaaagtct ccagcaccag    6060
caacaacctg atcagcacca tccctctga caacctggct gctggcactg acaacaccag    6120
cagcctgggc cccccagca tgcctgtgca ctatgacagc cagctggaca ccaccctgtt    6180
tggcaagaag agcagcccc tgactgagtc tggggcccc ctgagcctgt ctgaggaaa    6240 caatgacagc aagctgctgg agtctggcct gatgaacagc caggagagca gctgggcaa    6300 gaatgtgagc agcagggaga tcaccaggac caccctgcag tctgaccagg aggagattga    6360
ctatgatgac accatctctg tggagatgaa gaaggaggac tttgacatct acgacgagga    6420
```

-continued

```
cgagaaccag agccccagga gcttccagaa gaagaccagg cactacttca ttgctgctgt    6480
ggagaggctg tgggactatg gcatgagcag cagcccccat gtgctgagga cagggccca     6540
gtctggctct gtgcccagt tcaagaaggt ggtgttccag gagttcactg atggcagctt     6600
cacccagccc ctgtacagag gggagctgaa tgagcacctg gcctgctgg gcccctacat     6660
cagggctgag gtggaggaca acatcatggt gaccttcagg aaccaggcca gcaggcccta    6720
cagcttctac agcagcctga tcagctatga ggaggaccag aggcagggg ctgagcccag     6780
gaagaacttt gtgaagccca tgaaaccaa gacctacttc tggaaggtgc agcaccacat     6840
ggcccccacc aaggatgagt tgactgcaa ggcctgggcc tacttctctg atgtggacct     6900
ggagaaggat gtgcactctg gcctgattgg ccccctgctg gtgtgccaca ccaacaccct    6960
gaaccctgcc catggcaggc aggtgactgt gcaggagttt gccctgttct tcaccatctt    7020
tgatgaaacc aagagctggt acttcactga gaacatggag aggaactgca gggcccctg    7080
caacatccag atggaggacc ccaccttcaa ggagaactac aggttccatg ccatcaatgg    7140
ctacatcatg gacaccctgc ctggcctggt gatggcccag gaccagagga tcaggtggta    7200
cctgctgagc atgggcagca atgagaacat ccacagcatc cacttctctg gccatgtgtt    7260
cactgtgagg aagaaggagg agtacaagat ggccctgtac aacctgtacc ctgggtgtt    7320
tgagactgtg gagatgctgc ccagcaaggc tggcatctgg agggtggagt gcctgattgg    7380
ggagcacctg catgctggca tgagcaccct gttcctggtg tacagcaaca agtgccagac    7440
cccctgggc atggcctctg ccacatcag ggacttccag atcactgcct ctggccagta     7500
tggccagtgg gccccaagc tggccaggct gcactactct ggcagcatca atgcctggag    7560
caccaaggag cccttcagct ggatcaaggt ggacctgctg gcccccatga tcatccatgg    7620
catcaagacc caggggcca ggcagaagtt cagcagcctg tacatcagcc agttcatcat    7680
catgtacagc ctggatggca agaagtggca gacctacagg ggcaacagca ctggcaccct    7740
gatggtgttc tttggcaatg tggacagctc tggcatcaag cacaacatct tcaaccccc    7800
catcattgcc agatacatca ggctgcaccc cacccactac agcatcagga gcaccctgag    7860
gatggagctg atgggctgtg acctgaacag ctgcagcatg cccctgggca tggagagcaa    7920
ggccatctct gatgcccaga tcactgccag cagctacttc accaacatgt tgccacctg     7980
gagcccagc aaggccaggc tgcacctgca gggcaggagc aatgcctgga ggccccaggt    8040
caacaacccc aaggagtggc tgcaggtgga cttccagaag accatgaagg tgactggggt    8100
gaccacccag ggggtgaaga gcctgctgac cagcatgtat gtgaaggagt cctgatcag     8160
cagcagccag gatggccacc agtggaccct gttcttccag aatggcaagg tgaaggtgtt    8220
ccagggcaac caggacagct tcaccccgt ggtgaacagc ctggaccccc ccctgctgac    8280
cagatacctg aggattcacc cccagagctg ggtgcaccag attgccctga ggatggaggt    8340
gctgggctgt gaggcccagg acctgtactg agcggccgcg ggcccaatca acctctggat    8400
tacaaaattt gtgaaagatt gactggtatt cttaactatg ttgctccttt tacgctatgt    8460
ggatacgctg ctttaatgcc tttgtatcat gctattgctt cccgtatggc tttcattttc    8520
tcctccttgt ataaatcctg gttgctgtct ctttatgagg agttgtggcc cgttgtcagg    8580
caacgtggcg tggtgtgcac tgtgtttgct gacgcaaccc ccactggttg ggcattgcc    8640
accacctgtc agctccttc cgggacttc gctttccccc tcctattgc cacggcggaa       8700
ctcatcgccg cctgccttgc ccgctgctgg acagggctc ggctgttggg cactgacaat    8760
tccgtggtgt tgtcggggaa atcatcgtcc tttccttggc tgctcgcctg tgttgccacc    8820
```

```
tggattctgc gcgggacgtc cttctgctac gtcccttcgg ccctcaatcc agcggacctt    8880
ccttcccgcg gcctgctgcc ggctctgcgg cctcttccgc gtcttcgcct tcgccctcag    8940
acgagtcgga tctcccttg ggccgcctcc ccgcaagctt cgcactttt aaaagaaaag     9000
ggaggactga atgggattta ttactccgat aggacgctgg cttgtaactc agtctcttac    9060
taggagacca gcttgagcct gggtgttcgc tggttagcct aacctggttg gccaccaggg    9120
gtaaggactc cttggcttag aaagctaata aacttgcctg cattagagct cttacgcgtc    9180
ccgggctcga gatccgcatc tcaattagtc agcaaccata gtcccgcccc taactccgcc    9240
catcccgccc ctaactccgc ccagttccgc ccattctccg ccccatggct gactaatttt    9300
ttttatttat gcagaggccg aggccgcctc ggcctctgag ctattccaga agtagtgagg    9360
aggctttttt ggaggcctag gcttttgcaa aaagctaact tgtttattgc agcttataat    9420
ggttacaaat aaagcaatag catcacaaat ttcacaaata aagcatttt ttcactgcat     9480
tctagttgtg gtttgtccaa actcatcaat gtatcttatc atgtctgtcc gcttcctcgc    9540
tcactgactc gctgcgctcg gtcgttcggc tgcggcgagc ggtatcagct cactcaaagg    9600
cggtaatacg gttatccaca gaatcagggg ataacgcagg aaagaacatg tgagcaaaag    9660
gccagcaaaa ggccaggaac cgtaaaaagg ccgcgttgct ggcgtttttc cataggctcc    9720
gcccccctga cgagcatcac aaaaatcgac gctcaagtca gaggtggcga acccgacag     9780
gactataaag ataccaggcg tttccccctg gaagctccct cgtgcgctct cctgttccga    9840
ccctgccgct taccggatac ctgtccgcct ttctcccttc gggaagcgtg gcgctttctc    9900
atagctcacg ctgtaggtat ctcagttcgg tgtaggtcgt tcgctccaag ctgggctgtg    9960
tgcacgaacc ccccgttcag cccgaccgct gcgccttatc cggtaactat cgtcttgagt   10020
ccaacccggt aagacacgac ttatcgccac tggcagcagc cactggtaac aggattagca   10080
gagcgaggta tgtaggcggt gctacagagt tcttgaagtg gtggcctaac tacggctaca   10140
ctagaagaac agtatttggt atctgcgctc tgctgaagcc agttaccttc ggaaaaagag   10200
ttggtagctc ttgatccggc aaacaaacca ccgctggtag cggtggtttt tttgtttgca   10260
agcagcagat tacgcgcaga aaaaaaggat ctcaagaaga tcctttgatc ttttctacgg   10320
ggtctgacgc tcagtggaac gaaaactcac gttaagggat tttggtcatg agattatcaa   10380
aaaggatctt cacctagatc cttttaaatt aaaaatgaag ttttaaatca atctaaagta   10440
tatatgagta aacttggtct gacagttaga aaaactcatc gagcatcaaa tgaaactgca   10500
atttattcat atcaggatta tcaataccat attttgaaa aagccgtttc tgtaatgaag    10560
gagaaaactc accgaggcag ttccatagga tggcaagatc ctggtatcgg tctgcgattc   10620
cgactcgtcc aacatcaata aacctatta atttcccctc gtcaaaaata aggttatcaa    10680
gtgagaaatc accatgagtg acgactgaat ccggtgagaa tggcaacagc ttatgcattt   10740
ctttccagac ttgttcaaca ggccagccat tacgctcgtc atcaaaatca ctcgcatcaa   10800
ccaaaccgtt attcattcgt gattgcgcct gagcgagacg aaatacgcga tcgctgttaa   10860
aaggacaatt acaaacagga atcgaatgca accggcgcag gaacactgcc agcgcatcaa   10920
caatattttc acctgaatca ggatattctt ctaatacctg gaatgctgtt tttccgggga   10980
tcgcagtggt gagtaaccat gcatcatcag gagtacggat aaaatgcttg atggtcggaa   11040
gaggcataaa ttccgtcagc cagtttagtc tgaccatctc atctgtaaca tcattggcaa   11100
cgctaccttt gccatgtttc agaaacaact ctggcgcatc gggcttccca tacaatcgat   11160
```

```
agattgtcgc acctgattgc ccgacattat cgcgagccca tttataccca tataaatcag    11220
catccatgtt ggaatttaat cgcggcctag agcaagacgt ttcccgttga atatggctca    11280
taacacccct tgtattactg tttatgtaag cagacagttt tattgttcat gatgatatat    11340
ttttatcttg tgcaatgtaa catcagagat tttgagacac aacaattggt cgacggatcc    11400

<210> SEQ ID NO 14
<211> LENGTH: 11108
<212> TYPE: DNA
<213> ORGANISM: Artificial Sequence
<220> FEATURE:
<223> OTHER INFORMATION: pGM414 plasmid

<400> SEQUENCE: 14
ggtacctcaa tattggccat tagccatatt attcattggt tatatagcat aaatcaatat      60
tggctattgg ccattgcata cgttgtatct atatcataat atgtacattt atattggctc     120
atgtccaata tgaccgccat gttggcattg attattgact agttattaat agtaatcaat     180
tacgggtcat tagttcata gcccatatat ggagttccgc gttacataac ttacggtaaa     240
tggcccgcct ggctgaccgc ccaacgaccc cgcccattg acgtcaataa tgacgtatgt     300
tcccatagta acgccaatag ggactttcca ttgacgtcaa tgggtggagt atttacggta     360
aactgcccac ttggcagtac atcaagtgta tcatatgcca gtccgcccc ctattgacgt     420 caatgacggt aaatggcccg cctggcatta tgcccagtac atgaccttac gggactttcc     480
tacttggcag tacatctacg tattagtcat cgctattacc atggtgatgc ggttttggca     540
gtacaccaat gggcgtggat agcggtttga ctcacgggga tttccaagtc tccacccat     600 tgacgtcaat gggagtttgt tttggcacca aaatcaacgg gactttccaa aatgtcgtaa     660
caactgcgat cgcccgcccc gttgacgcaa atgggcggta ggcgtgtacg gtgggaggtc     720
tatataagca gagctcgctg gcttgtaact cagtctctta ctaggagacc agcttgagcc     780
tgggtgttcg ctggttagcc taacctggtt ggccaccagg ggtaaggact ccttggctta     840
gaaagctaat aaacttgcct gcattagagc ttatctgagt caagtgtcct cattgacgcc     900
tcactctctt gaacgggaat cttccttact gggttctctc tctgacccag gcagagaaa     960 ctccagcagt ggcgcccgaa cagggacttg agtgagagtg taggcacgta cagctgagaa    1020
ggcgtcggac gcgaaggaag cgcggggtgc gacgcgacca agaaggagac ttggtgagta    1080
ggcttctcga gtgccgggaa aaagctcgag cctagttaga ggactaggag aggccgtagc    1140
cgtaactact cttgggcaag tagggcaggc ggtgggtacg caatggggc ggctacctca    1200 gcactaaata ggagacaatt agaccaattt gagaaaatac gacttcgccc gaacggaaag    1260
aaaaagtacc aaattaaaca tttaatatgg gcaggcaagg agatggagcg cttcggcctc    1320
catgagaggt tgttggagac agaggagggg tgtaaaagaa tcatagaagt cctctacccc    1380
ctagaaccaa caggatcgga gggcttaaaa agtctgttca atcttgtgtg cgtgctatat    1440
tgcttgcaca aggaacagaa agtgaaagac acagaggaag cagtagcaac agtaagacaa    1500
cactgccatc tagtggaaaa agaaaaaagt gcaacagaga catctagtgg acaaaagaaa    1560
aatgacaagg gaatagcagc gccacctggt ggcagtcaga attttccagc gcaacaacaa    1620
ggaaatgcct gggtacatgt acccttgtca ccgcgcacct taaatgcgtg gtaaaagca    1680 gtagaggaga aaaatttgg agcagaaata gtacccatgt ttcaagccct atcgaattcc    1740
cgtttgtgct agggttctta ggcttcttgg gggctgctgg aactgcaatg ggagcagcgg    1800
cgacagccct gacggtccag tctcagcatt tgcttgctgg gatactgcag cagcagaaga    1860
```

```
atctgctggc ggctgtggag gctcaacagc agatgttgaa gctgaccatt tggggtgtta    1920
aaaacctcaa tgcccgcgtc acagcccttg agaagtacct agaggatcag gcacgactaa    1980
actcctgggg gtgcgcatgg aaacaagtat gtcataccac agtggagtgg ccctggacaa    2040
atcggactcc ggattggcaa atatgactt ggttggagtg ggaaagacaa atagctgatt     2100
tggaaagcaa cattacgaga caattagtga aggctagaga acaagaggaa aagaatctag    2160
atgcctatca gaagttaact agttggtcag atttctggtc ttggttcgat ttctcaaaat   2220
ggcttaacat tttaaaaatg ggatttttag taatagtagg aataataggg ttaagattac    2280
tttacacagt atatggatgt atagtgaggg ttaggcaggg atatgttcct ctatctccac    2340
agatccatat ccgcggcaat tttaaaagaa agggaggaat aggggacag acttcagcag     2400
agagactaat taatataata acaacacaat tagaaataca acatttacaa accaaaattc    2460
aaaaaatttt aaattttaga gccgcggaga tctgttacat aacttatggt aaatggcctg    2520
cctggctgac tgcccaatga cccctgccca atgatgtcaa taatgatgta tgttcccatg    2580
taatgccaat agggactttc cattgatgtc aatgggtgga gtatttatgg taactgccca    2640
cttggcagta catcaagtgt atcatatgcc aagtatgccc cctattgatg tcaatgatgg    2700
taaatggcct gcctggcatt atgcccagta catgacctta tgggactttc ctacttggca    2760
gtacatctat gtattagtca ttgctattac catgggaatt cactagtgga gaagagcatg    2820
cttgagggct gagtgcccct cagtgggcag agagcacatg gcccacagtc cctgagaagt    2880
tggggggagg ggtgggcaat tgaactggtg cctagagaag gtggggcttg ggtaaactgg    2940
gaaagtgatg tggtgtactg gctccacctt tttccccagg gtgggggaga accatatata    3000
agtgcagtag tctctgtgaa cattcaagct tctgccttct ccctcctgtg agtttgctag    3060
ccaccaatgc agattgagct gagcacctgc ttcttcctgt gcctgctgag gttctgcttc    3120
tctgccacca ggagatacta cctggggct gtggagctga gctgggacta catgcagtct     3180
gacctggggg agctgcctgt ggatgccagg ttccccccca gagtgcccaa gagcttcccc    3240
ttcaacacct ctgtggtgta caagaagacc ctgtttgtgg agttcactga ccacctgttc    3300
aacattgcca agcccaggcc ccctggatg ggcctgctgg gccccaccat ccaggctgag     3360
gtgtatgaca ctgtggtgat caccctgaag aacatggcca gccacctgt gagcctgcat     3420
gctgtggggg tgagctactg gaaggcctct gagggggctg agtatgatga ccagaccagc    3480
cagagggaga aggaggatga caaggtgttc cctggggca gccacaccta tgtgtggcag     3540
gtgctgaagg agaatggccc catggcctct gaccccctgt gcctgaccta cagctacctg    3600
agccatgtgg acctggtgaa ggacctgaac tctggcctga ttggggccct gctggtgtgc    3660
agggagggca gcctggccaa ggagaagacc cagaccctgc acaagttcat cctgctgttt    3720
gctgtgtttg atgagggcaa gagctggcac tctgaaacca gaacagcct gatgcaggac     3780
agggatgctg cctctgccag ggcctggccc aagatgcaca ctgtgaatgg ctatgtgaac    3840
aggagcctgc ctggcctgat tggctgccac aggaagtctg tgtactggca tgtgattggc    3900
atgggcacca cccctgaggt gcacagcatc ttcctggagg ccacaccttt cctggtcagg    3960
aaccacaggc aggccagcct ggagatcagc cccatcacct tcctgactgc ccagaccctg    4020
ctgatggacc tgggccagtt cctgctgttc tgccacatca gcagccacca gcatgatggc    4080
atggaggcct atgtgaaggt ggacagctgc cctgaggagc cccagctgag gatgaagaac    4140
aatgaggagg ctgaggacta tgatgatgac ctgactgact ctgagatgga tgtggtgagg    4200
```

```
tttgatgatg acaacagccc cagcttcatc cagatcaggt ctgtggccaa gaagcacccc    4260
aagacctggg tgcactacat tgctgctgag gaggaggact gggactatgc ccccctggtg    4320
ctggcccctg atgacaggag ctacaagagc cagtacctga caatggccc ccagaggatt     4380 ggcaggaagt acaagaaggt caggttcatg gcctacactg atgaaacctt caagaccagg    4440
gaggccatcc agcatgagtc tggcatcctg gccccctgc tgtatgggga ggtgggggac     4500
accctgctga tcatcttcaa gaaccaggcc agcaggccct acaacatcta cccccatggc    4560
atcactgatg tgaggcccct gtacagcagg aggctgccca aggggtgaa gcacctgaag     4620 gacttcccca tcctgcctgg ggagatcttc aagtacaagt ggactgtgac tgtggaggat    4680
ggccccacca agtctgaccc caggtgcctg accagatact acagcagctt tgtgaacatg    4740
gagagggacc tggcctctgg cctgattggc cccctgctga tctgctacaa ggagtctgtg    4800
gaccagaggg gcaaccagat catgtctgac aagaggaatg tgatcctgtt ctctgtgttt    4860
gatgagaaca ggagctggta cctgactgag aacatccaga ggttcctgcc caaccctgct    4920
ggggtgcagc tggaggaccc tgagttccag gccagcaaca tcatgcacag catcaatggc    4980
tatgtgtttg acagcctgca gctgtctgtg tgcctgcatg aggtggccta ctggtacatc    5040
ctgagcattg ggcccagac tgacttcctg tctgtgttct tctctggcta cacccttcaag    5100 cacaagatgg tgtatgagga cacccctgacc ctgttcccct tctctgggga gactgtgttc    5160
atgagcatgg agaaccctgg cctgtggatt ctgggctgcc acaactctga cttcaggaac    5220
aggggcatga ctgccctgct gaaagtctcc agctgtgaca agaacactgg ggactactat    5280
gaggacagct atgaggacat ctctgcctac ctgctgagca agaacaatgc cattgagccc    5340
aggagcttca gccagaacag caggcacccc agcaccaggc agaagcagtt caatgccacc    5400
accatccctg agaatgacat agagaagaca gacccatggt tgcccaccg gacccccatg    5460 cccaagatcc agaatgtgag cagctctgac ctgctgatgc tgctgaggca gagccccacc    5520
ccccatggcc tgagcctgtc tgacctgcag gaggccaagt atgaaacctt ctctgatgac    5580
cccagccctg ggccattga cagcaacaac agcctgtctg agatgaccca cttcaggccc    5640
cagctgcacc actctgggga catggtgttc accctgagt ctggcctgca gctgaggctg    5700
aatgagaagc tgggcaccac tgctgccact gagctgaaga agctggactt caaagtctcc    5760
agcaccagca caacctgat cagcaccatc ccctctgaca acctggctgc tggcactgac    5820
aacaccagca gcctgggccc cccagcatg cctgtgcact atgacagcca gctggacacc    5880
accctgtttg gcaagaagag cagccccctg actgagtctg ggggcccct gagcctgtct    5940 gaggagaaca atgacagcaa gctgctggag tctggcctga tgaacagcca ggagagcagc    6000
tggggcaaga atgtgagcag cagggagatc accaggacca ccctgcagtc tgaccaggag    6060
gagattgact atgatgacac catctctgtg gagatgaaga aggaggactt tgacatctac    6120
gacgaggacg agaaccagag ccccaggagc ttccagaaga gaccaggca ctacttcatt    6180 gctgctgtgg agaggctgtg ggactatggc atgagcagca ccccatgt gctgaggaac     6240 agggcccagt ctggctctgt gccccagttc aagaaggtgg tgttccagga gttcactgat    6300
ggcagcttca cccagcccct gtacagaggg gagctgaatg agcacctggg cctgctgggc    6360
ccctacatca gggctgaggt ggaggacaac atcatggtga ccttcaggaa ccaggccagc    6420
aggccctaca gcttctacag cagcctgatc agctatgagg aggaccagag gcagggggct    6480
gagcccagga gaactttgt gaagcccaat gaaaccaaga cctacttctg gaaggtgcag    6540
caccacatgg cccccaccaa ggatgagttt gactgcaagg cctgggccta cttctctgat    6600
```

```
gtggacctgg agaaggatgt gcactctggc ctgattggcc ccctgctggt gtgccacacc    6660
aacaccctga accctgccca tggcaggcag gtgactgtgc aggagtttgc cctgttcttc    6720
accatctttg atgaaaccaa gagctggtac ttcactgaga acatggagag gaactgcagg    6780 gcccctgca acatccagat ggaggacccc accttcaagg agaactacag gttccatgcc     6840
atcaatggct acatcatgga caccctgcct ggcctggtga tggcccagga ccagaggatc    6900
aggtggtacc tgctgagcat gggcagcaat gagaacatcc acagcatcca cttctctggc    6960
catgtgttca ctgtgaggaa gaggaggag tacaagatgg ccctgtacaa cctgtaccct     7020
ggggtgtttg agactgtgga gatgctgccc agcaaggctg gcatctggag ggtggagtgc    7080
ctgattgggg agcacctgca tgctggcatg agcaccctgt tcctggtgta cagcaacaag    7140
tgccagaccc ccctgggcat ggcctctggc cacatcaggg acttccagat cactgcctct    7200
ggccagtatg ccagtgggc ccccaagctg gccaggctgc actactctgg cagcatcaat     7260
gcctggagca ccaaggagcc cttcagctgg atcaaggtgg acctgctggc ccccatgatc    7320
atccatggca tcaagaccca gggggccagg cagaagttca gcagcctgta catcagccag    7380
ttcatcatca tgtacagcct ggatggcaag aagtggcaga cctacagggg caacagcact    7440 ggcacctga tggtgttctt tggcaatgtg acagctctg gcatcaagca aacatcttc       7500 aaccccccca tcattgccag atacatcagg ctgcaccca ccctactcag catcaggagc     7560
accctgagga tggagctgat gggctgtgac ctgaacagct gcagcatgcc cctgggcatg    7620
gagagcaagg ccatctctga tgcccagatc actgccagca gctacttcac caacatgttt    7680
gccacctgga gccccagcaa ggccaggctg cacctgcagg gcaggagcaa tgcctggagg    7740
ccccaggtca caaccccaa ggagtggctg caggtggact tccagaagac catgaaggtg     7800 actgggtga ccacccaggg ggtgaagagc ctgctgacca gcatgtatgt gaaggagttc     7860
ctgatcagca gcagccagga tggccaccag tggaccctgt tcttccagaa tggcaaggtg    7920
aaggtgttcc agggcaacca ggacagcttc accctgtgg tgaacagcct ggaccccccc     7980
ctgctgacca gatacctgag gattcacccc cagagctggg tgcaccagat tgccctgagg    8040
atggaggtgc tgggctgtga ggcccaggac ctgtactgag cggccgcggg cccaatcaac    8100
ctctggatta caaaatttgt gaaagattga ctggtattct taactatgtt gctccttta    8160 cgctatgtgg atacgctgct ttaatgcctt tgtatcatgc tattgcttcc cgtatggctt    8220
tcattttctc ctccttgtat aaatcctggt tgctgtctct ttatgaggag ttgtggcccg    8280
ttgtcaggca acgtggcgtg gtgtgcactg tgtttgctga cgcaaccccc actggttggg    8340
gcattgccac cacctgtcag ctccttccg ggactttcgc tttccccctc cctattgcca     8400
cggcggaact catcgccgcc tgccttgccc gctgctggac aggggctcgg ctgttgggca    8460
ctgacaattc cgtggtgttg tcggggaaat catcgtcctt tccttggctg ctcgcctgtg    8520
ttgccacctg gattctgcgc gggacgtcct tctgctacgt cccttcggcc ctcaatccag    8580
cggaccttcc ttcccgcggc ctgctgccgg ctctgcggcc tcttccgcgt cttcgccttc    8640
gccctcagac gagtcggatc tccctttggg ccgcctcccc gcaagcttcg cactttttaa    8700
aagaaaaggg aggactggat gggatttatt actccgatag gacgctggct tgtaactcag    8760
tctcttacta ggagaccagc ttgagctgg tgttcgctg ttagcctaa cctggttggc        8820 caccaggggt aaggactcct tggcttagaa agctaataaa cttgcctgca ttagagctct    8880
tacgcgtccc gggctcgaga tccgcatctc aattagtcag caaccatagt cccgccccta    8940
```

```
actccgccca tcccgcccct aactccgccc agttccgccc attctccgcc ccatggctga    9000
ctaattttt  ttatttatgc agaggccgag gccgcctcgg cctctgagct attccagaag   9060
tagtgaggag gctttttgg  aggcctaggc ttttgcaaaa agctaacttg tttattgcag   9120
cttataatgg ttacaaataa agcaatagca tcacaaattt cacaaataaa gcattttttt   9180
cactgcattc tagttgtggt tgtccaaac  tcatcaatgt atcttatcat gtctgtccgc   9240
ttcctcgctc actgactcgc tgcgctcggt cgttcggctg cggcgagcgg tatcagctca   9300
ctcaaaggcg gtaatacggt tatccacaga atcagggat  aacgcaggaa agaacatgtg   9360
agcaaaaggc cagcaaaagg ccaggaaccg taaaaaggcc gcgttgctgg cgttttcca   9420
taggctccgc cccctgacg  agcatcacaa aaatcgacgc tcaagtcaga ggtggcgaaa   9480
cccgacagga ctataaagat accaggcgtt ccccctgga  agctccctcg tgcgctctcc   9540
tgttccgacc ctgccgctta ccggatacct gtccgccttt ctcccttcgg gaagcgtggc   9600
gctttctcat agctcacgct gtaggtatct cagttcggtg taggtcgttc gctccaagct   9660
gggctgtgtg cacgaacccc ccgttcagcc cgaccgctgc gccttatccg gtaactatcg   9720
tcttgagtcc aacccggtaa gacacgactt atcgccactg gcagcagcca ctggtaacag   9780
gattagcaga gcgaggtatg taggcggtgc tacagagttc ttgaagtggt ggcctaacta   9840
cggctacact agaagaacag tatttggtat ctgcgctctg ctgaagccag ttaccttcgg   9900
aaaaagagtt ggtagctctt gatccggcaa acaaaccacc gctggtagcg gtggttttt   9960
tgtttgcaag cagcagatta cgcgcagaaa aaaggatct  caagaagatc ctttgatctt  10020
ttctacgggg tctgacgctc agtggaacga aaactcacgt taagggattt tggtcatgag  10080
attatcaaaa aggatcttca cctagatcct tttaaattaa aaatgaagtt ttaaatcaat  10140
ctaaagtata tatgagtaaa cttggtctga cagttagaaa aactcatcga gcatcaaatg  10200
aaactgcaat ttattcatat caggattatc aataccatat ttttgaaaaa gccgtttctg  10260
taatgaagga gaaaactcac cgaggcagtt ccataggatg gcaagatcct ggtatcggtc  10320
tgcgattccg actcgtccaa catcaataca acctattaat ttcccctcgt caaaaataag  10380
gttatcaagt gagaaatcac catgagtgac gactgaatcc ggtgagaatg gcaacagctt  10440
atgcatttct ttccagactt gttcaacagg ccagccatta cgctcgtcat caaaatcact  10500
cgcatcaacc aaaccgttat tcattcgtga ttgcgcctga gcgagacgaa atacgcgatc  10560
gctgttaaaa ggacaattac aaacaggaat cgaatgcaac cggcgcagga acactgccag  10620
cgcatcaaca atattttcac ctgaatcagg atattcttct aatacctgga atgctgtttt  10680
tccgggatc  gcagtggtga gtaaccatgc atcatcagga gtacggataa aatgcttgat  10740
ggtcggaaga ggcataaatt ccgtcagcca gtttagtctg accatctcat ctgtaacatc  10800
attggcaacg ctacctttgc catgtttcag aaacaactct ggcgcatcgg gcttcccata  10860
caatcgatag attgtcgcac ctgattgccc gacattatcg cgagcccatt tatacccata  10920
taaatcagca tccatgttgg aatttaatcg cggcctagag caagacgttt cccgttgaat  10980
atggctcata cacccccttg tattactgtt tatgtaagca gacagttta  ttgttcatga  11040
tgatatattt ttatcttgtg caatgtaaca tcagagattt tgagacacaa caattggtcg  11100
acggatcc                                                            11108
```

<210> SEQ ID NO 15
<211> LENGTH: 1257
<212> TYPE: DNA
<213> ORGANISM: Artificial Sequence
<220> FEATURE:
<223> OTHER INFORMATION: codon-optimised CpG depleted A1AT transgene

<400> SEQUENCE: 15

```
atgcccagct ctgtgtcctg gggcattctg ctgctggctg gcctgtgctg tctggtgcct      60
gtgtccctgg ctgaggaccc tcaggggat gctgcccaga aaacagacac ctcccaccat     120
gaccaggacc accccacctt caacaagatc accccccaacc tggcagagtt tgccttcagc    180
ctgtacagac agctggccca ccagagcaac agcaccaaca tctttttcag ccctgtgtcc    240
attgccacag cctttgccat gctgagcctg ggcaccaagg ctgacaccca tgatgagatc    300
ctggaaggcc tgaacttcaa cctgacagag atccctgagg cccagatcca tgagggcttc    360
caggaactgc tgagaaccct gaaccagcca gacagccagc tgcagctgac aacaggcaat    420
gggctgttcc tgtctgaggg cctgaagctg gtggacaagt tctggaaga tgtgaagaag     480
ctgtaccact ctgaggcctt cacagtgaac tttggggaca cagaagaggc caagaaacag    540
atcaatgact atgtggaaaa gggcacccag ggcaagattg tggaccttgt gaaagagctg    600
gacagggaca ctgtgtttgc ccttgtgaac tacatcttct tcaagggcaa gtgggagagg    660
ccctttgaag tgaaggacac tgaggaagag gacttccatg tggaccaagt gaccacagtg    720
aaggtgccaa tgatgaagag actggggatg ttcaatatcc agcactgcaa gaaactgagc    780
agctgggtgc tgctgatgaa gtacctgggc aatgctacag ccatattctt tctgcctgat    840
gagggcaagc tgcagcacct ggaaaatgag ctgacccatg acatcatcac caaatttctg    900
gaaaatgagg acagaagatc tgccagcctg catctgccca gctgagcat cacaggcaca    960
tatgacctga gtctgtgct gggacagctg gaatcacca aggtgttcag caatggggca   1020
gacctgagtg gagtgacaga ggaagccct ctgaagctgt ccaaggctgt gcacaaggca   1080
gtgctgacca ttgatgagaa gggcacagag gctgctgggg ccatgtttct ggaagccatc   1140
cccatgtcca ccccccaga agtgaagttc aacaagccct tgtgttcct gatgattgag   1200
cagaacacca agagccccct gttcatgggc aaggttgtga ccccaccca gaaatga      1257
```

<210> SEQ ID NO 16
<211> LENGTH: 5013
<212> TYPE: DNA
<213> ORGANISM: Artificial Sequence
<220> FEATURE:
<223> OTHER INFORMATION: codon-optimised CpG depleted FVIII transgene
       (N6)

<400> SEQUENCE: 16

```
atgcagattg agctgagcac ctgcttcttc ctgtgcctgc tgaggttctg cttctctgcc     60
accaggagat actacctggg ggctgtggag ctgagctggg actacatgca gtctgacctg    120
ggggagctgc ctgtggatgc caggttcccc cccagagtgc ccaagagctt cccttcaac    180
acctctgtgg tgtacaagaa gaccctgttt gtggagttca ctgaccacct gttcaacatt    240
gccaagccca ggcccccctg gatgggcctg ctgggcccca ccatccaggc tgaggtgtat    300
gacactgtgg tgatcaccct gaagaacatg gccagccacc ctgtgagcct gcatgctgtg    360
ggggtgagct actggaaggc ctctgagggg ctgagtatg atgaccagac cagccagagg    420
gagaaggagg atgacaaggt gttccctggg ggcagccaca cctatgtgtg gcaggtgctg    480
aaggagaatg gccccatggc ctctgacccc ctgtgcctga ctacagcta cctgagccat    540
gtggacctgt tgaggacct gaactctggc ctgattgggg ccctgctggt gtgcaggag    600
ggcagcctgg ccaaggagaa gacccagacc ctgcacaagt tcatcctgct gtttgctgtg    660
```

```
tttgatgagg gcaagagctg gcactctgaa accaagaaca gcctgatgca ggacagggat      720
gctgcctctg ccagggcctg gcccaagatg cacactgtga atggctatgt gaacaggagc      780
ctgcctggcc tgattggctg ccacaggaag tctgtgtact ggcatgtgat tggcatgggc      840
accaccoctg aggtgcacag catcttcctg gagggccaca ccttcctggt caggaaccac      900
aggcaggcca gcctggagat cagccccatc accttcctga ctgcccagac cctgctgatg      960
gacctgggcc agttcctgct gttctgccac atcagcagcc accagcatga tggcatggag     1020
gcctatgtga aggtggacag ctgccctgag agccccagc tgaggatgaa gaacaatgag      1080
gaggctgagg actatgatga tgacctgact gactctgaga tggatgtggt gaggtttgat     1140
gatgacaaca gccccagctt catccagatc aggtctgtgg ccaagaagca ccccaagacc     1200
tgggtgcact acattgctgc tgaggaggag actgggact atgcccccct ggtgctggcc      1260
cctgatgaca ggagctacaa gagccagtac ctgaacaatg ccccccagag gattggcagg     1320
aagtacaaga aggtcaggtt catggcctac actgatgaaa ccttcaagac cagggaggcc     1380
atccagcatg agtctggcat cctgggcccc ctgctgtatg gggaggtggg ggacaccctg     1440
ctgatcatct tcaagaacca ggccagcagg ccctacaaca tctacccca tggcatcact      1500
gatgtgaggc ccctgtacag caggaggctg cccaaggggg tgaagcacct gaaggacttc     1560
cccatcctgc ctggggagat cttcaagtac aagtggactg tgactgtgga ggatggcccc     1620
accaagtctg accccaggtg cctgaccaga tactacagca gctttgtgaa catggagagg     1680
gacctggcct ctggcctgat tggccccctg ctgatctgct acaaggagtc tgtggaccag     1740
aggggcaacc agatcatgtc tgacaagagg aatgtgatcc tgttctctgt gtttgatgag     1800
aacaggagct ggtacctgac tgagaacatc cagaggttcc tgcccaaccc tgctggggtg     1860
cagctggagg accctgagtt ccaggccagc aacatcatgc acagcatcaa tggctatgtg     1920
tttgacagcc tgcagctgtc tgtgtgcctg catgaggtgg cctactggta catcctgagc     1980
attggggccc agactgactt cctgtctgtg ttcttctctg gctacacctt caagcacaag     2040
atggtgtatg aggacaccct gaccctgttc cccttctctg gggagactgt gttcatgagc     2100
atggagaacc tggcctgtg gattctgggc tgccacaact ctgacttcag gaacaggggc     2160
atgactgccc tgctgaaagt ctccagctgt gacaagaaca ctggggacta ctatgaggac     2220
agctatgagg acatctctgc ctacctgctg agcaagaaca atgccattga gcccaggagc     2280
ttcagccaga acagcaggca ccccagcacc aggcagaagc agttcaatgc caccaccatc     2340
cctgagaata catagagaa gacagaccca tggtttgccc accggacccc catgcccaag     2400
atccagaatg tgagcagctc tgacctgctg atgctgctga ggcagagccc cacccccat      2460
ggcctgagcc tgtctgacct gcaggaggcc aagtatgaaa ccttctctga tgaccccagc     2520
cctggggcca ttgacagcaa caacagcctg tctgagatga cccacttcag gccccagctg     2580
caccactctg ggacatggt gttcaccct gagtctggcc tgcagctgag gctgaatgag      2640
aagctgggca ccactgctgc cactgagctg aagaagctgg acttcaaagt ctccagcacc     2700
agcaacaacc tgatcagcac catcccctct gacaacctgg ctgctggcac tgacaacacc     2760
agcagcctgg gccccccag catgcctgtg cactatgaca gcagctggaa caccaccctg     2820
tttggcaaga gagcagccc cctgactgag tctgggggcc ccctgagcct gtctgaggag     2880
aacaatgaca gcaagctgct ggagtctggc ctgatgaaca gccaggagag cagctggggc     2940
aagaatgtga gcagcaggga gatcaccagg accacccctgc agtctgacca ggaggagatt     3000
```

```
gactatgatg acaccatctc tgtggagatg aagaaggagg actttgacat ctacgacgag      3060
gacgagaacc agagcccag  gagcttccag aagaagacca ggcactactt cattgctgct      3120
gtggagaggc tgtgggacta tggcatgagc agcagccccc atgtgctgag gaacagggcc      3180
cagtctggct ctgtgcccca gttcaagaag gtggtgttcc aggagttcac tgatggcagc      3240
ttcacccagc ccctgtacag aggggagctg aatgagcacc tgggcctgct gggcccctac      3300
atcagggctg aggtggagga caacatcatg gtgaccttca ggaaccaggc cagcaggccc      3360
tacagcttct acagcagcct gatcagctat gaggaggacc agaggcaggg ggctgagccc      3420
aggaagaact ttgtgaagcc caatgaaacc aagacctact tctggaaggt gcagcaccac      3480
atggccccca ccaaggatga gtttgactgc aaggcctggg cctacttctc tgatgtggac      3540
ctggagaagg atgtgcactc tggcctgatt ggccccctgc tggtgtgcca caccaacacc      3600
ctgaaccctg cccatggcag gcaggtgact gtgcaggagt ttgccctgtt cttcaccatc      3660
tttgatgaaa ccaagagctg gtacttcact gagaacatgg agaggaactg cagggccccc      3720
tgcaacatcc agatggagga ccccaccttc aaggagaact acaggttcca tgccatcaat      3780
ggctacatca tggacaccct gcctggcctg gtgatggccc aggaccagag gatcaggtgg      3840
tacctgctga gcatgggcag caatgagaac atccacagca tccacttctc tggccatgtg      3900
ttcactgtga ggaagaagga ggagtacaag atggccctgt acaacctgta ccctggggtg      3960
tttgagactg tggagatgct gccccagcaa gctggcatct ggagggtgga gtgcctgatt      4020
ggggagcacc tgcatgctgg catgagcacc ctgttcctgg tgtacagcaa caagtgccag      4080 accccctgg  gcatggcctc tggccacatc agggacttcc agatcactgc ctctggccag      4140
tatggccagt gggccccccaa gctggccagg ctgcactact ctggcagcat caatgcctgg      4200
agcaccaagg agcccttcag ctggatcaag gtggacctgc tggcccccat gatcatccat      4260
ggcatcaaga cccagggggc caggcagaag ttcagcagcc tgtacatcag ccagttcatc      4320
atcatgtaca gcctggatgg caagaagtgg cagacctaca gggcaacag  cactggcacc      4380 ctgatggtgt tctttggcaa tgtggacagc tctggcatca gcacaacat  cttcaacccc      4440 cccatcattg ccagatacat caggctgcac cccaccccact acagcatcag gagcaccctg      4500
aggatggagc tgatgggctg tgacctgaac agctgcagca tgccctggg  catggagagc      4560 aaggccatct ctgatgccca gatcactgcc agcagctact tcaccaacat gtttgccacc      4620
tggagcccca gcaaggccag gctgcacctg cagggcagga gcaatgcctg gaggccccag      4680
gtcaacaacc ccaaggagtg gctgcaggtg gacttccaga gaccatgaa  ggtgactggg      4740 gtgaccaccc agggggtgaa gagcctgctg accagcatgt atgtgaagga gttcctgatc      4800
agcagcagcc aggatggcca ccagtggacc ctgttcttcc agaatggcaa ggtgaaggtg      4860
ttccagggca ccaggacag  cttcaccccct gtggtgaaca gcctggaccc ccccctgctg      4920
accagatacc tgaggattca cccccagagc tgggtgcacc agattgccct gaggatggag      4980
gtgctgggct gtgaggccca ggacctgtac tga                                   5013
```

<210> SEQ ID NO 17
<211> LENGTH: 873
<212> TYPE: DNA
<213> ORGANISM: Cytomegalovirus

<400> SEQUENCE: 17

```
ccgcggagat ctcaatattg gccattagcc atattattca ttggttatat agcataaatc         60
aatattggct attggccatt gcatacgttg tatctatatc ataatatgta catttatatt        120
```

```
ggctcatgtc caatatgacc gccatgttgg cattgattat tgactagtta ttaatagtaa    180
tcaattacgg ggtcattagt tcatagccca tatatggagt tccgcgttac ataacttacg    240
gtaaatggcc cgcctggctg accgcccaac gaccccgcc cattgacgtc aataatgacg     300
tatgttccca gtaacgcc aatagggact ttccattgac gtcaatgggt ggagtattta      360
cggtaaactg cccacttggc agtacatcaa gtgtatcata tgccaagtcc gcccctatt     420 gacgtcaatg acggtaaatg gcccgcctgg cattatgccc agtacatgac cttacgggac    480
tttcctactt ggcagtacat ctacgtatta gtcatcgcta ttaccatggt gatgcggttt    540
tggcagtaca ccaatgggcg tggatagcgg tttgactcac ggggatttcc aagtctccac    600
cccattgacg tcaatgggag tttgttttgg caccaaaatc aacgggactt tccaaaatgt    660
cgtaataacc ccgccccgtt gacgcaaatg ggcggtaggc gtgtacggtg ggaggtctat    720
ataagcagag ctcgtttagt gaaccgtcag atcactagaa gctttattgc ggtagtttat    780
cacagttaaa ttgctaacgc agtcagtgct tctgacacaa cagtctcgaa cttaagctgc    840
agaagttggt cgtgaggcac tgggcaggct agc                                 873

<210> SEQ ID NO 18
<211> LENGTH: 67
<212> TYPE: DNA
<213> ORGANISM: Artificial Sequence
<220> FEATURE:
<223> OTHER INFORMATION: primer

<400> SEQUENCE: 18
tcgagatgtg gtctgagtta aaaatcagga gcaacgacgg aggtgaagga ccagacgcca    60
acgaccc                                                              67

<210> SEQ ID NO 19
<211> LENGTH: 67
<212> TYPE: DNA
<213> ORGANISM: Artificial Sequence
<220> FEATURE:
<223> OTHER INFORMATION: primer

<400> SEQUENCE: 19
ccgggggtcg ttggcgtctg gtccttcacc tccgtcgttg ctcctgattt ttaactcaga    60
ccacatc                                                              67

<210> SEQ ID NO 20
<211> LENGTH: 57
<212> TYPE: DNA
<213> ORGANISM: Artificial Sequence
<220> FEATURE:
<223> OTHER INFORMATION: primer

<400> SEQUENCE: 20
ccggggaaag ggggtgcaac acatccatat ccagccatct ctacctgttt atggaca       57

<210> SEQ ID NO 21
<211> LENGTH: 58
<212> TYPE: DNA
<213> ORGANISM: Artificial Sequence
<220> FEATURE:
<223> OTHER INFORMATION: primer

<400> SEQUENCE: 21
accctctgtc cataaacagg tagagatggc tggatatgga tgtgttgcac ccctttcc      58
```

```
<210> SEQ ID NO 22
<211> LENGTH: 39
<212> TYPE: DNA
<213> ORGANISM: Artificial Sequence
<220> FEATURE:
<223> OTHER INFORMATION: primer

<400> SEQUENCE: 22
gggttaggtg gttgctgatt ctctcattca cccagtggg            39

<210> SEQ ID NO 23
<211> LENGTH: 39
<212> TYPE: DNA
<213> ORGANISM: Artificial Sequence
<220> FEATURE:
<223> OTHER INFORMATION: primer

<400> SEQUENCE: 23
gatccccact gggtgaatga gagaatcagc aaccaccta            39

<210> SEQ ID NO 24
<211> LENGTH: 34
<212> TYPE: DNA
<213> ORGANISM: Artificial Sequence
<220> FEATURE:
<223> OTHER INFORMATION: primer

<400> SEQUENCE: 24
gagactcgag atgtggtctg agttaaaaat cagg                 34

<210> SEQ ID NO 25
<211> LENGTH: 62
<212> TYPE: DNA
<213> ORGANISM: Artificial Sequence
<220> FEATURE:
<223> OTHER INFORMATION: primer

<400> SEQUENCE: 25
agaggtagac cagtacgagt cacgtttgcc cctatcacca tccctaaccc tctgtcataa   60
ac                                                                 62

<210> SEQ ID NO 26
<211> LENGTH: 1257
<212> TYPE: DNA
<213> ORGANISM: Artificial Sequence
<220> FEATURE:
<223> OTHER INFORMATION: complementary strand of codon-optimised CpG
      depleted A1AT transgene

<400> SEQUENCE: 26
tacgggtcga gacacaggac cccgtaagac gacgaccgac cggacacgac agaccacgga   60
cacagggacc gactcctggg agtcccccta cgacgggtct tttgtctgtg gagggtggta   120
ctggtcctgg tggggtggaa gttgttctag tgggggttgg accgtctcaa acggaagtcg   180
gacatgtctg tcgaccgggt ggtctcgttg tcgtggttgt agaaaaagtc gggacacagg   240
taacggtgtc ggaaacggta cgactcggac ccgtggttcc gactgtgggt actactctag   300
gaccttccgg acttgaagtt ggactgtctc tagggactcc gggtctaggt actcccgaag   360
gtccttgacg actcttggga cttggtcggt ctgtcggtcg acgtcgactg ttgtccgtta   420
cccgacaagg acagactccc ggacttcgac cacctgttca aagaccttct acacttcttc   480
gacatggtga gactccggaa gtgtcacttg aaaccccgtg gtcttctccg gttctttgtc   540
```

-continued

```
tagttactga tacacctttt cccgtgggtc ccgttctaac acctggaaca ctttctcgac    600
ctgtccctgt gacacaaacg ggaacacttg atgtagaaga agttcccgtt caccctctcc    660
gggaaacttc acttcctgtg actccttctc ctgaaggtac acctggttca ctggtgtcac    720
ttccacggtt actacttctc tgaccccTac aagttatagg tcgtgacgtt ctttgactcg    780
tcgacccacg acgactactt catggacccg ttacgatgtc ggtataagaa agacggacta    840
ctcccgttcg acgtcgtgga ccttttactc gactgggtac tgtagtagtg gtttaaagac    900
cttttactcc tgtcttctag acggtcggac gtagacgggt cgactcgta gtgtccgtgt     960 atactggact tcagacacga ccctgtcgac ccttagtggt tccacaagtc gttacccgt    1020 ctggactcac ctcactgtct ccttcgggga gacttcgaca ggttccgaca cgtgttccgt    1080
cacgactggt aactactctt cccgtgtctc gacgacccc ggtacaaaga ccttcggtag    1140
gggtacaggt aggggggtct tcacttcaag ttgttcggga aacacaagga ctactaactc    1200
gtcttgtggt tctcggggga caagtacccg ttccaacact tggggtgggt ctttact      1257
```

<210> SEQ ID NO 27
<211> LENGTH: 419
<212> TYPE: PRT
<213> ORGANISM: Artificial Sequence
<220> FEATURE:
<223> OTHER INFORMATION: peptide coded by codon-optimised CpG depleted A1AT transgene

<400> SEQUENCE: 27

```
Ala Glu Asp Pro Gln Gly Asp Ala Ala Gln Lys Thr Asp Thr Ser His
1               5                   10                  15

His Asp Gln Asp His Pro Thr Phe Ala Glu Asp Pro Gln Gly Asp Ala
                20                  25                  30

Ala Gln Lys Thr Asp Thr Ser His His Asp Gln Asp His Pro Thr Phe
            35                  40                  45

Asn Lys Ile Thr Pro Asn Leu Ala Glu Phe Ala Phe Ser Leu Tyr Arg
        50                  55                  60

Gln Leu Ala His Gln Ser Asn Ser Thr Asn Ile Phe Phe Ser Pro Val
65                  70                  75                  80

Ser Ile Ala Thr Ala Phe Ala Met Leu Ser Leu Gly Thr Lys Ala Asp
                85                  90                  95

Thr His Asp Glu Ile Leu Glu Gly Leu Asn Phe Asn Leu Thr Glu Ile
            100                 105                 110

Pro Glu Ala Gln Ile His Glu Gly Phe Gln Glu Leu Leu Arg Thr Leu
        115                 120                 125

Asn Gln Pro Asp Ser Gln Leu Gln Leu Thr Thr Gly Asn Gly Leu Phe
    130                 135                 140

Leu Ser Glu Gly Leu Lys Leu Val Asp Lys Phe Leu Glu Asp Val Lys
145                 150                 155                 160

Lys Leu Tyr His Ser Glu Ala Phe Thr Val Asn Phe Gly Asp Thr Glu
                165                 170                 175

Glu Ala Lys Lys Gln Ile Asn Asp Tyr Val Glu Lys Gly Thr Gln Gly
            180                 185                 190

Lys Ile Val Asp Leu Val Lys Glu Leu Asp Arg Asp Thr Val Phe Ala
        195                 200                 205

Leu Val Asn Tyr Ile Phe Phe Lys Gly Lys Trp Glu Arg Pro Phe Glu
    210                 215                 220

Val Lys Asp Thr Glu Glu Glu Asp Phe His Val Asp Gln Val Thr Thr
225                 230                 235                 240
```

Val Lys Val Pro Met Met Lys Arg Leu Gly Met Phe Asn Ile Gln His
            245                 250                 255
Cys Lys Lys Leu Ser Ser Trp Val Leu Leu Met Lys Tyr Leu Gly Asn
        260                 265                 270
Ala Thr Ala Ile Phe Phe Leu Pro Asp Glu Gly Lys Leu Gln His Leu
    275                 280                 285
Glu Asn Glu Leu Thr His Asp Ile Ile Thr Lys Phe Leu Glu Asn Glu
290                 295                 300
Asp Arg Arg Ser Ala Ser Leu His Leu Pro Lys Leu Ser Ile Thr Gly
305                 310                 315                 320
Thr Tyr Asp Leu Lys Ser Val Leu Gly Gln Leu Gly Ile Thr Lys Val
                325                 330                 335
Phe Ser Asn Gly Ala Asp Leu Ser Gly Val Thr Glu Glu Ala Pro Leu
            340                 345                 350
Lys Leu Ser Lys Ala Val His Lys Ala Val Leu Thr Ile Asp Glu Lys
        355                 360                 365
Gly Thr Glu Ala Ala Gly Ala Met Phe Leu Glu Ala Ile Pro Met Ser
    370                 375                 380
Ile Pro Pro Glu Val Lys Phe Asn Lys Pro Phe Val Phe Leu Met Ile
385                 390                 395                 400
Glu Gln Asn Thr Lys Ser Pro Leu Phe Met Gly Lys Val Val Asn Pro
                405                 410                 415
Thr Gln Lys

<210> SEQ ID NO 28
<211> LENGTH: 5013
<212> TYPE: DNA
<213> ORGANISM: Artificial Sequence
<220> FEATURE:
<223> OTHER INFORMATION: complementary strand of codon-optimised CpG
    depleted FVIII transgene (N6)

<400> SEQUENCE: 28
tacgtctaac tcgactcgtg gacgaagaag gacacggacg actccaagac gaagagacgg    60
tggtcctcta tgatggaccc ccgacacctc gactcgaccc tgatgtacgt cagactggac   120
cccctcgacg gacacctacg gtccaagggg gggtctcacg ggttctcgaa ggggaagttg   180
tggagacacc acatgttctt ctgggacaaa cacctcaagt gactggtgga caagttgtaa   240
cggttcgggt ccgggggggac ctacccggac gacccggggt ggtaggtccg actccacata   300
ctgtgacacc actagtggga cttcttgtac cggtcggtgg gacactcgga cgtacgacac   360
ccccactcga tgaccttccg gagactcccc cgactcatac tactggtctg gtcggtctcc   420
ctcttcctcc tactgttcca caagggaccc cgtcggtgt ggatacacac cgtccacgac   480
ttcctcttac cgggtaccg gagactgggg gacacggact ggatgtcgat ggactcggta   540
cacctggacc acttcctgga cttgagaccg gactaacccc gggacgacca cacgtccctc   600
ccgtcggacc ggttcctctt ctgggtctgg gacgtgttca gtaggacga caaacgacac   660 aaactactcc cgttctcgac cgtgagactt tggttcttgt cggactacgt cctgtcccta   720
cgacggagac ggtcccggac cgggttctac gtgtgacact taccgataca cttgtcctcg   780
gacggaccgg actaaccgac ggtgtcctcc agacacatga ccgtacacta accgtacccg   840 tggtgggac tccacgtgtc gtagaaggac ctcccggtgt ggaaggacca gtccttggtg   900
tccgtccggt cggacctcta gtcggggtag tggaaggact gacgggtctg ggacgactac   960

```
ctggacccgg tcaaggacga caagacggtg tagtcgtcgg tggtcgtact accgtacctc    1020
cggatacact tccacctgtc gacgggactc ctcggggtcg actcctactt cttgttactc    1080
ctccgactcc tgatactact actggactga ctgagactct acctacacca ctccaaacta    1140
ctactgttgt cggggtcgaa gtaggtctag tccagacacc ggttcttcgt ggggttctgg    1200
acccacgtga tgtaacgacg actcctcctc ctgaccctga tacggggga ccacgaccgg     1260 ggactactgt cctcgatgtt ctcggtcatg gacttgttac cggggtctc ctaaccgtcc     1320 ttcatgttct tccagtccaa gtaccggatg tgactacttt ggaagttctg gtccctccgg    1380
taggtcgtac tcagaccgta ggacccgggg gacgacatac ccctccaccc cctgtgggac    1440
gactagtaga agttcttggt ccggtcgtcc gggatgttgt agatgggggt accgtagtga    1500
ctacactccg gggacatgtc gtcctccgac gggttccccc acttcgtgga cttcctgaag    1560
gggtaggacg gacccctcta gaagttcatg ttcacctgac actgacacct cctaccgggg    1620
tggttcagac tggggtccac ggactggtct atgatgtcgt cgaaacactt gtacctctcc    1680
ctggaccgga gaccggacta accggggac gactagacga tgttcctcag acacctggtc     1740
tccccgttgg tctagtacag actgttctcc ttacactagg acaagagaca caaactactc    1800
ttgtcctcga ccatggactg actcttgtag gtctccaagg acgggttggg acgacccac     1860 gtcgacctcc tgggactcaa ggtccggtcg ttgtagtacg tgtcgtagtt accgatacac    1920
aaactgtcgg acgtcgacag acacgggac gtactccacc ggatgaccat gtaggactcg    1980
taaccccggg tctgactgaa ggacagacac aagaagagac cgatgtggaa gttcgtgttc    2040
taccacatac tcctgtggga ctgggacaag gggaagagac ccctctgaca caagtactcg    2100
tacctcttgg gaccggacac ctaagacccg acggtgttga gactgaagtc cttgtccccg    2160
tactgacggg acgactttca gaggtcgaca ctgttcttgt gaccctgat gatactcctg     2220 tcgatactcc tgtagagacg gatggacgac tcgttcttgt tacggtaact cgggtcctcg    2280
aagtcggtct tgtcgtccgt ggggtcgtgg tccgtcttcg tcaagttacg gtggtggtag    2340
ggactcttac tgtatctctt ctgtctgggt accaaacggg tggcctgggg gtacgggttc    2400
taggtcttac actcgtcgag actggacgac tacgacgact ccgtctcggg gtgggggta     2460 ccggactcgg acagactgga cgtcctccgg ttcatacttt ggaagagact actggggtcg    2520
ggaccccggt aactgtcgtt gttgtcggac agactctact gggtgaagtc cggggtcgac    2580
gtggtgagac ccctgtacca caagtgggga ctcagaccgg acgtcgactc cgacttactc    2640
ttcgacccgt ggtgacgacg gtgactcgac ttccttgacc tgaagtttca gaggtcgtgg    2700
tcgttgttgg actagtcgtg gtaggggaga ctgttggacc gacgaccgtg actgttgtgg    2760
tcgtcggacc cggggggggtc gtacggacac gtgatactgt cggtcgacct gtggtgggac    2820
aaaccgttct tctcgtcggg ggactgactc agaccccgg gggactcgga cagactcctc     2880
ttgttactgt cgttcgacga cctcagaccg gactacttgt cggtcctctc gtcgaccccg    2940
ttcttacact cgtcgtccct ctagtggtcc tggtgggacg tcagactggt cctcctctaa    3000
ctgatactac tgtggtagag acacctctac ttcttcctcc tgaaactgta gatgctgctc    3060
ctgctcttgg tctcggggtc ctcgaaggtc ttcttctggt ccgtgatgaa gtaacgacga    3120
cacctctccg acaccctgat accgtactcg tcgtcggggg tacacgactc cttgtcccgg    3180
gtcagaccga gacacggggt caagttcttc caccacaagg tcctcaagtg actaccgtcg    3240
aagtgggtcg gggacatgtc tcccctcgac ttactcgtgg acccgacga cccggggatg     3300 tagtcccgac tccacctcct gttgtagtac cactggaagt ccttggtccg gtcgtccggg    3360
```

```
atgtcgaaga tgtcgtcgga ctagtcgata ctcctcctgg tctccgtccc ccgactcggg    3420
tccttcttga aacacttcgg gttactttgg ttctggatga agaccttcca cgtcgtggtg    3480
taccgggggt ggttcctact caaactgacg ttccggaccc ggatgaagag actacacctg    3540
gacctcttcc tacacgtgag accggactaa ccggggacg accacacggt gtggttgtgg    3600
gacttgggac gggtaccgtc cgtccactga cacgtcctca acgggacaa gaagtggtag     3660
aaactacttt ggttctcgac catgaagtga ctcttgtacc tctccttgac gtcccggggg    3720
acgttgtagg tctacctcct ggggtggaag ttcctcttga tgtccaaggt acggtagtta    3780
ccgatgtagt acctgtggga cggaccggac cactaccggg tcctggtctc ctagtccacc    3840
atggacgact cgtacccgtc gttactcttg taggtgtcgt aggtgaagag accggtacac    3900
aagtgacact ccttcttcct cctcatgttc taccgggaca tgttggacat ggacccccac    3960
aaactctgac acctctacga cgggtcgttc cgaccgtaga cctcccacct cacggactaa    4020
ccctcgtgg acgtacgacc gtactcgtgg gacaaggacc acatgtcgtt gttcacggtc    4080
tgggggacc cgtaccggag accggtgtag tccctgaagg tctagtgacg gagaccggtc    4140
ataccggtca cccggggggtt cgaccggtcc gacgtgatga accgtcgta gttacggacc    4200
tcgtggttcc tcgggaagtc gacctagttc cacctggacg accggggta ctagtaggta    4260
ccgtagttct gggtccccg gtccgtcttc aagtcgtcgg acatgtagtc ggtcaagtag    4320
tagtacatgt cggacctacc gttcttcacc gtctggatgt ccccgttgtc gtgaccgtgg    4380
gactaccaca agaaaccgtt acacctgtcg agaccgtagt tcgtgttgta gaagttgggg    4440
gggtagtaac ggtctatgta gtccgacgtg gggtgggtga tgtcgtagtc ctcgtgggac    4500
tcctacctcg actacccgac actgacttg tcgacgtcgt acgggaccc gtacctctcg     4560
ttccggtaga gactacgggt ctagtgacgg tcgtcgatga agtggttgta caaacggtgg    4620
acctcggggt cgttccggtc cgacgtggac gtcccgtcct cgttacggac ctccggggtc    4680
cagttgttgg ggttcctcac cgacgtccac ctgaaggtct tctggtactt ccactgaccc    4740
cactggtggg tccccccactt ctcggacgac tggtcgtaca tacacttcct caaggactag   4800
tcgtcgtcgg tcctaccggt ggtcacctgg gacaagaagg tcttaccgtt ccacttccac    4860
aaggtcccgt tggtcctgtc gaagtgggga caccacttgt cggacctggg ggggacgac    4920
tggtctatgg actcctaagt gggggtctcg acccacgtgg tctaacggga ctcctacctc    4980
cacgacccga cactccgggt cctggacatg act                                 5013
```

<210> SEQ ID NO 29
<211> LENGTH: 1670
<212> TYPE: PRT
<213> ORGANISM: Artificial Sequence
<220> FEATURE:
<223> OTHER INFORMATION: peptide coded by codon-optimised CpG depleted FVIII transgene (N6)

<400> SEQUENCE: 29

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60
```

```
Tyr Lys Lys Thr Leu Phe Val Glu Phe Thr Asp His Leu Phe Asn Ile
 65                  70                  75                  80

Ala Lys Pro Arg Pro Pro Trp Met Gly Leu Leu Gly Pro Thr Ile Gln
                 85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Lys Val Arg Phe Met
        435                 440                 445

Ala Tyr Thr Asp Glu Thr Phe Lys Thr Arg Glu Ala Ile Gln His Glu
    450                 455                 460

Ser Gly Ile Leu Gly Pro Leu Leu Tyr Gly Glu Val Gly Asp Thr Leu
465                 470                 475                 480
```

```
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
            500                 505                 510
Gly Val Lys His Leu Lys Asp Phe Pro Ile Leu Pro Gly Glu Ile Phe
        515                 520                 525
Lys Tyr Lys Trp Thr Val Thr Val Glu Asp Gly Pro Thr Lys Ser Asp
    530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
            580                 585                 590
Ile Leu Phe Ser Val Phe Asp Glu Asn Arg Ser Trp Tyr Leu Thr Glu
        595                 600                 605
Asn Ile Gln Arg Phe Leu Pro Asn Pro Ala Gly Val Gln Leu Glu Asp
    610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
            660                 665                 670
Ser Gly Tyr Thr Phe Lys His Lys Met Val Tyr Glu Asp Thr Leu Thr
        675                 680                 685
Leu Phe Pro Phe Ser Gly Glu Thr Val Phe Met Ser Met Glu Asn Pro
    690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
            740                 745                 750
Asn Asn Ala Ile Glu Pro Arg Ser Phe Ser Gln Asn Ser Arg His Pro
        755                 760                 765
Ser Thr Arg Gln Lys Gln Phe Asn Ala Thr Thr Ile Pro Glu Asn Asp
    770                 775                 780
Ile Glu Lys Thr Asp Pro Trp Phe Ala His Arg Thr Pro Met Pro Lys
785                 790                 795                 800
Ile Gln Asn Val Ser Ser Ser Asp Leu Leu Met Leu Leu Arg Gln Ser
                805                 810                 815
Pro Thr Pro His Gly Leu Ser Leu Ser Asp Leu Gln Glu Ala Lys Tyr
            820                 825                 830
Glu Thr Phe Ser Asp Asp Pro Ser Pro Gly Ala Ile Asp Ser Asn Asn
        835                 840                 845
Ser Leu Ser Glu Met Thr His Phe Arg Pro Gln Leu His His Ser Gly
    850                 855                 860
Asp Met Val Phe Thr Pro Glu Ser Gly Leu Gln Leu Arg Leu Asn Glu
865                 870                 875                 880
Lys Leu Gly Thr Thr Ala Ala Thr Glu Leu Lys Lys Leu Asp Phe Lys
                885                 890                 895
Val Ser Ser Thr Ser Asn Asn Leu Ile Ser Thr Ile Pro Ser Asp Asn
```

```
                900             905             910
Leu Ala Ala Gly Thr Asp Asn Thr Ser Ser Leu Gly Pro Pro Ser Met
        915             920             925

Pro Val His Tyr Asp Ser Gln Leu Asp Thr Thr Leu Phe Gly Lys Lys
        930             935             940

Ser Ser Pro Leu Thr Glu Ser Gly Gly Pro Leu Ser Leu Ser Glu Glu
945             950             955             960

Asn Asn Asp Ser Lys Leu Leu Glu Ser Gly Leu Met Asn Ser Gln Glu
            965             970             975

Ser Ser Trp Gly Lys Asn Val Ser Ser Arg Glu Ile Thr Arg Thr Thr
            980             985             990

Leu Gln Ser Asp Gln Glu Glu Ile Asp Tyr Asp Asp Thr Ile Ser Val
        995             1000            1005

Glu Met Lys Lys Glu Asp Phe Asp Ile Tyr Asp Glu Asp Glu Asn
    1010            1015            1020

Gln Ser Pro Arg Ser Phe Gln Lys Lys Thr Arg His Tyr Phe Ile
    1025            1030            1035

Ala Ala Val Glu Arg Leu Trp Asp Tyr Gly Met Ser Ser Ser Pro
    1040            1045            1050

His Val Leu Arg Asn Arg Ala Gln Ser Gly Ser Val Pro Gln Phe
    1055            1060            1065

Lys Lys Val Val Phe Gln Glu Phe Thr Asp Gly Ser Phe Thr Gln
    1070            1075            1080

Pro Leu Tyr Arg Gly Glu Leu Asn Glu His Leu Gly Leu Leu Gly
    1085            1090            1095

Pro Tyr Ile Arg Ala Glu Val Glu Asp Asn Ile Met Val Thr Phe
    1100            1105            1110

Arg Asn Gln Ala Ser Arg Pro Tyr Ser Phe Tyr Ser Ser Leu Ile
    1115            1120            1125

Ser Tyr Glu Glu Asp Gln Arg Gln Gly Ala Glu Pro Arg Lys Asn
    1130            1135            1140

Phe Val Lys Pro Asn Glu Thr Lys Thr Tyr Phe Trp Lys Val Gln
    1145            1150            1155

His His Met Ala Pro Thr Lys Asp Glu Phe Asp Cys Lys Ala Trp
    1160            1165            1170

Ala Tyr Phe Ser Asp Val Asp Leu Glu Lys Asp Val His Ser Gly
    1175            1180            1185

Leu Ile Gly Pro Leu Leu Val Cys His Thr Asn Thr Leu Asn Pro
    1190            1195            1200

Ala His Gly Arg Gln Val Thr Val Gln Glu Phe Ala Leu Phe Phe
    1205            1210            1215

Thr Ile Phe Asp Glu Thr Lys Ser Trp Tyr Phe Thr Glu Asn Met
    1220            1225            1230

Glu Arg Asn Cys Arg Ala Pro Cys Asn Ile Gln Met Glu Asp Pro
    1235            1240            1245

Thr Phe Lys Glu Asn Tyr Arg Phe His Ala Ile Asn Gly Tyr Ile
    1250            1255            1260

Met Asp Thr Leu Pro Gly Leu Val Met Ala Gln Asp Gln Arg Ile
    1265            1270            1275

Arg Trp Tyr Leu Leu Ser Met Gly Ser Asn Glu Asn Ile His Ser
    1280            1285            1290

Ile His Phe Ser Gly His Val Phe Thr Val Arg Lys Lys Glu Glu
    1295            1300            1305
```

```
Tyr Lys Met Ala Leu Tyr Asn Leu Tyr Pro Gly Val Phe Glu Thr
1310                1315                1320

Val Glu Met Leu Pro Ser Lys Ala Gly Ile Trp Arg Val Glu Cys
1325                1330                1335

Leu Ile Gly Glu His Leu His Ala Gly Met Ser Thr Leu Phe Leu
1340                1345                1350

Val Tyr Ser Asn Lys Cys Gln Thr Pro Leu Gly Met Ala Ser Gly
1355                1360                1365

His Ile Arg Asp Phe Gln Ile Thr Ala Ser Gly Gln Tyr Gly Gln
1370                1375                1380

Trp Ala Pro Lys Leu Ala Arg Leu His Tyr Ser Gly Ser Ile Asn
1385                1390                1395

Ala Trp Ser Thr Lys Glu Pro Phe Ser Trp Ile Lys Val Asp Leu
1400                1405                1410

Leu Ala Pro Met Ile Ile His Gly Ile Lys Thr Gln Gly Ala Arg
1415                1420                1425

Gln Lys Phe Ser Ser Leu Tyr Ile Ser Gln Phe Ile Ile Met Tyr
1430                1435                1440

Ser Leu Asp Gly Lys Lys Trp Gln Thr Tyr Arg Gly Asn Ser Thr
1445                1450                1455

Gly Thr Leu Met Val Phe Phe Gly Asn Val Asp Ser Ser Gly Ile
1460                1465                1470

Lys His Asn Ile Phe Asn Pro Pro Ile Ile Ala Arg Tyr Ile Arg
1475                1480                1485

Leu His Pro Thr His Tyr Ser Ile Arg Ser Thr Leu Arg Met Glu
1490                1495                1500

Leu Met Gly Cys Asp Leu Asn Ser Cys Ser Met Pro Leu Gly Met
1505                1510                1515

Glu Ser Lys Ala Ile Ser Asp Ala Gln Ile Thr Ala Ser Ser Tyr
1520                1525                1530

Phe Thr Asn Met Phe Ala Thr Trp Ser Pro Ser Lys Ala Arg Leu
1535                1540                1545

His Leu Gln Gly Arg Ser Asn Ala Trp Arg Pro Gln Val Asn Asn
1550                1555                1560

Pro Lys Glu Trp Leu Gln Val Asp Phe Gln Lys Thr Met Lys Val
1565                1570                1575

Thr Gly Val Thr Thr Gln Gly Val Lys Ser Leu Leu Thr Ser Met
1580                1585                1590

Tyr Val Lys Glu Phe Leu Ile Ser Ser Ser Gln Asp Gly His Gln
1595                1600                1605

Trp Thr Leu Phe Phe Gln Asn Gly Lys Val Lys Val Phe Gln Gly
1610                1615                1620

Asn Gln Asp Ser Phe Thr Pro Val Val Asn Ser Leu Asp Pro Pro
1625                1630                1635

Leu Leu Thr Arg Tyr Leu Arg Ile His Pro Gln Ser Trp Val His
1640                1645                1650

Gln Ile Ala Leu Arg Met Glu Val Leu Gly Cys Glu Ala Gln Asp
1655                1660                1665

Leu Tyr
1670

<210> SEQ ID NO 30
<211> LENGTH: 4425
```

<212> TYPE: DNA
<213> ORGANISM: Artificial Sequence
<220> FEATURE:
<223> OTHER INFORMATION: codon-optimised CpG depleted FVIII transgene (V3)

<400> SEQUENCE: 30

```
atgcagattg agctgagcac ctgcttcttc ctgtgcctgc tgaggttctg cttctctgcc      60
accaggagat actacctggg ggctgtggag ctgagctggg actacatgca gtctgacctg     120
ggggagctgc ctgtggatgc caggttcccc cccagagtgc caagagcttc ccccttcaac     180
acctctgtgg tgtacaagaa gaccctgttt gtggagttca ctgaccacct gttcaacatt     240
gccaagccca ggcccccctg gatgggcctg ctgggcccca ccatccaggc tgaggtgtat     300
gacactgtgg tgatcaccct gaagaacatg gccagccacc ctgtgagcct gcatgctgtg     360
ggggtgagct actggaaggc ctctgagggg gctgagtatg atgaccagac cagccagagg     420
gagaaggagg atgacaaggt gttccctggg ggcagccaca cctatgtgtg gcaggtgctg     480
aaggagaatg cccccatggc ctctgacccc ctgtgcctga cctacagcta cctgagccat     540
gtggacctgg tgaaggacct gaactctggc ctgattgggg ccctgctggt gtgcagggag     600
ggcagcctgg ccaaggagaa gacccagacc tgcacaagt tcatcctgct gtttgctgtg     660
tttgatgagg gcaagagctg gcactctgaa accaagaaca gcctgatgca ggacagggat     720
gctgcctctg ccagggcctg gcccaagatg cacactgtga atggctatgt gaacaggagc     780
ctgcctggcc tgattggctg ccacaggaag tctgtgtact ggcatgtgat tggcatgggc     840
accacccctg aggtgcacag catcttcctg gagggccaca ccttcctggt caggaaccac     900
aggcaggcca gctggagat cagcccccatc accttcctga ctgcccagac cctgctgatg     960
gacctgggca gttcctgct gttctgccac atcagcagcc accagcatga tggcatggag    1020
gcctatgtga aggtggacag ctgccctgag gagccccagc tgaggatgaa gaacaatgag    1080
gaggctgagg actatgatga tgacctgact gactctgaga tggatgtggt gaggtttgat    1140
gatgacaaca gccccagctt catccagatc aggtctgtgg ccaagaagca ccccaagacc    1200
tgggtgcact acattgctgc tgaggaggag gactgggact atgccccct ggtgctggcc    1260
cctgatgaca ggagctacaa gagccagtac ctgaacaatg ccccccagag gattggcagg    1320
aagtacaaga aggtcaggtt catggcctac actgatgaaa ccttcaagac cagggaggcc    1380
atccagcatg agtctggcat cctgggcccc ctgctgtatg gggaggtggg ggacaccctg    1440
ctgatcatct tcaagaacca ggccagcagg ccctacaaca tctaccccca tggcatcact    1500
gatgtgaggc ccctgtacag caggaggctg cccaagggg tgaagcacct gaaggacttc    1560
cccatcctgc ctggggagat cttcaagtac aagtggactg tgactgtgga ggatggcccc    1620
accaagtctg accccaggtg cctgaccaga tactacagca gctttgtgaa catggagagg    1680
gacctggcct ctggcctgat ggcccccctg ctgatctgct acaaggagtc tgtggaccag    1740
agggcaacc agatcatgtc tgacaagagg aatgtgatcc tgttctctgt gtttgatgag    1800
aacaggagct ggtacctgac tgagaacatc cagaggttcc tgcccaaccc tgctggggtg    1860
cagctggagg accctgagtt ccaggccagc aacatcatgc acagcatcaa tggctatgtg    1920
tttgacagcc tgcagctgtc tgtgtgcctg catgaggtgg cctactggta catcctgagc    1980
attggggccc agactgactt cctgtctgtg ttcttctctg gctacacctt caagcacaag    2040
atggtgtatg aggacacct gaccctgttc cccttctctg ggagactgt gttcatgagc    2100
atggagaacc ctggcctgtg gattctgggc tgccacaact ctgacttcag gaacagggc    2160
```

```
atgactgccc tgctgaaagt ctccagctgt gacaagaaca ctggggacta ctatgaggac    2220
agctatgagg acatctctgc ctacctgctg agcaagaaca atgccattga gcccaggagc    2280
ttcagccaga atgccactaa tgtgtctaac aacagcaaca ccagcaatga cagcaatgtg    2340
tctcccccag tgctgaagag gcaccagagg gagatcacca ggaccaccct gcagtctgac    2400
caggaggaga ttgactatga tgacaccatc tctgtggaga tgaagaagga ggactttgac    2460
atctacgacg aggacgagaa ccagagcccc aggagcttcc agaagaagac caggcactac    2520
ttcattgctg ctgtggagag gctgtgggac tatggcatga gcagcagccc ccatgtgctg    2580
aggaacaggg cccagtctgg ctctgtgccc cagttcaaga aggtggtgtt ccaggagttc    2640
actgatggca gcttcaccca gcccctgtac agagggagc tgaatgagca cctgggcctg    2700
ctgggcccct acatcagggc tgaggtggag acaacatca tggtgacctt caggaaccag    2760
gccagcaggc cctacagctt ctacagcagc ctgatcagct atgaggagga ccagaggcag    2820
ggggctgagc ccaggaagaa ctttgtgaag cccaatgaaa ccaagaccta cttctggaag    2880
gtgcagcacc acatggcccc caccaaggat gagtttgact gcaaggcctg gcctacttc     2940
tctgatgtgg acctggagaa ggatgtgcac tctggcctga ttggcccct gctggtgtgc    3000
cacaccaaca ccctgaaccc tgcccatggc aggcaggtga ctgtgcagga gtttgccctg    3060
ttcttcacca tctttgatga aaccaagagc tggtacttca ctgagaacat ggagaggaac    3120
tgcagggccc cctgcaacat ccagatggag accccacct tcaaggagaa ctacaggttc    3180
catgccatca atggctacat catggacacc ctgcctggcc tggtgatggc ccaggaccag    3240
aggatcaggt ggtacctgct gagcatgggc agcaatgaga acatccacag catccacttc    3300
tctggccatg tgttcactgt gaggaagaag gaggagtaca agatggccct gtacaacctg    3360
taccctgggg tgtttgagac tgtggagatg ctgcccagca aggctggcat ctggagggtg    3420
gagtgcctga ttggggagca cctgcatgct ggcatgagca ccctgttcct ggtgtacagc    3480
aacaagtgcc agacccccct gggcatggcc tctggccaca tcagggactt ccagatcact    3540
gcctctggcc agtatggcca gtgggccccc aagctggcca ggctgcacta ctctggcagc    3600
atcaatgcct ggagcaccaa ggagcccttc agctggatca aggtggacct gctggccccc    3660
atgatcatcc atggcatcaa gacccagggg gccaggcaga agttcagcag cctgtacatc    3720
agccagttca tcatcatgta cagcctggat ggcaagaagt ggcagaccta caggggcaac    3780
agcactggca ccctgatggt gttctttggc aatgtggaca gctctggcat caagcacaac    3840
atcttcaacc cccccatcat tgccagatac atcaggctgc acccccaccca ctacagcatc    3900
aggagcaccc tgaggatgga gctgatgggc tgtgacctga acagctgcag catgcccctg    3960
ggcatggaga gcaaggccat ctctgatgcc cagatcactg ccagcagcta cttcaccaac    4020
atgtttgcca cctggagccc cagcaaggcc aggctgcacc tgcagggcag gagcaatgcc    4080
tggaggcccc aggtcaacaa ccccaaggag tggctgcagg tggacttcca gaagaccatg    4140
aaggtgactg gggtgaccac ccaggggggtg aagagcctgc tgaccagcat gtatgtgaag    4200
gagttcctga tcagcagcag ccaggatggc caccagtgga cctgttctt ccagaatggc    4260
aaggtgaagg tgttccaggg caaccaggac agcttcaccc ctgtggtgaa cagcctggac    4320
ccccccctgc tgaccagata cctgaggatt caccccagaa gctgggtgca ccagattgcc    4380
ctgaggatgg aggtgctggg ctgtgaggcc caggacctgt actga                    4425
```

<210> SEQ ID NO 31

<211> LENGTH: 4425
<212> TYPE: DNA
<213> ORGANISM: Artificial Sequence
<220> FEATURE:
<223> OTHER INFORMATION: complementary strand of codon-optimised CpG
      depleted FVIII transgene (V3)

<400> SEQUENCE: 31

| | |
|---|---:|
| tacgtctaac tcgactcgtg gacgaagaag gacacggacg actccaagac gaagagacgg | 60 |
| tggtcctcta tgatggaccc ccgacacctc gactcgaccc tgatgtacgt cagactggac | 120 |
| cccctcgacg gacacctacg gtccaagggg gggtctcacg ggttctcgaa ggggaagttg | 180 |
| tggagacacc acatgttctt ctgggacaaa cacctcaagt gactggtgga caagttgtaa | 240 |
| cggttcgggt ccgggggggac ctacccggac gacccggggt ggtaggtccg actccacata | 300 |
| ctgtgacacc actagtggga cttcttgtac cggtcggtgg gacactcgga cgtacgacac | 360 |
| ccccactcga tgaccttccg gagactcccc cgactcatac tactggtctg gtcggtctcc | 420 |
| ctcttcctcc tactgttcca caagggaccc cgtcggtgt ggatacacac cgtccacgac | 480 |
| ttcctcttac cggggtaccg gagactgggg gacacggact ggatgtcgat ggactcggta | 540 |
| cacctggacc acttcctgga cttgagaccg gactaaccccc gggacgacca cacgtccctc | 600 |
| ccgtcggacc ggttcctctt ctgggtctgg gacgtgttca gtaggacga caaacgacac | 660 |
| aaactactcc cgttctcgac cgtgagactt tggttcttgt cggactacgt cctgtcccta | 720 |
| cgacggagac ggtcccggac cgggttctac gtgtgacact taccgataca cttgtcctcg | 780 |
| gacggaccgg actaaccgac ggtgtccttc agacacatga ccgtacacta accgtacccg | 840 |
| tggtggggac tccacgtgtc gtagaaggac ctcccggtgt ggaaggacca gtccttggtg | 900 |
| tccgtccggt cggacctcta gtcggggtag tggaaggact gacgggtctg ggacgactac | 960 |
| ctggacccgg tcaaggacga caagacggtg tagtcgtcgg tggtcgtact accgtacctc | 1020 |
| cggatacact tccacctgtc gacgggactc tcggggtcg actcctactt cttgttactc | 1080 |
| ctccgactcc tgatactact actggactga ctgagactct acctacacca ctccaaacta | 1140 |
| ctactgttgt cggggtcgaa gtaggtctag tccagacacc ggttcttcgt ggggttctgg | 1200 |
| acccacgtga tgtaacgacg actcctcctc ctgaccctga tacgggggga ccacgaccgg | 1260 |
| ggactactgt cctcgatgtt ctcggtcatg gacttgttac cggggggtctc ctaaccgtcc | 1320 |
| ttcatgttct tccagtccaa gtaccggatg tgactacttt ggaagttctg gtccctccgg | 1380 |
| taggtcgtac tcagaccgta ggacccgggg gacgacatac ccctccaccc cctgtgggac | 1440 |
| gactagtaga agttcttggt ccggtcgtcc gggatgttgt agatgggggt accgtagtga | 1500 |
| ctacactccg gggacatgtc gtcctccgac gggttcccccc acttcgtgga cttcctgaag | 1560 |
| gggtaggacg gacccctcta gaagttcatg ttcacctgac actgacacct cctaccgggg | 1620 |
| tggttcagac tggggtccac ggactggtct atgatgtcgt cgaaacactt gtacctctcc | 1680 |
| ctggaccgga gaccggacta accgggggac gactagacga tgttcctcag acacctggtc | 1740 |
| tccccgttgg tctagtacag actgttctcc ttacactagg acaagagaca caaactactc | 1800 |
| ttgtcctcga ccatgggactg actcttgtag gtctccaagg acgggttggg acgaccccac | 1860 |
| gtcgacctcc tgggactcaa ggtccggtcg ttgtagtacg tgtcgtagtt accgatacac | 1920 |
| aaactgtcgg acgtcgacag acacacggac gtactccacc ggatgaccat gtaggactcg | 1980 |
| taaccccggg tctgactgaa ggacagacac aagaagagac cgatgtggaa gttcgtgttc | 2040 |
| taccacatac tcctgtggga ctgggacaag gggaagagac ccctctgaca caagtactcg | 2100 |

```
tacctcttgg gaccggacac ctaagacccg acggtgttga gactgaagtc cttgtccccg   2160
tactgacggg acgactttca gaggtcgaca ctgttcttgt gaccectgat gatactcctg   2220
tcgatactcc tgtagagacg gatggacgac tcgttcttgt tacggtaact cgggtcctcg   2280
aagtcggtct tacggtgatt acacagattg ttgtcgttgg ggtcgttact gtcgttacac   2340
agaggggtc acgacttctc cgtggtctcc ctctagtggt cctggtggga cgtcagactg    2400
gtcctcctct aactgatact actgtggtag agacacctct acttcttcct cctgaaactg   2460
tagatgctgc tcctgctctt ggtctcgggg tcctcgaagg tcttcttctg gtccgtgatg   2520
aagtaacgac gacacctctc cgacaccctg ataccgtact cgtcgtcggg ggtacacgac   2580
tccttgtccc gggtcagacc gagacacggg gtcaagttct tccaccacaa ggtcctcaag   2640
tgactaccgt cgaagtgggt cggggacatg tctcccctcg acttactcgt ggacccggac   2700
gacccgggga tgtagtcccg actccacctc ctgttgtagt accactggaa gtccttggtc   2760
cggtcgtccg ggatgtcgaa gatgtcgtcg gactagtcga tactcctcct ggtctccgtc   2820
ccccgactcg ggtccttctt gaaacacttc gggttactt  ggttctggat gaagaccttc   2880
cacgtcgtgg tgtaccgggg gtggttccta ctcaaactga cgttccggac ccggatgaag   2940
agactacacc tggacctctt cctacacgtg agaccggact aaccggggga cgaccacacg   3000
gtgtggttgt gggacttggg acgggtaccg tccgtccact gacacgtcct caaacgggac   3060
aagaagtggt agaaactact ttggttctcg accatgaagt gactcttgta cctctccttg   3120
acgtcccggg ggacgttgta ggtctacctc ctggggtgga agttcctctt gatgtccaag   3180
gtacggtagt taccgatgta gtacctgtgg gacggaccgg accactaccg ggtcctggtc   3240
tcctagtcca ccatggacga ctcgtacccg tcgttactct tgtaggtgtc gtaggtgaag   3300
agaccggtac acaagtgaca ctccttcttc ctcctcatgt tctaccggga catgttggac   3360
atgggacccc acaaactctg acacctctac gacgggtcgt tccgaccgta gacctcccac   3420
ctcacggact aacccctcgt ggacgtacga ccgtactcgt gggacaagga ccacatgtcg   3480
ttgttcacgg tctgggggga cccgtaccgg agaccggtgt agtccctgaa ggtctagtga   3540
cggagaccgg tcataccggt cacccggggg ttcgaccggt ccgacgtgat gagaccgtcg   3600
tagttacgga cctcgtggtt cctcgggaag tcgacctagt tccacctgga cgaccggggg   3660
tactagtagg taccgtagtt ctgggtcccc cggtccgtct tcaagtcgtc ggacatgtag   3720
tcggtcaagt agtagtacat gtcggaccta ccgttcttca ccgtctggat gtccccgttg   3780
tcgtgaccgt gggactacca caagaaaccg ttacacctgt cgagaccgta gttcgtgttg   3840
tagaagttgg gggggtagta acggtctatg tagtccgacg tggggtgggt gatgtcgtag   3900
tcctcgtggg actcctacct cgactacccg acactggact tgtcgacgtc gtacggggac   3960
ccgtacctct cgttccggta gagactacgg gtctagtgac ggtcgtcgat gaagtggttg   4020
tacaaacggt ggacctcggg gtcgttccgg tccgacgtgg acgtcccgtc ctcgttacgg   4080
acctccgggg tccagttgtt ggggttcctc accgacgtcc acctgaaggt cttctggtac   4140
ttccactgac cccactggtg ggtcccccac ttctcggacg actggtcgta catacacttc   4200
ctcaaggact agtcgtcgtc ggtcctaccg gtggtcacct gggacaagaa ggtcttaccg   4260
ttccacttcc acaaggtccc gttggtcctg tcgaagtggg gacaccactt gtcggacctg   4320
ggggggacg  actggtctat ggactcctaa gtgggggtct cgacccacgt ggtctaacgg   4380
gactcctacc tccacgaccc gacactccgg gtcctggaca tgact             4425
```

<210> SEQ ID NO 32
<211> LENGTH: 1474
<212> TYPE: PRT
<213> ORGANISM: Artificial Sequence
<220> FEATURE:
<223> OTHER INFORMATION: peptide coded by codon-optimised CpG depleted
      FVIII transgene (V3)

<400> SEQUENCE: 32

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
    290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365
```

Leu Thr Asp Ser Glu Met Asp Val Val Arg Phe Asp Asp Asn Ser
370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
            405                 410                 415

Leu Val Leu Ala Pro Asp Asp Arg Ser Tyr Lys Ser Gln Tyr Leu Asn
            420                 425                 430

Asn Gly Pro Gln Arg Ile Gly Arg Lys Tyr Lys Val Arg Phe Met
        435                 440                 445

Ala Tyr Thr Asp Glu Thr Phe Lys Thr Arg Glu Ala Ile Gln His Glu
450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
            500                 505                 510

Gly Val Lys His Leu Lys Asp Phe Pro Ile Leu Pro Gly Glu Ile Phe
        515                 520                 525

Lys Tyr Lys Trp Thr Val Thr Val Glu Asp Gly Pro Thr Lys Ser Asp
530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
            580                 585                 590

Ile Leu Phe Ser Val Phe Asp Glu Asn Arg Ser Trp Tyr Leu Thr Glu
        595                 600                 605

Asn Ile Gln Arg Phe Leu Pro Asn Pro Ala Gly Val Gln Leu Glu Asp
610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
            660                 665                 670

Ser Gly Tyr Thr Phe Lys His Lys Met Val Tyr Glu Asp Thr Leu Thr
        675                 680                 685

Leu Phe Pro Phe Ser Gly Glu Thr Val Phe Met Ser Met Glu Asn Pro
690                 695                 700

Gly Leu Trp Ile Leu Gly Cys His Asn Ser Asp Phe Arg Asn Arg Gly
705                 710                 715                 720

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ala Thr Asn Val
        755                 760                 765

Ser Asn Asn Ser Asn Thr Ser Asn Asp Ser Asn Val Ser Pro Pro Val
770                 775                 780

Leu Lys Arg His Gln Arg Glu Ile Thr Arg Thr Thr Leu Gln Ser Asp

```
                785                 790                 795                 800
        Gln Glu Glu Ile Asp Tyr Asp Asp Thr Ile Ser Val Glu Met Lys Lys
                        805                 810                 815
        Glu Asp Phe Asp Ile Tyr Asp Glu Asp Glu Asn Gln Ser Pro Arg Ser
                        820                 825                 830
        Phe Gln Lys Lys Thr Arg His Tyr Phe Ile Ala Ala Val Glu Arg Leu
                        835                 840                 845
        Trp Asp Tyr Gly Met Ser Ser Ser Pro His Val Leu Arg Asn Arg Ala
                        850                 855                 860
        Gln Ser Gly Ser Val Pro Gln Phe Lys Lys Val Val Phe Gln Glu Phe
        865                 870                 875                 880
        Thr Asp Gly Ser Phe Thr Gln Pro Leu Tyr Arg Gly Glu Leu Asn Glu
                        885                 890                 895
        His Leu Gly Leu Leu Gly Pro Tyr Ile Arg Ala Glu Val Glu Asp Asn
                        900                 905                 910
        Ile Met Val Thr Phe Arg Asn Gln Ala Ser Arg Pro Tyr Ser Phe Tyr
                        915                 920                 925
        Ser Ser Leu Ile Ser Tyr Glu Glu Asp Gln Arg Gln Gly Ala Glu Pro
                930                 935                 940
        Arg Lys Asn Phe Val Lys Pro Asn Glu Thr Lys Thr Tyr Phe Trp Lys
        945                 950                 955                 960
        Val Gln His His Met Ala Pro Thr Lys Asp Glu Phe Asp Cys Lys Ala
                        965                 970                 975
        Trp Ala Tyr Phe Ser Asp Val Asp Leu Glu Lys Asp Val His Ser Gly
                        980                 985                 990
        Leu Ile Gly Pro Leu Leu Val Cys  His Thr Asn Thr Leu  Asn Pro Ala
                995                 1000                1005
        His Gly  Arg Gln Val Thr Val  Gln Glu Phe Ala Leu  Phe Phe Thr
                1010                1015                1020
        Ile Phe  Asp Glu Thr Lys Ser  Trp Tyr Phe Thr Glu  Asn Met Glu
                1025                1030                1035
        Arg Asn  Cys Arg Ala Pro Cys  Asn Ile Gln Met Glu  Asp Pro Thr
                1040                1045                1050
        Phe Lys  Glu Asn Tyr Arg Phe  His Ala Ile Asn Gly  Tyr Ile Met
                1055                1060                1065
        Asp Thr  Leu Pro Gly Leu Val  Met Ala Gln Asp Gln  Arg Ile Arg
                1070                1075                1080
        Trp Tyr  Leu Leu Ser Met Gly  Ser Asn Glu Asn Ile  His Ser Ile
                1085                1090                1095
        His Phe  Ser Gly His Val Phe  Thr Val Arg Lys Lys  Glu Glu Tyr
                1100                1105                1110
        Lys Met  Ala Leu Tyr Asn Leu  Tyr Pro Gly Val Phe  Glu Thr Val
                1115                1120                1125
        Glu Met  Leu Pro Ser Lys Ala  Gly Ile Trp Arg Val  Glu Cys Leu
                1130                1135                1140
        Ile Gly  Glu His Leu His Ala  Gly Met Ser Thr Leu  Phe Leu Val
                1145                1150                1155
        Tyr Ser  Asn Lys Cys Gln Thr  Pro Leu Gly Met Ala  Ser Gly His
                1160                1165                1170
        Ile Arg  Asp Phe Gln Ile Thr  Ala Ser Gly Gln Tyr  Gly Gln Trp
                1175                1180                1185
        Ala Pro  Lys Leu Ala Arg Leu  His Tyr Ser Gly Ser  Ile Asn Ala
                1190                1195                1200
```

| Trp | Ser | Thr | Lys | Glu | Pro | Phe | Ser | Trp | Ile | Lys | Val | Asp | Leu | Leu |
|-----|-----|-----|-----|-----|-----|-----|-----|-----|-----|-----|-----|-----|-----|-----|
|     | 1205 |     |     |     | 1210 |     |     |     | 1215 |     |     |     |     |     |

| Ala | Pro | Met | Ile | Ile | His | Gly | Ile | Lys | Thr | Gln | Gly | Ala | Arg | Gln |
|-----|-----|-----|-----|-----|-----|-----|-----|-----|-----|-----|-----|-----|-----|-----|
| 1220 |     |     |     |     | 1225 |     |     |     |     | 1230 |     |     |     |     |

| Lys | Phe | Ser | Ser | Leu | Tyr | Ile | Ser | Gln | Phe | Ile | Ile | Met | Tyr | Ser |
|-----|-----|-----|-----|-----|-----|-----|-----|-----|-----|-----|-----|-----|-----|-----|
| 1235 |     |     |     |     | 1240 |     |     |     |     | 1245 |     |     |     |     |

| Leu | Asp | Gly | Lys | Lys | Trp | Gln | Thr | Tyr | Arg | Gly | Asn | Ser | Thr | Gly |
|-----|-----|-----|-----|-----|-----|-----|-----|-----|-----|-----|-----|-----|-----|-----|
| 1250 |     |     |     |     | 1255 |     |     |     |     | 1260 |     |     |     |     |

| Thr | Leu | Met | Val | Phe | Phe | Gly | Asn | Val | Asp | Ser | Ser | Gly | Ile | Lys |
|-----|-----|-----|-----|-----|-----|-----|-----|-----|-----|-----|-----|-----|-----|-----|
| 1265 |     |     |     |     | 1270 |     |     |     |     | 1275 |     |     |     |     |

| His | Asn | Ile | Phe | Asn | Pro | Pro | Ile | Ile | Ala | Arg | Tyr | Ile | Arg | Leu |
|-----|-----|-----|-----|-----|-----|-----|-----|-----|-----|-----|-----|-----|-----|-----|
| 1280 |     |     |     |     | 1285 |     |     |     |     | 1290 |     |     |     |     |

| His | Pro | Thr | His | Tyr | Ser | Ile | Arg | Ser | Thr | Leu | Arg | Met | Glu | Leu |
|-----|-----|-----|-----|-----|-----|-----|-----|-----|-----|-----|-----|-----|-----|-----|
| 1295 |     |     |     |     | 1300 |     |     |     |     | 1305 |     |     |     |     |

| Met | Gly | Cys | Asp | Leu | Asn | Ser | Cys | Ser | Met | Pro | Leu | Gly | Met | Glu |
|-----|-----|-----|-----|-----|-----|-----|-----|-----|-----|-----|-----|-----|-----|-----|
| 1310 |     |     |     |     | 1315 |     |     |     |     | 1320 |     |     |     |     |

| Ser | Lys | Ala | Ile | Ser | Asp | Ala | Gln | Ile | Thr | Ala | Ser | Ser | Tyr | Phe |
|-----|-----|-----|-----|-----|-----|-----|-----|-----|-----|-----|-----|-----|-----|-----|
| 1325 |     |     |     |     | 1330 |     |     |     |     | 1335 |     |     |     |     |

| Thr | Asn | Met | Phe | Ala | Thr | Trp | Ser | Pro | Ser | Lys | Ala | Arg | Leu | His |
|-----|-----|-----|-----|-----|-----|-----|-----|-----|-----|-----|-----|-----|-----|-----|
| 1340 |     |     |     |     | 1345 |     |     |     |     | 1350 |     |     |     |     |

| Leu | Gln | Gly | Arg | Ser | Asn | Ala | Trp | Arg | Pro | Gln | Val | Asn | Asn | Pro |
|-----|-----|-----|-----|-----|-----|-----|-----|-----|-----|-----|-----|-----|-----|-----|
| 1355 |     |     |     |     | 1360 |     |     |     |     | 1365 |     |     |     |     |

| Lys | Glu | Trp | Leu | Gln | Val | Asp | Phe | Gln | Lys | Thr | Met | Lys | Val | Thr |
|-----|-----|-----|-----|-----|-----|-----|-----|-----|-----|-----|-----|-----|-----|-----|
| 1370 |     |     |     |     | 1375 |     |     |     |     | 1380 |     |     |     |     |

| Gly | Val | Thr | Thr | Gln | Gly | Val | Lys | Ser | Leu | Leu | Thr | Ser | Met | Tyr |
|-----|-----|-----|-----|-----|-----|-----|-----|-----|-----|-----|-----|-----|-----|-----|
| 1385 |     |     |     |     | 1390 |     |     |     |     | 1395 |     |     |     |     |

| Val | Lys | Glu | Phe | Leu | Ile | Ser | Ser | Ser | Gln | Asp | Gly | His | Gln | Trp |
|-----|-----|-----|-----|-----|-----|-----|-----|-----|-----|-----|-----|-----|-----|-----|
| 1400 |     |     |     |     | 1405 |     |     |     |     | 1410 |     |     |     |     |

| Thr | Leu | Phe | Phe | Gln | Asn | Gly | Lys | Val | Lys | Val | Phe | Gln | Gly | Asn |
|-----|-----|-----|-----|-----|-----|-----|-----|-----|-----|-----|-----|-----|-----|-----|
| 1415 |     |     |     |     | 1420 |     |     |     |     | 1425 |     |     |     |     |

| Gln | Asp | Ser | Phe | Thr | Pro | Val | Val | Asn | Ser | Leu | Asp | Pro | Pro | Leu |
|-----|-----|-----|-----|-----|-----|-----|-----|-----|-----|-----|-----|-----|-----|-----|
| 1430 |     |     |     |     | 1435 |     |     |     |     | 1440 |     |     |     |     |

| Leu | Thr | Arg | Tyr | Leu | Arg | Ile | His | Pro | Gln | Ser | Trp | Val | His | Gln |
|-----|-----|-----|-----|-----|-----|-----|-----|-----|-----|-----|-----|-----|-----|-----|
| 1445 |     |     |     |     | 1450 |     |     |     |     | 1455 |     |     |     |     |

| Ile | Ala | Leu | Arg | Met | Glu | Val | Leu | Gly | Cys | Glu | Ala | Gln | Asp | Leu |
|-----|-----|-----|-----|-----|-----|-----|-----|-----|-----|-----|-----|-----|-----|-----|
| 1460 |     |     |     |     | 1465 |     |     |     |     | 1470 |     |     |     |     |

Tyr

<210> SEQ ID NO 33
<211> LENGTH: 873
<212> TYPE: DNA
<213> ORGANISM: Cytomegalovirus

<400> SEQUENCE: 33

```
ggcgcctcta gagttataac cggtaatcgg tataataagt aaccaatata tcgtatttag      60
ttataaccga taaccggtaa cgtatgcaac atagatatag tattatacat gtaaatataa     120
ccgagtacag gttatactgg cggtacaacc gtaactaata actgatcaat aattatcatt     180
agttaatgcc ccagtaatca gtatcgggt atatacctca aggcgcaatg tattgaatgc      240
catttaccgg gcggaccgac tggcgggttg ctggggcgg gtaactgcag ttattactgc      300
atacaagggt atcattgcgg ttatccctga aggtaactg cagttaccca cctcataaat      360
gccatttgac gggtgaaccg tcatgtagtt cacatagtat acggttcagg cggggataa      420
```

```
ctgcagttac tgccatttac cgggcggacc gtaatacggg tcatgtactg gaatgccctg    480
aaaggatgaa ccgtcatgta gatgcataat cagtagcgat aatggtacca ctacgccaaa    540
accgtcatgt ggttacccgc acctatcgcc aaactgagtg cccctaaagg ttcagaggtg    600
gggtaactgc agttaccctc aaacaaaacc gtggttttag ttgccctgaa aggttttaca    660
gcattattgg ggcggggcaa ctgcgtttac ccgccatccg cacatgccac cctccagata    720
tattcgtctc gagcaaatca cttggcagtc tagtgatctt cgaaataacg ccatcaaata    780
gtgtcaattt aacgattgcg tcagtcacga agactgtgtt gtcagagctt gaattcgacg    840
tcttcaacca gcactccgtg acccgtccga tcg                                 873

<210> SEQ ID NO 34
<211> LENGTH: 20
<212> TYPE: DNA
<213> ORGANISM: Artificial Sequence
<220> FEATURE:
<223> OTHER INFORMATION: Forward primer

<400> SEQUENCE: 34
ggatacgctg ctttaatgcc                                                20

<210> SEQ ID NO 35
<211> LENGTH: 20
<212> TYPE: DNA
<213> ORGANISM: Artificial Sequence
<220> FEATURE:
<223> OTHER INFORMATION: Reverse primer

<400> SEQUENCE: 35
acgccacgtt gcctgacaac                                                20
```

LENTIVIRAL VECTORS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 270077_402USPC_SEQUENCE_LISTING.txt. The text file is 192 KB, was created on Nov. 14, 2016, and is being submitted electronically via EFS-Web.

The present invention relates to lentiviral gene transfer vectors pseudotyped with hemagglutinin-neuraminidase (HN) and fusion (F) proteins from a respiratory paramyxovirus, comprising a promoter and a transgene; and methods of making the same. The present invention also relates to the use of said vectors in gene therapy, particularly for the treatment of respiratory tract diseases such as Cystic Fibrosis (CF).

BACKGROUND TO THE INVENTION

Lentiviruses belong to a genus of viruses of the Retroviridae family, and are characterised by a long incubation period. Lentiviruses can deliver a significant amount of viral RNA into the DNA of the host cell and have the unique ability among retroviruses of being able to infect non-dividing cells, so they are one of the most efficient methods of a gene delivery vector.

Lentiviral vectors, especially those derived from HIV-1, are widely studied and frequently used vectors. The evolution of the lentiviral vectors backbone and the ability of viruses to deliver recombinant DNA molecules (transgenes) into target cells have led to their use in many applications. Two possible applications of viral vectors include restoration of functional genes in genetic therapy and in vitro recombinant protein production.

Pseudotyping is the process of producing viruses or viral vectors in combination with foreign viral envelope proteins. As such, the foreign viral envelope proteins can be used to alter host tropism or an increased/decreased stability of the virus particles. For example, pseudotyping allows one to specify the character of the envelope proteins. A frequently used protein is the glycoprotein G of the Vesicular stomatitis virus (VSV), short VSV-G.

Efficient and controllable retroviral expression of a transgene is understood to require the presence of intron sequences. However, incorporation of such introns into retroviral vectors involves elaborate and time-consuming methods owing to the multi-step processes employed.

To date, viral gene transfer agents have not been useful for the treatment of diseases, without the transduction of stem cell populations, because of the host adaptive immune response, which prevents successful repeat administration.

Moreover, gene transfer to the airway epithelium has proven more difficult than originally anticipated. For example, the use of lentiviral pseudotypes that require disruption of epithelial integrity to transduce the airways, for example by the use of detergents such as lysophosphatidylcholine or ethylene glycol bis(2-aminoethyl ether)-N,N,N'N'-tetraacetic acid, has been linked to an increased risk of sepsis.

One example of a clinical setting which would benefit from gene transfer to the airway epithelium is treatment of Cystic Fibrosis (CF). CF is a fatal genetic disorder caused by mutations in the CF transmembrane conductance regulator (CFTR) gene, which acts as a chloride channel in airway epithelial cells. CF is characterised by recurrent chest infections, increased airway secretions, and eventually respiratory failure. In the UK, the current median age at death is ~25 years. For most genotypes, there are no treatments targeting the basic defect; current treatments for symptomatic relief require hours of self-administered therapy daily. Gene therapy, unlike small molecule drugs, is independent of CFTR mutational class and is thus applicable to all affected CF individuals. However, to date no viral vector has met the requirements for clinical use, and the same applies to other diseases, particularly many other respiratory tract diseases.

In this regard, at least three major problems have been encountered. Gene transfer efficiency is generally poor, at least in part because the respective receptors for many viral vectors appear to be predominantly localised to the basolateral surface of the airway epithelium. Second, penetration of the respiratory tract mucus layer is generally poor. Finally, the ability to administer viral vectors repeatedly, mandatory for the life-long treatment of a self-renewing epithelium, is limited.

Administration of the vectors for clinical application is another pertinent factor. Therefore, viral stability through use of clinically relevant devices (e.g. bronchoscope and nebuliser) must be maintained for treatment efficacy.

Another example of a potential target for gene therapy is α1-antitrypsin (A1AT) deficiency. A1AT deficiency is an inherited disorder that may cause lung disease and liver disease. Symptoms include shortness of breath/wheezing, reduced ability to exercise, weight loss, recurring respiratory infections, fatigue and rapid heartbeat upon standing. Affected individuals often develop emphysema. About 10-15% percent of patients with A1AT deficiency develop liver disease. Individuals with A1AT deficiency are also at risk of developing a hepatocellular carcinoma.

A1AT is a secreted protein, produced mainly in the liver and then trafficked to the lung, with smaller amounts also being produced in the lung itself. The main function of A1AT is to bind and neutralise neutrophil elastase. A1AT gene therapy is likely to be of therapeutic value in patients with A1AT deficiency, CF and chronic obstructive pulmonary disease (COPD), where increasing or introducing A1AT may improve lung function.

A1AT therapy is also potentially valuable for the treatment of non-respiratory/non-pulmonary diseases, such as type 1 and type 2 diabetes, acute myocardial infarction, rheumatoid arthritis, inflammatory bowel disease, transplant rejection, graft versus host (GvH) disease, multiple sclerosis and infections, particularly viral infections, due to the effect of A1AT deficiency on other tissues/organs, such as the liver and pancreas (see, for example, Lewis Mol. Med. 2012; 18:957-970, which is herein incorporated by reference).

A1AT deficiency is an attractive target disease for gene therapy because the therapeutic threshold levels are well defined. A comparison of A1AT levels in subjects with the risk of developing emphysema/COPD determined a protective threshold level of 11 µM in serum, with levels below 11 µM are used as threshold for initiating protein augmentation therapy where available. A1AT levels in airway lining fluid are only ~10% of serum level, because the lung epithelium constitutes a barrier and the therapeutic threshold in airway surface lining fluid is therefore considered to be 1.1 µM (see Ferraroti et al. Thorax. 2012 August; 67(8):669-74 and Abusriwil & Stockley 2006 Current Opinion in Pulmonary Medicine 12:125-131, each of which is herein incorporated by reference).

Six FDA-approved commercial formulations of A1AT protein isolated from pooled human blood are in clinical use in the US for the treatment of patients with severe A1AT deficiency (via weekly intravenous injections). Enzyme replacement therapy (ERT) is expensive ($100,000/year) and although biochemical efficacy for ERT protein augmentation therapy has been proven clinical efficacy has been more difficult to prove.

A1AT ERT is currently not accessible in all countries and currently not available in the UK. In addition, it is difficult to achieve sufficiently sustained tissue levels using current therapies, which may in part be responsible for the modest clinical efficacy observed so far.

Other attractive targets for gene therapy include cardiovascular diseases and blood disorders, particularly blood clotting deficiencies such as Haemophilia (A and B), von Willebrand disease and Factor VII deficiency.

Haemophilia, particularly Haemophilia A, is an attractive target for gene therapy. Haemophilia A is an inherited bleeding disorder caused by a deficiency or mutation of Factor VIII (FVIII). Its inheritance is sex-linked, with almost all patients being male. Bleeding is typically into the joints. Bleeding into the muscle, mucosal tissue and central nervous system (CNS) is uncommon but can occur. Disease severity is inversely proportional to the level of FVIII: less than 1% (<0.01 IU/ml) results in severe disease, with bleeding after minimal injury; between 1-5% (0.01 IU/ml-0.05 IU/ml) causes moderate disease, with bleeding after mild injury; and greater than 5% (>0.05 IU/ml) causes mild disease, with bleeding only after significant trauma or surgery.

There is accordingly a need for a gene therapy vector that is able to circumvent one or more of the problems described above.

SUMMARY OF THE INVENTION

The present inventors have developed a lentiviral vector, which has been pseudotyped with hemagglutinin-neuraminidase (HN) and fusion (F) proteins from a respiratory paramyxovirus, comprising a promoter and a transgene. Typically the backbone of the vector is from a simian immunodeficiency virus (SIV), such as SIV1 or African green monkey SIV (SIV-AGM). Preferably the backbone of a viral vector of the invention is from SIV-AGM. The HN and F proteins function, respectively, to attach to sialic acids and mediate cell fusion for vector entry to target cells. The present inventors have discovered that this specifically F/HN-pseudotyped lentiviral vector can efficiently transduce airway epithelium, resulting in transgene expression sustained for periods beyond the proposed lifespan of airway epithelial cells. Importantly, the present inventors have also found that re-administration does not result in a loss of efficacy. These features make the vectors of the present invention attractive candidates for treating diseases via their use in expressing therapeutic proteins: (i) within the cells of the respiratory tract; (ii) secreted into the lumen of the respiratory tract; and (iii) secreted into the circulatory system.

The present invention addresses one or more of the above needs by providing lentiviral vectors pseudotyped with hemagglutinin-neuraminidase (HN) and fusion (F) proteins from a respiratory paramyxovirus, comprising a promoter and a transgene. In one embodiment, the promoter is preferably a hybrid human CMV enhancer/EF1a (hCEF) promoter. The present invention also provides methods of manufacturing said vectors, compositions comprising said vectors, and uses thereof in therapy.

The vectors of the present invention enable higher and sustained gene expression through efficient gene transfer. The above-identified problems are addressed by the present invention which provides F/HN-pseudotyped lentiviral vectors which are capable of: (i) airway transduction without disruption of epithelial integrity; (ii) persistent gene expression; (iii) lack of chronic toxicity; and (iv) efficient repeat administration. Long term/persistent stable gene expression, preferably at a therapeutically-effective level, may be achieved using repeat doses of a vector of the present invention. Alternatively, a single dose may be used to achieve the desired long-term expression.

By contrast with known lentiviral vectors, the lentiviral vectors of the invention exhibit efficient airway cell uptake, enhanced transgene expression, and suffer no loss of efficacy upon repeated administration.

Thus, advantageously, the lentiviral vectors of the present invention can be used in gene therapy. By way of example, the efficient airway cell uptake properties of the vectors of the invention make them highly suitable for treating respiratory tract diseases. The lentiviral vectors of the invention can also be used in methods of gene therapy to promote secretion of therapeutic proteins. By way of further example, the invention provides secretion of therapeutic proteins into the lumen of the respiratory tract or the circulatory system. Thus, administration of a vector of the invention and its uptake by airway cells may enable the use of the lungs (or nose or airways) as a "factory" to produce a therapeutic protein that is then secreted and enters the general circulation at therapeutic levels, where it can travel to cells/tissues of interest to elicit a therapeutic effect. In contrast to intracellular or membrane proteins, the production of such secreted proteins does not rely on specific disease target cells being transduced, which is a significant advantage and achieves high levels of protein expression. Thus, other diseases which are not respiratory tract diseases, such as cardiovascular diseases and blood disorders, particularly blood clotting deficiencies, can also be treated by the vectors of the present invention.

As an example, Alpha-1 Antitrypsin (A1AT) is a secreted anti-protease that is produced mainly in the liver and then trafficked to the lung, with smaller amounts also being produced in the lung itself. The main function of A1AT is to bind and neutralise/inhibit neutrophil elastase. Gene therapy with A1AT according to the present invention is relevant to A1AT deficient patient, as well as in other lung diseases such as cystic fibrosis or chronic obstructive pulmonary disease (COPD), and offers the opportunity to overcome some of the problems encountered by enzyme replacement therapy.

The present inventors have previously demonstrated that there is a significant correlation between neutrophil elastase (NE) and A1AT in sputum samples from cystic fibrosis patients, showing that the body produces A1AT in response to NE challenge. The present inventors have also shown that there is a statistically significant correlation between NE and lung clearance index, a marker of small airways disease, implying that increased NE has a negative impact on lung function. As presented herein, the inventors have now surprisingly demonstrated that the lentiviral vectors of the invention can achieve high concentrations of A1AT and long term (at least 90 days) A1AT expression in vivo. Thus, gene therapy with A1AT may neutralise NE, improving the lung function of patients with cystic fibrosis and/or COPD (and having a therapeutic effect in other indications as described herein). Accordingly, the present invention relates to the use of a lentiviral vector as described herein for the administration of an A1AT transgene and gene therapy of conditions including, but not limited to, A1AT deficiency, cystic fibrosis and/or COPD. Administration of lentiviral A1AT directly to the nasal epithelium and/or lung may overcome some of the limitations currently faced by enzyme replacement therapy (A1AT isolated from human blood and administered intravenously every week), providing stable, long-lasting expression in the target tissue (lung/nasal epithelium), ease of administration and unlimited availability.

In some embodiments, transduction with a lentiviral vector of the invention leads to secretion of the recombinant protein into the lumen of the lung as well as into the circulation. One benefit of this is that the therapeutic protein reaches the interstitium. In the case of A1AT deficiency, this is advantageous because NE inhibition is also required at this site. A1AT gene therapy may therefore also be beneficial in other disease indications, non-limiting examples of which include type 1 and type 2 diabetes, acute myocardial infarction, ischemic heart disease, rheumatoid arthritis, inflammatory bowel disease, transplant rejection, graft versus host (GvH) disease, multiple sclerosis, liver disease, cirrhosis, vasculitides and infections, such as bacterial and/or viral infections.

A1AT has numerous other anti-inflammatory and tissue-protective effects, for example in pre-clinical models of diabetes, graft versus host disease and inflammatory bowel disease. The production of A1AT in the lung and/or nose following transduction according to the present invention may, therefore, be more widely applicable, including to these indications.

Other examples of diseases that may be treated with gene therapy of a secreted protein according to the present invention include cardiovascular diseases and blood disorders, particularly blood clotting deficiencies such as haemophilia (A and B), von Willebrand disease and Factor VII deficiency.

In some embodiments, Haemophilia A may be treated according to the present invention. Disease severity is inversely proportional to the level of FVIII, and an increase in FVIII of 2-5% (0.02-0.05 IU/ml) is enough to be therapeutically effective.

In some embodiments the nose is a preferred production site for a therapeutic protein using a gene therapy vector of the invention for at least one of the following reasons: (i) extracellular barriers such as inflammatory cells and sputum are less pronounced in the nose; (ii) ease of vector administration; (iii) smaller quantities of vector required; and (iv) ethical considerations. Thus, transduction of nasal epithelial cells with a lentiviral vector of the invention may result in efficient (high-level) and long-lasting expression of the therapeutic transgene of interest.

The vectors of the present invention enable long term gene expression, resulting in long term expression of a therapeutic protein. As described herein, the phrases "long term expression", "sustained expression" and "persistent expression" are used interchangeably. Long term expression according to the present invention means expression of a therapeutic gene and/or protein, preferably at therapeutic levels, for at least 45 days, at least 60 days, at least 90 days, at least 120 days, at least 180 days, at least 250 days, at least 360 days, at least 450 days, at least 730 days or more. Preferably long term expression means expression for at least 90 days, at least 120 days, at least 180 days, at least 250 days, at least 360 days, at least 450 days, at least 720 days or more, more preferably at least 360 days, at least 450 days, at least 720 days or more. This long term expression may be achieved by repeated doses or by a single dose.

Repeated doses may be administered twice-daily, daily, twice-weekly, weekly, monthly, every two months, every three months, every four months, every six months, yearly, every two years, or more. Dosing may be continued for as long as required, for example, for at least six months, at least one year, two years, three years, four years, five years, ten years, fifteen years, twenty years, or more, up to for the lifetime of the patient to be treated.

Lentiviral vectors, such as those of the invention, can integrate into the genome of transduced cells and lead to long-lasting expression, making them suitable for transduction of stem/progenitor cells. In the lung, several cell types with regenerative capacity have been identified as responsible for maintaining specific cell lineages in the conducting airways and alveoli. These include basal cells and submucosal gland duct cells in the upper airways, Clara cells and neuroendocrine cells in the bronchiolar airways, bronchioalveolar stem cells in the terminal bronchioles and type II pneumocytes in the alveoli. Therefore, and without being bound by theory, it is believed that the vectors of the present invention bring about long term gene expression of the transgene of interest by introducing the transgene into one or more long-lived airway epithelial cells or cell types, such as basal cells and submucosal gland duct cells in the upper airways, Clara cells and neuroendocrine cells in the bronchiolar airways, bronchioalveolar stem cells in the terminal bronchioles and type II pneumocytes in the alveoli.

Accordingly, the lentiviral vectors of the invention may transduce one or more cells or cell lines with regenerative potential within the lung (including the airways and respiratory tract) to achieve long term gene expression. In a preferred embodiment the lentiviral vector of the invention transduces basal cells, such as those in the upper airways/respiratory tract. Basal cells have a central role in processes of epithelial maintenance and repair following injury. In addition, basal cells are widely distributed along the human respiratory epithelium, with a relative distribution ranging from 30% (larger airways) to 6% (smaller airways).

The lentiviral vectors of the invention may be used to transduce isolated and expanded stem/progenitor cells ex vivo prior administration to a patient. Preferably, the lentiviral vectors of the invention are used to transduce cells within the lung (or airways/respiratory tract) in vivo.

The vectors of the present invention enable high levels of gene expression, resulting in high levels (preferably therapeutic levels) of expression of a therapeutic protein. Expression may be measured by any appropriate method (qualitative or quantitative, preferably quantitative), and concentrations given in any appropriate unit of measurement, for example ng/ml. A high level of expression according to the present invention may mean expression of a therapeutic gene and/or protein at a concentration of at least 10 ng/ml, at least 20 ng/ml, at least 30 ng/ml, at least 40 ng/ml, at least 50 ng/ml, at least 60 ng/ml, at least 70 ng/ml, at least 80 ng/ml, at least 90 ng/ml, at least 100 ng/ml, at least 200 ng/ml, at least 300 ng/ml, at least 400 ng/ml, at least 500 ng/ml, at least 600 ng/ml, at least 700 ng/ml, at least 800 ng/ml, at least 900 ng/ml, at least 1,000 ng/ml, at least 2,000 ng/ml, at least 3,000 ng/ml, at least 4,000 ng/ml, at least 5,000 ng/ml, at least 10,000, at least 15,000 ng/ml, at least 20,000 ng/ml or more. Therapeutic expression may be defined using these same values.

The lentiviral vectors of the present invention typically provide high expression levels of a transgene when administered to a patient. The terms high expression and therapeutic expression are used interchangeably herein.

A high level of expression according to the present invention may mean expression of a therapeutic gene and/or protein at a concentration of at least about 100 nM, at least about 200 nM, at least about 300 nM, at least about 400 nM, at least about 500 nM, at least about 600 nM, at least about 700 nM, at least about 800 nM, at least about 900 nM, at least about 1 µM, at least about 1.1 µM, at least about 1.2 µM, at least about 1.3 µM, at least about 1.4 µM, at least about 1.5 µM, at least about 2 µM, at least about 3 µM, at least about 4 µM, at least about 5 µM, at least about 6 µM, at least about 7 µM, at least about 8 µM, at least about 9 µM, at least about 10 µM, at least about 11 µM, at least about 12 µM, at least about 13 µM, at least about 14 µM, at least about 15 µM, at least about 20 µM, at least about 25 µM, at least about 30 µM, at least about 40 µM, at least about 50 µM, at least about 75 µM, or at least about 100 µM or more. Therapeutic expression may be defined using these same values.

A high level of expression according to the present invention may mean expression of a therapeutic gene (typically measured by mRNA expression) at least about 1%, at least about 2%, at least about 3%, at least about 4%, at least about 5%, at least about 6%, at least about 7%, at least about 8%, at least about 9%, at least about 10%, at least about 15%, at least about 20% or more compared with the expression level of the corresponding endogenous (defective) mRNA. Therapeutic expression may be defined using these same values. For example, a typical expression level of endogenous CFTR mRNA may be quantified in terms of the number of copies of the mRNA per lung cell, for example one copy of the endogenous CFTR mRNA per lung cell, two copies of the endogenous CFTR mRNA per lung cell, three copies of the endogenous CFTR mRNA per lung cell, four copies of the endogenous CFTR mRNA per lung cell, five copies of the endogenous CFTR mRNA per lung cell, or more, preferably two copies of the endogenous CFTR mRNA per lung cell. The expression of the therapeutic gene of the invention, such as a functional CFTR gene, may be quantified relative to the endogenous gene, such as the endogenous (dysfunctional) CFTR genes in terms of mRNA copies per cell or any other appropriate unit.

A high level of expression according to the present invention may mean expression of a therapeutic gene and/or protein at a concentration of at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, at least about 60%, at least about 70%, at least about 80%, at least about 90%, at least about 95%, at least about 96%, at least about 97%, at least about 98%, at least about 99%, or more compared with the wild type level of the therapeutic gene and/or protein, wherein the wild type level is the level in a normal individual without the disease. In some embodiments, wild type expression is given as 100%, with any improvement in gene expression measured relative to that. As a non-limiting example, if in a normal individual without the disease the expression of the functional gene is given as 100%, and in an individual with the disease, the expression of the functional gene is 0%, a therapeutic level of expression of the gene or protein may be at least about 0.5%, at least about 1%, at least about 2%, at least about 3%, at least about 4%, at least about 5%, at least about 6%, at least about 7%, at least about 8%, at least about 9%, at least about 10%, at least about 15%, at least about 20%, at least about 25%, at least about 30%, at least about 40%, at least about 50%, or more compared with the wild type level of the therapeutic gene and/or protein. As another non-limiting example, if in a normal individual without the disease the expression of the functional gene is given as 100%, and in an individual with the disease, the expression of the functional gene is 50%, a therapeutic level of expression of the gene or protein may be at least about 55%, at least about 60%, at least about 70%, at least about 80%, at least about 90%, at least 95%, at least about 96%, at least about 97%, at least about 98%, at least about 99%, or more compared with the wild type level of the therapeutic gene and/or protein.

For secreted proteins such as A1AT, typically the concentration in the lung or epithelial lining fluid (as measured using BAL) is approximately ten times that in serum. As a non-limiting example, if the concentration of secreted protein in the lung or epithelial lining fluid is in the region of 750 ng/ml, the serum concentration of the protein is in the region of 75 ng/ml.

Expression levels of a therapeutic gene and/or protein of the invention may be measured in the lung tissue, epithelial lining fluid and/or serum/plasma as appropriate. A high and/or therapeutic expression level may therefore refer to the concentration in the lung, epithelial lining fluid and/or serum/plasma.

As a non-limiting example, a therapeutic expression level of CFTR is typically 1-5% of the therapeutic CFTR mRNA compared with the expression level of the endogenous (defective) CFTR mRNA.

As another non-limiting example, a therapeutic expression level of A1AT is typically at least about 1 µM in the epithelial lining fluid, and/or at least about 0.1 µM in the serum. In a preferred embodiment, a therapeutic expression level of A1AT in the epithelial lining fluid is at least about 1.1 µM, and/or a therapeutic serum expression level of A1AT according to the present invention is at least about 11 µM. As another non-limiting example, a therapeutic expression level of A1AT in the epithelial lining fluid (ELF, i.e. the fluid lining the airways and airspaces in the lungs) is 70 µg/ml (compared with a "normal" target level of ATT (A1AT) in the ELF of 200 µg/ml).

As another non-limiting example, a therapeutic expression level of FVIII protein is typically at least about 1-3% or at least about 1-6% of the expression level in a normal individual who does not suffer from haemophilia.

The therapeutic gene included in the vector of the invention may be modified to facilitate expression. For example, the gene sequence may be in CpG-depleted and/or codon-optimised form to facilitate gene expression. Standard techniques for modifying the gene sequence in this way are known in the art.

The promoter included in the vector of the invention may be specifically selected and/or modified to further refine regulation of expression of the therapeutic gene. Again, suitable promoters and standard techniques for their modification are known in the art. As a non-limiting example, a number of suitable (CpG-free) promoters suitable for use in the present invention are described in Pringle et al. (J. Mol. Med. Berl. 2012, 90(12): 1487-96), which is herein incorporated by reference in its entirety.

The vector of the invention may be modified to allow shut down of gene expression. Standard techniques for modifying the vector in this way are known in the art. As a non-limiting example, Tet-responsive promoters are widely used.

The vectors of the present invention also demonstrate remarkable resistance to shear forces with only modest reduction in transduction ability when passaged through clinically-relevant delivery devices such as bronchoscopes, spray bottles and nebulisers.

In one embodiment, the invention provides F/HN lentiviral vectors comprising a promoter and a transgene, having no intron positioned between the promoter and the transgene. In one embodiment, the vector of the present invention is delivered to cells of the respiratory tract. In embodiment, the lentivirus is SIV. In one embodiment, the promoter is a hybrid human CMV enhancer/EF1a (hCEF) promoter. Typically said promoter of the invention lacks the intron corresponding to nucleotides 570-709 and the exon corresponding to nucleotides 728-733 of the hCEF promoter. A preferred example of an hCEF promoter sequence of the invention is provided by SEQ ID NO: 6. The promoter may be a CMV promoter. An example of a CMV promoter sequence is provided by SEQ ID NO: 17. Other promoters for transgene expression are known in the art and their suitability for the lentiviral vectors of the invention determined using routine techniques known in the art. Non-limiting examples of other promoters include UbC and UCOE. As described herein, the promoter may be modified to further regulate expression of the transgene of the invention.

In one embodiment, the transgene encodes a CFTR. An example of a CFTR cDNA is provided by SEQ ID NO: 7.

In one embodiment, the transgene encodes an A1AT. An example of an A1AT transgene is provided by SEQ ID NO: 15, or by the complementary sequence of SEQ ID NO: 26. SEQ ID NO: 15 is a codon-optimized CpG depleted A1AT transgene designed by the present inventors to enhance translation in human cells. Such optimisation has been shown to enhance gene expression by up to 15-fold. Thus, in one embodiment, the invention provides a polynucleotide comprising or consisting of the nucleotide sequence of SEQ ID NO: 15. Variants of same sequence (as defined herein) which possess the same technical effect of enhancing translation compared with the unmodified (wild-type) A1AT gene sequence are also encompassed by the present invention. The invention further provides a polypeptide encoded by said A1AT transgene, as exemplified by the polypeptide of SEQ ID NO: 27, plasmids (particularly vector genome plasmids as defined herein) and lentiviral vectors comprising said A1AT transgene. In a preferred embodiment, aspects of the invention relating to A1AT gene therapy according to the present invention use the A1AT transgene sequence of SEQ ID NO: 15.

In one embodiment, the transgene encodes a FVIII. Examples of a FVIII transgene are provided by SEQ ID NOs: 16 and 30, or by the respective complementary sequences of SEQ ID NO: 28 and 31.

Lentiviral vectors suitable for use in the present invention include Human immunodeficiency virus (HIV), Simian immunodeficiency virus (SIV), Feline immunodeficiency virus (FIV), Equine infectious anaemia virus (EIAV), and Visna/maedi virus. In one embodiment of the invention, an SIV vector is used, preferably SIV-AGM. In another embodiment, an HIV vector is used.

The lentiviral vectors of the present invention are pseudotyped with hemagglutinin-neuraminidase (HN) and fusion (F) proteins from a respiratory paramyxovirus. In one embodiment, the respiratory paramyxovirus is a Sendai virus (murine parainfluenza virus type 1).

In one embodiment of the invention, the lentiviral vector is integrase-competent (IC). In an alternative embodiment, the lentiviral vector is integrase-deficient (ID).

In another embodiment of the invention, the transgene of the invention is any one or more of DNAH5, DNAH11, DNAI1, and DNAI2, or other known related gene.

In one embodiment of the invention, the respiratory tract epithelium is targeted for delivery of the vector. In this embodiment, the transgene encodes Alpha-1 Antitrypsin (A1AT), Surfactant Protein B (SFTPB), or Granulocyte-Macrophage Colony-Stimulating Factor (GM-CSF). In another embodiment, the transgene encodes a monoclonal antibody (mAb) against an infectious agent. In one embodiment, transgene encodes anti-TNF alpha. In a further embodiment, the transgene encodes a therapeutic protein implicated in an inflammatory, immune or metabolic condition.

In one embodiment of the invention, the vector is delivered to the cells of the respiratory tract to allow production of proteins to be secreted into circulatory system. In this embodiment, the transgene encodes for Factor VII, Factor VIII, Factor IX, Factor X, Factor XI and/or von Willebrand's factor. Such a vector may be used in the treatment of diseases, particularly cardiovascular diseases and blood disorders, preferably blood clotting deficiencies such as Haemophilia. In another embodiment, the transgene encodes a monoclonal antibody (mAb) against an infectious agent. In one embodiment, the transgene encodes a protein implicated in an inflammatory, immune or metabolic condition, such as, lysosomal storage disease.

In accordance with the invention, there is provided an F/HN-SIV lentiviral vector comprising an hCEF promoter and a CFTR transgene, having no intron positioned between the promoter and the transgene. Similarly, there is no intron between the promoter and the transgene in the vector genome (pDNA1) plasmid (for example, pGM326 as described herein, illustrated in FIG. 1A and with the sequence of SEQ ID NO: 1).

The invention also provides an F/HN-SIV lentiviral vector comprising an hCEF promoter and an A1AT transgene, having no intron positioned between the promoter and the transgene. Such a lentiviral vector may be produced by the method described herein, using a plasmid carrying the A1AT transgene and a promoter. Similarly, there is no intron between the promoter and the A1AT transgene in the vector genome (pDNA1) plasmid. An exemplary sequence of such a plasmid is given in SEQ ID NO: 9 (F/HN-SIV-hCEF-soA1AT, illustrated in FIG. 15A).

The invention also provides an F/HN-SIV lentiviral vector comprising (i) an hCEF promoter or a CMV promoter; and (ii) an FVIII transgene; wherein no intron is positioned between the promoter and the transgene. Such a lentiviral vector may be produced by the method described herein, using a plasmid carrying the FVIII transgene and a promoter. Similarly, there is no intron between the promoter and the FVIII transgene in the vector genome (pDNA1) plasmid. Exemplary sequences of such plasmids are given in SEQ ID NO: 11 to 14 (illustrated in FIG. 22A to E).

The lentiviral vector as described above comprises a transgene. The transgene comprises a nucleic acid sequence encoding a gene product, e.g., a protein.

For example, in one embodiment, the nucleic acid sequence encoding a CFTR, A1AT or FVIII comprises (or consists of) a nucleic acid sequence having at least 90% (such as at least 90, 92, 94, 95, 96, 97, 98, 99 or 100%) sequence identity to the CFTR, A1AT or FVIII nucleic acid sequence respectively. In a further embodiment, the nucleic acid sequence encoding CFTR, A1AT or FVIII comprises (or consists of) a nucleic acid sequence having at least 95% (such as at least 95, 96, 97, 98, 99 or 100%) sequence identity to the CFTR, A1AT or FVIII nucleic acid sequence respectively. In one embodiment, the nucleic acid sequence encoding CFTR is provided by SEQ ID NO: 7, the nucleic acid sequence encoding A1AT is provided by SEQ ID NO: 15, or by the complementary sequence of SEQ ID NO: 26 and/or the nucleic acid sequence encoding FVIII is provided by SEQ ID NO: 16 and 30, or by the respective complementary sequences of SEQ ID NO: 28 and 31, or variants thereof.

The term "polypeptide" as used herein also encompasses variant sequences. Thus, the polypeptide encoded by the transgene of the invention may have at least 90% (such as at least 90, 92, 94, 95, 96, 97, 98, 99 or 100%) sequence identity to a functional CFTR, A1AT or FVIII polypeptide sequence respectively. In a further embodiment, the amino acid sequence of the CFTR, A1AT or FVIII transgene comprises (or consists of) an amino acid sequence having at least 95% (such as at least 95, 96, 97, 98, 99 or 100%) sequence identity to the functional CFTR, A1AT or FVIII polypeptide sequence respectively. In one embodiment, the amino acid sequence of the A1AT protein encoded by the transgene of the invention comprises (or consists of) the amino acid sequence of SEQ ID NO: 27, or variants thereof. Preferably said variant A1AT proteins of the invention have at least 90% (such as at least 90, 92, 94, 95, 96, 97, 98, 99 or 100%), more preferably at least 95% or more sequence identity with SEQ ID NO: 27.

In one embodiment, the nucleic acid sequence encoding CFTR, A1AT or FVIII comprises (or consists of) the CFTR, A1AT or FVII complementary DNA sequence respectively. In one embodiment, the CFTR, A1AT or FVIII transgene is a sequence-optimised CFTR, A1AT or FVIII (soCFTR2, soA1AT or FVIII). An example is provided by SEQ ID NOS: 7, 15 and 16 respectively. An exemplary complementary sequence-optimised A1AT sequence is given by SEQ ID NO: 26. Exemplary complementary sequence optimised FVIII sequences are given by SEQ ID NOs: 28 and 31.

In one embodiment of the invention, the F/HN vector transgene expression is driven by cytomegalovirus (CMV) promoter. In another embodiment, the vector transgene expression is driven by elongation factor 1a (EF1a) promoter. In a preferred embodiment, the vector transgene expression is driven by hybrid human CMV enhancer/EF1a (hCEF) promoter. In one embodiment, the hCEF promoter has all CG dinucleotides replaced with any one of AG, TG or GT. Thus, in one embodiment, the hCEF promoter is CpG-free.

In one embodiment, the lentiviral vector may be produced using the F/HN-SIV-hCEF-soCFTR2-IC plasmid. In this embodiment, CFTR is expressed under control of the hCEF promoter. This lentiviral vector may be described as comprising F/HN-SIV-hCEF-soCFTR2-IC, as it comprises the SIV F/HN elements, as well as an integrase competent expression cassette comprising CFTR under the control of the hCEF promoter. This lentiviral vector of the invention is capable of producing long-lasting, repeatable, high-level expression in airway cells without inducing an undue immune response. Consequently, the invention provides an efficient means of in vivo gene therapy, for example, CFTR gene transfer into the CF lung for the treatment of CF lung disease.

In a preferred embodiment, the lentiviral vector may be produced using the F/HN-SIV-hCEF-soA1AT plasmid. In this embodiment, A1AT is expressed under control of the hCEF promoter. This lentiviral vector may be described as comprising F/HN-SIV-hCEF-soA1AT, as it comprises the SIV F/HN elements, as well as an expression cassette comprising A1AT under the control of the hCEF promoter. This lentiviral vector of the invention is capable of producing long-lasting, repeatable, high-level expression in airway cells without inducing an undue immune response. Consequently, the invention provides an efficient means of in vivo gene therapy, for example, A1AT gene transfer into a patient's lung or nose for the production of A1AT which is then secreted into the circulatory system (as described herein). Thus, this vector and other vectors of the invention comprising the A1AT transgene may be used in the treatment of A1AT deficiency, or other indications as described herein.

In another preferred embodiment, the lentiviral vectors may be produced using the F/HN-SIV-CMV-HFVIII-V3, F/HN-SIV-hCEF-HFVIII-V3, F/HN-Sly-CMV-HFVIII-N6-co and/or F/HN-SIV-hCEF-HFVIII-N6-co plasmids. HFVIII refers to human FVIII. In this embodiment, FVIII is expressed under control of the hCEF or CMV promoter. These lentiviral vectors may be described as comprising F/HN-SIV-CMV-HFVIII-V3, F/HN-SIV-hCEF-HFVIII-V3, F/HN-SIV-CMV-HFVIII-N6-co and F/HN-Sly-hCEF-HFVIII-N6-co respectively, as they comprise the SIV F/HN elements, as well as an expression cassette comprising FVIII under the control of the hCEF/CMV promoter. Viral vector products produced using the F/HN-SIV-CMV-HFVIII-V3, F/HN-SIV-hCEF-HFVIII-V3, F/HN-SIV-CMV-HFVIII-N6-co and/or F/HN-SIV-hCEF-HFVIII-N6-co plasmids are also known as vGM126, vGM127, vGM142 and vGM129 (see FIG. 22). These lentiviral vectors of the invention are capable of producing long-lasting, repeatable, high-level expression in airway cells without inducing an undue immune response. Consequently, the invention provides an efficient means of in vivo gene therapy, for example, FVIII gene transfer into a patient's lung or nose for the production of FVIII which is then secreted into the circulatory system (as described herein). Thus, these vectors and other vectors of the invention comprising the FVIII transgene may be used in the treatment of haemophilia, or other indications as described herein.

The lentiviral vectors of the invention do not contain an intron between the promoter and the transgene. Similarly, the vector genome plasmids of the invention (used to generate said lentiviral vectors as described herein) also do not contain an intron between the promoter and the transgene. The invention therefore provides, in one embodiment, no intron between the hCEF promoter and the coding sequences to be expressed. In one preferred embodiment, the coding sequence to be expressed is a CFTR, A1AT and/or FVIII nucleic acid sequence.

In one embodiment, the vectors of the invention comprise central polypurine tract (cPPT) and the Woodchuck hepatitis virus posttranscriptional regulatory elements (WPRE). In one embodiment, the WPRE sequence is provided by SEQ ID NO: 8.

In one embodiment the vector of the invention is used for gene therapy. In one embodiment the disease to be treated is CF. In another embodiment of the invention, the disease to be treated is Primary Ciliary Dyskinesia (PCD). In one embodiment, the vector is used to treat acute lung injury. In one embodiment of the invention, the disease to be treated is Surfactant Protein B (SP-B) deficiency, Alpha 1-antitrypsin Deficiency (A1AD), Pulmonary Alveolar Proteinosis (PAP), Chronic obstructive pulmonary disease (COPD). In another embodiment, the disease is an inflammatory, immune or metabolic condition.

The disease to be treated may be a cardiovascular disease or blood disorder, particularly a blood clotting deficiency. Thus, in some embodiments, the disease to be treated is Haemophilia A, Haemophilia B, or Haemophilia C, Factor VII deficiency and/or von Willebrand disease. In yet another embodiment, the disease to be treated is an inflammatory disease, infectious disease or metabolic condition, such as, lysosomal storage disease.

Non-limiting examples of diseases which may be treated using A1AT gene therapy according to the present invention include type 1 and type 2 diabetes, acute myocardial infarction, ischemic heart disease, rheumatoid arthritis, inflammatory bowel disease, transplant rejection, graft versus host (GvH) disease, multiple sclerosis, liver disease, cirrhosis, vasculitides and infections, such as bacterial and/or viral infections.

In one aspect of the invention, the vector can effectively treat a disease by providing a transgene for the correction of the disease. For example, inserting a functional copy of the CFTR gene to ameliorate or prevent lung disease in CF patients, independent of the underlying mutation.

In another embodiment of the invention, a lentiviral production method is provided. In this embodiment, the method of the invention is a scalable GMP-compatible method. Thus, the method of the invention allows the generation of high titre purified F/HN vectors.

The method of the invention comprises the following steps:
(a) growing cells in suspension;
(b) transfecting the cells with one or more plasmids;
(c) adding a nuclease;
(d) harvesting the lentivirus;
(e) adding trypsin; and
(f) purification.

In one embodiment of the method of the invention, the one or more plasmids provide the vector genome, the Gag-Pol, Rev, F and HN. Thus, there can be five plasmids for each of the vector genome, the Gag-Pol, Rev, F and HN, respectively. In the preferred 5 plasmid method of the invention, the vector genome plasmid encodes all the genetic material that is packaged into final lentiviral vector, including the transgene. Typically only a portion of the genetic material found in the vector genome plasmid ends up in the virus. The vector genome plasmid may be designated herein as "pDNA1". The other four plasmids are manufacturing plasmids encoding the Gag-Pol, Rev, F and HN proteins. These plasmids may be designated "pDNA2a", "pDNA2b", "pDNA3a" and "pDNA3b" respectively.

In one embodiment of the invention, the lentivirus is SIV, such as SIV1, preferably SIV-AGM. In one embodiment, the F and HN proteins are derived from a Paramyxovirus, such as Sendai virus. In one embodiment, the vector genome plasmid (pDNA1) comprises the transgene and the transgene promoter.

In a specific embodiment relating to CFTR, the five plasmids are characterised by FIGS. 1A-1E, thus pDNA1 is the pGM326 plasmid of FIG. 1A, pDNA2a is the pGM299 plasmid of FIG. 1B, pDNA2b is the pGM299 plasmid of FIG. 1C, pDNA3a is the pGM301 plasmid of FIG. 1D and pDNA3b is the pGM303 plasmid of FIG. 1E. In this embodiment, the final CFTR containing lentiviral vector may be referred to as vGM058 (see the Examples). The vGM058 vector is a preferred embodiment of the invention.

In an embodiment relating to A1AT, the five plasmids may be characterised by FIG. 15A (thus plasmid pDNA1 may be pGM407) and 1B-E (as above for the specific CFTR embodiment).

In an embodiment relating to FVIII, the five plasmids may be characterised by FIGS. 22C-F (thus plasmid pDNA1 may be pGM411, pGM412, pGM413 or pGM414) and 1B-E.

In these embodiments of the invention, the plasmid as defined in FIG. 1A is represented by SEQ ID NO: 1; the plasmid as defined in FIG. 1B is represented by SEQ ID NO: 2; the plasmid as defined in FIG. 10 is represented by SEQ ID NO: 3; the plasmid as defined in FIG. 1D is represented by SEQ ID NO: 4; the plasmid as defined in FIG. 1E is represented by SEQ ID NO: 5; the plasmid as defined in FIG. 15A is represented by SEQ ID NO: 9 and the F/HN-SIV-CMV-HFVIII-V3, F/HN-SIV-hCEF-HFVIII-V3, F/HN-SIV-CMV-HFVIII-N6-co and/or F/HN-SIV-hCEF-HFVIII-N6-co plasmids as defined in FIG. 22B are represented by SEQ ID NOs: 11 to 14 respectively.

In the 5 plasmid method of the invention all five plasmids contribute to the formation of the final lentiviral vector. During manufacture of the lentiviral vector, the vector genome plasmid (pDNA1) provides the enhancer/promoter, Psi, RRE, cPPT, mWPRE, SIN LTR, SV40 polyA (see FIG. 1A), which are important for viral manufacture. Using pGM326 as a non-limiting example of a pDNA1, the CMV enhancer/promoter, SV40 polyA, colE1 Ori and Kan® are involved in manufacture of the lentiviral vector of the invention (e.g. vGM058), but are not found in the final viral vector. The RRE, cPPT (central polypurine tract), hCEF, soCFTR2 (transgene) and mWPRE from pGM326 are found in the final viral vector. SIN LTR (long terminal repeats, SIN/IN self inactivating) and Psi (packaging signal) may be found in the final viral vector.

For other lentiviral vectors of the invention, corresponding elements from the other vector genome plasmids (pDNA1) are required for manufacture (but not found in the final vector), or are present in the final viral vector.

The F and HN proteins from pDNA3a and pDNA3b (preferably Sendai F and HN proteins) are important for infection of target cells with the final lentiviral vector, i.e. for entry of a patients epithelial cells (typically lung or nasal cells as described herein). The products of the pDNA2a and pDNA2b plasmids are important for virus transduction, i.e. for inserting the lentiviral DNA into the host's genome. The promoter, regulatory elements (such as WPRE) and transgene are important for transgene expression within the target cell(s).

In one embodiment, steps (a)-(f) are carried out sequentially. In one embodiment, the cells are HEK293 cells or 293T/17 cells. In one embodiment, the cells are grown in animal-component free (serum-free) media. In one embodiment, the transfection is carried out by the use of PEIPro™. In one embodiment, the nuclease is an endonuclease, for example, Benzonase®. In one embodiment, the trypsin activity is provided by an animal origin free, recombinant enzyme such as TrypLE Select™.

In one embodiment of the invention, the addition of the nuclease is at the pre-harvest stage. In an alternative embodiment, the addition of the nuclease is at the post-harvest stage. In another embodiment, the addition of trypsin is at the pre-harvest stage. In another embodiment, the addition of the trypsin is at the post-harvest stage.

In one embodiment, the purification step comprises a chromatography step. In this embodiment, mixed-mode size exclusion chromatography (SEC) is used. In one embodiment, anion exchange chromatography is used. In this embodiment, no salt gradient is used for the elution step.

In one embodiment, this method is used to produce the lentiviral vectors of the invention. In this embodiment, the vector of the invention comprises the CFTR, A1AT and/or FVIII gene. In an alternative embodiment, the vector of the invention comprises any of the above-mentioned genes, or the genes encoding the above-mentioned proteins.

In one embodiment of the method of the invention, any combination of one or more of the specific plasmid constructs provided by FIGS. 1A-1E, FIG. 15A and/or FIG. 22C-22F is used to provide a vector of the invention.

The invention further provides a method of treating a disease, the method comprising administering a lentiviral vector of the invention to a subject. In this embodiment, the invention provides a lentiviral vector of the invention for use in treatment of a lung disease. In one embodiment, disease is a chronic disease. In a specific embodiment, a method of treating CF is provided. In other embodiments, a method of treating Primary Ciliary Dyskinesia (PCD), Surfactant Protein B (SP-B) deficiency, Alpha 1-antitrypsin Deficiency (A1AD), Pulmonary Alveolar Proteinosis (PAP), Chronic obstructive pulmonary disease (COPD) is provided. In another embodiment, the disease is an inflammatory, immune or metabolic condition.

In another embodiment, the disease may be a cardiovascular disease or blood disorder, particularly a blood clotting deficiency, such as Haemophilia A, Haemophilia B, Haemophilia C, Factor VII deficiency and/or von Willebrand disease, an inflammatory disease, infectious disease or metabolic condition, such as, lysosomal storage disease.

The disease may be type 1 and type 2 diabetes, acute myocardial infarction, ischemic heart disease, rheumatoid arthritis, inflammatory bowel disease, transplant rejection, graft versus host (GvH) disease, multiple sclerosis, liver disease, cirrhosis, vasculitides and infections, such as bacterial and/or viral infections.

The lentiviral vectors of the invention may be administered in any dosage appropriate for achieving the desired therapeutic effect. Appropriate dosages may be determined by a clinician or other medical practitioner using standard techniques and within the normal course of their work. Non-limiting examples of suitable dosages include $1\times10^8$ transduction units (TU), $1\times10^9$ TU, $1\times10^{10}$ TU, $1\times10^{11}$ TU or more.

The invention also provides compositions comprising the lentiviral vectors described above, and a pharmaceutically-acceptable carrier. Non-limiting examples of pharmaceutically acceptable carriers include water, saline, and phosphate-buffered saline. In some embodiments, however, the composition is in lyophilized form, in which case it may include a stabilizer, such as bovine serum albumin (BSA). In some embodiments, it may be desirable to formulate the composition with a preservative, such as thiomersal or sodium azide, to facilitate long-term storage.

The vectors of the invention may be administered by any appropriate route. It may be desired to direct the compositions of the present invention (as described above) to the respiratory system of a subject. Efficient transmission of a therapeutic/prophylactic composition or medicament to the site of infection in the respiratory tract may be achieved by oral or intra-nasal administration, for example, as aerosols (e.g. nasal sprays), or by catheters. Typically the lentiviral vectors of the invention are stable in clinically relevant nebulisers, catheters and aerosols, etc.

Formulations for intra-nasal administration may be in the form of nasal droplets or a nasal spray. An intra-nasal formulation may comprise droplets having approximate diameters in the range of 100-5000 µm, such as 500-4000 µm, 1000-3000 µm or 100-1000 µm. Alternatively, in terms of volume, the droplets may be in the range of about 0.001-100 µl, such as 0.1-50 µl or 1.0-25 µl, or such as 0.001-1 µl.

The aerosol formulation may take the form of a powder, suspension or solution. The size of aerosol particles is relevant to the delivery capability of an aerosol. Smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli. In the case of aerosol delivery of the medicament, the particles may have diameters in the approximate range of 0.1-50 µm, preferably 1-25 µm, more preferably 1-5 µm.

Aerosol particles may be for delivery using a nebulizer (e.g. via the mouth) or nasal spray. An aerosol formulation may optionally contain a propellant and/or surfactant.

As used herein, the terms "nucleic acid sequence" and "polynucleotide" are used interchangeably and do not imply any length restriction. As used herein, the terms "nucleic acid" and "nucleotide" are used interchangeably. The terms "nucleic acid sequence" and "polynucleotide" embrace DNA (including cDNA) and RNA sequences. The terms "transgene" and "gene" are also used interchangeably and both terms encompass fragments or variants thereof encoding the target protein.

The transgenes of the present invention include nucleic acid sequences that have been removed from their naturally occurring environment, recombinant or cloned DNA isolates, and chemically synthesized analogues or analogues biologically synthesized by heterologous systems.

The polynucleotides of the present invention may be prepared by any means known in the art. For example, large amounts of the polynucleotides may be produced by replication in a suitable host cell. The natural or synthetic DNA fragments coding for a desired fragment will be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured insect, mammalian, plant or other eukaryotic cell lines.

The polynucleotides of the present invention may also be produced by chemical synthesis, e.g. by the phosphoramidite method or the tri-ester method, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

When applied to a nucleic acid sequence, the term "isolated" in the context of the present invention denotes that the polynucleotide sequence has been removed from its natural genetic milieu and is thus free of other extraneous or unwanted coding sequences (but may include naturally occurring 5' and 3' untranslated regions such as promoters and terminators), and is in a form suitable for use within genetically engineered protein production systems. Such isolated molecules are those that are separated from their natural environment.

In view of the degeneracy of the genetic code, considerable sequence variation is possible among the polynucleotides of the present invention. Degenerate codons encompassing all possible codons for a given amino acid are set forth below:

| Amino Acid | Codons | Degenerate Codon |
|---|---|---|
| Cys | TGC TGT | TGY |
| Ser | AGC ACT TCA TCC TCG TCT | WSN |
| Thr | ACA ACC ACG ACT | ACN |
| Pro | CCA CCC CCG CCT | CCN |
| Ala | GCA GCC GCG GCT | GCN |
| Gly | GGA GGC GGG GGT | GGN |
| Asn | AAC AAT | AAY |
| Asp | GAC GAT | GAY |
| Glu | GAA GAG | GAR |
| Gln | CAA CAG | CAR |
| His | CAC CAT | CAY |
| Arg | AGA AGG CGA CGC CGG CGT | MGN |
| Lys | AAA AAG | AAR |
| Met | ATG | ATG |
| Ile | ATA ATC ATT | ATH |
| Leu | CTA CTC CTG CTT TTA TTG | YTN |
| Val | GTA GTC GTG GTT | GTN |
| Phe | TTC TTT | TTY |
| Tyr | TAC TAT | TAY |
| Trp | TGG | TGG |
| Ter | TAA TAG TGA | TRR |
| Asn/ Asp | | RAY |
| Glu/ Gln | | SAR |
| Any | | NNN |

One of ordinary skill in the art will appreciate that flexibility exists when determining a degenerate codon, representative of all possible codons encoding each amino acid. For example, some polynucleotides encompassed by the degenerate sequence may encode variant amino acid sequences, but one of ordinary skill in the art can easily identify such variant sequences by reference to the amino acid sequences of the present invention.

A "variant" nucleic acid sequence has substantial homology or substantial similarity to a reference nucleic acid sequence (or a fragment thereof). A nucleic acid sequence or fragment thereof is "substantially homologous" (or "substantially identical") to a reference sequence if, when optimally aligned (with appropriate nucleotide insertions or deletions) with the other nucleic acid (or its complementary strand), there is nucleotide sequence identity in at least about 70%, 75%, 80%, 82, 84, 86, 88, 90, 92, 94, 96, 98 or 99% of the nucleotide bases. Methods for homology determination of nucleic acid sequences are known in the art.

Alternatively, a "variant" nucleic acid sequence is substantially homologous with (or substantially identical to) a reference sequence (or a fragment thereof) if the "variant" and the reference sequence they are capable of hybridizing under stringent (e.g. highly stringent) hybridization conditions. Nucleic acid sequence hybridization will be affected by such conditions as salt concentration (e.g. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. The combination of parameters is much more important than any single parameter.

Methods of determining nucleic acid percentage sequence identity are known in the art. By way of example, when assessing nucleic acid sequence identity, a sequence having a defined number of contiguous nucleotides may be aligned with a nucleic acid sequence (having the same number of contiguous nucleotides) from the corresponding portion of a nucleic acid sequence of the present invention. Tools known in the art for determining nucleic acid percentage sequence identity include Nucleotide BLAST.

One of ordinary skill in the art appreciates that different species exhibit "preferential codon usage". As used herein, the term "preferential codon usage" refers to codons that are most frequently used in cells of a certain species, thus favouring one or a few representatives of the possible codons encoding each amino acid. For example, the amino acid threonine (Thr) may be encoded by ACA, ACC, ACG, or ACT, but in mammalian host cells ACC is the most commonly used codon; in other species, different codons may be preferential. Preferential codons for a particular host cell species can be introduced into the polynucleotides of the present invention by a variety of methods known in the art. Introduction of preferential codon sequences into recombinant DNA can, for example, enhance production of the protein by making protein translation more efficient within a particular cell type or species.

Thus, in one embodiment of the invention, the nucleic acid sequence is codon optimized for expression in a host cell.

A "fragment" of a polynucleotide of interest comprises a series of consecutive nucleotides from the sequence of said full-length polynucleotide. By way of example, a "fragment" of a polynucleotide of interest may comprise (or consist of) at least 30 consecutive nucleotides from the sequence of said polynucleotide (e.g. at least 35, 50, 75, 100, 150, 200, 250, 300, 350, 400, 450, 500, 550, 600, 650, 700, 750, 800 850, 900, 950 or 1000 consecutive nucleic acid residues of said polynucleotide). A fragment may include at least one antigenic determinant and/or may encode at least one antigenic epitope of the corresponding polypeptide of interest. Typically a fragment as defined herein retains the same function as the full-length polynucleotide or polypeptide.

DESCRIPTION OF THE DRAWINGS

The present invention will now be described by way of example only with reference to the accompanying drawings, in which:

FIG. 9A shows that transduction of human nasal brushing cells (MOI 250) and human and sheep lung slices cultured ex vivo (1E7 TU/slice) with F/HN-SIV-CMV-Lux results in substantial luciferase transgene expression 24-48 hours post-transduction. FIGS. 9B and 9C display transduction of $(1\times10^5)$ primary human CF lung cells cultured at the air-liquid interface (CF hALIs) with (3E7 TU) F/HN-SIV-soCFTR2 vectors containing CMV- and hCEF transgene promoters. (B) Vector copy number (copies of pro-viral DNA per copy of endogenous CFTR DNA) at 6-8 days post-transduction. (C) CFTR mRNA expression level (% VE: copies of CFTR mRNA per copy of endogenous CFTR mRNA×100) at 6-8 days post-transduction. The horizontal line in (C) represents target expression level of 5% VE—thought to represent the therapeutic threshold. Following in vivo delivery of F/HN-SIV-EGFPLux vectors containing CMV-, EF1aS and hCEF promoters in integrase defective (ID) or integrase competent form (IC or no label) airway cells transgene expression was determined in the nasal (D) and lung (E) murine epithelium (n=6-10/group). Time course of luciferase transgene expression was monitored by repeated in vivo bioluminescence imaging and as normalised to delivered dose. FIG. 9F shows representative bioluminescence images following in vivo murine transduction at day 14 post transduction. FIG. 9G portrays representative bioluminescence images following in vitro transduction of non-CF hALI at day 5-6 post transduction. FIG. 9H represents EGFP expression at 14 days post transduction in the murine nasal epithelium following delivery of 1.6E8 TU of F/HN-SIV-hCEF-EGFPLux (vGM020). EGFP visualised by immunohistochemistry, nuclei visualised by DAPI. FIG. 9I shows time-course of luciferase transgene expression in non-CF ALIs was monitored by repeated bioluminescence imaging and was normalised to delivered dose.

FIG. 10B is a diagrammatic representation of the sheep lung (trachea centre/top). Green circle represents region in (A). In (B), line indicates passage of bronchoscope to deliver 3×100 μL aliquots of 2.2E9 TU/mL (6.6E8 TU total) F/HN SIV CMV-EGFPLux to n=3 individual sheep (animal codes T121, T156 & T251). At seven days post-delivery, 5-6 tissue sample blocks were taken at post-mortem at ~1 cm intervals from the site of instillation. Blocks were divided into 2-3 approximately equivalent samples and analysed for transgene expression by (C) luciferase assays normalised to protein content; and (D) quantitative RT-PCR normalised to endogenous CFTR mRNA levels. Horizontal line in (C) represents highest luciferase activity noted in any sample treated with a non-viral gene transfer vector, and (D) target expression level of 5% VE—thought to represent the therapeutic threshold.

FIGS. 12A-F provide a comparison of IS profiles from F/HN-SIV transduced mouse lung and VSV-G-HIV vector transduced mouse retina (Bartholomae et al, Mol Ther (2011) 19:703-710). IS profiles for (A,C,E) were derived from deep sequencing of lung DNA from two mice transduced with F/HN-SIV, and for (B,D,F) from retinal VSV-G-HIV IS sequences (Schmidt laboratory). (A,B) Aggregated IS sites (lung, 2862; retina, 262) plotted on karyograms generated via the Ensembl genome browser. (C,D) IS distances to transcription start sites (TSS). Numbers of IS in each distance bin are shown above bars. The sum exceeds the total number of IS analysed because a typical IS is located near to several TSS. Graphs were generated by use of the UCSC genome browser and the GREAT genome analyser (great.stanford.edu). (E,F) Quick-Map (www.gtsg.org) comparison between random (diamond) and observed (square) insertion frequencies per chromosome. (G) Survival of mice treated with progenitor F/HN-SIV vector (virus vector manufactured in accordance with known method using adherent cells: black line, 24 months of data) and current generation vector (GTC: dark grey line, 8 months of data) compared with buffer treated mice (light grey line, 24 months of data). Data aggregated from various experiments involving mice treated with buffer or ~1E7 TU virus by nasal sniffing.

FIG. 20A: lung homogenate; FIG. 20B: BAL; and FIG. 20C: serum.

EXAMPLES

Figures 1, 1A:
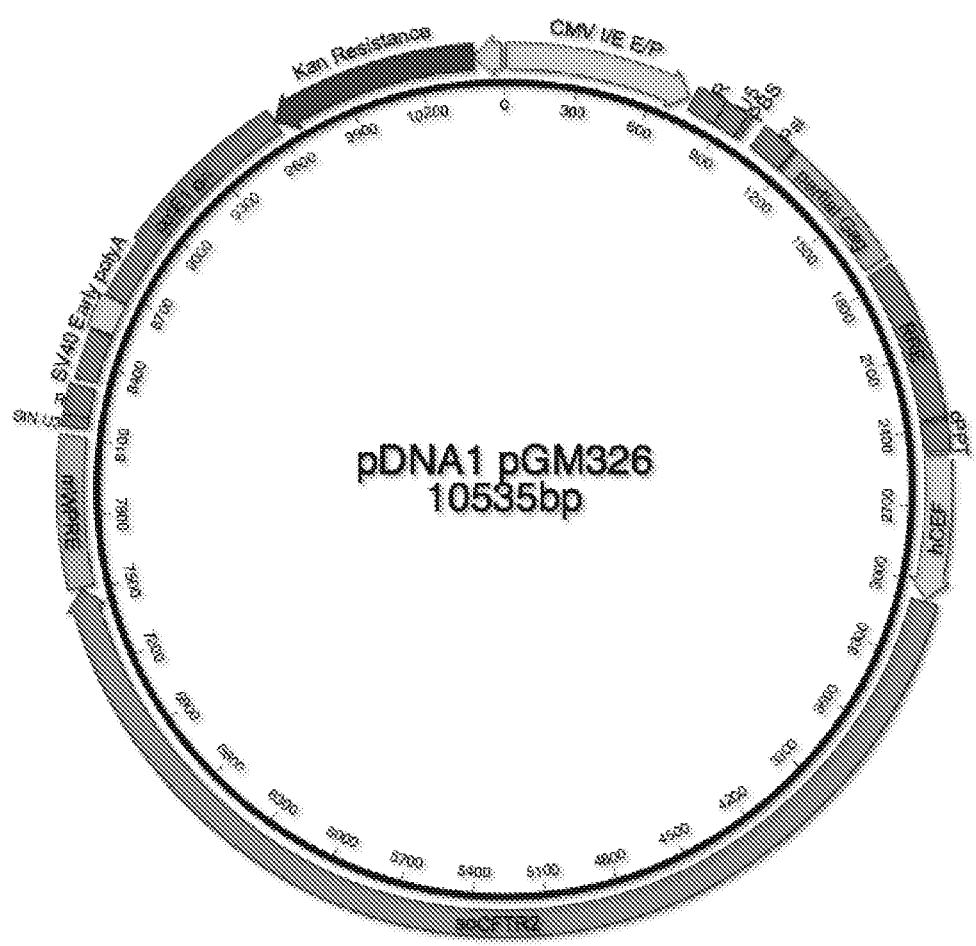
FIG. 1 shows exemplary plasmids utilised in the invention.
FIGS. 1A-1E show schematic drawings of plasmids used for production of the vectors of the invention. In one embodiment of the invention, FIG. 1A provides a tool of the invention.

The invention is now described with reference to the Examples below. These are not limiting on the scope of the invention, and a person skilled in the art would appreciate that suitable equivalents could be used within the scope of the present invention. Thus, the Examples may be considered component parts of the invention, and the individual

Example 1: Cell Culture

HEK293T, Freestyle 293F (Life Technologies, Paisley, UK) and 293T/17 cells (CRL-11268; ATCC, Manassas, Va.) were maintained in Dulbecco's minimal Eagle's medium (Invitrogen, Carlsbad, Calif.) containing 10% fetal bovine serum and supplemented with penicillin (100 U/ml) and streptomycin (100 µg/ml) or Freestyle™ 293 Expression Medium (Life Technologies).

Example 2: Plasmid Construction pCAGGS-Fct4 and pCAGGS-SIVct+HN were constructed as follows:

(i) Plasmid SIVct/HN contains the gene encoding the cytoplasmic tail of SIVagm TMP (reversed) fused to the ectodomain and transmembrane regions of SeV HN protein. Three oligonucleotide pairs were synthesized: pair 1, 5'-TCGAGATGTGGTCTGAGTTAAAAATCAGGAGCAAC-GACGGAGGTGAAGGACCAGACGCCAACGACCC-3' (SEQ ID NO: 18) and 5'-CCGGGGGTCGTTGGCGTCTG-GTCCTTCACCTCCGTCGTTGCTCCTGATTTT-TAACTCAGACCACATC-3' (SEQ ID NO: 19); pair 2, 5'-CCGGGGAAAGGGGGTGCAACACATCCATATCCA-GCCATCTCTACCTGTTTATGGACAGA-3' (SEQ ID NO: 20) and 5'-ACCCTCTGTCCATAAACAGGTAGAGATG-GCTGGATATGGATGTGTTGCACCCCTTTCC-3' (SEQ ID NO: 21); and pair 3, 5'-GGGTTAGGTGGTTGCTGAT-TCTCTCATTCACCCAGTGGG-3' (SEQ ID NO: 22) and 5'-GATCCCCACTGGGTGAATGAGAGAATCAGCAAC-CACCTA-3' (SEQ ID NO: 23).

These oligonucleotide pairs were annealed and cloned into the XhoI and BamHI sites of pBluescript KS+ (Stratagene) to yield pKS+SIVct. pCAGGS-SIVct/HN was constructed by cloning the 160-bp XhoI-DraIII fragment from pKS+SIVct and a 1.5-kbp DraIII-Bsu36I fragment from pCAGGS-HN, which carries the wild-type HN gene (HNwt), in the XhoI site of pCAGGS vector, into the XhoI and Bsu36I sites of pCAGGS. This plasmid was constructed so that the cytoplasmic tail of the HN protein was replaced with the cytoplasmic tail of SIVagm TMP.

For construction of pCAGGS-SIVct+HN, the genes encoding the cytoplasmic tail of SIVagm TMP and the N terminus of HN protein were first amplified by PCR from pCAGGS-SIVct/HN with the primer pair 5'-GAGACTC-GAGATGTGGTCTGAGTTAAAAATCAGG-3' (SEQ ID NO: 24) and 5'-AGAGGTAGACCAGTACGAGT-CACGTTTGCCCCTATCACCATCCCTAACCCTCTGT-CATAAAC-3' (SEQ ID NO: 25). The resulting PCR fragment was cloned into the XhoI and AccI sites of pKS+SIVct to generate pKS+SIVct-H. Then a XhoI-DraIII fragment from pKS+SIVct-H and a DraIII-Bsu36I fragment from pCAGGS-HN were cloned into the XhoI and Bsu36I sites of pCAGGS to yield pCAGGS-SIVct+HN.

The cPPT and WPRE sequences were inserted in the SIV-derived gene transfer plasmid. An example of the WPRE sequence used is provided in SEQ ID NO: 8.

The plasmid pGM101 contains the colE1 origin of replication, kanamycin resistance gene and promoter and was created by synthetic gene synthesis (GeneArt, Regensburg, Germany; now LifeTechnologies Ltd).

The hybrid CMV/SIV R U5 LTR, partial Gag, RRE, cPPT, SIN U3 and R sequences from pBS/CG2-Rc/s-CMV-D U (Nakajima et al. 2000 Human Gene Therapy 11:1863) were amplified by PCR and inserted along with the hCEF enhancer/Promoter sequence amplified by PCR from pGM169 (Hyde et al. Nature Biotechnology 26:549) and the soCFTR2 cDNA isolated from pGM169 on a NheI-ApaI restriction enzyme fragment into pGM101 to create pGM326.

The CMV enhancer/chicken beta actin promoter along with associated exon/intron sequences, SIV GagPol and RRE sequences and the SV40 polyA/origin of replication were amplified by PCR from pCAGGS/Sagm-gtr (Nakajima et al. 2000 Human Gene Therapy 11:1863) to create pGM297. The CMV enhancer/promoter along with associated exon/intron sequences and SV40 polyA sequence from pCI (Promega, Madison, Wis., USA) were isolated on a BglII-BamHI restriction enzyme fragment and the SIV Rev sequence derived from pCAGGS/Sagm-gtr amplified by PCR were inserted into pGM101 to create pGM299.

The CMV enhancer/chicken beta actin promoter along with associated exon/intron sequences, the Fct4 cDNA and SV40 polyA/origin from pCAGGS-Fct4 were isolated on a SalI-HindIII restriction enzyme fragment by a combination of gene synthesis, PCR and restriction enzyme fragment recombination and inserted into pGM101 to create pGM301.

The CMV enhancer/chicken beta actin promoter along with associated exon/intron sequences, the SIVct+HN cDNA and SV40 polyA/origin from pCAGGS-SIVct+HN were isolated on a SalI-HindIII restriction enzyme fragment by a combination of gene synthesis, PCR and restriction enzyme fragment recombination and inserted into pGM101 to create pGM303.

Other pGM plasmids of the invention were made using standard techniques and in accordance with the above disclosure.

Throughout these plasmid DNA assembly approaches, restriction enzymes and PCR polymerases were supplied by New England Biolabs (Ipswich, Mass., USA) and DNA purification reagents were supplied by Qiagen (Limburg, Netherlands).

Example 3: Production of SIV Vector

Four Plasmid System:

Replication-defective self-inactivating SIV vector was constructed with minor modifications. Briefly, the SeV-F/HN-pseudotyped SIV vector was produced by transfecting 293T/17 cells (15 cm diameter culture dishes) with four plasmids complexed to Lipofectamine/Plus reagents (Invitrogen) according to the manufacturer's recommendations [Plasmid-1: 10 µg SIV-derived transfer plasmid carrying a GFP, a luciferase (lux) reporter gene, or a GFP-CFTR fusion construct, Plasmid-2: 3 µg packaging plasmid, Plasmid-3: 2 µg pCAGGS-Fct4, Plasmid 4: 2 µg pCAGGS-SIVct+HN; FIGS. 1A-E show schematic drawings of plasmids used for the production of vectors of the invention]. The VSV-G pseudotyped SIV vector was produced using a similar protocol, but a pVSV-G plasmid (2 µg; Clontech, Mountain View, Calif.) was used instead of pCAGGS-Fct4 and pCAGGS-SIVct+HN. At 12 hours after transfection the culture medium was replaced with 30 ml serum-free Dulbecco's modified Eagle medium containing 5 mmol/l sodium butyrate. Sodium butyrate stimulates the vector production to inhibit histone deacetylase. The culture supernatant containing the SIV vector was harvested 48 hours after transfection, filtered through a 0.45 µm filter membrane, and further concentrated by high-speed centrifugation (20,000 g for 4 hours at 4° C., Avanti JA18 rotor; Beckman Coulter, Brea, Calif.). The vector pellets were suspended in PBS (Invitrogen) to 100- to 200-fold concentration and stored at −80° C.

Figure 1B:
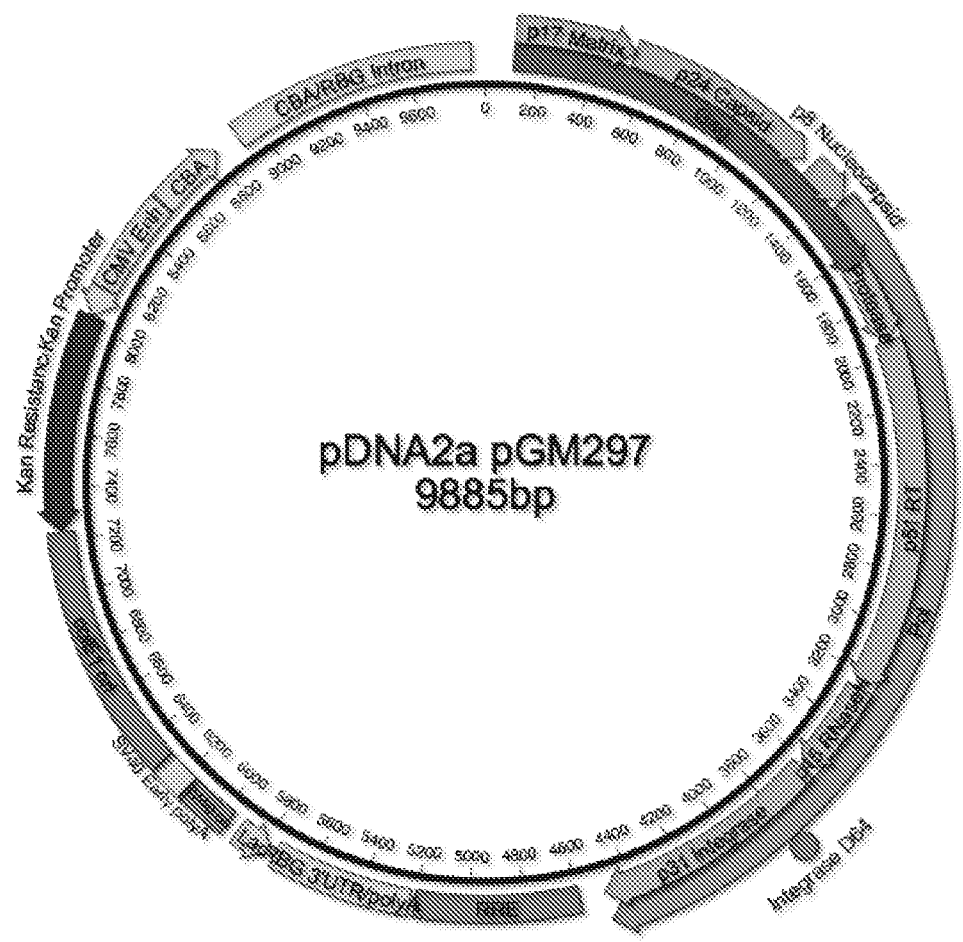
Figure 1C:
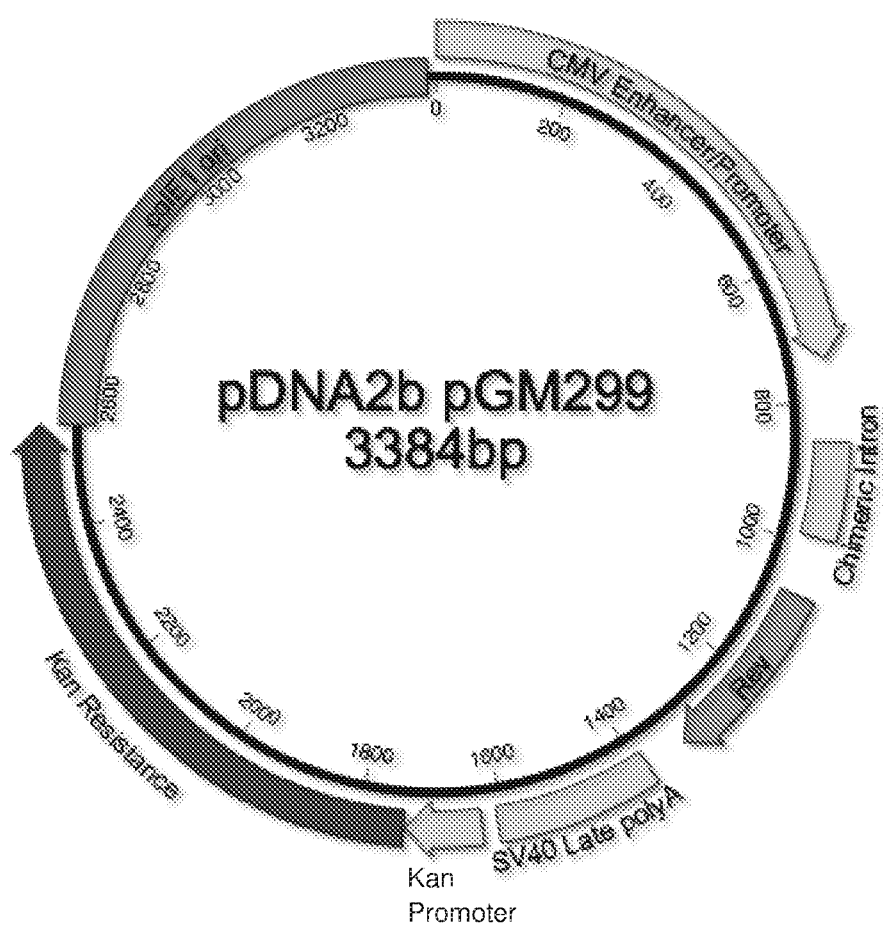
Figure 1D:
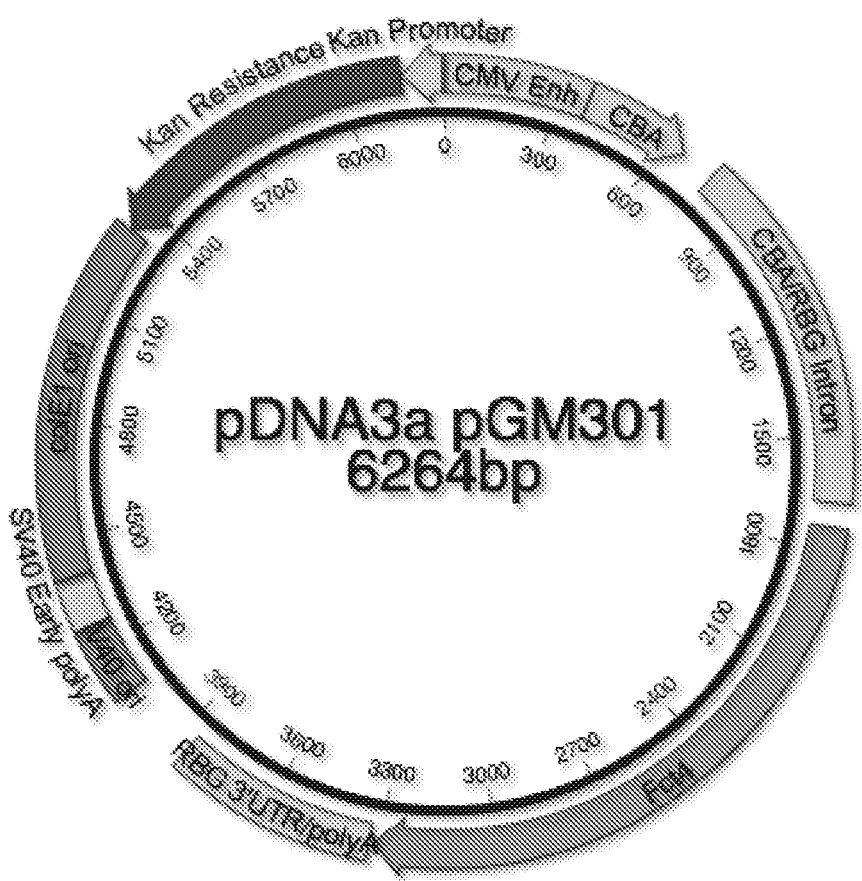
Figure 1E:
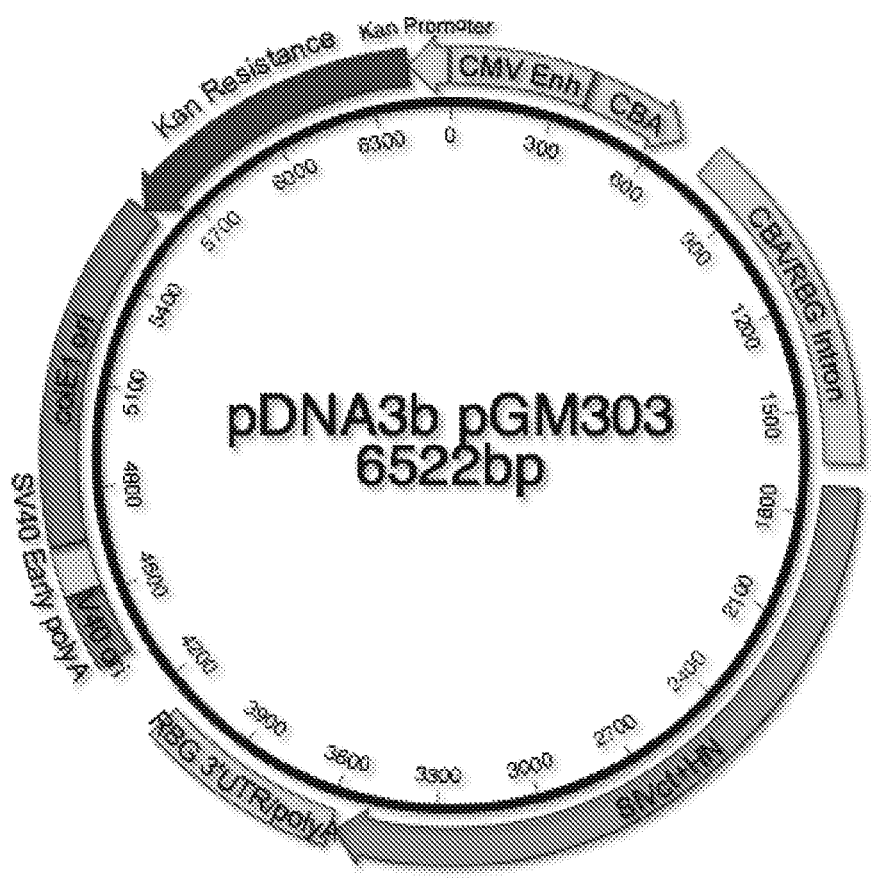

Five Plasmid System (Preferred):

SeV-F/HN-pseudotyped SIV vector was produced by transfecting HEK293T or 293T/17 cells cultured in Free-Style™ 293 Expression Medium with a mixture of five plasmids with the following characteristics: pDNA1 (for example pGM326; FIG. 1A) encodes the lentiviral vector mRNA; pDNA2a (for example pGM297; FIG. 1B) encodes SIV Gag and Pol proteins; pDNA2b (for example pGM299: FIG. 1C) encodes SIV Rev proteins; pDNA3a (for example pGM301; FIG. 1D) encodes the Sendai virus-derived Fct4 protein [Kobayashi et al., 2003 J. Virol. 77:2607]; and pDNA3b (for example pGM303; FIG. 1E) encodes the Sendai virus-derived SIVct+HN [Kobayashi et al., 2003 J. Virol. 77:2607] complexed with PEIpro (Polyplus, Illkirch, France).

Cell culture media was supplemented at 12-24 post-transfection with sodium butyrate. Sodium butyrate stimulates vector production via inhibiting histone deacetylase resulting in increasing expression of the SIV and Sendai virus fusion protein components encoded by the five plasmids. Cell culture media was supplemented at 44-52 hours and/or 68-76 hours post-transfection with 5 units/mL Benzonase Nuclease (Merck Millipore, Nottingham, UK). The culture supernatant containing the SIV vector was harvested 68-76.5 hours after transfection, and clarified by filtration through a 0.45 μm membrane. The SIV vector is treated by digestion with a protease containing trypsin activity—for example an animal origin free, recombinant enzyme such as TrypLE Select™. Subsequently, SIV vector is typically further purified and concentrated by anion-exchange chromatography and/or tangential flow filtration ultra-filtration/dia-filtration.

Figure 15:
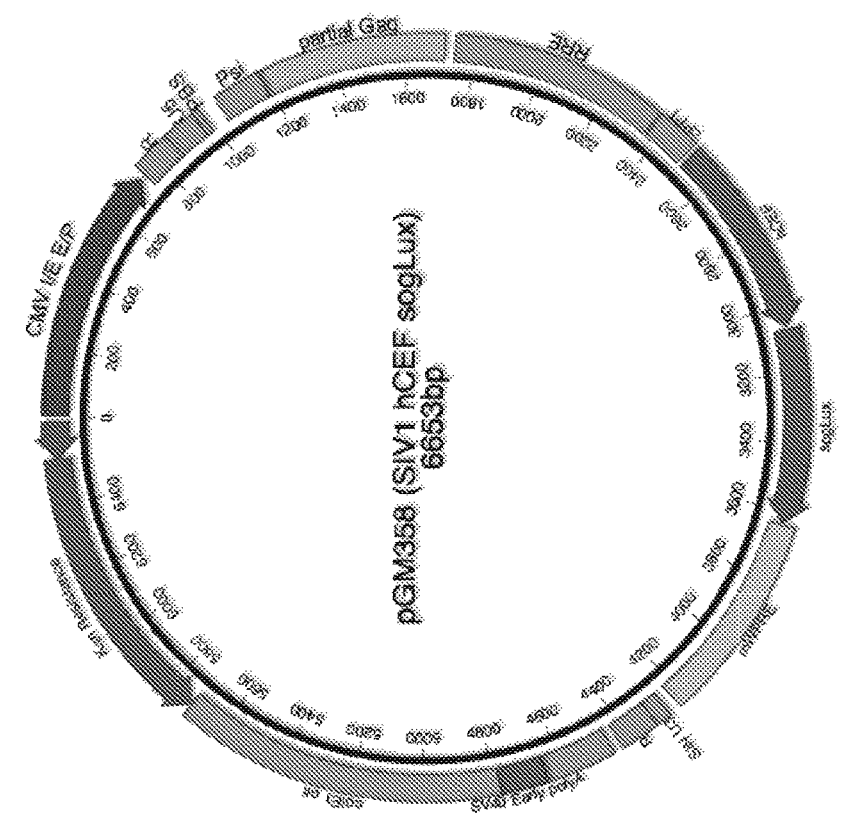
FIG. 15A shows a schematic drawings of a plasmid used for production of the A1AT vectors of the invention. In one embodiment of the invention, FIG. 15A provides a tool of the invention.
FIG. 15B shows a control plasmid encoding the Gaussia luciferase reporter gene.
Figure 15:
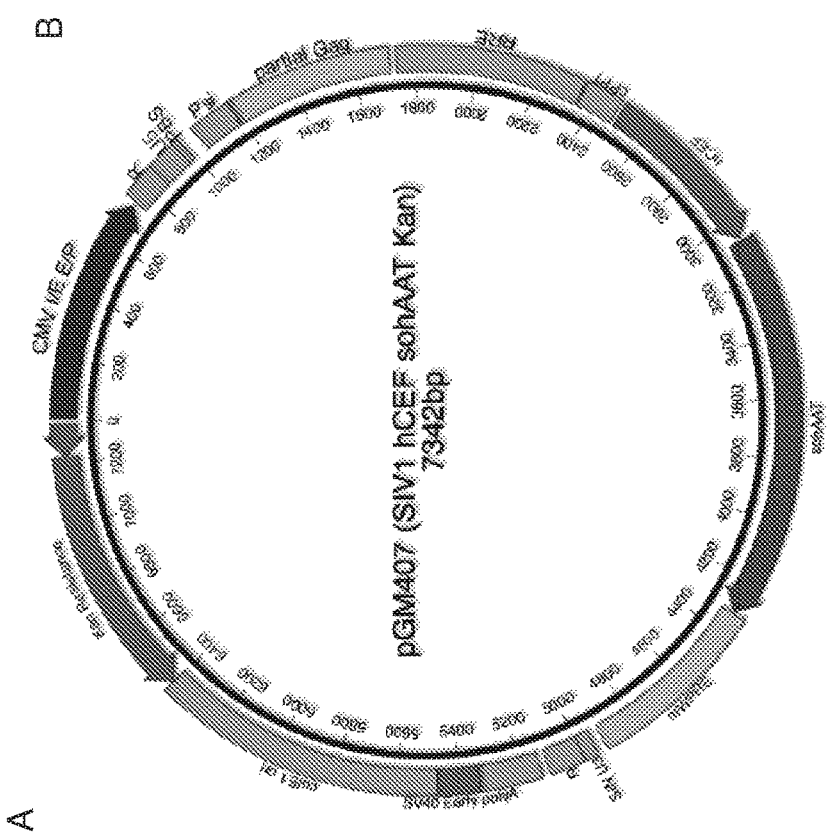
Figure 22:
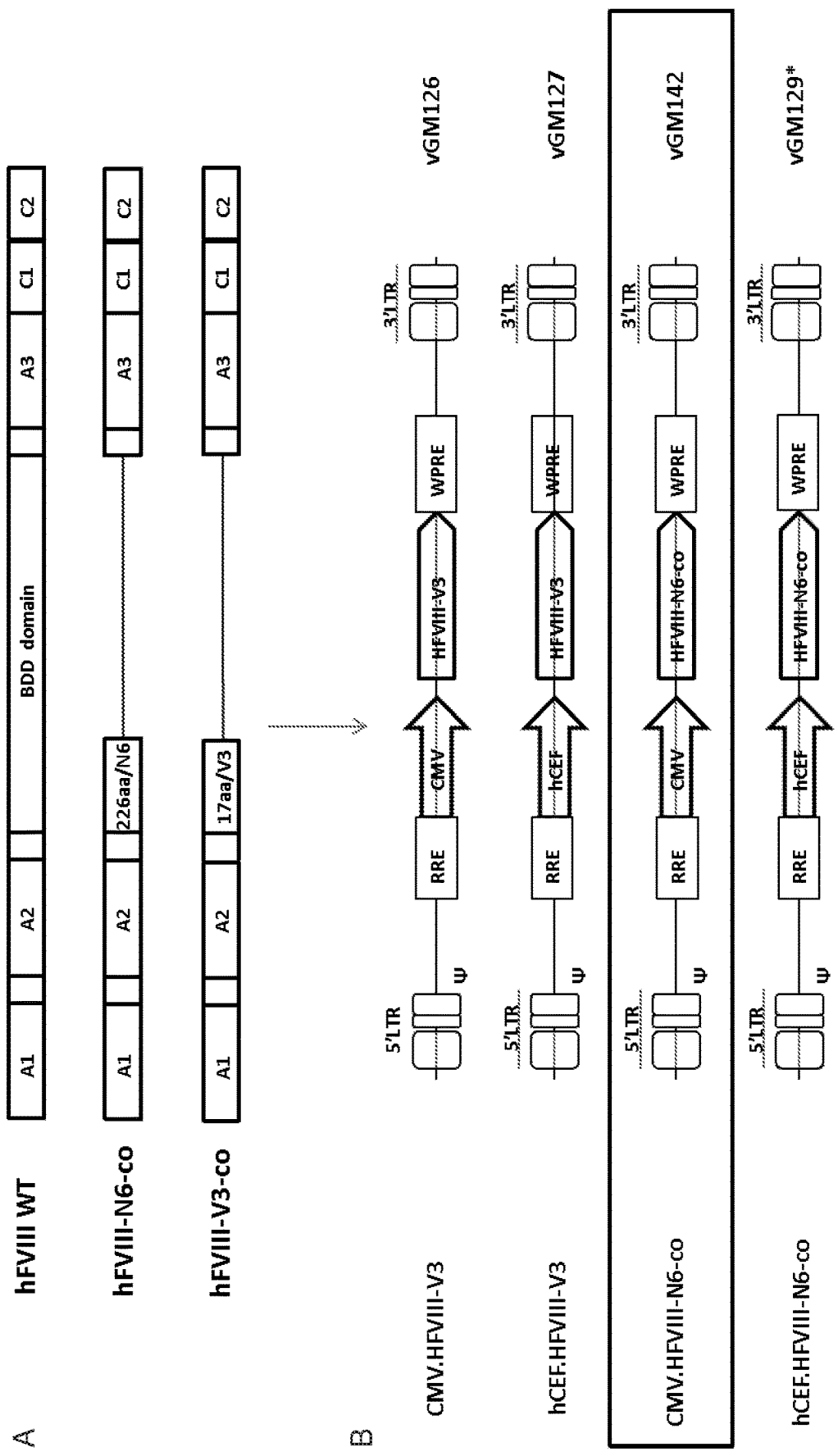
FIG. 22A shows schematic drawings of FVIII cDNA constructs used for production of the FVIII vectors of the invention.
FIG. 22B shows viral vectors of the invention. In one embodiment of the invention, FIG. 22B provides a tool of the invention.
FIGS. 22C-F show schematic drawings of pDNA1 plasmids used for production of the FVIII vectors of the invention. In one embodiment of the invention, FIGS. 22C-F provide tools of the invention.
Figure 22:
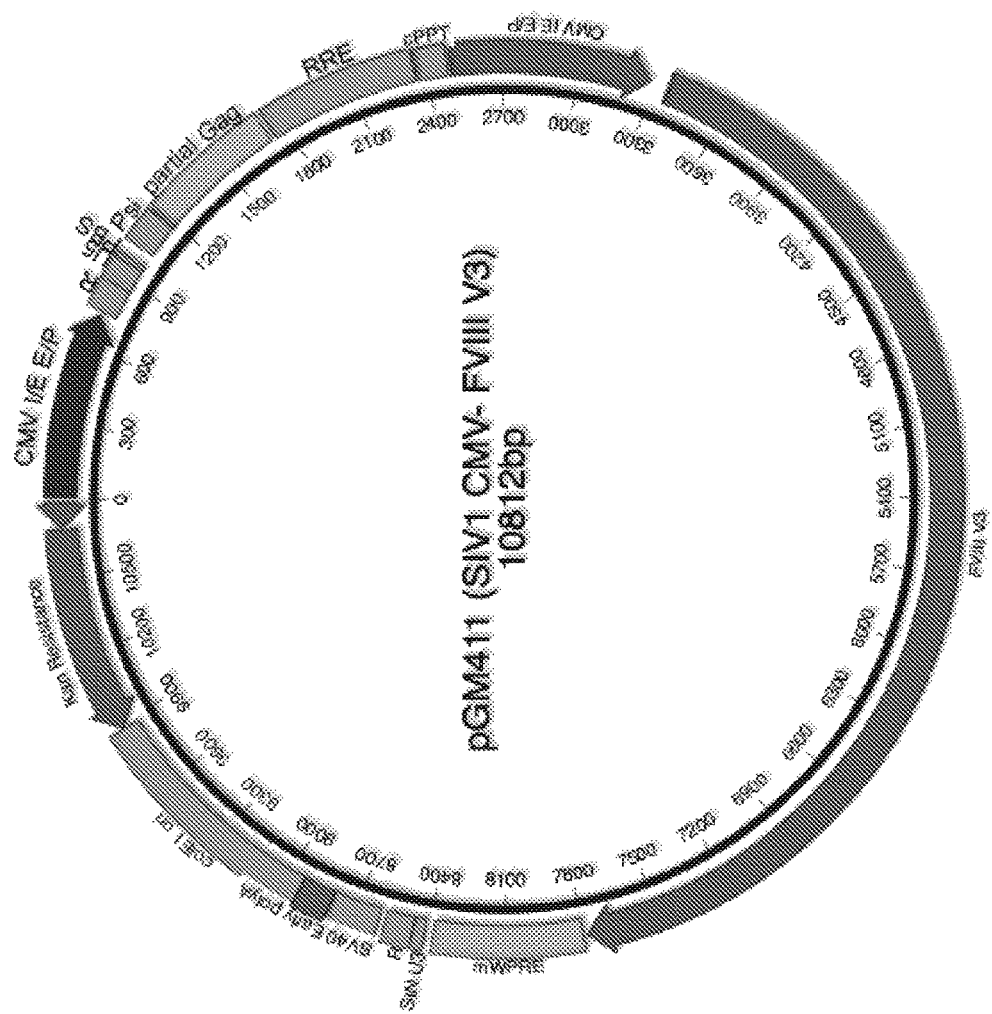
Figure 22:
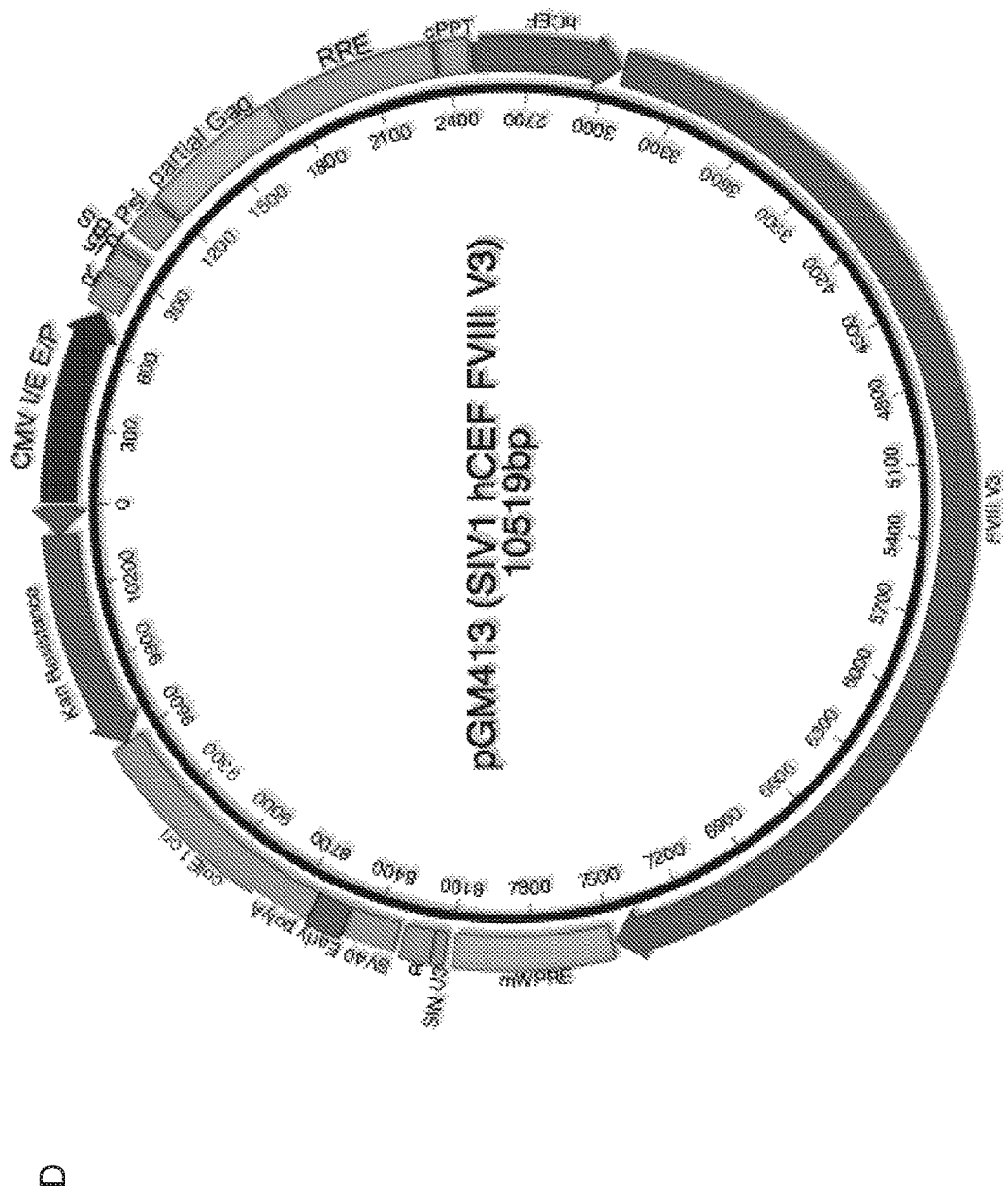
Figure 22:
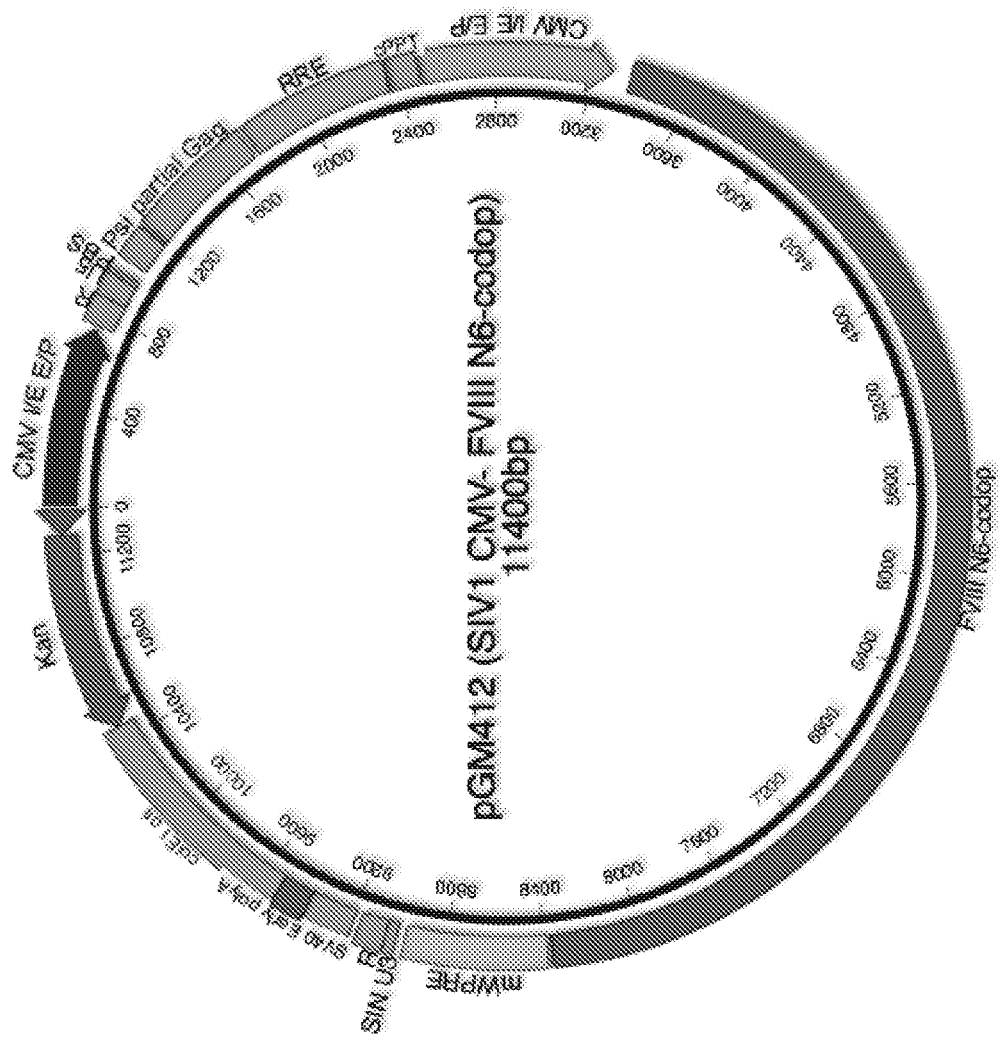
Figure 22:
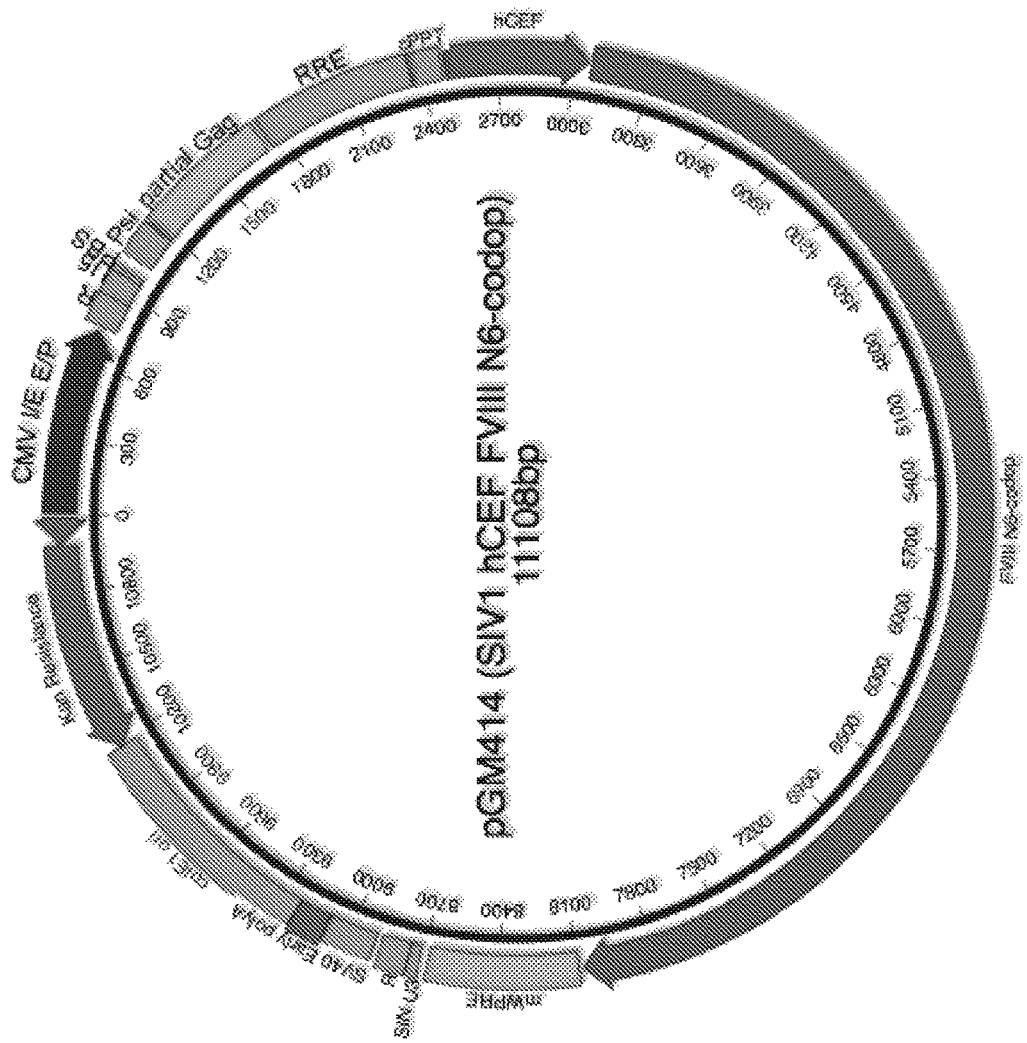

This same method was used to generate lentiviral vectors comprising the A1AT and FVIII transgenes, with the plasmids of FIG. 15A and FIG. 22B replacing that of FIG. 1A to provide the appropriate transgene (see Examples 15 and 20).

Example 4: Vector Titration

Method 1:

The particle titre was determined using real-time reverse transcriptase-PCR. Virus RNA was purified using a QIAamp viral RNA mini-kit (QIAGEN, Strasse, Germany), and reverse transcribed using Superscript II (Invitrogen). The QuantiTect probe PCR system (QIAGEN) and primers for amplifying 131 nucleotides (bp) spanning the WPRE sequence (forward primer: 5'-ggatacgctgctttaatgcc-3' (SEQ ID NO: 34), reverse primer: 5'-acgccacgttgcctgacaac-3' (SEQ ID NO: 35)) were used according to the manufacturer's protocol in an ABI PRISM 7700 Sequence Detector System (PE Applied Biosystems, Foster City, Calif.). SIV gene transfer plasmid DNA ($3\times10^4$ to $2\times10^6$ molecules) was used as standard.

Transduction units (TU/ml) were determined by transducing 293T cells with serial dilutions of vector stock and quantification of transduced cells by GFP fluorescence (for F/HN-SIV-GFP and VSV-G-SIV-GFP) or staining with anti-luciferase antibody (for F/HN-SIV-lux).

Method 2 (Preferred):

The particle titre (VP/mL) was typically determined using real-time reverse transcriptase-PCR. Virus RNA was purified using a QIAamp viral RNA mini-kit (QIAGEN, Strasse, Germany), and reverse transcribed using reverse transcriptase (Life Technologies). TaqMan quantitative PCR system (Life Technologies) using primers amplifying a portion of the WPRE sequence in an ABI PRISM 7700 Sequence Detector System (Life Technologies). In vitro transcribed WPRE RNA molecules were used as quantitative standards.

Transduction units (TU/mL) were determined by transducing 293T/17 or Freestyle 293F cells with serial dilutions of SIV vector and quantification of WPRE containing provirus DNA by TaqMan quantitative PCR system (Life Technologies) using primers amplifying a portion of the WPRE sequence in an ABI PRISM 7700 Sequence Detector System (Life Technologies). Plasmid DNA molecules containing WPRE sequences were used as quantitative standards.

Example 5: Generation of Basal Cells-Enriched tEC Cultures

Murine tracheal epithelial cells (tEC) were isolated as follows. C57BL/6N Mice were culled and the tracheas were excised from the larynx to the main bronchial branches using sterile surgical instruments. The tissues were placed in a tube containing cold Ham's F-12 medium with 100 U/ml penicillin (P), 100 μg/ml streptomycin (S) and 2.5 mg/ml amphotericin B (A) (Ham's F12/PSA medium) and kept on ice. In a sterile tissue culture hood, the tracheas were cleaned from adherent muscles and connective tissue, cut longitudinally to expose the internal respiratory epithelium, and placed in 0.15% pronase solution in F-12 medium (~5 ml in 15 ml tube). Tissue digestion was performed overnight (15-18 hr) at 4° C. To block the enzymatic reaction, 10% fetal bovine serum (FBS) was added to the tissue digest. After gently inverting the tube to detach more cells, the tracheas were placed into a new tube containing 10% FBS/Ham's F-12/PS solution, and inverted as before. This step was repeated two more times. The content of the four tubes was pooled together and centrifuged at 500 g for 10 min at 4° C. The pellet was re-suspended in DNase solution (0.5 mg/ml crude pancreatic DNase plus 10 mg/ml BSA in FBS/Ham's F-12/PS solution, about 200 μl/trachea), incubated on ice for 5 minutes, and centrifuged as before.

After removing the supernatant, tEC were resuspended in Progenitor Cell Targeted (PCT) medium (CnT-17, CELLn-TEC, Bern, Switzerland), an antibiotics and antimycotics-free formulation specifically designed for human and mouse airways progenitor cells isolation and proliferation. tEC were then plated in a Primaria tissue culture dish (Becton Dickinson Labwere, Franklin Lakes, N.J., USA) and incubated for 3-4 hr in 5% $CO_2$ at 37° C. Non-adherent cells were collected and centrifuged at 500 g for 5 min at 4° C. and counted in a haemocytometer. To generate basal cells-enriched cultures, tEC were suspended in PCT medium and seeded on a Nunclon™ Δ plate (Nunc A/S, Roskilde, Denmark), coated with 50 μg/ml type 1 rat tail collagen at a recommended seeding density of $4\times10^3$ cells/cm². tEC were also cultured in a control basic medium, containing DMEM/Ham's F12 supplemented with L-glutamine (4 mM), HEPES (15 mM) and NaHCO3 (3.4 mM). Plates were incubated at 37° C. with 5% $CO_2$. To determine the proportion of basal cells in the tEC population before and after expansion in PCT medium, cytospin preparations were stained with the anti-KRT5 antibody and the appropriate secondary antibody.

The pool of tEC produced comprised both fully differentiated cells (Clara and ciliated cells) and basal cells. Once seeded onto permeable membranes tEC were able to generate an air liquid interface (ALI) culture system as a result of basal cell proliferation and redifferentiation into secretory and ciliated cells. To establish an alternative and rapid protocol for basal cell expansion, two-dimensional (2D) tEC cultures using a commercially available proprietary Progenitor Cell Targeted (PCT) medium, specifically formulated to support the proliferation of airway progenitor cells while maintaining them in an undifferentiated status were assessed. As a negative control, tEC were exposed to a basic media formulation without addition of specific growth factors. tEC seeded on collagen-coated plastic surfaces ($4 \times 10^3$ cells/cm$^2$) and exposed to PCT medium were able to grow rapidly and became confluent within 5-8 days whereas tEC exposed to the growth factor-deficient control medium were unable to adhere and propagate. To establish whether the use of PCT medium resulted in a substantial enrichment of the basal cell population, tEC were harvested at approximately 80% confluence (n=6 wells), fixed and treated with an anti-keratin 5 (Krt5) antibody, a specific marker of basal cells. Freshly isolated tEC were used as controls (n=3 unique preparations). The proportion of Krt5 positive basal cells after expansion in PCT medium was higher (78±1.4%) than in freshly isolated pools of tEC (33±0.6%), demonstrating that murine airway basal cells can be selectively and rapidly expanded from a mixed pool of tEC using a commercial medium.

Example 6: Ex Vivo Transduction of Basal Cells-Enriched tEC Cultures with F/HN-SIV-GFP To determine whether the F/HN-SIV vector can effectively transduce basal cells ex vivo, tEC prepared in Example 5 were grown to approximately 70% confluence over 7 days in PCT medium and transduced with F/HN-SIV carrying a green fluorescent protein reporter gene (F/HN-SIV-GFP) at an MOI 100 and incubated at 37° C. with 5% $CO_2$ for 3 days. tEC derived from wild-type and GFP transgenic animals were cultured under the same conditions and used as negative (no viral transduction) and positive control groups, respectively (n=3-6 wells/group).

To quantify the proportion of GFP-positive cells, basal cells-enriched tEC cultures were detached with the enzyme accutase (CELLnTEC), re-suspended in PBS/1% BSA and subjected to FACS analysis, counting an average of 20.277±2.478 cells/group. The F/HN-SIV vector transduced 26%±0.9% of basal cells-enriched tEC (p<0.0001 when compared to untransduced controls).

To assess whether transduced GFP-expressing cells were basal cells, three days post-infection cells were double stained with antibodies against Krt5 and GFP. Immunofluorescence staining of cultured cells showed that approximately 40% of Krt5-expressing cells also expressed the GFP reporter gene, showing that the F/HN-SIV vector can transduce progenitor basal cells ex vivo.

Example 7: In Vivo Administration to the Mouse Nose

Figure 2:
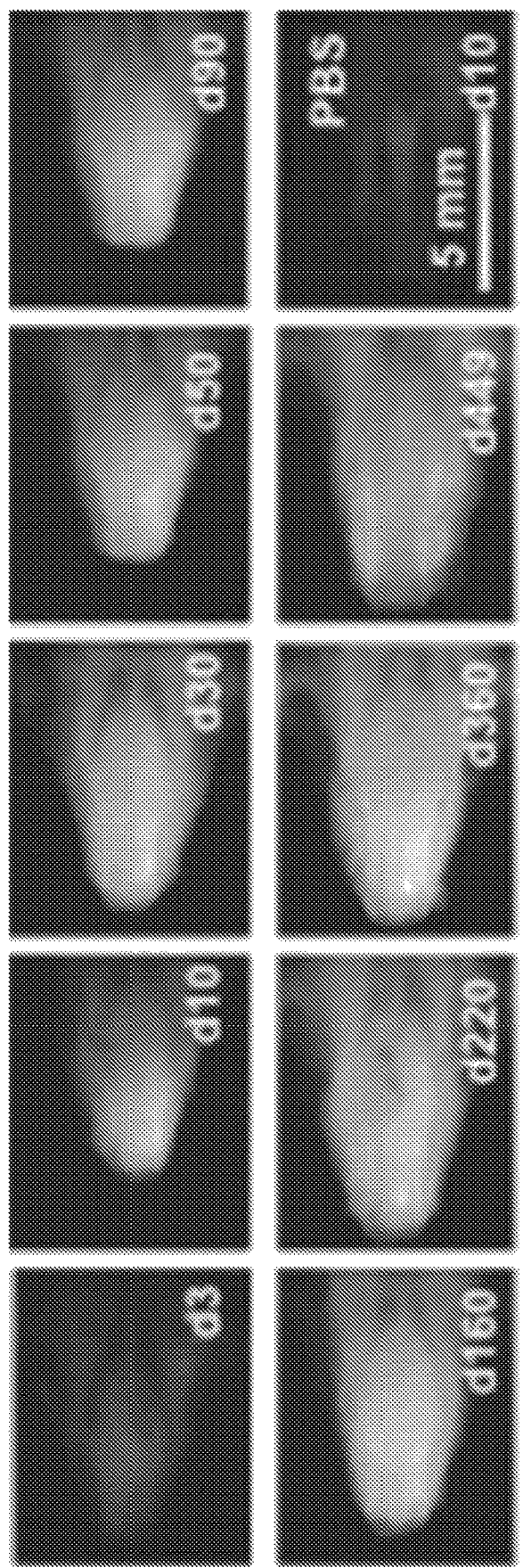
FIG. 2 shows the duration of F/HN-SIV transgene expression in mouse nasal tissue, which was perfused with $4\times10^8$ TU F/HN-SIV-CMV-EGFP and EGFP expression determined at the indicated number of days post-treatment. A negative control is shown where nasal tissue was perfused with vector diluent (PBS).
Figure 3:
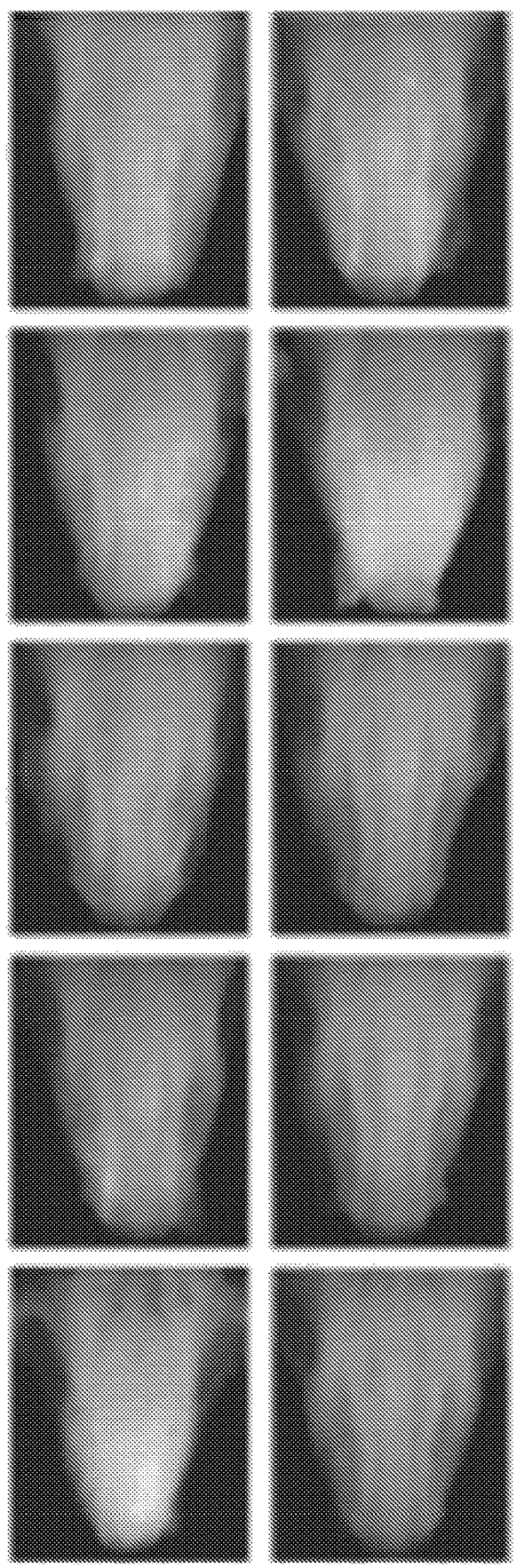
FIG. 3 demonstrates consistency of F/HN-SIV transgene expression, by showing at 1 year post-treatment. EGFP expression was determined in 10 independent mice at 360 days post-treatment.

C57BL/6N mice (female, 6-8 weeks) were used. Mice were anesthetized, placed horizontally on their backs onto a heated board, and a thin catheter (<0.5 mm outer diameter) was inserted ~2.5 mm from the tip of nose into the left nostril. Using a syringe pump (Cole-Parmer, Vernon Hills, Ill.), vector (100 µl) was then slowly perfused onto the nasal epithelium (1.3 µl/min) for 75 minutes. Despite perfusion of virus into the left nostril, we routinely observe transfection in both left and right nostrils, which is due to dispersion of the solutions throughout the entire nasal cavity. PBS and VSV-G-SIV transduced mice preconditioned with 1% lyso-phosphatidylcholine as described by Limberis et al., 2002, were used as controls. At indicated time points (3-360 days after transduction), mice were culled to visualize GFP expression. As shown in FIG. 2, GFP expression was observed for at least 449 days post-transduction, whereas the negative control showed no GFP expression. As shown in FIG. 3, transgene expression with the F/NH-SIV vector was consistent, with observable GFP expression at least 360 days post-transduction in 10 independently tested mice.

Figure 13:
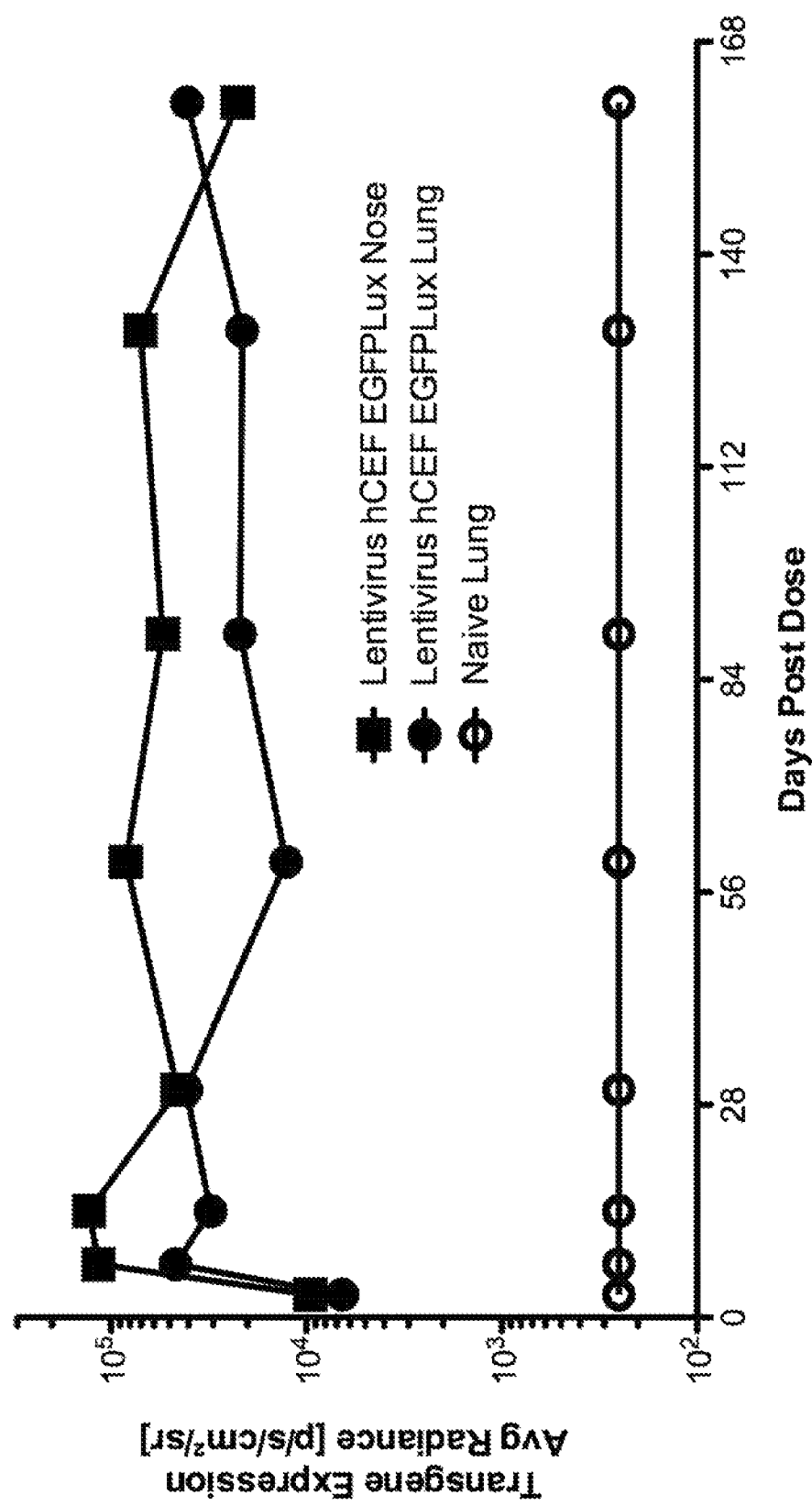
FIG. 13 shows hCEF mediated respiratory transgene expression—using lentivirus gene transfer with a CpG rich transgene—transgene expression (average radiance $p/s/cm^2/sr$) against days post dose. High levels of Gaussia luciferase reporter gene expression compared with the control (naïve lung) was observed in both the lung (square) and nose (circle) for at least 168 days after dosing.

Similarly, as shown in FIG. 13, transduction with an F/HN-SIV vector of the invention comprising an hCEF promoter resulted in long-term expression of a CpG rich reporter gene (luciferase). High levels of expression relative to the control were observed in both the lung and the nose for at least 169 days post-transduction.

In the repeat administration experiments groups of mice were transduced with either one dose of F/HN-SIV-lux (single-dose group), or two doses of F/HN-SIV-GFP (day 0, day 28), followed by F/HN-SIV-lux on day 56 (repeat-dose group). Importantly, mice receiving F/HN-SIV-lux (single-dose group) and F/HN-SIV-lux on day 56 (repeat-dose group) were of similar age and were transduced at the same time. Gene expression was analysed 30 days after F/HN-SIV-lux administration. For comparison, mice were transfected with the cationic lipid GL67A complexed to a luciferase reporter gene as previously described (Griesenbach, U. et al., *Methods Mol Biol.* 2008; 433:229-42) and luciferase expression was measured 2 days after transfection.

Figure 6:
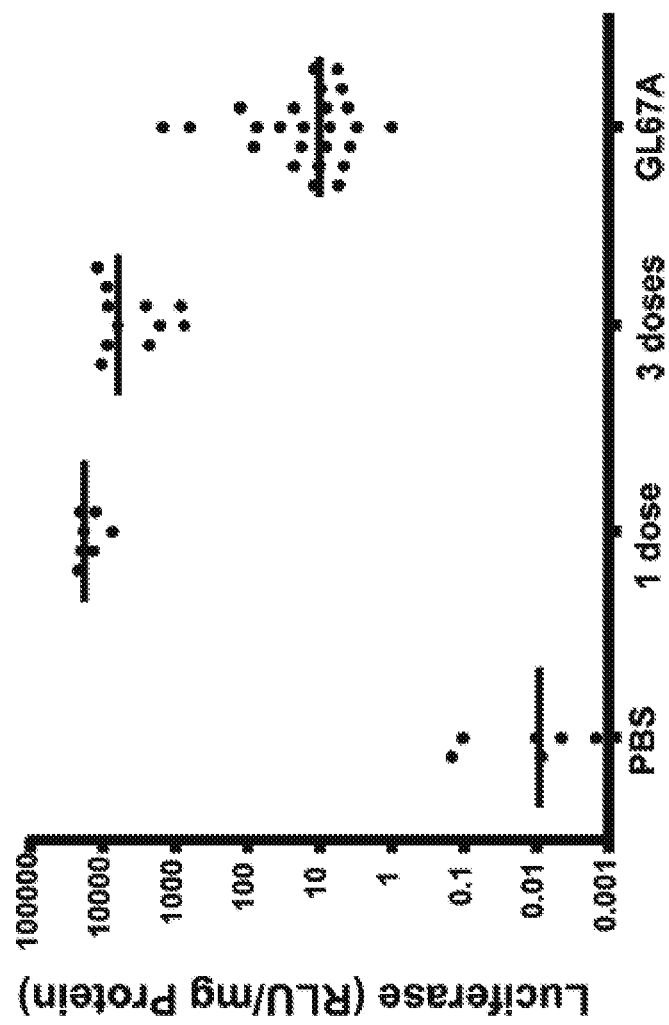
FIG. 6 shows repeat administration of F/HN-SIV to the mouse nose. Mouse nasal tissue which was transduced (as FIG. 1) with one dose of F/HN-SIV-CMV-Lux or, two doses of F/HN-SIV-CMV-EGFP followed by one dose of F/HN-SIV-CMV-Lux at 28 day intervals. Thus, repeat administration of F/HN-SIV to the mouse nose does not alter gene expression levels. Transgene expression is compared to a leading non-viral gene transfer formulation (CMV-Lux plasmid complexed with GL67A).
Figure 7:
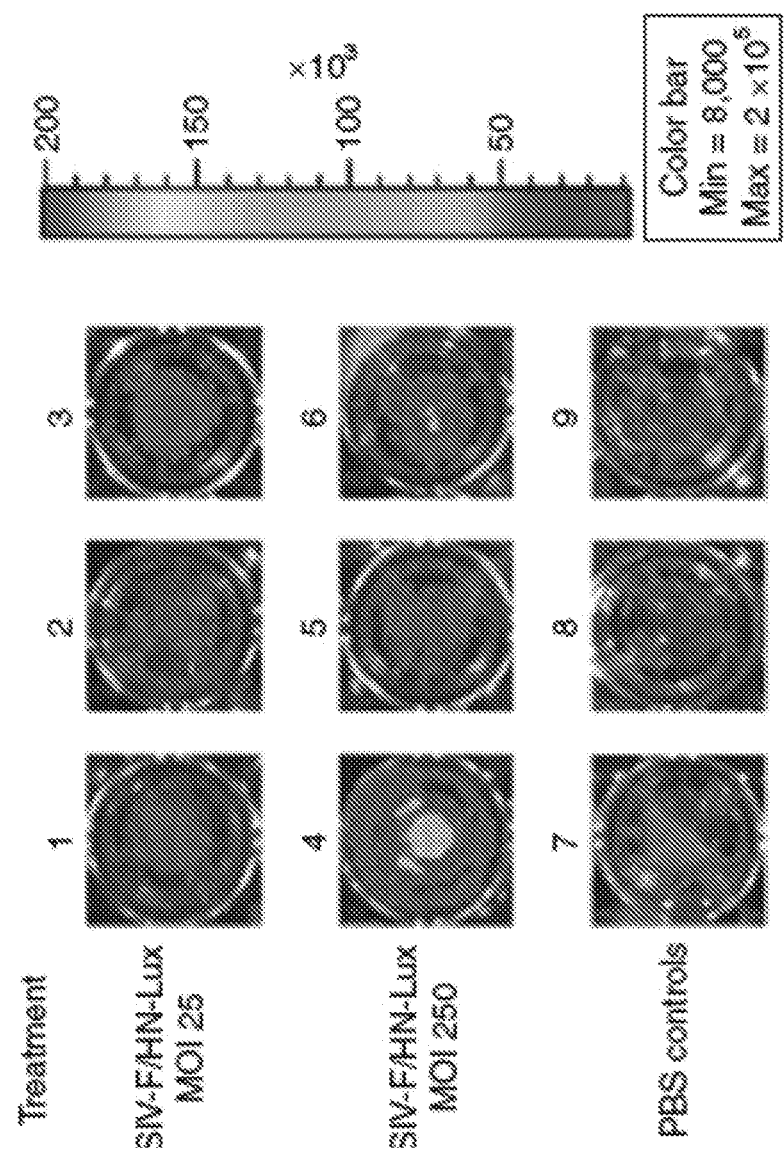
FIG. 7 displays transduction of human air liquid interface (ALI) respiratory cell cultures. Human ALI cultures were transduced with F/HN-SIV-Lux at the indicated multiplicity of infection (MOI) and imaged for Lux expression at 5 days post-treatment.
Figure 8:
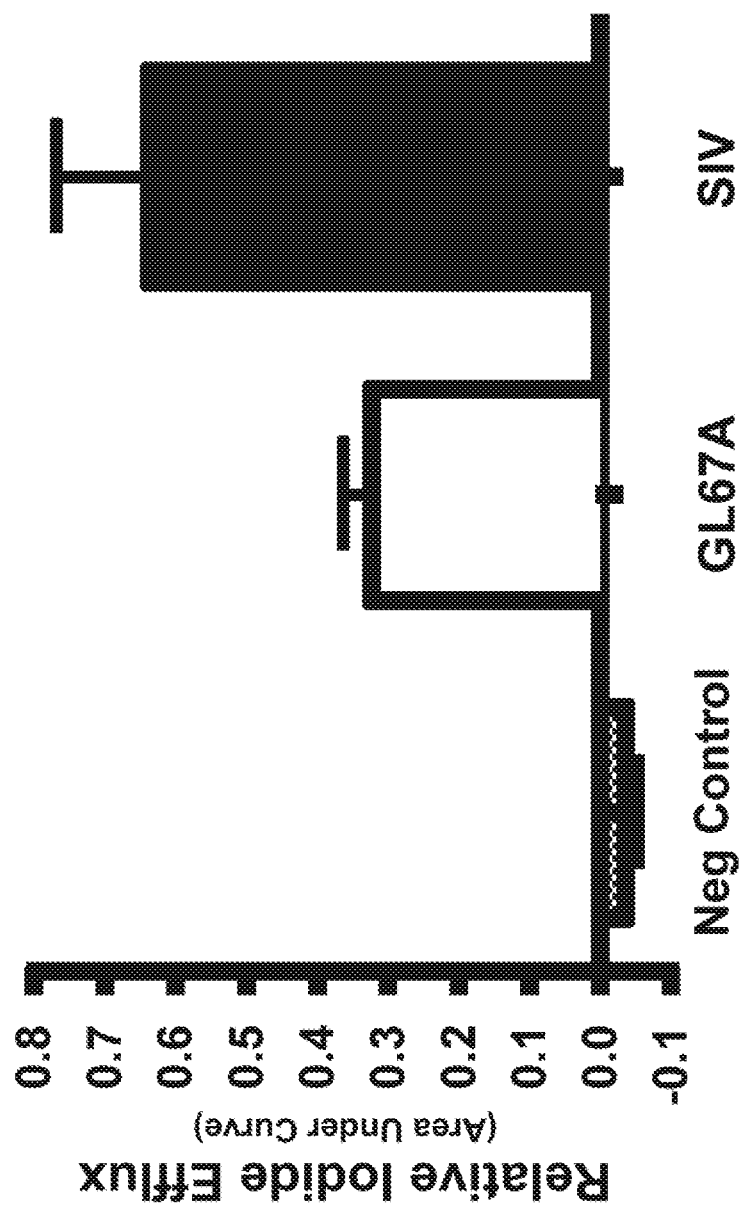
FIG. 8 demonstrates that F/HN-SIV can direct functional CFTR expression. HEK293T cells were transduced with F/HN-SIV-CMV-EGFP-CFTR at 500 MOI and CFTR functional activity was determined by iodide efflux. F/HN-SIV-CMV-EGFP served as a negative control.

As shown in FIG. 6, repeat administration of F/HN-SIV to the mouse nose does not alter gene expression levels. Transgene expression is compared to a leading non-viral gene transfer formulation (CMV-Lux plasmid complexed with GL67A).

Figure 12:
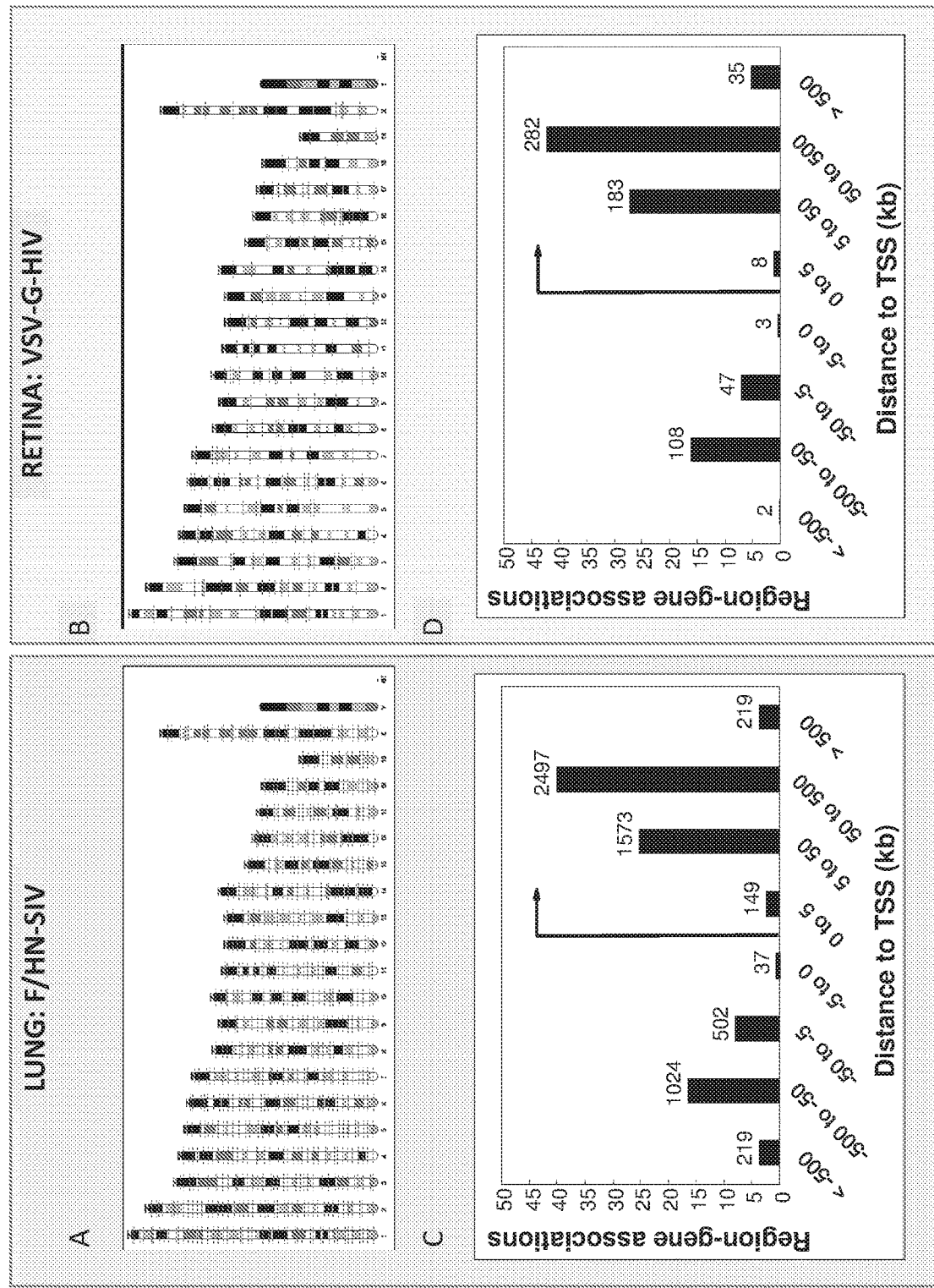
FIG. 12 displays insertion site (IS) profiling and survival of transduced mice.
Figure 12:
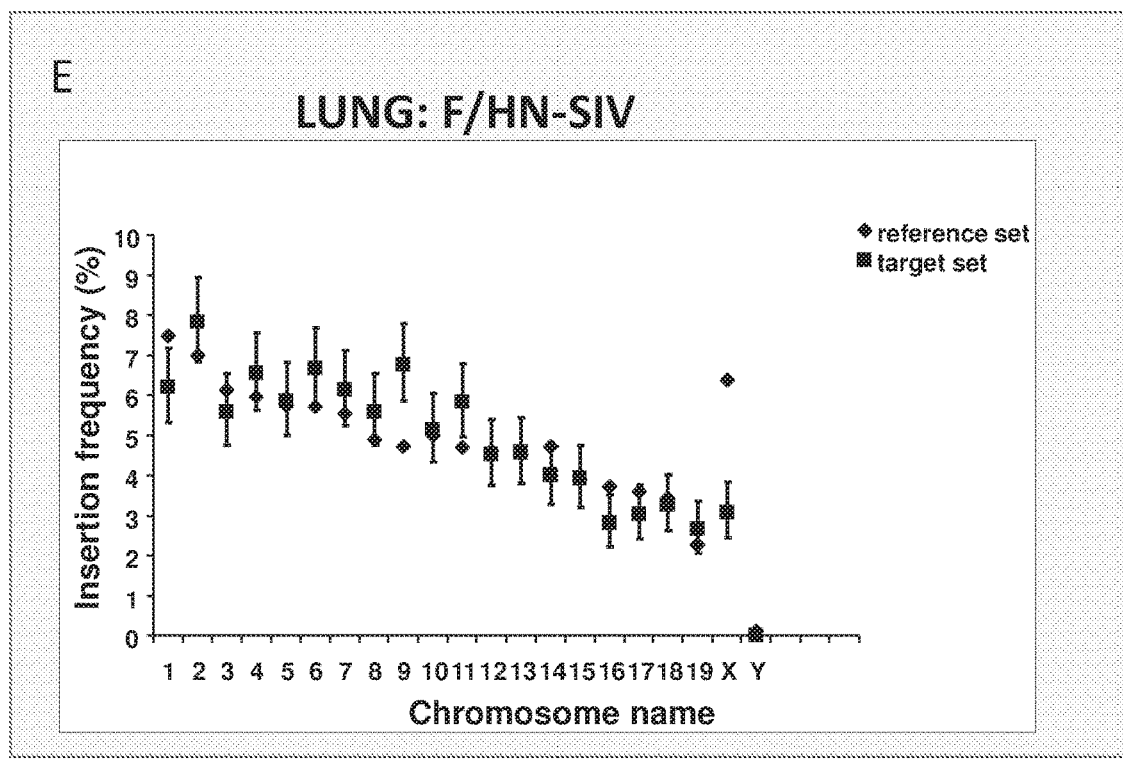
Figure 12:
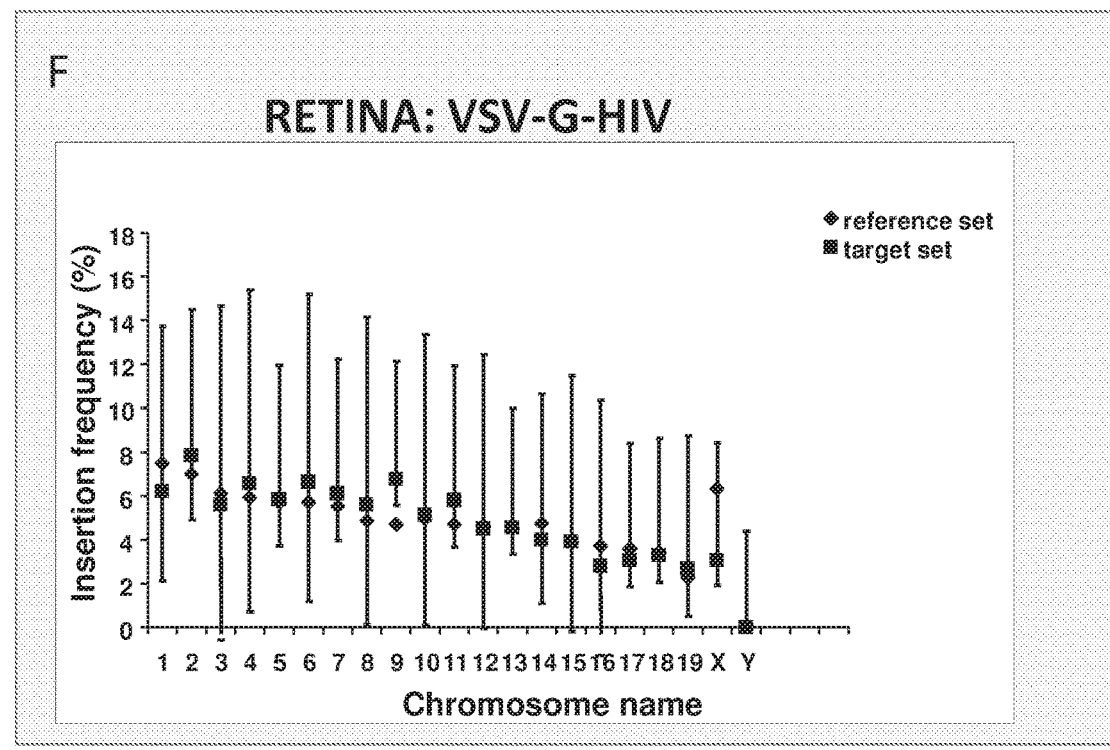
Figure 12:
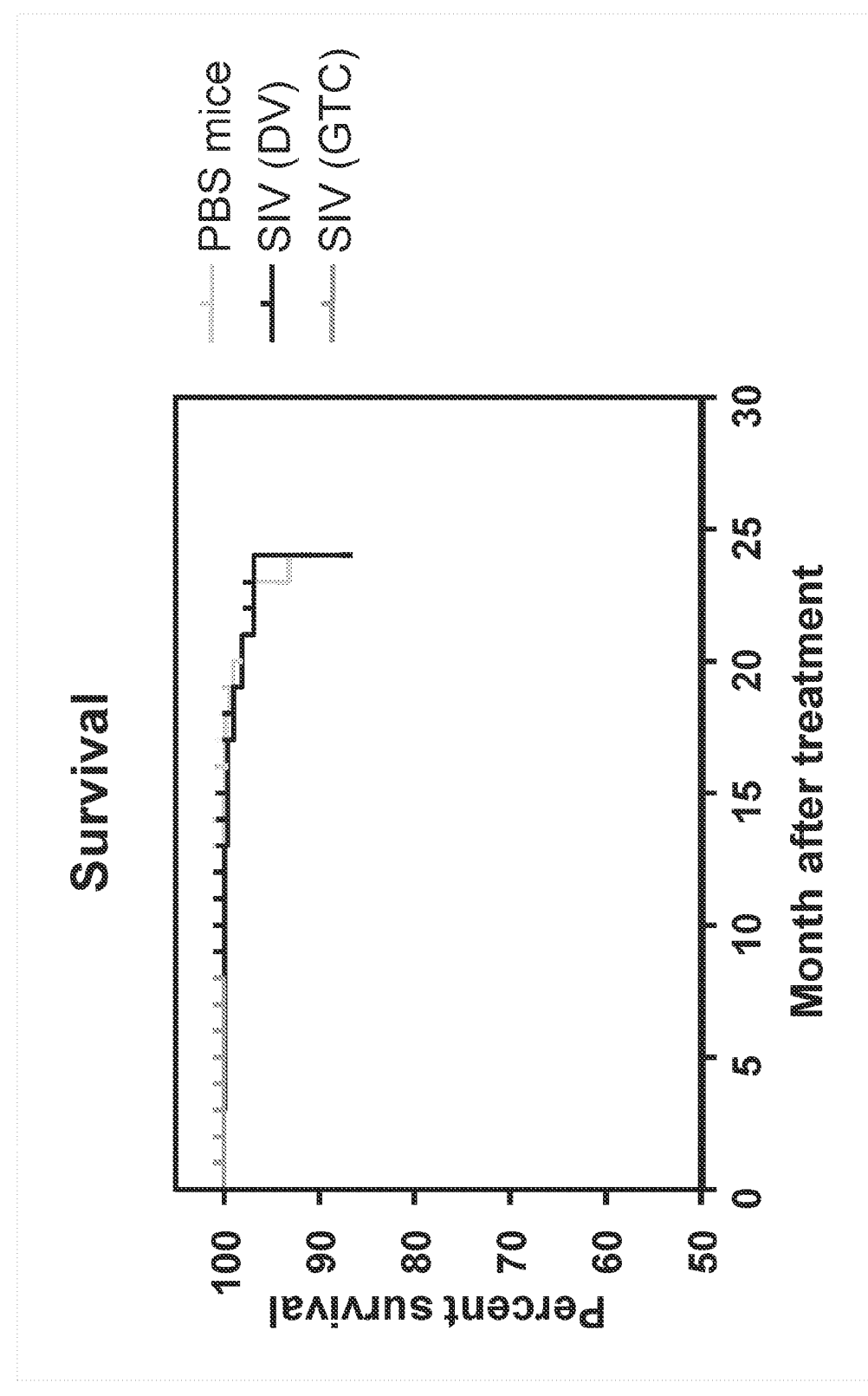

Insertion site profiling was conducted on transduced mice, and survival time investigated as set out in the description of FIG. 12 above. Transduction using the F/HN-SIV vector of the invention was not observed to have any adverse effect on mouse survival compared with an existing F/HN-SIV vector or negative (buffer only) control (see FIG. 12G).

Example 8: Induced Regeneration of Nasal Epithelial Cells by Polidocanol Treatment Nasal epithelial cells were stripped by polidocanol treatment according to the method described (Borthwick et al., *Am J Respir Cell Mol Biol.* 2001 June; 24(6):662-70), with some modification. In brief, mice were anesthetized and 10 µl polidocanol (2%) was administered to the nose as a bolus by "nasal sniffing". To confirm the stripping and regeneration of nasal epithelial cells, nasal tissue was perfused with 10 µl of 2% (vol/vol in PBS) polidocanol (nonaethylene glycol mono-dodecyl ether; SIGMA, St Louis, Mo.) and histological analysis undertaken 24 hours and 7 days after treatment (n=3/group).

To analyse transduction of possible progenitor or stem cells, we first administered F/HN-SIV-GFP ($4 \times 10^8$ TU/mouse) vector to mouse nasal epithelium. Seven days after transduction, nasal tissue was perfused with 10 µl of 2% (vol/vol in PBS) polidocanol, and this treatment was repeated again 3 weeks later. Histological sections were analysed 58 days after vector administration (30 days after the last polidocanol treatment).

Example 9: Bioluminescent Imaging

Mice were injected intraperitoneally with 150 mg/kg of D-luciferin (Xenogen, Alameda, Calif.) 10 minutes before imaging and were anesthetized with isoflurane. Bioluminescence (photons/s/cm2/sr) from living mice was measured using an IVIS50 system (Xenogen) at a binning of 4 for 10 minutes, using the software programme Living Image (Xenogen). For anatomical localization a pseudocolor image representing light intensity (blue: least intense, red: most intense) was generated using Living Image software and superimposed over the grayscale reference image. To quantify bioluminescence in the nose, photon emission in a defined area (red box) was measured by marking a standardized area for quantification. The size of the red box was kept constant and was placed over the heads of the animals as indicated in the figure. Importantly, the areas were marked using the grayscale reference image to avoid bias.

Example 10: Tissue Preparation for Histological Assessment of GFP Expression and/or Basal Cell Detection Mice were culled and the skin was removed. The head was cut at eye level and skin, jaw, tongue, and the soft tip of the nose were carefully removed. For in situ imaging of GFP expression in the nasal cavity, GFP fluorescence was detected using fluorescence stereoscopic microscopy (Leica, Ernst Leitz Optische Werke, Germany). Subsequently, the tissue was fixed in 4% paraformaldehyde (pH 7.4) overnight at room temperature and was then submerged in 20% EDTA (pH 7.5 for 5 days) for decalcification. The EDTA solution was changed at least every second day. After decalcification, the tissue was incubated in 15% sucrose overnight at room temperature and was then embedded in Tissue Mount (Chiba Medical, Soka, Japan). Ten micrometer sections were cut at six different positions in each mouse head (~0-6 mm from the tip of nasal bone). GFP expression was observed using a fluorescent microscope (Leica). Quantification and identification of cell types were carried out on six levels per mouse using a ×40 or ×63 objective. Prolonged image exposure was necessary to capture the structure of the nasal epithelium using fluorescent microscopy. This led to pixel saturation of GFP-positive cells and caused GFP-positive cells to appear almost white rather than the common green appearance that we, and others, observe under higher magnification.

Figure 4:
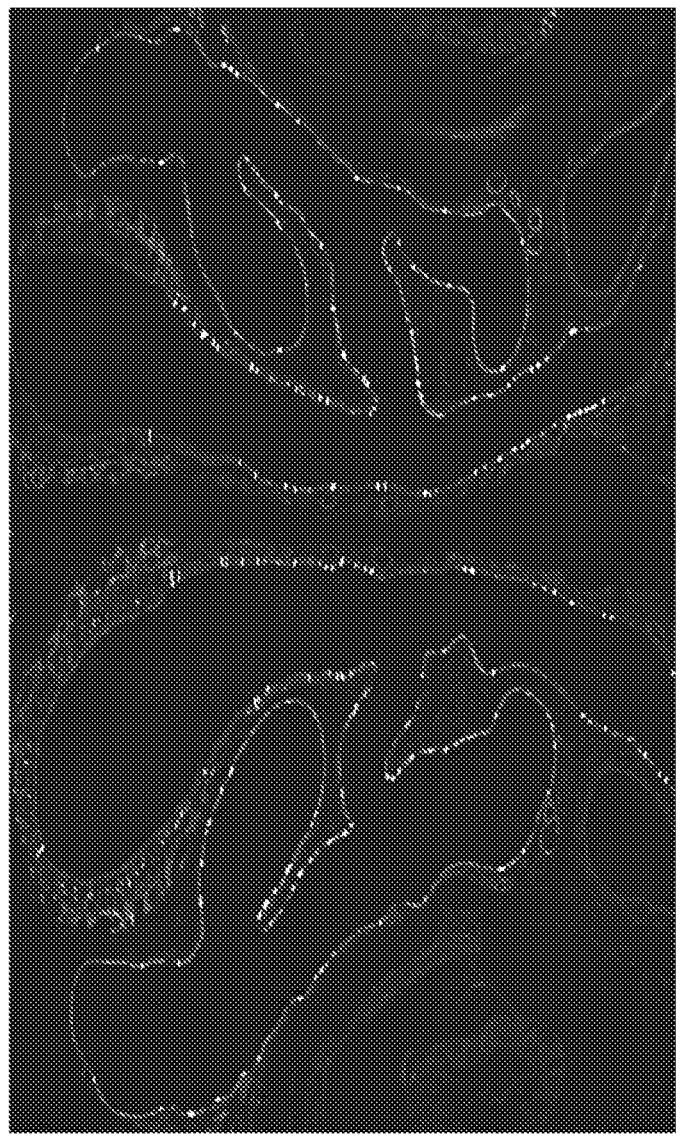
FIG. 4 shows cellular distribution of F/HN-SIV transgene expression. EGFP expression was determined in histological sections of the mouse nasal cavity (2 mm from tip of nose) at 30 days post-treatment. EGFP positive cells produce a white punctate signal.

Cellular distribution of F/NH-SIV transgene expression was investigated in histological sections. Specifically, EGFP expression was determined in histological sections of the mouse nasal cavity (2 mm from the tip of the nose) at 30 days post treatment. FIG. 4 shows the location of EGFP expression (FIG. 4, white punctate signal).

Figure 5:
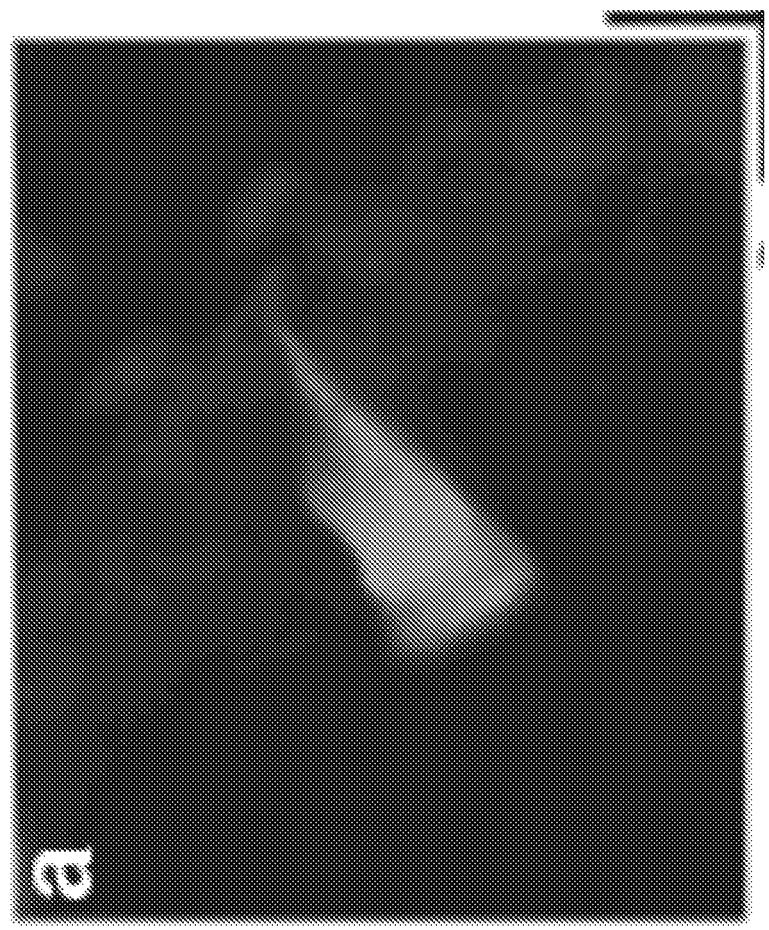
FIG. 5 shows cell types transduced by F/HN-SIV treatment of the mouse nose. 69% of the cells transduced in the mouse nasal cavity were ciliated respiratory epithelial cells. Other cell types transduced included neuronal cells in the olfactory epithelium (21%) and squamous cells (7%).

FIG. 5 shows the cell types transduced by /NH-SIV transgene treatment of the mouse nose. 69% of the cells transduced in the mouse nasal cavity were ciliated respiratory epithelial cells. Other transduced cell types included neuronal cells in the olfactory epithelium (21%) and squamous cells (7%).

To detect basal cells following polidocanol treatment horseradish peroxidase (HRP)-based immunostaining was performed using the Envision kit (Dako, Glostrup, Denmark). Briefly, slides were treated with 0.6% hydrogen peroxide in methanol for 15 min, washed in tap water and incubated with 1.5% normal goat serum (Abcam) for 30 min. Slides were then incubated with a rabbit polyclonal anti-Cytokeratin 5 antibody (1:500) (Abcam) for 1 hr following a Goat anti-rabbit IgG conjugated to HRP (provided with the kit) for 30 min. Sections were then washed in PBS and incubated with the peroxidase substrate 3-amino-9-ethylcarbazole (AEC) (provided with the kit) for 5 min. Finally, slides were washed in distilled $H_2O$, counterstained with aqueous Harris' hematoxylin (BDH) for 15 seconds, washed in tap water, and then in distilled $H_2O$.

Immunofluorescence detection of GFP-positive transduced nasal epithelial cells and Krt5 positive basal cells was performed using the following primary and secondary antibodies: goat polyclonal anti-GFP antibody (1:250) (Abcam), rabbit monoclonal anti-KRT5 antibody (1:500) (Abcam), Alexa Fluor 488 donkey anti-Goat IgG (1:200) (Invitrogen, Paisley, UK) and Alexa Fluor 594 goat anti-rabbit IgG (1:200) (Invitrogen). To improve antibody performance, sections were subjected to heat-mediated antigen retrieval in citrate buffer (10 mM citric acid, 0.05% Tween20, pH 6.0) for 20 min on a water bath at 100° C. Stained sections were mounted in ProLong® Gold Antifade Reagent with DAPI (Invitrogen) and analysed with a confocal microscope as before (all Zeiss). GFP-positive basal cells (identification based on morphology and location within the epithelial layer) were quantified on a total of 13 sections/mouse. Sections that displayed putative GFP positive basal cells were selected for double staining with the anti-KRT5 and anti-GFP antibodies to confirm the basal cell phenotype.

Example 11: Transduction of ALI Cultures

Fully differentiated airway epithelial cells grown as ALI cultures were purchased from Epithelix (Geneva, Switzerland). ALIs were transfected with F/HN-SIV-lux at a multiplicity of infection ranging from ~25 to ~300 TU/cell. After 6 hours, the virus was removed and ALIs were incubated for 10-26 days. The basolateral medium was changed every 48 hours during this incubation period. At specified time points, the ALIs were lysed in 100 μl reporter lysis buffer and luciferase expression was quantified using the Luciferase Assay System (Promega, Southampton, UK) according to the manufacturer's instructions. The total protein content of the cultures was quantified using the BioRad protein assay kit (BioRad, Hemel Hempstead, UK). Each sample was assayed in duplicate. Luciferase expression was then presented as relative light units/mg total protein. For bioluminescence imaging 100 μg luciferin in PBS were added to the apical membrane.

As shown in FIG. 7, cells in ALI cultures were successfully transduced with F/HN-SIV-Lux, as evidenced by luciferase expression. Luciferase expression was greater at MOI 250 compared with MOI 25.

Example 12: Iodide Efflux Assay

HEK293T cells were transfected with F/HN-SIV-GFP-CFTR or an F/HN-SIV-GFP control virus at a multiplicity of infection of 500 TU/cell and cultured for 2 days. CFTR chloride channel activity was assayed by measuring the rate of $^{125}$iodide efflux as previously described (Derand, R., et al., 2003). The $^{125}$iodide efflux rates were normalized to the time of forskolin/IBMX addition (time 0). Curves were constructed by plotting rates of $^{125}$iodide efflux against time. To reflect the cumulative levels of $^{125}$iodide efflux following agonist-stimulation, all comparisons are based on areas under the time-$^{125}$iodide efflux curves. The area under the curve was calculated by the trapezium rule. Experiments were carried out in duplicate (n=6 wells/group/experiment).

As shown in FIG. 8, F/HN-SIV can direct functional CFTR expression, with a relative $^{125}$iodide efflux of 0.65. In contrast, the GL67A plasmid vector achieved a lower $^{125}$iodide efflux value of 0.33.

Example 13: Transduction of Sheep and Human Primary Lung Cells and Mouse Lung F/HN-SIV efficiently transduces sheep & human primary lung cells and mouse lung.

Figure 9:
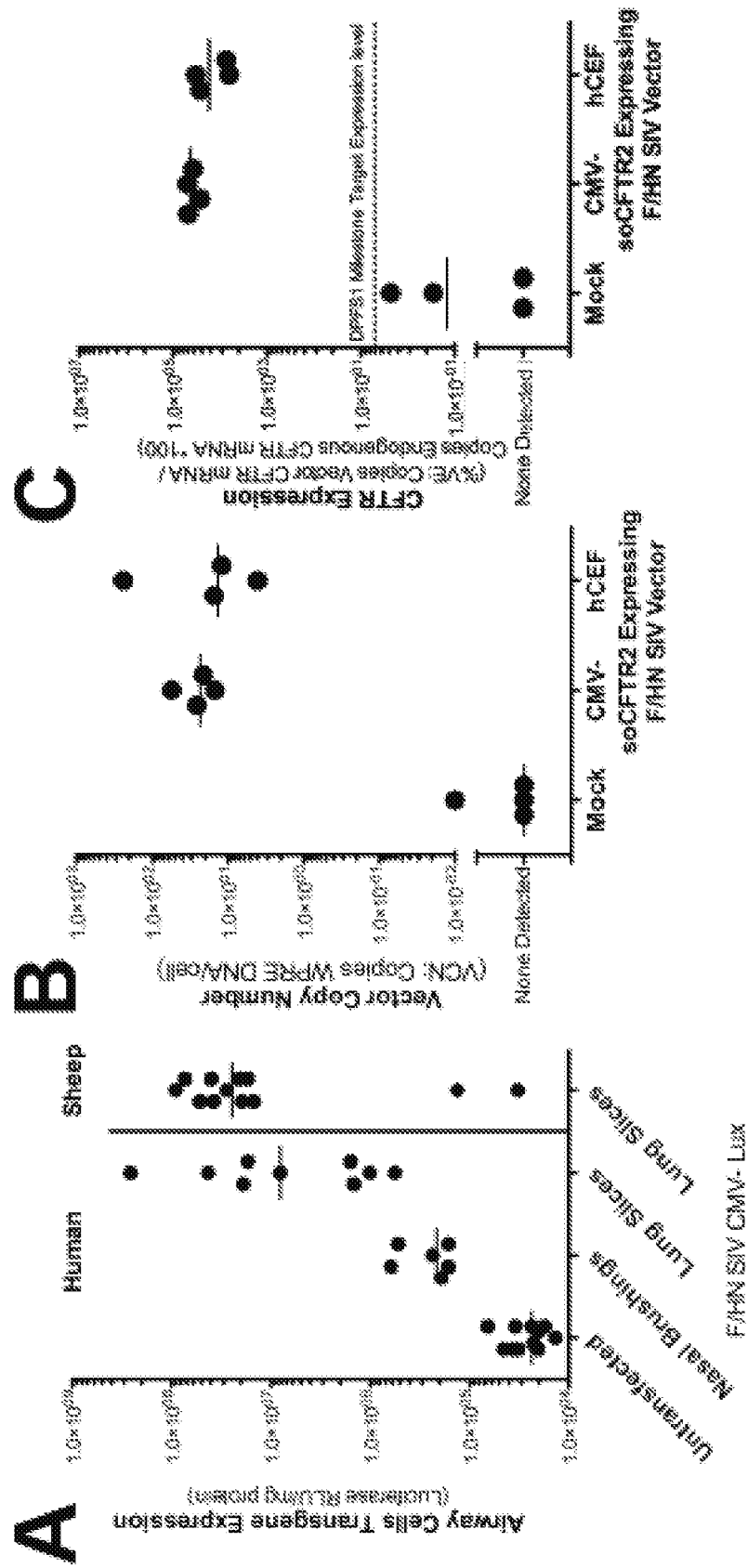
FIG. 9 exhibits that F/HN-SIV efficiently transduces sheep & human primary lung cells and mouse lung.
Figure 9:
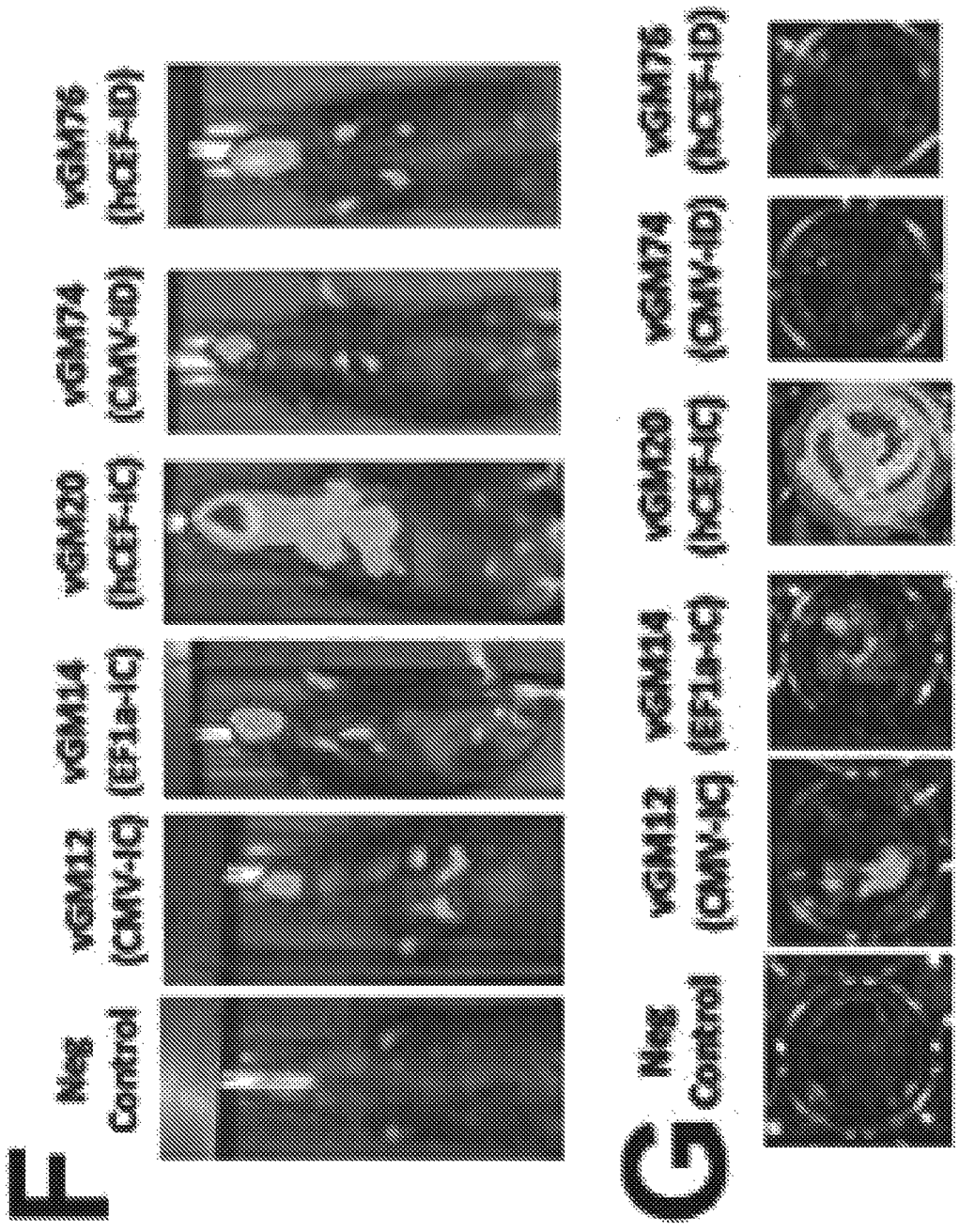
Figure 9:
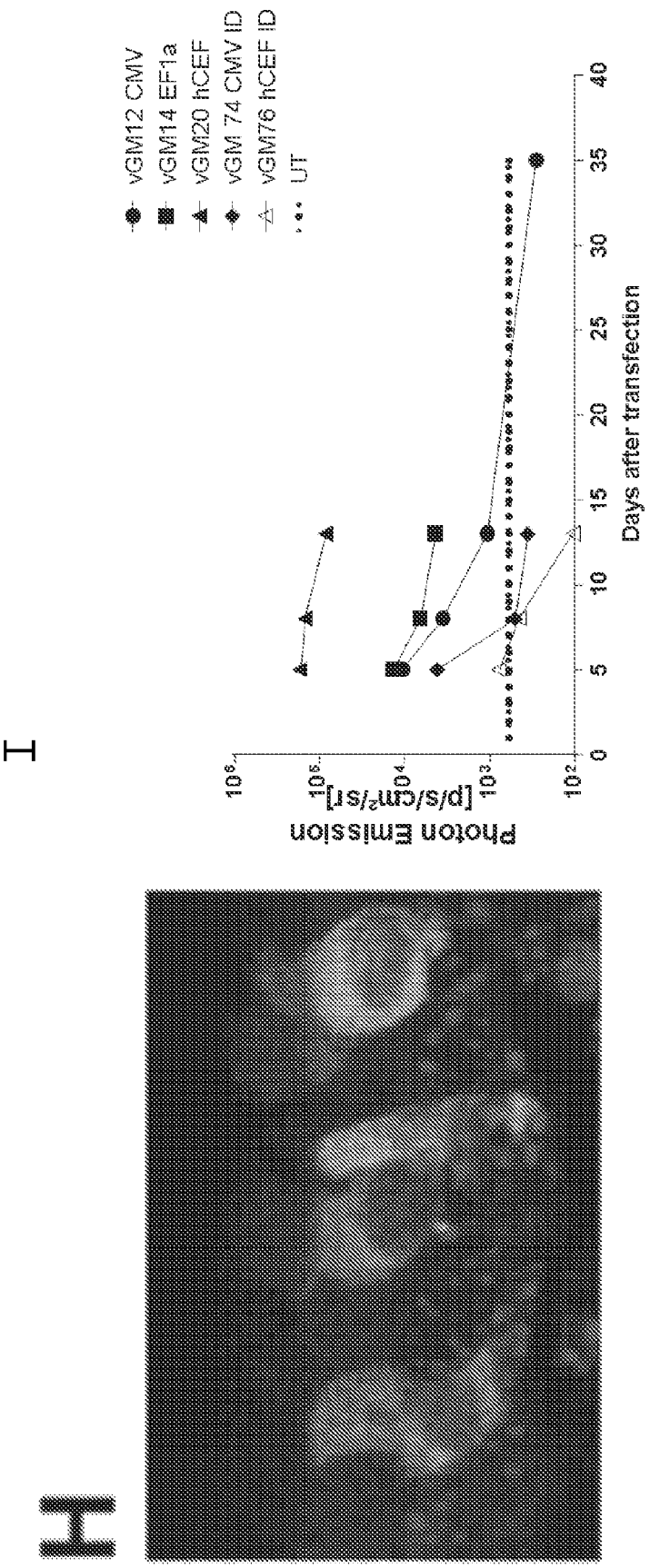

F/HN-SIV-CMV-Lux was used to transduce human nasal brushings (MOI 250) and human and sheep lung slices cultured ex vivo ($1 \times 10^7$ TU/slice). As shown in FIG. 9A, transduction of both the human nasal brushing cells and human and sheep lung slices resulted in substantial luciferase transgene expression (average values in the region of $2 \times 10^2$ RLU/mg protein for the human nasal brushings, $1 \times 10^7$ RLU/mg protein for the human lung slices and $2 \times 10^7$ RLU/mg protein for the sheep lung slices) 24-48 hours post-transduction.

Primary human CF lung cells cultured at the air-liquid interface (CF hALIs, $\sim 1 \times 10^5$) were transduced with ($3 \times 10^7$ TU) F/HN-SIV-soCFTR2 vectors containing CMV- and hCEF transgene promoters. Vector copy number (copies of pro-viral DNA per copy of endogenous CFTR DNA) was measured at 6-8 days post-transduction. Both the CMW and hCEF promoters were able to achieve a vector copy number of at least $1 \times 10^1$ (FIG. 9B).

CFTR mRNA expression level (% VE: copies of CFTR mRNA per copy of endogenous CFTR mRNA×100) at 6-8 days post-transduction was also measured. The horizontal dotted line in FIG. 9C represents a target expression level of 5% VE, which is thought to represent the therapeutic threshold. Both the F/HN-SIV-soCFTR-CMV and F/HN-SIV-soCFTR2-hCEF induced expression significantly above this target (in the region of 40583±10687 and 18509±13588 respectively, mean±SD, n=4).

Following in vivo delivery of F/HN-SIV-EGFPLux vectors containing CMV, EF1a and hCEF promoters in integrase defective (ID) or integrase competent form (IC or no label) airway cells transgene expression was determined in the nasal (FIG. 9D) and lung (FIG. 9E) murine epithelium (n=6-10/group). The time course of luciferase transgene expression was monitored by repeated in vivo bioluminescence imaging and was normalised to delivered dose. Four of the five vectors tested (vGM012 CMW, vGM014 EF1a, vGM020 hCEF and vGM076 hCEF ID) achieved expression in the nose above the target level for the whole time course of the experiment. The fifth vector, vGM074 CMV ID, achieved expression in the nose above the accepted expression level for the whole time course of the experiment.

Two of the five vectors tested (vGM014 EF1a and vGM020 hCEF) achieved expression in the lung above the target level for the whole time course of the experiment. One vector, vGM012 CMW, achieved expression in the lung above the accepted expression level for the whole time course of the experiment.

Bioluminescence was detected following in vivo murine transduction at day 14 post transduction. Representative images are shown in FIG. 9F. The vGM020 hCEF vector achieved the highest level of in vivo expression out of the five vectors tested.

Bioluminescence was also detected following in vitro transduction of non-CF hALI at day 5-6 post transduction. Representative images are shown FIG. 9G. Again, the vGM020 hCEF vector achieved the highest level of expression out of the five vectors tested.

FIG. 9H shows EGFP expression at 14 days post transduction in the murine nasal epithelium following delivery of $1.6 \times 10^8$ TU of F/HN-SIV-hCEF-EGFPLux (vGM020), as visualised by immunohistochemistry (nuclei stained with DAPI).

The time-course of luciferase transgene expression in non-CF ALIs was monitored by repeated bioluminescence imaging and was normalised to the delivered dose. As shown in FIG. 9I, the vGM014 EF1a and vGM020 hCEF vectors achieved the highest level of expression.

F/HN-SIV also efficiently transduces sheep lung in vivo. Acriflavine was instilled ($3 \times 100$ μL aliquots over ~5 minutes) to a proximal airway under direct bronchoscopic visualisation. The distribution of the acriflavine can be appreciated by the orange colouration of the dissected airway at postmortem (FIG. 10A).

The acriflavine was largely restricted to the conducting airways and absent from the alveolar regions. The arrow in FIG. 10A indicates the approximate site of instillation. The numbers on the ruler are in cm.

Figure 10:
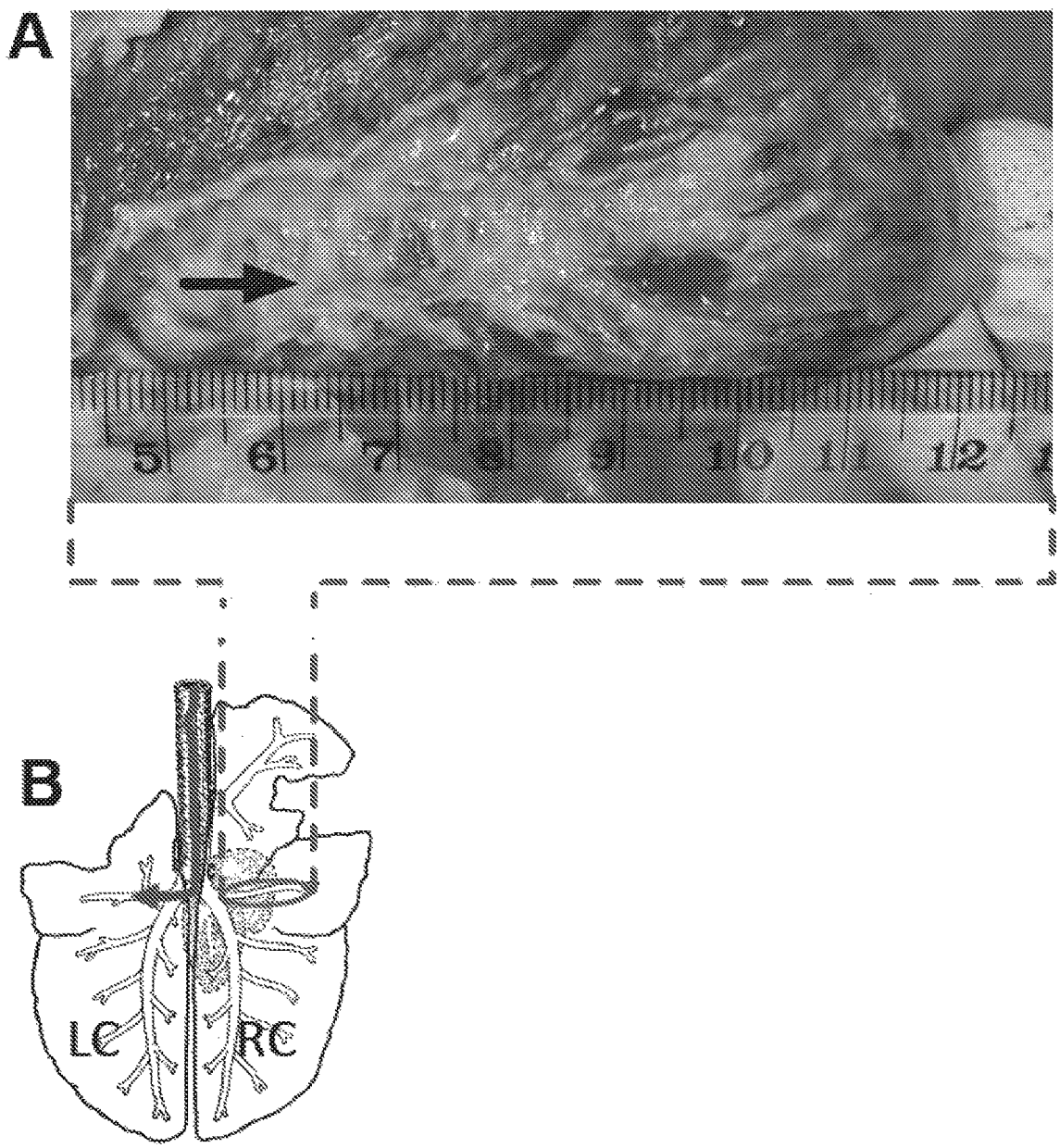
FIG. 10 shows that F/HN-SIV efficiently transduces sheep lung in vivo. Figure A shows that to model virus delivery to the sheep lung, we instilled (3×100 μL aliquots over ~5 minutes) acriflavine to a proximal airway under direct bronchoscopic visualisation. The distribution of the acriflavine can be appreciated by the orange colouration of the dissected airway at postmortem. Note the acriflavine is largely restricted to the conducting airways and absent from the alveolar regions. Arrow indicates the approximate site of instillation. Numbers on ruler are cm.
Figure 10:
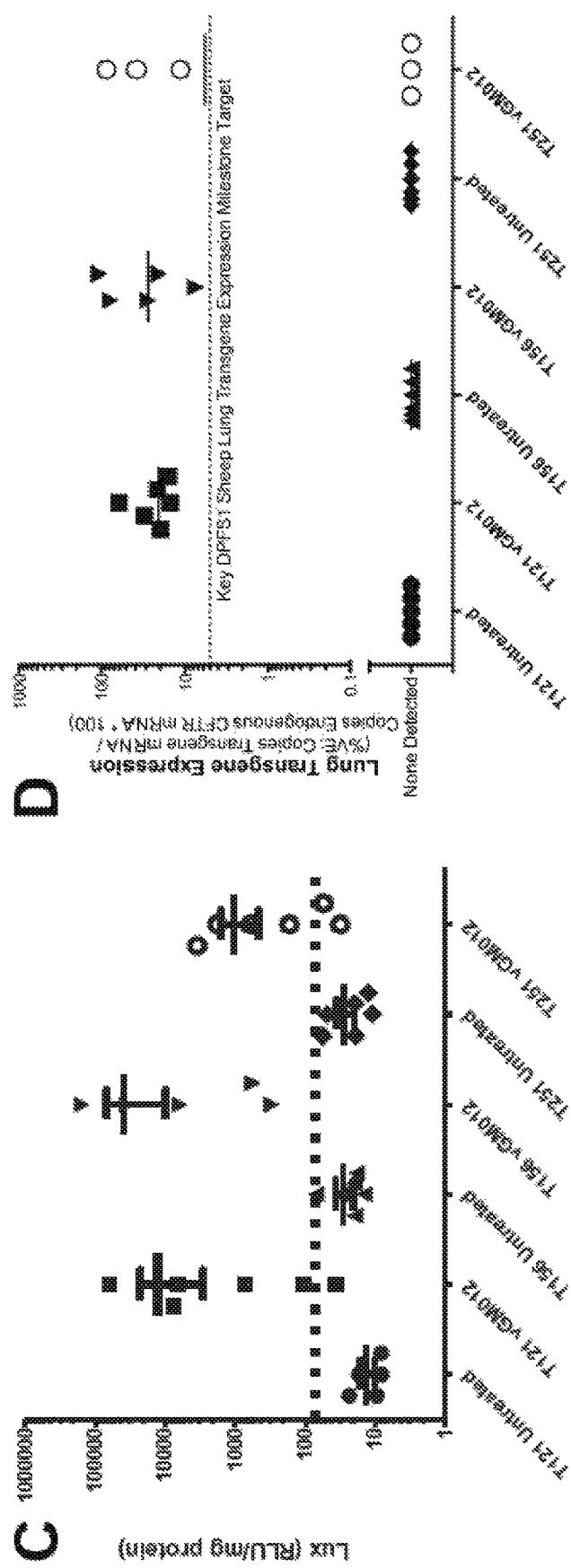
Figure 11:
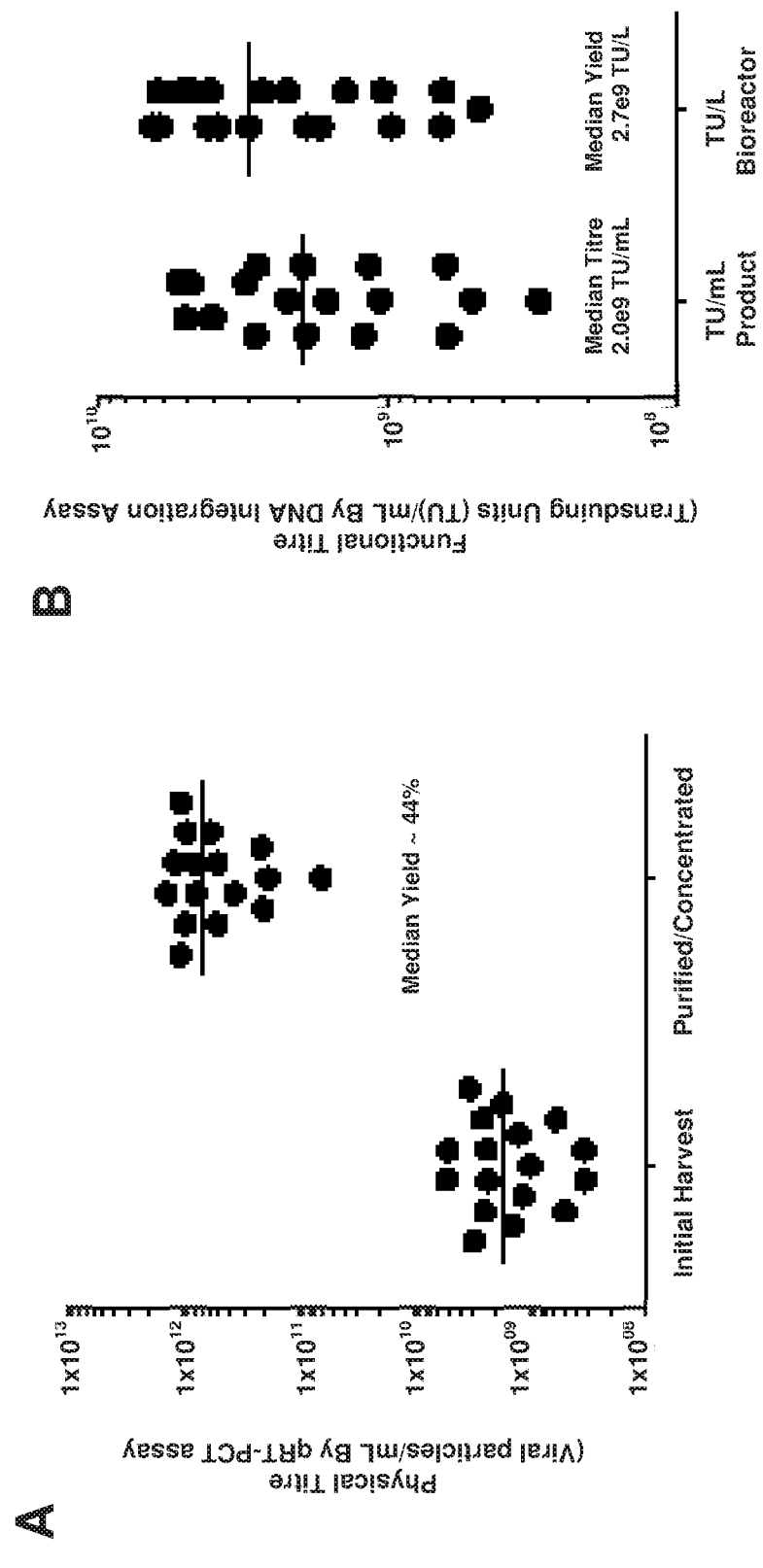
FIG. 11 depicts the production and purification of F/HN SIV Vectors. F/HN SIV Vectors were produced by 5 plasmid (pDNA) PEI-mediated transient transfection of 293T cells grown in suspension at 1 L scale in pH controlled WAVE Bioreactors (GE), using scalable methods of the invention. Vectors were clarified by depth/end-filtration (GE/Pall), contaminating nucleic acids were removed with Benzonase® (Merck), vectors were activated with TrypLE Select™ (Life Technology), purified and concentrated by anion exchange membrane chromatography (Pall) and tangential-flow filtration (Spectrum). All process vessels, containers and columns were single-use cGMP compliant. All reagents except plasmid DNA were animal-free cGMP compliant. Data from a variety of vector configurations (transgene promoter, transgene, integrase status) are shown. Physical and functional titres were determined using Q-PCR. (A) Physical titre from initial clarified harvest and final purified product. Median process yield is ~44%. (B) Functional titre of final product. Median functional titre is $~2\times10^9$ TU/mL product and $~3\times10^9$ TU/L bioreactor volume. Target productivity and yields were exceeded. Lower yielding CFTR vectors utilise CMV transgene promoter. Higher yielding CFTR vectors utilise EF1aS and hCEF transgene promoters. (C) Final product particle: infectivity ratio is tightly clustered and similar to values from other high quality vector manufacturers (Oxford BioMedica, BlueBirdBio). Median particle: infectivity ratio is ~300. Product consistency has been achieved with the use of "Design of Experiments" methods supporting ultimate transition to QbD-based regulatory agency approval of manufacturing process. (D) Final product functional titre is strongly correlated with initial physical titre indicating non-saturating process conditions with no vector concentration limiting process steps—suggests purification scale-up will be efficient.
Figure 11:
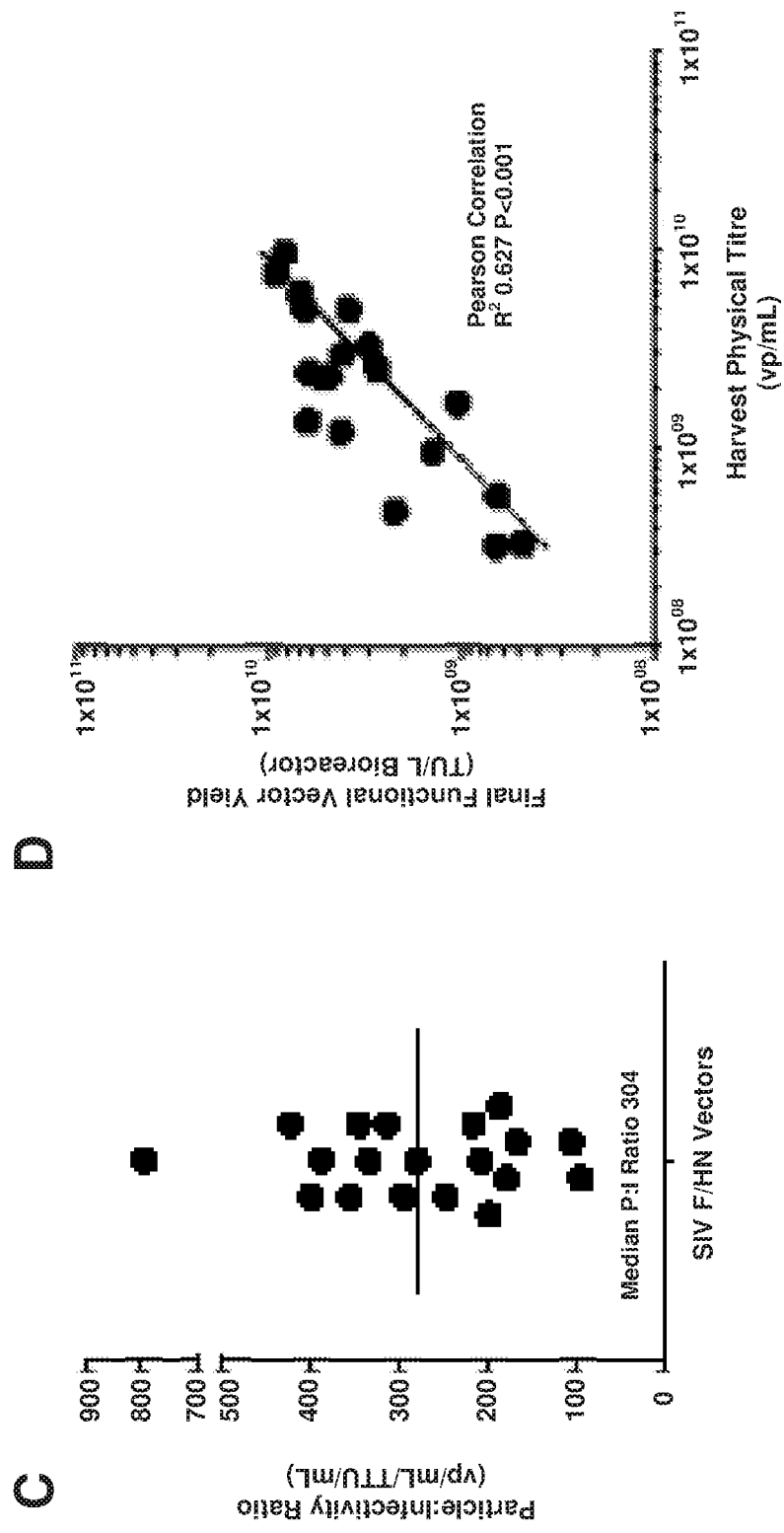

FIG. 10B is a diagrammatic representation of the sheep lung (trachea centre/top). The circle represents the region in (FIG. 10A). In FIG. 10B, the arrow indicates passage of bronchoscope to deliver $3 \times 100$ μL aliquots of 2.2E9 TU/mL (6.6E8 TU total) F/HN SIV CMV-EGFPLux to n=3 individual sheep (animal codes T121, T156 & T251). At seven days post-delivery, 5-6 tissue sample blocks were taken at post-mortem at ~1 cm intervals from the site of instillation.

The sample blocks were divided into 2-3 approximately equivalent samples and analysed for transgene expression, the results of which are shown in FIG. 10C as luciferase assays normalised to protein content; and In FIG. 10D as quantitative RT-PCR normalised to endogenous CFTR mRNA levels. The horizontal line in FIG. 10O represents the highest luciferase activity noted in any sample treated with a non-viral gene transfer vector, and in FIG. 10D the target expression level of 5% VE (thought to represent the therapeutic threshold, see above). For each treatment group the average was higher than the non-viral vector comparison (FIG. 10O), and also achieved expression above the target 5% VE threshold.

Figure 14:
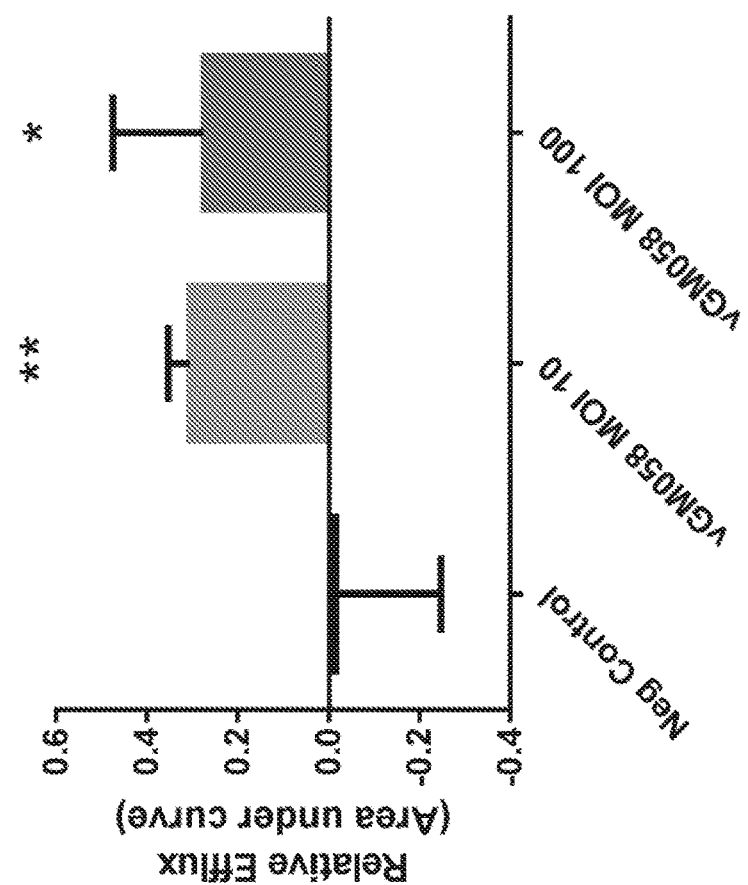
FIG. 14 shows the effect of transduction of human intestinal organoids with a CFTR lentiviral vector (vGM058) of the invention. The left-hand panel shows that forskolin induced swelling was significantly ($p<0.001$) reduced in vGM058 transduced organoids. In the right-hand panel, A549 cells were transduced with vGM058 or a control virus and CFTR function quantified using a radioactive iodide-efflux assay. Significant ($p<0.05$) levels of CFTR-mediated iodide efflux were detected in vGM058 transduced cells.
Figure 14:
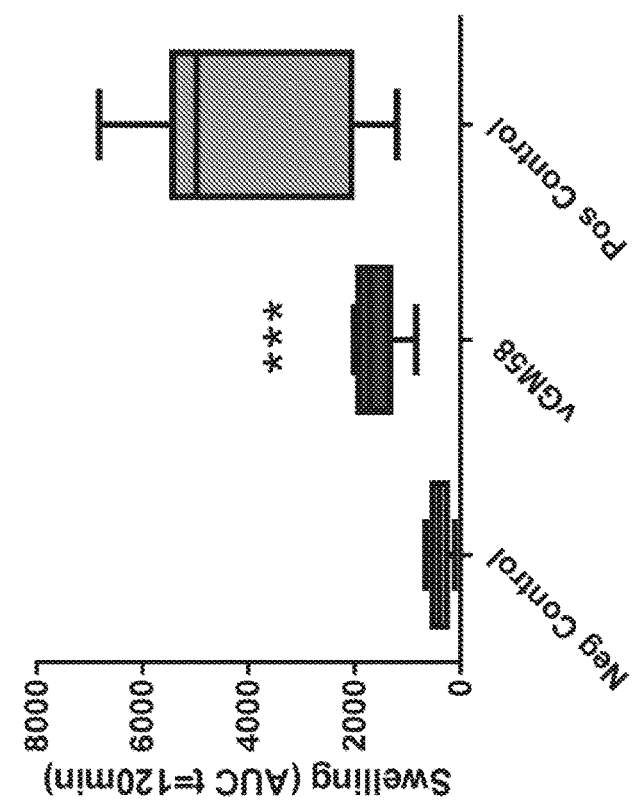

Example 14: CFTR Expression and Function Measured Using Human CF Intestinal Organoids Human CF intestinal organoids were generated as described by Dekkers J F et al, (Nature Medicine 2013, 19(7): 939-945). Briefly, intestinal biopsies were washed in EDTA containing solutions to dissociate crypt cells. Crypt cells were then transduced with vGM058 (approximately $1 \times 10^7$ transduction units) or a control virus (n=3 wells/condition) and embedded in Matrigel and allowed to form organoids for 3-4 days. CFTR function was assessed by exposing the organoids to forskolin (approximately 5 μM forskolin) which increases intracellular cAMP levels and thereby activates CFTR. In response the CFTR activation the organoids increase chloride transport which leads to water uptake and swelling. Organoids (minimum 10/well) were directly analysed by confocal live-cell microscopy (LSM710, Zeiss, ×5 objective). Forskolin-stimulated organoid swelling was automatically quantified using Volocity imaging software (Improvision). The total organoid area (xy plane) increase relative to that at t=0 of forskolin treatment was calculated and averaged. Forskolin induced swelling was significantly ($p<0.001$) increased in vGM058 transduced organoids compared to controls (see FIG. 14A). Significant levels of CFTR-mediated iodide efflux ($p<0.05$) were also detected in vGM058 transduced cells (FIG. 14B) using the iodide efflux assay disclosed herein (see Example 12).

Example 15: Generation of Lentiviral Vectors for A1AT

Lentiviral vectors were prepared using the SIV backbone and 5 plasmid method described above in Examples 2 and 3 (for the CFTR lentivirus) and using the hCEF promoter as described herein. Two separate lentiviral constructs were generated: one with a human alpha-1-antitrypsin (hAAT) transgene; one with a Gaussia luciferase (Glux) transgene (see FIGS. 15A and B, SEQ ID NOs: 9 and 10 respectively). The cDNAs contained within these vectors were codon-optimised and CpG-depleted.

Example 16: Air-Liquid Interface (ALI) Culture Using Lux Reporter Gene Lentiviral Vector Fully differentiated wild-type human ALI cultures (MuciIAir) were purchased from Epithelix SARL (Geneva, CH). ALIs were cultured at 37° C. and 5% $CO_2$ and the basolateral culture medium changed every 2-3 days. The culture medium was stored at −20° C. until further analysis.

ALIs were transduced (on day 0) by pipetting 100 µl of virus ($1 \times 10^7$ Taqman transfection units (TTU) onto the apical surface. The virus was removed after 4 hours incubation at 37° C., and the basolateral medium replaced.

At indicated timepoints post-transduction, the apical surface of the ALIs was washed by incubating with sterile PBS for one hour. The washings were removed and stored at −20° C. until further analysis.

A Gaussia luciferase assay (New England Biolabs, Ipswich, USA) was performed according to manufacturer's recommendations. 15 µl of sample was analysed in duplicate, and luminescence determined in an Appliskan plate reader. Glux expression was expressed as RLU/µl fluid (RUL=relative light units).

Figure 16:
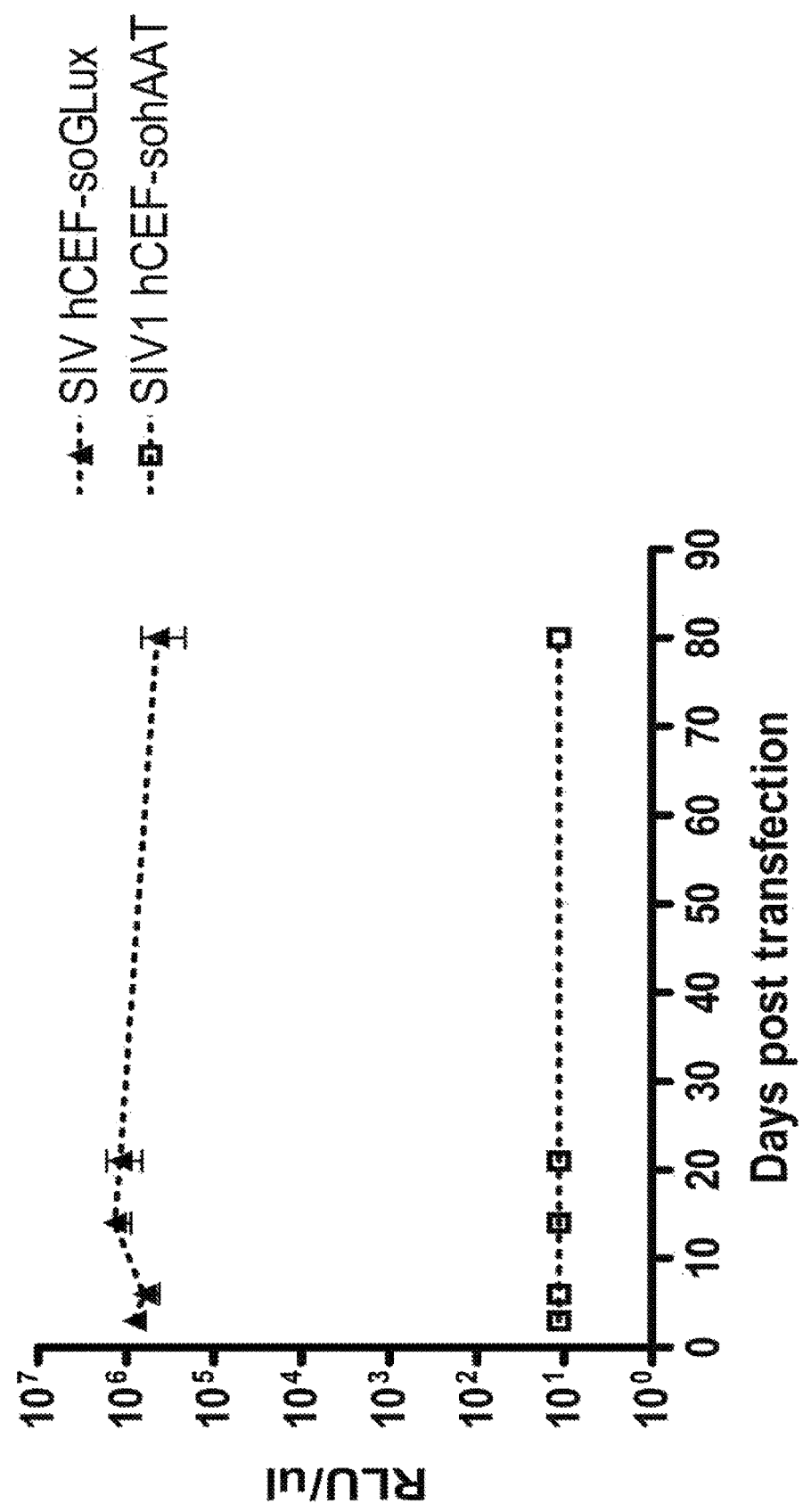
FIG. 16 shows that F/HN-SIV efficiently transduces human primary lung cells in ALI culture. In particular, transduction of human ALI cultures results in substantial luciferase transgene expression for at least 80 days post-transduction. Each point represents the mean value of RLU/µl in the media from n=6 ALIs at the timepoint shown. Vertical bars represent the standard error of the mean.

FIG. 16 provides the results, with each point representing the mean value of RLU/µl in the media from n=6 ALIs at the time point shown (standard error indicated by error bars).

Lentiviral-mediated gene transfer in human air-liquid interfaces resulted in the long-term expression of secreted reporter protein Gaussia luciferase.

Example 17: Transgene Expression in Lung Slice Cultures Using A1AT and Lux Reporter Gene Lentiviral Vectors Precision-cut human lung slices were prepared as described in Moreno L et al, Respir Res 2006 Aug. 21; 7:111. Lung slices were placed in 12-well tissue culture plates (1 slice per well) in 1 ml of media and incubated at 37° C. and 5% $CO_2$. The media was changed daily and stored at −20° C. until further analysis.

On day 0 lung slices (n=6 per group) were transduced with SIV hCEF-sogLux ($1 \times 10^6$ TTU) or SIV1 hCEF-sohAAT ($2 \times 10^6$ TTU) virus diluted in medium to a final volume of 1000 µl and incubated for 4 hours. After the incubation, medium was replaced and stored at −20° C. until further analysis.

Figure 17:
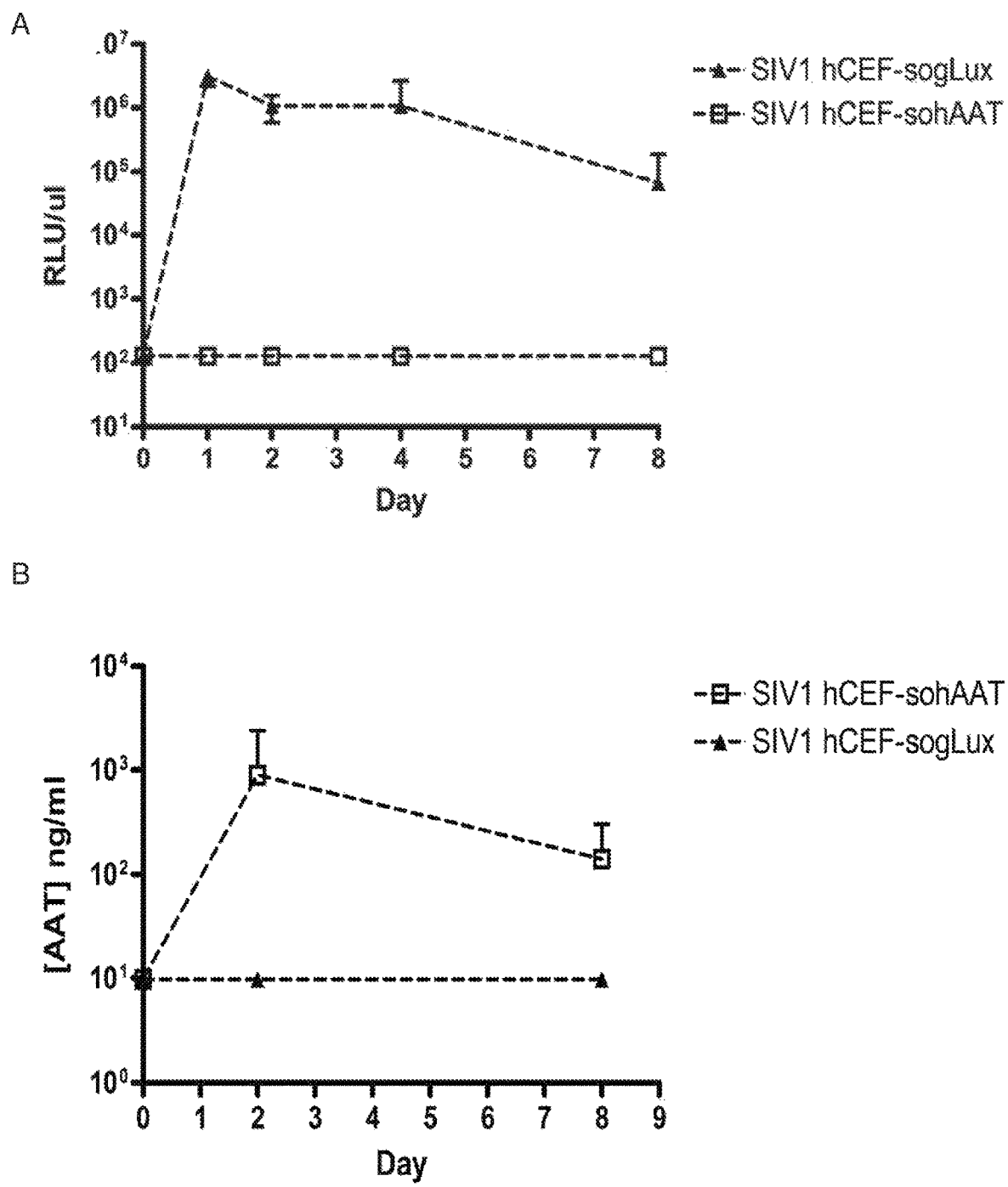
FIG. 17 shows gene expression following transduction of human lung slices (n=6 per group) with SIV1 hCEF-sogLux (FIG. 17A) and SIV1 hCEF-sohAAT (FIG. 17B). High levels of expression were observed. Each point represents the mean value of RLU/µl in the media from n=6 lung slices at the timepoint shown. Vertical bars represent the standard error of the mean.

Gaussia luciferase expression was determined as described above (Example 16). As shown in FIG. 17A, high levels of expression of secreted reporter protein Gaussia luciferase followed lentiviral-mediated gene transfer in human lung slices. AAT (also referred to herein as A1AT) expression was determined using a sandwich ELISA (Abcam, Cambridge, UK), performed according to the manufacturer's recommendations. 50 µl of sample was assayed in duplicate, and measured on a microplate reader at 450 nm.

As shown in FIG. 17B, high levels of expression of alpha-1-antitrypsin (AAT/A1AT) followed lentiviral-mediated gene transfer in human lung slices.

Example 18: In Vivo Administration of A1AT and Lux Reporter Gene Lentiviral Vectors to the Mouse Nose Mouse Lung Transduction:

Female C57BL/6 mice (Charles River, UK) were anaesthetised with isoflurane and given 100 ul of virus by nasal instillation as described in Xenariou S et al, Gene Ther 2007 May; 14(9): 768-75. Animals were given between 1 and 5 doses and observed daily for signs of toxicity.

For Gaussia luciferase, female C57BL/6 mice were anaesthetised on day 0 using isoflurane and given a single 100 ul dose of the SIV1 hCEF-soGLux virus ($1 \times 10^6$ TTU) by nasal instillation. Control animals were treated with DMEM (tissue culture medium), the main constituent of the viral preparation used in the study.

For A1AT, female C57bl/6 mice (n=5 per group) were treated with 3 doses of SIV1 hCEF-sohAAT at 10-day intervals (100 µl per dose, $6.8 \times 10^7$ TTU; total dose $2.4 \times 10^8$ TTU). Control animals were instilled with 100 ul of sterilised PBS (the main constituent of the lentivirus production batch used in the study) at each dosing point.

10 days after the third dose, animals were sacrificed and lung tissue homogenate, broncho-alveolar lavage fluid and serum analysed for AAT expression.

In addition, long term expression of A1AT was investigated. On days 1 to 5 of the experiment, C57bl/6 mice were treated with 100 µl of SIV1 hCEF-sohAAT by nasal instillation (5 doses of $4 \times 10^5$ TTU, i.e. $2 \times 10e^6$ TTU per animal in total). Control animals were instilled with 100 ul of DMEM (tissue culture medium), the main constituent of the lentivirus production batch used in the study. Animals were sacrificed at various timepoints post-transduction and lung tissue homogenate, broncho-alveolar lavage fluid and serum were analysed for AAT expression.

Mouse Tissue Collection:

Mice were sacrificed at the indicated time-points post transduction. Blood was collected by puncturing the left ventricle, and centrifuged at 760 $g_{av}$ for 10 minutes to prepare serum. Serum was subsequently frozen at −80° C.

A bronco-alveolar lavage (BAL) was performed by dissecting the neck, inserting a cannula into the trachea and securing it in place with suture thread. 500 µl of PBS was instilled into the lung, and aspirated three times to obtain thorough washing of the epithelial lining. The sample was immediately snap frozen in liquid nitrogen, and stored at −80° C. for further analysis.

Lungs were then dissected and snap-frozen in liquid nitrogen, and subsequently homogenised in lysing matrix D tubes (MP Biomedicals), centrifuged in a FastPrep machine (ThermoFisher Scientific, Waltham, Mass., USA) at 4 m/s for 45 seconds, and stored at −80° C. for further analysis.

Figure 18:
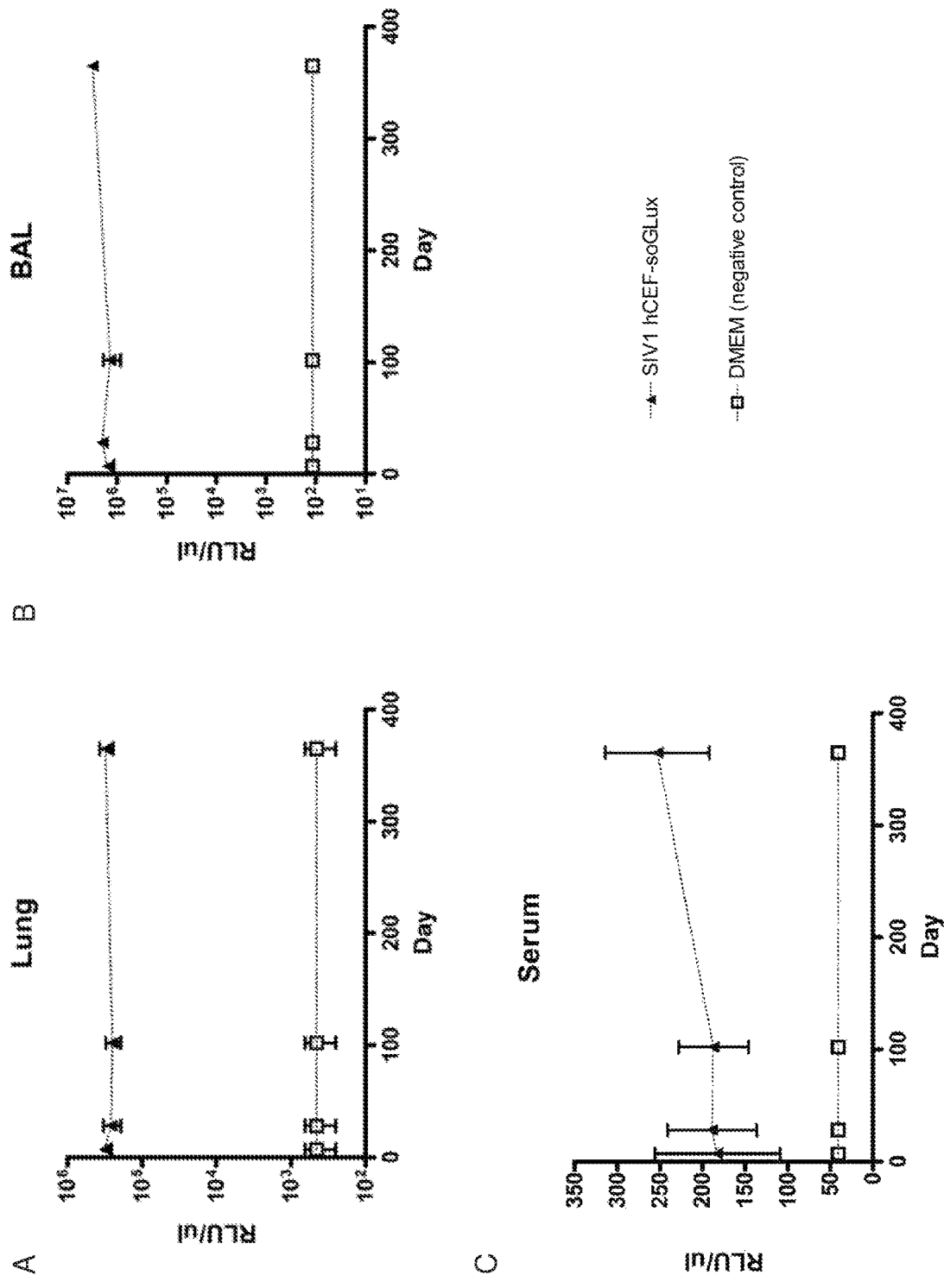
FIG. 18 shows long term expression (>12 months) of Gaussia luciferase following lentiviral-mediated gene transfer (SIV1 hCEF-soGLux) in vivo. A: lung tissue homogenate; B: broncho-alveolar lavage (BAL) fluid; C: serum. Each point represents the mean value of RLU/µl in one group of animals (n=5 or 6 per group) harvested at the timepoint shown. Vertical bars represent standard error of the mean.

AAT (A1AT) and Gaussia luciferase (Glux) expression was determined as described in Examples 16 and 17 above. In vivo transduction of mouse airway cells with a single dose of the lux reporter gene lentiviral vector of Example 15 resulted in long-term expression (at least 12 months) of the secreted reporter protein Gaussia luciferase, in lung homogenate (FIG. 18A), bronco-alveolar lavage fluid (BAL, FIG. 18B) and serum (FIG. 18C).

Figure 19:
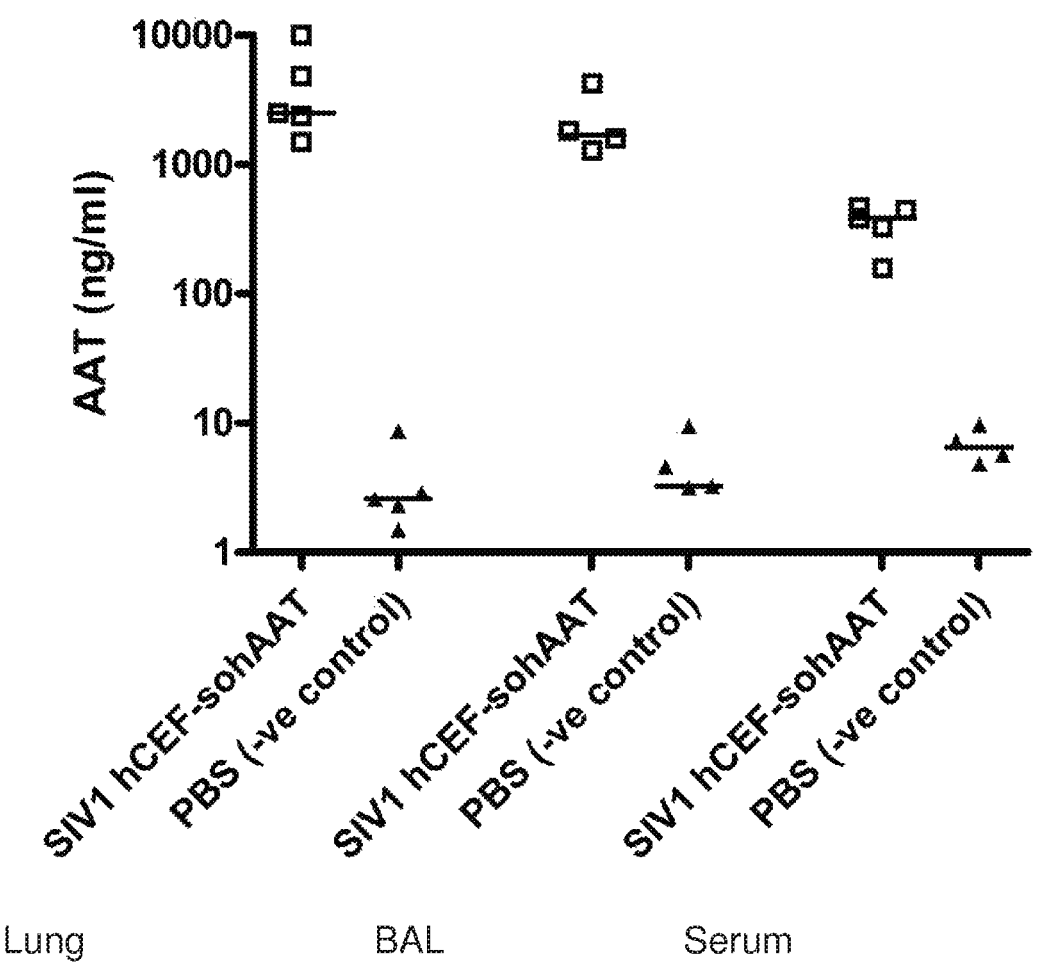
FIG. 19 shows high levels of expression of A1AT expression following lentiviral-mediated gene transfer (SIV1 hCEF-sohAAT) in vivo. Each point represents one animal. Horizontal bars represent the median of each group.

High levels of expression of A1AT were observed in lung homogenate, BAL and serum following lentiviral-mediated transfer of the AAT (A1AT) gene in vivo (FIG. 19), with over a 100-fold increase in ATT (A1AT) expression in the lung homogenate and BAL observed compared with the corresponding negative (PBS) controls. A significant increase (at least one order of magnitude) in ATT (A1AT) expression was also observed in the serum.

Figure 20:
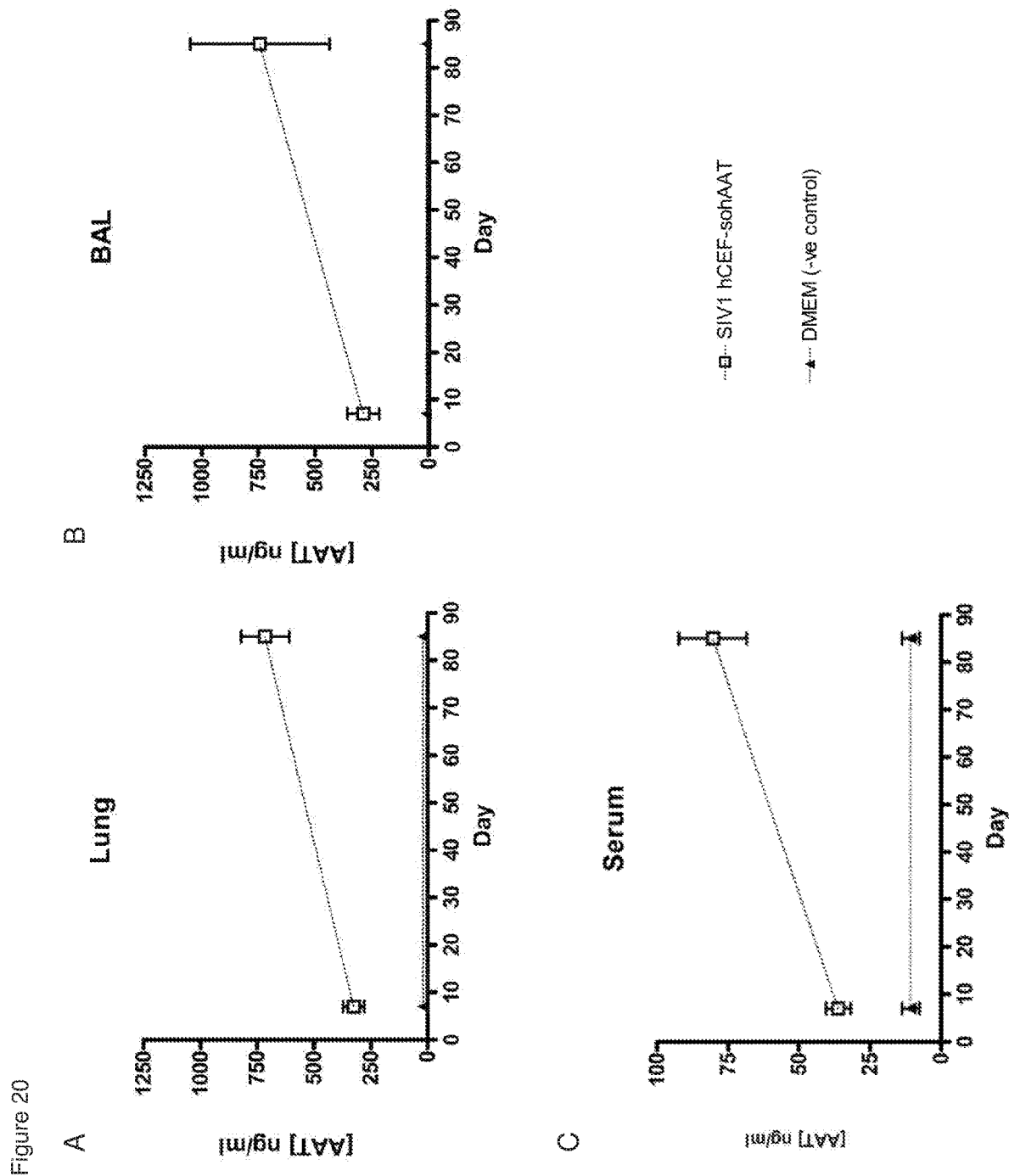
FIG. 20 shows long term expression of A1AT following lentiviral-mediated gene transfer of the AAT (A1AT) gene in vivo.

In addition, long-term expression (at least 90 days) of alpha-1-antitrypsin was observed in lung homogenate (FIG. 20A), BAL (FIG. 20B) and serum (FIG. 20C) following lentiviral-mediated gene transfer of the AAT (A1AT) gene in vivo.

Example 19: Urea Assay

C57bl/6 mice (n=5 per group) were treated with 3 doses of SIV1 hCEF-sohAAT at 10-day intervals (100 μl per dose, $6.8 \times 10^7$ TTU; total dose $2.4 \times 10^8$ TTU). Control animals were instilled with 100 ul of sterilised PBS (the main constituent of the lentivirus production batch used in the study) at each dosing point.

10 days after the third dose, animals were sacrificed and lung tissue homogenate, broncho-alveoloar lavage fluid and serum analysed for A1AT expression.

A urea assay (Abcam, Cambridge, UK) was performed according to the manufacturer's instructions.

Firstly, serial dilutions of murine serum and BAL fluid samples were prepared and analysed to determine the appropriate dilution to use in further experiments.

Secondly, corresponding serum and BAL fluid samples from single mice (n=14) were analysed to calculate the fold-difference between urea concentration in serum and BAL fluid, equivalent to the dilutional effect of BAL on epithelial lining fluid (as per Rennard SI et al, J Appl Physiol (1985). 1986 February; 60(2):532-8). The mean dilution of BAL was 41-fold (range 24-88).

Taking into account this dilutional effect, the concentration of ATT (A1AT) in the epithelial lining fluid was calculated. Specifically, the concentration of AAT in the broncho-alveolar lavage fluid was multiplied by the dilution factor, to provide an estimate of the 'true' AAT concentration in epithelial lining fluid.

Figure 21:
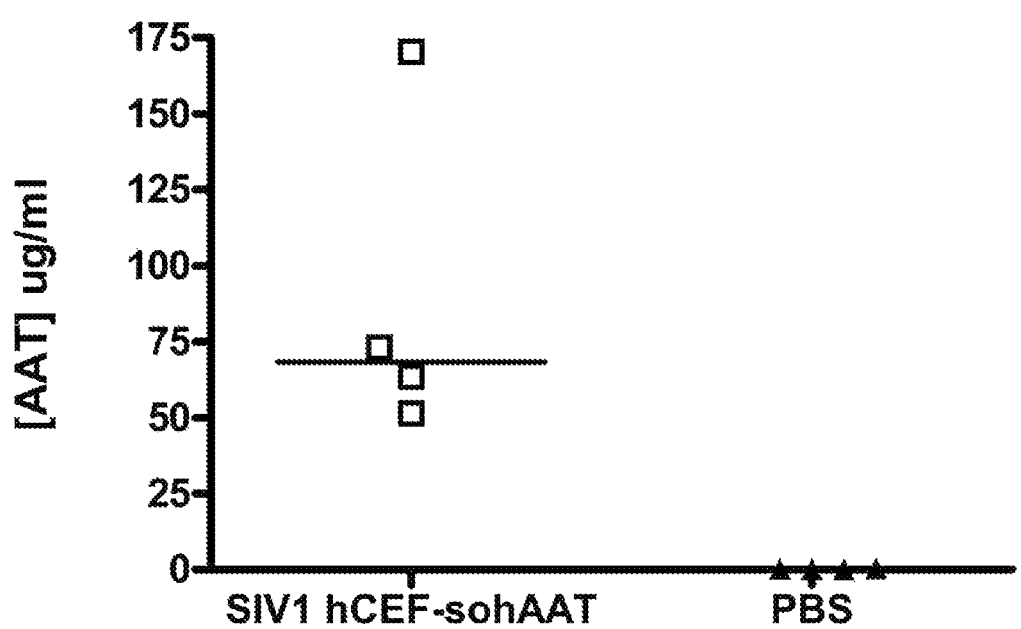
FIG. 21 shows the level of A1A1 in the epithelial lining fluid following lentiviral mediated gene transfer (SIV1 hCEF-sohAAT) in vivo. lentiviral mediated gene transfer (SIV1 hCEF-sohAAT) in vivo.

A "protective" target level of ATT (A1AT) in the epithelial lining fluid (ELF, i.e. the fluid lining the airways and airspaces in the lungs) is 70 μg/ml (compared with a "normal" target level of ATT (A1AT) in the ELF of 200 μg/ml). As shown in FIG. 21, therapeutic levels of alpha-1-antitrypsin in epithelial lining fluid followed ATT (A1AT) lentiviral-mediated gene transfer in vivo.

Example 20: Generation of Lentiviral Vectors for FVIII

Four different FVIII lentiviral vectors were prepared using the SIV backbone and 5 plasmid method described above in Examples 2 and 3 (for the CFTR lentivirus) and 15 (for the A1AT lentivirus). The promoter-transgene plasmids have SEQ ID NOs: 11 to 14 respectively.

The SIV sequence was identical to the CFTR constructs (Examples 2 and 3) except for the promoter and cDNA. The human cytomegalovirus promoter (CMV) or tissue specific hCEFI promoter/enhancer was used as indicated (FIG. 22) to drive expression of FVIII transgenes.

SIV-F/HN-FVIII-N6-co contained the wild type human FVIII cDNA from which the BDD domain has been deleted and replaced with codon optimised 226 amino acid 6N-glycosylation fragment.

SIV-FVIII-V3 contains the wild type human FVIII cDNA from which the 226 amino acid glycosylation site has been deleted and replaced with 17 amino acid peptide which expresses 6N-glycosylation triples within the B domain (McIntosh et al., Blood 2013 121(17); 3335-3344).

Example 21: Quantification of hFVIII Antigen and Activity Levels in In Vivo and In Vitro Models Human FVIII antigen levels in a murine model were quantified by enzyme-linked immunosorbent assay (ELISA) according to the manufacturer's protocol. Briefly, plasma, BAL and lung were analysed for the presence of FVIII antigen using Asserachrom (FVIII:Ag) Elisa (Stago Diagnostics, France).

Samples were diluted 1:2 and incubated on a mouse monoclonal anti-human factor VIII fragment-coated 96-well plate for 2 hours at room temperature. Following washing, anti-mouse secondary antibody coupled with peroxidase was added to the plate and incubation was carried out for 2 hours at RT. hFVIII:Ag levels were determined spectrophotometric at 450 nm using TMB substrate (data not shown).

Another ELISA assay was used to evaluate FVIII activity in an in vitro HEK293T model (FVIII:C, Affinity Biological, Canada). Supernatants were collected 48 and 72 hours after HEK293T transduction with SIV-F/HN-FVIII-N6 or SIV-F/HN-FVIII-N3. FVIII activity was evaluated by following the manufacturer's instructions using 50 μl supernatants assayed in duplicate. As a negative control the supernatant from untreated HEK293T cells was tested. hFVIII activity was calculated from a standard curve generated using a series of dilutions of normal human pooled plasma (13th British Standard for blood coagulation Factor VIII concentrate, Human; NIBSC).

HEK293T cells were transduced with two different batches of vGM142 (Batch 1-$5.9 \times 10^8$ TTU/ml and Batch 2-$2.8 \times 10^8$ TTU/ml). HEK293T cells were transduced with vGM142 Batch 1 vector (FIG. 23A) and vGM142 Batch 2 vector (FIG. 23B) at 3 different MOIs (MOI 1; 10; 100), and collected 48 and 72 hours post-transduction.

Figure 23:
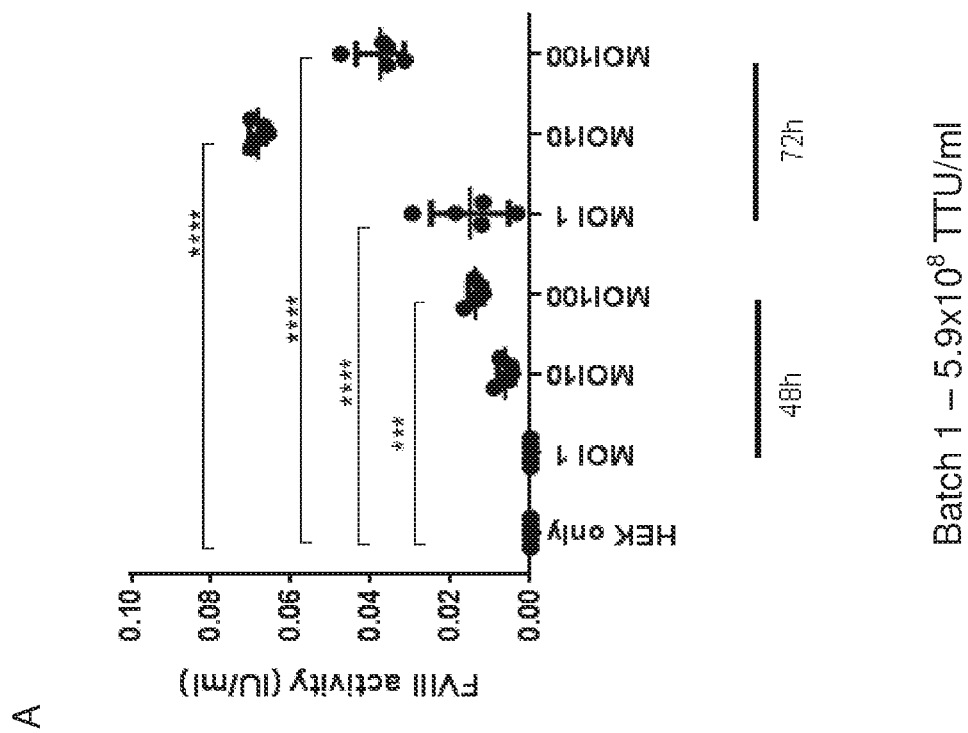
FIG. 23 shows HEK293T transduction efficiency with vGM142 (SIV-F/HN-FVIII-N6-co) for batch 1 (A) and batch 2 (B). The graphs show FVIII activity for each MOI at 48 and 72 hours post-transduction. Each symbol represents an independent experiment (n=5-6 experiments). The horizontal bar indicates group mean+/−SD. Analysis was performed using One-way Anova (GraphPad Prism) with multiple comparisons to untreated control $p<0.01$; *$p<0.001$; ****$p<0.0001$.

As is clear from FIG. 23, increasing FVIII activity was observed with increasing MOI for both Batch 1 and Batch 2 of vGM142 at both 48 and 72 hours post-transduction. Furthermore, FVIII activity increased from 48 hours to 72 hours for each MOI tested.

Example 22: In Vivo Administration of FVIII and Lux Reporter Gene Lentiviral Vectors to the Mouse Nose Mouse Lung Transduction:
All animal procedures were performed in accordance with the conditions and limitation of the UK Home Office Project and Personal licence regulations under the Animal Scientific Procedure Act (1986).

Wild type C57BL/6 female mice aged 6-8 weeks old (Charles River, UK were anaesthetised using isofluorane and given 100 μl of virus in Dulbecco's phosphate-buffered saline (D-PBS), as described previously (Griesenbach et al., 2012) and the presence of FVIII antigen was assessed.

In two experiments (Group 1 and 2) mice received 3 doses (every other day) of SIV-F/HN-FVIII-N6 (vGM142) and were culled 10 days after the first dose. Group 1 (n=4) were treated with a total vector dose of $1.4 \times 10^6$ TTU/mouse. Group 2 (n=3) were treated with a total vector dose of $1.57 \times 10^8$ TTU/mouse In one experiment (Group 3) mice were treated with 12 doses (every other day) of SIV-F/HN-FVIII-N6 (vGM142) and culled 28 days after the first dose. Group 3 (n=4) were treated with a total vector dose of $3.36 \times 10^8$ TTU/mouse)

Plasma, BAL fluid and Lung were collected (as described in Example 14). Briefly, the mice were sacrificed at the indicated time-points post transduction. Blood was then collected from heart into the 3.2 trisodium citrate anticoagulant collection tubes, before being centrifuged at 2000-2500×g to obtain plasma. BAL fluid was collected by applying 3 consecutive installations of PBS (500 µl) into mouse lung at room temperature. Supernatants were stored at −80° C. Lungs were collected and stored at −80° C. prior to tissue homogenisation.

The presence of FVIII expression was then assessed. FVIII levels were assessed in lung tissue homogenates (FIG. 24A), BAL fluid (FIG. 24B) and plasma (FIG. 24C) collected separately in 3 independent experiments at 10 and/or 28 days post SIV-F/HN-FVIII-N6 treatment. Analysis was performed using One-way Anova (GraphPad Prism) with multiple comparisons between treated groups (**** p<0.0001).

Figure 24:
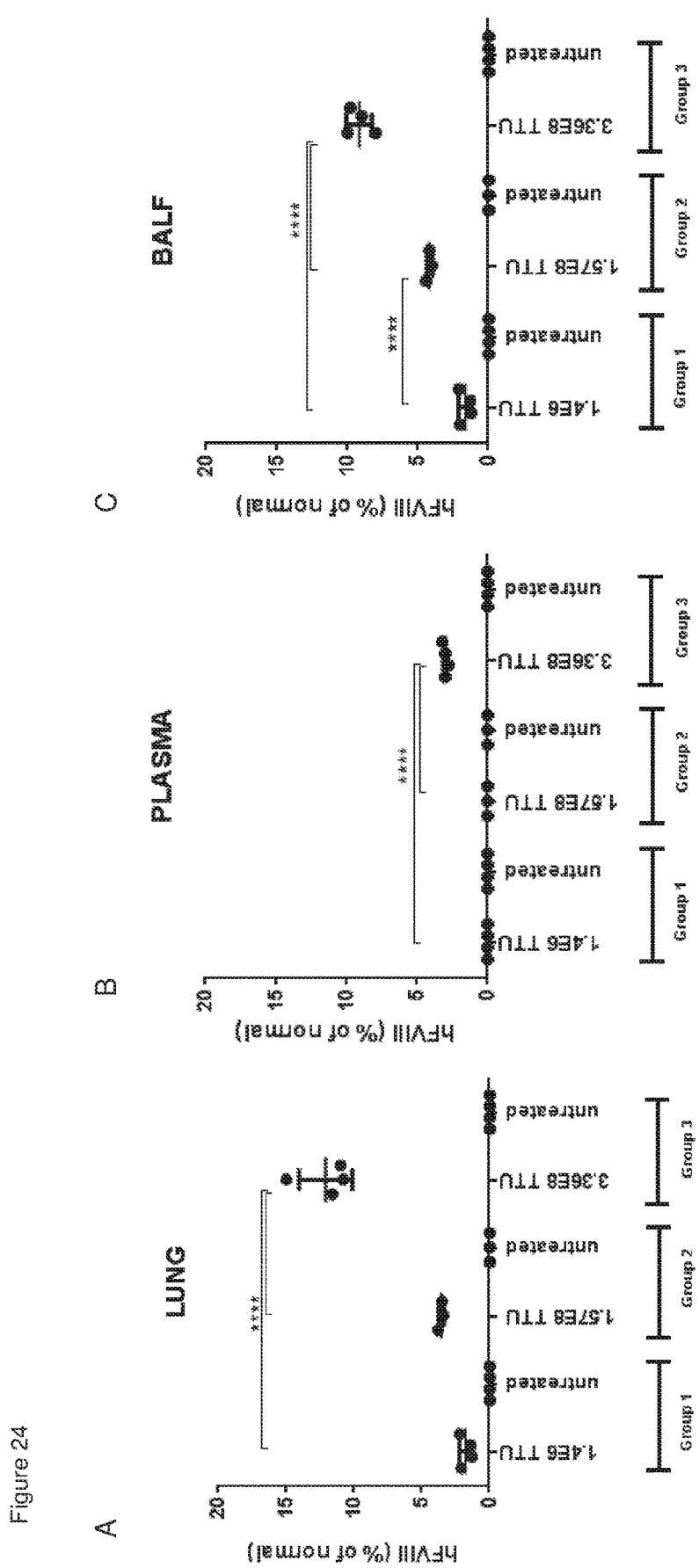
FIG. 24 shows the assessment of vGM142 in an in vivo system (murine model). A: lung; B: BAL fluid; C: plasma. The graphs show the level of hFVIII (as a percentage of the normal level) against the different treatments for Groups 1 to 3 (Groups 1 and 2-10 day treatment, 3 doses/week of 100 µl vector per mouse (total amount of doses was equal 3 per animal); Group 3-28 day treatment, 3 doses/week of 100 µl vector per mouse (total amount of doses was equal 12 per animal)). Each symbol represents an individual mouse (Group 1 (n=4) treated with total vector dose of $1.4 \times 10^6$ TTU/mouse; Group 2 (n=3) treated with total vector dose of $1.57 \times 10^8$ TTU/mouse and Group 3 (n=4) treated with total vector dose of $3.36 \times 10^8$ TTU/mouse). The horizontal bar indicates mean FVIII:Ag levels+/−SD. Analysis was performed using One-way Anova (GraphPad Prism) with multiple comparisons between treated groups ****$p<0.0001$.

As is clear from FIG. 24A, all three treatment groups produced an observable increase in hFVIII levels within the lung tissue compared with the corresponding control (D-PBS). The 28 day treatment of Group 3 resulted in a significant increase in hFVIII expression compared with the 10 day treatments of Groups 1 and 2. Similar results were observed for the BAL fluid samples (FIG. 24B), although in these

| Sequences |
|---|

SEQ ID NO: 1
```
   1 GGTACCTCAA TATTGGCCAT TAGCCATATT ATTCATTGGT TATATAGCAT
     AAATCAATAT
  61 TGGCTATTGG CCATTGCATA CGTTGTATCT ATATCATAAT ATGTACATTT
     ATATTGGCTC
 121 ATGTCCAATA TGACCGCCAT GTTGGCATTG ATTATTGACT AGTTATTAAT
     AGTAATCAAT
 181 TACGGGGTCA TTAGTTCATA GCCCATATAT GGAGTTCCGC GTTACATAAC
     TTACGGTAAA
 241 TGGCCCGCCT GGCTGACCGC CCAACGACCC CCGCCCATTG ACGTCAATAA
     TGACGTATGT
 301 TCCCATAGTA ACGCCAATAG GGACTTTCCA TTGACGTCAA TGGGTGGAGT
     ATTTACGGTA
 361 AACTGCCCAC TTGGCAGTAC ATCAAGTGTA TCATATGCCA AGTCCGCCCC
     CTATTGACGT
 421 CAATGACGGT AAATGGCCCG CCTGGCATTA TGCCCAGTAC ATGACCTTAC
     GGGACTTTCC
 481 TACTTGGCAG TACATCTACG TATTAGTCAT CGCTATTACC ATGGTGATGC
     GGTTTTGGCA
 541 GTACACCAAT GGGCGTGGAT AGCGGTTTGA CTCACGGGGA TTTCCAAGTC
     TCCACCCCAT
 601 TGACGTCAAT GGGAGTTTGT TTTGGCACCA AAATCAACGG GACTTTCCAA
     AATGTCGTAA
 661 CAACTGCGAT CGCCCGCCCC GTTGACGCAA ATGGGCGGTA GGCGTGTACG
     GTGGGAGGTC
 721 TATATAAGCA GAGCTCGCTG GCTTGTAACT CAGTCTCTTA CTAGGAGACC
     AGCTTGAGCC
 781 TGGGTGTTCG CTGGTTAGCC TAACCTGGTT GGCCACCAGG GGTAAGGACT
     CCTTGGCTTA
 841 GAAAGCTAAT AAACTTGCCT GCATTAGAGC TTATCTGAGT CAAGTGTCCT
     CATTGACGCC
 901 TCACTCTCTT GAACGGGAAT CTTCCTTACT GGGTTCTCTC TCTGACCCAG
     GCGAGAGAAA
 961 CTCCAGCAGT GGCGCCCGAA CAGGGACTTG AGTGAGAGTG TAGGCACGTA
     CAGCTGAGAA
1021 GGCGTCGGAC GCGAAGGAAG CGCGGGTGC GACGCGACCA AGAAGGAGAC
     TTGGTGAGTA
1081 GGCTTCTCGA GTGCCGGGAA AAAGCTCGAG CCTAGTTAGA GGACTAGGAG
     AGGCCGTAGC
1141 CGTAACTACT CTTGGGCAAG TAGGGCAGGC GGTGGGTACG CAATGGGGGC
     GGCTACCTCA
1201 GCACTAAATA GGAGACAATT AGACCAATTT GAGAAAATAC GACTTCGCCC
     GAACGGAAAG
1261 AAAAAGTACC AAATTAAACA TTTAATATGG GCAGGCAAGG AGATGGAGCG
     CTTCGGCCTC
1321 CATGAGAGGT TGTTGGAGAC AGAGGAGGGG TGTAAAAGAA TCATAGAAGT
     CCTCTACCCC
1381 CTAGAACCAA CAGGATCGGA GGGCTTAAAA AGTCTGTTCA ATCTTGTGTG
     CGTGCTATAT
1441 TGCTTGCACA AGGAACAGAA AGTGAAAGAC ACAGAGGAAG CAGTAGCAAC
     AGTAAGACAA
1501 CACTGCCATC TAGTGGAAAA AGAAAAAAGT GCAACAGAGA CATCTAGTGG
     ACAAAAGAAA
1561 AATGACAAGG GAATAGCAGC GCCACCTGGT GGCAGTCAGA ATTTTCCAGC
     GCAACAACAA
1621 GGAAATGCCT GGGTACATGT ACCCTTGTCA CCGCGCACCT TAAATGCGTG
     GGTAAAAGCA
1681 GTAGAGGAGA AAAATTTGG AGCAGAAATA GTACCCATTT TTTTGTTTCA
     AGCCCTATCG
1741 AATTCCCGTT TGTGCTAGGG TTCTTAGGCT TCTTGGGGGC TGCTGGAACT
     GCAATGGGAG
1801 CAGCGGCGAC AGCCCTGACG GTCCAGTCTC AGCATTTGCT TGCTGGGATA
     CTGCAGCAGC
1861 AGAAGAATCT GCTGGCGGCT GTGGAGGCTC AACAGCAGAT GTTGAAGCTG
     ACCATTTGGG
1921 GTGTTAAAAA CCTCAATGCC CGCGTCACAG CCCTTGAGAA GTACCTAGAG
     GATCAGGCAC
1981 GACTAAACTC CTGGGGGTGC GCATGGAAAC AAGTATGTCA TACCACAGTG
     GAGTGGCCCT
2041 GGACAAATCG GACTCCGGAT TGGCAAAATA TGACTTGGTT GGAGTGGGAA
     AGACAAATAG
2101 CTGATTTGGA AAGCAACATT ACGAGACAAT TAGTGAAGGC TAGAGAACAA
     GAGGAAAAGA
2161 ATCTAGATGC CTATCAGAAG TTAACTAGTT GGTCAGATTT CTGGTCTTGG
     TTCGATTTCT
2221 CAAAATGGCT TAACATTTTA AAAATGGGAT TTTTAGTAAT AGTAGGAATA
     ATAGGGTTAA
2281 GATTACTTTA CACAGTATAT GGATGTATAG TGAGGGTTAG GCAGGGATAT
     GTTCCTCTAT
```

| | Sequences |
|---|---|
| 2341 | CTCCACAGAT CCATATCCGC GGCAATTTTA AAAGAAAGGG AGGAATAGGG GGACAGACTT |
| 2401 | CAGCAGAGAG ACTAATTAAT ATAATAACAA CACAATTAGA AATACAACAT TTACAAACCA |
| 2461 | AAATTCAAAA AATTTTAAAT TTTAGAGCCG CGGAGATCTG TTACATAACT TATGGTAAAT |
| 2521 | GGCCTGCCTG GCTGACTGCC CAATGACCCC TGCCCAATGA TGTCAATAAT GATGTATGTT |
| 2581 | CCCATGTAAT GCCAATAGGG ACTTTCCATT GATGTCAATG GGTGGAGTAT TTATGGTAAC |
| 2641 | TGCCCACTTG GCAGTACATC AAGTGTATCA TATGCCAAGT ATGCCCCCTA TTGATGTCAA |
| 2701 | TGATGGTAAA TGGCCTGCCT GGCATTATGC CCAGTACATG ACCTTATGGG ACTTTCCTAC |
| 2761 | TTGGCAGTAC ATCTATGTAT TAGTCATTGC TATTACCATG GAATTCACT AGTGGAGAAG |
| 2821 | AGCATGCTTG AGGGCTGAGT GCCCCTCAGT GGGCAGAGAG CACATGGCCC ACAGTCCCTG |
| 2881 | AGAAGTTGGG GGGAGGGGTG GGCAATTGAA CTGGTGCCTA GAGAAGGTGG GGCTTGGGTA |
| 2941 | AACTGGGAAA GTGATGTGGT GTACTGGCTC CACCTTTTTC CCCAGGGTGG GGGAGAACCA |
| 3001 | TATATAAGTG CAGTAGTCTC TGTGAACATT CAAGCTTCTG CCTTCTCCCT CCTGTGAGTT |
| 3061 | TGCTAGCCAC CATGCAGAGA AGCCCTCTGG AGAAGGCCTC TGTGGTGAGC AAGCTGTTCT |
| 3121 | TCAGCTGGAC CAGGCCCATC CTGAGGAAGG GCTACAGGCA GAGACTGGAG CTGTCTGACA |
| 3181 | TCTACCAGAT CCCCTCTGTG GACTCTGCTG ACAACCTGTC TGAGAAGCTG GAGAGGGAGT |
| 3241 | GGGATAGAGA GCTGGCCAGC AAGAAGAACC CCAAGCTGAT CAATGCCCTG AGGAGATGCT |
| 3301 | TCTTCTGGAG ATTCATGTTC TATGGCATCT TCCTGTACCT GGGGGAAGTG ACCAAGGCTG |
| 3361 | TGCAGCCTCT GCTGCTGGGC AGAATCATTG CCAGCTATGA CCCTGACAAC AAGGAGGAGA |
| 3421 | GGAGCATTGC CATCTACCTG GGCATTGGCC TGTGCCTGCT GTTCATTGTG AGGACCCTGC |
| 3481 | TGCTGCACCC TGCCATCTTT GGCCTGCACC ACATTGGCAT GCAGATGAGG ATTGCCATGT |
| 3541 | TCAGCCTGAT CTACAAGAAA ACCCTGAAGC TGTCCAGCAG AGTGCTGGAC AAGATCAGCA |
| 3601 | TTGGCCAGCT GGTGAGCCTG CTGAGCAACA ACCTGAACAA GTTTGATGAG GGCCTGGCCC |
| 3661 | TGGCCCACTT TGTGTGGATT GCCCCTCTGC AGGTGGCCCT GCTGATGGGC CTGATTTGGG |
| 3721 | AGCTGCTGCA GGCCTCTGCC TTTTGTGGCC TGGGCTTCCT GATTGTGCTG GCCCTGTTTC |
| 3781 | AGGCTGGCCT GGGCAGGATG ATGATGAAGT ACAGGGACCA GAGGGCAGGC AAGATCAGTG |
| 3841 | AGAGGCTGGT GATCACCTCT GAGATGATTG AGAACATCCA GTCTGTGAAG GCCTACTGTT |
| 3901 | GGGAGGAAGC TATGGAGAAG ATGATTGAAA ACCTGAGGCA GACAGAGCTG AAGCTGACCA |
| 3961 | GGAAGGCTGC CTATGTGAGA TACTTCAACA GCTCTGCCTT CTTCTTCTCT GGCTTCTTTG |
| 4021 | TGGTGTTCCT GTCTGTGCTG CCCTATGCCC TGATCAAGGG GATCATCCTG AGAAAGATTT |
| 4081 | TCACCACCAT CAGCTTCTGC ATTGTGCTGA GGATGGCTGT GACCAGACAG TTCCCCTGGG |
| 4141 | CTGTGCAGAC CTGGTATGAC AGCCTGGGGG CCATCAACAA GATCCAGGAC TTCCTGCAGA |
| 4201 | AGCAGGAGTA CAAGACCCTG GAGTACAACC TGACCACCAC AGAAGTGGTG ATGGAGAATG |
| 4261 | TGACAGCCTT CTGGGAGGAG GGCTTTGGGG AGCTGTTTGA GAAGGCCAAG CAGAACAACA |
| 4321 | ACAACAGAAA GACCAGCAAT GGGGATGACT CCCTGTTCTT CTCCAACTTC TCCCTGCTGG |
| 4381 | GCACACCTGT GCTGAAGGAC ATCAACTTCA AGATTGAGAG GGGGCAGCTC CTGGCTGTGG |
| 4441 | CTGGATCTAC AGGGGCTGGC AAGACCAGCC TGCTGATGAT GATCATGGGG GAGCTGGAGC |
| 4501 | CTTCTGAGGG CAAGATCAAG CACTCTGGCA GGATCAGCTT TTGCAGCCAG TTCAGCTGGA |
| 4561 | TCATGCCTGG CACCATCAAG GAGAACATCA TCTTTGGAGT GAGCTATGAT GAGTACAGAT |

| | Sequences |
|---|---|
| 4621 | ACAGGAGTGT GATCAAGGCC TGCCAGCTGG AGGAGGACAT CAGCAAGTTT GCTGAGAAGG |
| 4681 | ACAACATTGT GCTGGGGGAG GGAGGCATTA CACTGTCTGG GGGCCAGAGA GCCAGAATCA |
| 4741 | GCCTGGCCAG GGCTGTGTAC AAGGATGCTG ACCTGTACCT GCTGGACTCC CCCTTTGGCT |
| 4801 | ACCTGGATGT GCTGACAGAG AAGGAGATTT TTGAGAGCTG TGTGTGCAAG CTGATGGCCA |
| 4861 | ACAAGACCAG AATCCTGGTG ACCAGCAAGA TGGAGCACCT GAAGAAGGCT GACAAGATCC |
| 4921 | TGATCCTGCA TGAGGGCAGC AGCTACTTCT ATGGGACCTT CTCTGAGCTG CAGAACCTGC |
| 4981 | AGCCTGACTT CAGCTCTAAG CTGATGGGCT GTGACAGCTT TGACCAGTTC TCTGCTGAGA |
| 5041 | GGAGGAACAG CATCCTGACA GAGACCCTGC ACAGATTCAG CCTGGAGGGA GATGCCCCTG |
| 5101 | TGAGCTGGAC AGAGACCAAG AAGCAGAGCT TCAAGCAGAC AGGGGAGTTT GGGGAGAAGA |
| 5161 | GGAAGAACTC CATCCTGAAC CCCATCAACA GCATCAGGAA GTTCAGCATT GTGCAGAAAA |
| 5221 | CCCCCCTGCA GATGAATGGC ATTGAGGAAG ATTCTGATGA GCCCCTGGAG AGGAGACTGA |
| 5281 | GCCTGGTGCC TGATTCTGAG CAGGGAGAGG CCATCCTGCC TAGGATCTCT GTGATCAGCA |
| 5341 | CAGGCCCTAC ACTGCAGGCC AGAAGGAGGC AGTCTGTGCT GAACCTGATG ACCCACTCTG |
| 5401 | TGAACCAGGG CCAGAACATC CACAGGAAAA CCACAGCCTC CACCAGGAAA GTGAGCCTGG |
| 5461 | CCCCTCAGGC CAATCTGACA GAGCTGGACA TCTACAGCAG GAGGCTGTCT CAGGAGACAG |
| 5521 | GCCTGGAGAT TTCTGAGGAG ATCAATGAGG AGGACCTGAA AGAGTGCTTC TTTGATGACA |
| 5581 | TGGAGAGCAT CCCTGCTGTG ACCACCTGGA ACACCTACCT GAGATACATC ACAGTGCACA |
| 5641 | AGAGCCTGAT CTTTGTGCTG ATCTGGTGCC TGGTGATCTT CCTGGCTGAA GTGGCTGCCT |
| 5701 | CTCTGGTGGT GCTGTGGCTG CTGGGAAACA CCCCACTGCA GGACAAGGGC AACAGCACCC |
| 5761 | ACAGCAGGAA CAACAGCTAT GCTGTGATCA TCACCTCCAC CTCCAGCTAC TATGTGTTCT |
| 5821 | ACATCTATGT GGGAGTGGCT GATACCCTGC TGGCTATGGG CTTCTTTAGA GGCCTGCCCC |
| 5881 | TGGTGCACAC ACTGATCACA GTGAGCAAGA TCCTCCACCA CAAGATGCTG CACTCTGTGC |
| 5941 | TGCAGGCTCC TATGAGCACC CTGAATACCC TGAAGGCTGG GGGCATCCTG AACAGATTCT |
| 6001 | CCAAGGATAT TGCCATCCTG GATGACCTGC TGCCTCTCAC CATCTTTGAC TTCATCCAGC |
| 6061 | TGCTGCTGAT TGTGATTGGG GCCATTGCTG TGGTGGCAGT GCTGCAGCCC TACATCTTTG |
| 6121 | TGGCCACAGT GCCTGTGATT GTGGCCTTCA TCATGCTGAG GGCCTACTTT CTGCAGACCT |
| 6181 | CCCAGCAGCT GAAGCAGCTG GAGTCTGAGG GCAGAAGCCC CATCTTCACC CACCTGGTGA |
| 6241 | CAAGCCTGAA GGGCCTGTGG ACCCTGAGAG CCTTTGGCAG GCAGCCCTAC TTTGAGACCC |
| 6301 | TGTTCCACAA GGCCCTGAAC CTGCACACAG CCAACTGGTT CCTCTACCTG TCCACCCTGA |
| 6361 | GATGGTTCCA GATGAGAATT GAGATGATCT TTGTCATCTT CTTCATTGCT GTGACCTTCA |
| 6421 | TCAGCATTCT GACCACAGGA GAGGGAGAGG GCAGAGTGGG CATTATCCTG ACCCTGGCCA |
| 6481 | TGAACATCAT GAGCACACTG CAGTGGGCAG TGAACAGCAG CATTGATGTG GACAGCCTGA |
| 6541 | TGAGGAGTGT GAGCAGAGTG TTCAAGTTCA TTGATATGCC CACAGAGGGC AAGCCTACCA |
| 6601 | AGAGCACCAA GCCCTACAAG AATGGCCAGC TGAGCAAAGT GATGATCATT GAGAACAGCC |
| 6661 | ATGTGAAGAA GGATGATATC TGGCCCAGTG GAGGCCAGAT GACAGTGAAG GACCTGACAG |
| 6721 | CCAAGTACAC AGAGGGGGGC AATGCTATCC TGGAGAACAT CTCCTTCAGC ATCTCCCCTG |
| 6781 | GCCAGAGAGT GGGACTGCTG GGAAGAACAG GCTCTGGCAA GTCTACCCTG CTGTCTGCCT |
| 6841 | TCCTGAGGCT GCTGAACACA GAGGGAGAGA TCCAGATTGA TGGAGTGTCC TGGGACAGCA |

| | Sequences |
|---|---|
| 6901 | TCACACTGCA GCAGTGGAGG AAGGCCTTTG GTGTGATCCC CCAGAAAGTG TTCATCTTCA |
| 6961 | GTGGCACCTT CAGGAAGAAC CTGGACCCCT ATGAGCAGTG GTCTGACCAG GAGATTTGGA |
| 7021 | AAGTGGCTGA TGAAGTGGGC CTGAGAAGTG TGATTGAGCA GTTCCCTGGC AAGCTGGACT |
| 7081 | TTGTCCTGGT GGATGGGGGC TGTGTGCTGA GCCATGGCCA CAAGCAGCTG ATGTGCCTGG |
| 7141 | CCAGATCAGT GCTGAGCAAG GCCAAGATCC TGCTGCTGGA TGAGCCTTCT GCCCACCTGG |
| 7201 | ATCCTGTGAC CTACCAGATC ATCAGGAGGA CCCTCAAGCA GGCCTTTGCT GACTGCACAG |
| 7261 | TCATCCTGTG TGAGCACAGG ATTGAGGCCA TGCTGGAGTG CCAGCAGTTC CTGGTGATTG |
| 7321 | AGGAGAACAA AGTGAGGCAG TATGACAGCA TCCAGAAGCT GCTGAATGAG AGGAGCCTGT |
| 7381 | TCAGGCAGGC CATCAGCCCC TCTGATAGAG TGAAGCTGTT CCCCCACAGG AACAGCTCCA |
| 7441 | AGTGCAAGAG CAAGCCCCAG ATTGCTGCCC TGAAGGAGGA GACAGAGGAG GAAGTGCAGG |
| 7501 | ACACCAGGCT GTGAGGGCCC AATCAACCTC TGGATTACAA AATTTGTGAA AGATTGACTG |
| 7561 | GTATTCTTAA CTATGTTGCT CCTTTTACGC TATGTGGATA CGCTGCTTTA ATGCCTTTGT |
| 7621 | ATCATGCTAT TGCTTCCCGT ATGGCTTTCA TTTTCTCCTC CTTGTATAAA TCCTGGTTGC |
| 7681 | TGTCTCTTTA TGAGGAGTTG TGGCCCGTTG TCAGGCAACG TGGCGTGGTG TGCACTGTGT |
| 7741 | TTGCTGACGC AACCCCCACT GGTTGGGGCA TTGCCACCAC CTGTCAGCTC CTTTCCGGGA |
| 7801 | CTTTCGCTTT CCCCCTCCCT ATTGCCACGG CGGAACTCAT CGCCGCCTGC CTTGCCCGCT |
| 7861 | GCTGGACAGG GGCTCGGCTG TTGGGCACTG ACAATTCCGT GGTGTTGTCG GGGAAATCAT |
| 7921 | CGTCCTTTCC TTGGCTGCTC GCCTGTGTTG CCACCTGGAT TCTGCGCGGG ACGTCCTTCT |
| 7981 | GCTACGTCCC TTCGGCCCTC AATCCAGCGG ACCTTCCTTC CCGCGGCCTG CTGCCGGCTC |
| 8041 | TGCGGCCTCT TCCGCGTCTT CGCCTTCGCC CTCAGACGAG TCGGATCTCC CTTTGGGCCG |
| 8101 | CCTCCCCGCA AGCTTCGCAC TTTTTAAAAG AAAAGGGAGG ACTGGATGGG ATTTATTACT |
| 8161 | CCGATAGGAC GCTGGCTTGT AACTCAGTCT CTTACTAGGA GACCAGCTTG AGCCTGGGTG |
| 8221 | TTCGCTGGTT AGCCTAACCT GGTTGGCCAC CAGGGGTAAG GACTCCTTGG CTTAGAAAGC |
| 8281 | TAATAAACTT GCCTGCATTA GAGCTCTTAC GCGTCCCGGG CTCGAGATCC GCATCTCAAT |
| 8341 | TAGTCAGCAA CCATAGTCCC GCCCCTAACT CCGCCCATCC CGCCCCTAAC TCCGCCCAGT |
| 8401 | TCCGCCCATT CTCCGCCCCA TGGCTGACTA ATTTTTTTTA TTTATGCAGA GGCCGAGGCC |
| 8461 | GCCTCGGCCT CTGAGCTATT CCAGAAGTAG TGAGGAGGCT TTTTTGGAGG CCTAGGCTTT |
| 8521 | TGCAAAAAGC TAACTTGTTT ATTGCAGCTT ATAATGGTTA CAAATAAAGC AATAGCATCA |
| 8581 | CAAATTTCAC AAATAAAGCA TTTTTTTCAC TGCATTCTAG TTGTGGTTTG TCCAAACTCA |
| 8641 | TCAATGTATC TTATCATGTC TGTCCGCTTC CTCGCTCACT GACTCGCTGC GCTCGGTCGT |
| 8701 | TCGGCTGCGG CGAGCGGTAT CAGCTCACTC AAAGGCGGTA ATACGGTTAT CCACAGAATC |
| 8761 | AGGGGATAAC GCAGGAAAGA ACATGTGAGC AAAAGGCCAG CAAAAGGCCA GGAACCGTAA |
| 8821 | AAAGGCCGCG TTGCTGGCGT TTTTCCATAG GCTCCGCCCC CCTGACGAGC ATCACAAAAA |
| 8881 | TCGACGCTCA AGTCAGAGGT GGCGAAACCC GACAGGACTA TAAAGATACC AGGCGTTTCC |
| 8941 | CCCTGGAAGC TCCCTCGTGC GCTCTCCTGT TCCGACCCTG CCGCTTACCG GATACCTGTC |
| 9001 | CGCCTTTCTC CCTTCGGGAA GCGTGGCGCT TTCTCATAGC TCACGCTGTA GGTATCTCAG |
| 9061 | TTCGGTGTAG GTCGTTCGCT CCAAGCTGGG CTGTGTGCAC GAACCCCCCG TTCAGCCCGA |
| 9121 | CCGCTGCGCC TTATCCGGTA ACTATCGTCT TGAGTCCAAC CCGGTAAGAC ACGACTTATC |

-continued

| | Sequences |
|---|---|
| 9181 | GCCACTGGCA GCAGCCACTG GTAACAGGAT TAGCAGAGCG AGGTATGTAG GCGGTGCTAC |
| 9241 | AGAGTTCTTG AAGTGGTGGC CTAACTACGG CTACACTAGA AGAACAGTAT TTGGTATCTG |
| 9301 | CGCTCTGCTG AAGCCAGTTA CCTTCGGAAA AAGAGTTGGT AGCTCTTGAT CCGGCAAACA |
| 9361 | AACCACCGCT GGTAGCGGTG GTTTTTTTGT TTGCAAGCAG CAGATTACGC GCAGAAAAAA |
| 9421 | AGGATCTCAA GAAGATCCTT TGATCTTTTC TACGGGGTCT GACGCTCAGT GGAACGAAAA |
| 9481 | CTCACGTTAA GGGATTTTGG TCATGAGATT ATCAAAAGG ATCTTCACCT AGATCCTTTT |
| 9541 | AAATTAAAAA TGAAGTTTTA AATCAATCTA AAGTATATAT GAGTAAACTT GGTCTGACAG |
| 9601 | TTAGAAAAAC TCATCGAGCA TCAAATGAAA CTGCAATTTA TTCATATCAG GATTATCAAT |
| 9661 | ACCATATTTT TGAAAAAGCC GTTTCTGTAA TGAAGGAGAA AACTCACCGA GGCAGTTCCA |
| 9721 | TAGGATGGCA AGATCCTGGT ATCGGTCTGC GATTCCGACT CGTCCAACAT CAATACAACC |
| 9781 | TATTAATTTC CCCTCGTCAA AAATAAGGTT ATCAAGTGAG AAATCACCAT GAGTGACGAC |
| 9841 | TGAATCCGGT GAGAATGGCA ACAGCTTATG CATTTCTTTC CAGACTTGTT CAACAGGCCA |
| 9901 | GCCATTACGC TCGTCATCAA AATCACTCGC ATCAACCAAA CCGTTATTCA TTCGTGATTG |
| 9961 | CGCCTGAGCG AGACGAAATA CGCGATCGCT GTTAAAAGGA CAATTACAAA CAGGAATCGA |
| 10021 | ATGCAACCGG CGCAGGAACA CTGCCAGCGC ATCAACAATA TTTTCACCTG AATCAGGATA |
| 10081 | TTCTTCTAAT ACCTGGAATG CTGTTTTTCC GGGGATCGCA GTGGTGAGTA ACCATGCATC |
| 10141 | ATCAGGAGTA CGGATAAAAT GCTTGATGGT CGGAAGAGGC ATAAATTCCG TCAGCCAGTT |
| 10201 | TAGTCTGACC ATCTCATCTG TAACATCATT GGCAACGCTA CCTTTGCCAT GTTTCAGAAA |
| 10261 | CAACTCTGGC GCATCGGGCT TCCCATACAA TCGATAGATT GTCGCACCTG ATTGCCCGAC |
| 10321 | ATTATCGCGA GCCCATTTAT ACCCATATAA ATCAGCATCC ATGTTGGAAT TTAATCGCGG |
| 10381 | CCTAGAGCAA GACGTTTCCC GTTGAATATG GCTCATAACA CCCCTTGTAT TACTGTTTAT |
| 10441 | GTAAGCAGAC AGTTTTATTG TTCATGATGA TATATTTTTA TCTTGTGCAA TGTAACATCA |
| 10501 | GAGATTTTGA GACACAACAA TTGGTCGACG GATCC |

SEQ ID NO: 2

| | |
|---|---|
| 1 | GCTCGAGACT AGTGACTTGG TGAGTAGGCT TCGAGCCTAG TTAGAGGACT AGGAGAGGCC |
| 61 | GTAGCCGTAA CTACTCTGGG CAAGTAGGGC AGGCGGTGGG TACGCAATGG GGGCGGCTAC |
| 121 | CTCAGCACTA AATAGGAGAC AATTAGACCA ATTTGAGAAA ATACGACTTC GCCCGAACGG |
| 181 | AAAGAAAAAG TACCAAATTA AACATTTAAT ATGGGCAGGC AAGGAGATGG AGCGCTTCGG |
| 241 | CCTCCATGAG AGGTTGTTGG AGACAGAGGA GGGGTGTAAA AGAATCATAG AAGTCCTCTA |
| 301 | CCCCCTAGAA CCAACAGGAT CGGAGGGCTT AAAAGTCTG TTCAATCTTG TGTGCGTACT |
| 361 | ATATTGCTTG CACAAGGAAC AGAAAGTGAA AGACACAGAG GAAGCAGTAG CAACAGTAAG |
| 421 | ACAACACTGC CATCTAGTGG AAAAAGAAAA AAGTGCAACA GAGACATCTA GTGGACAAAA |
| 481 | GAAAAATGAC AAGGGAATAG CAGCGCCACC TGGTGGCAGT CAGAATTTTC CAGCGCAACA |
| 541 | ACAAGGAAAT GCCTGGGTAC ATGTACCCTT GTCACCGCGC ACCTTAAATG CGTGGGTAAA |
| 601 | AGCAGTAGAG GAGAAAAAAT TTGGAGCAGA AATAGTACCC ATGTTTCAAG CCCTATCAGA |
| 661 | AGGCTGCACA CCCTATGACA TTAATCAGAT GCTTAATGTG CTAGGAGATC ATCAAGGGGC |
| 721 | ATTACAAATA GTGAAAGAGA TCATTAATGA AGAAGCAGCC CAGTGGGATG TAACACACCC |
| 781 | ACTACCCGCA GGACCCCTAC CAGCAGGACA GCTCAGGGAC CCTCGCGGCT CAGATATAGC |
| 841 | AGGGACCACC AGCTCAGTAC AAGAACAGTT AGAATGGATC TATACTGCTA ACCCCCGGGT |

-continued

| | Sequences |
|---|---|
| 901 | AGATGTAGGT GCCATCTACC GGAGATGGAT TATTCTAGGA CTTCAAAAGT GTGTCAAAAT |
| 961 | GTACAACCCA GTATCAGTCC TAGACATTAG GCAGGGACCT AAAGAGCCCT TCAAGGATTA |
| 1021 | TGTGGACAGA TTTTACAAGG CAATTAGAGC AGAACAAGCC TCAGGGGAAG TGAAACAATG |
| 1081 | GATGACAGAA TCATTACTCA TTCAAAATGC TAATCCAGAT TGTAAGGTCA TCCTGAAGGG |
| 1141 | CCTAGGAATG CACCCCACCC TTGAAGAAAT GTTAACGGCT TGTCAGGGGG TAGGAGGCCC |
| 1201 | AAGCTACAAA GCAAAAGTAA TGGCAGAAAT GATGCAGACC ATGCAAAATC AAAACATGGT |
| 1261 | GCAGCAGGGA GGTCCAAAAA GACAAAGACC CCCACTAAGA TGTTATAATT GTGGAAAATT |
| 1321 | TGGCCATATG CAAAGACAAT GTCCGGAACC AAGGAAAACA AAATGTCTAA AGTGTGGAAA |
| 1381 | ATTGGGACAC CTAGCAAAAG ACTGCAGGGG ACAGGTGAAT TTTTTAGGGT ATGGACGGTG |
| 1441 | GATGGGGGCA AAACCGAGAA ATTTTCCCGC CGCTACTCTT GGAGCGGAAC CGAGTGCGCC |
| 1501 | TCCTCCACCG AGCGGCACCA CCCCATACGA CCCAGCAAAG AAGCTCCTGC AGCAATATGC |
| 1561 | AGAGAAAGGG AAACAACTGA GGGAGCAAAA GAGGAATCCA CCGGCAATGA ATCCGGATTG |
| 1621 | GACCGAGGGA TATTCTTTGA ACTCCCTCTT TGGAGAAGAC CAATAAAGAC AGTGTATATA |
| 1681 | GAAGGGGTCC CCATTAAGGC ACTGCTAGAC ACAGGGGCAG ATGACACCAT AATTAAAGAA |
| 1741 | AATGATTTAC AATTATCAGG TCCATGGAGA CCCAAAATTA TAGGGGGCAT AGGAGGAGGC |
| 1801 | CTTAATGTAA AAGAATATAA CGACAGGGGA GTAAAAATAG AAGATAAAAT TTTGAGAGGA |
| 1861 | ACAATATTGT TAGGAGCAAC TCCCATTAAT ATAATAGGTA GAAATTTGCT GGCCCCGGCA |
| 1921 | GGTGCCCGGT TAGTAATGGG ACAATTATCA GAAAAAATTC CTGTCACACC TGTCAAATTG |
| 1981 | AAGGAAGGGG CTCGGGGACC CTGTGTAAGA CAATGGCCTC TCTCTAAAGA GAAGATTGAA |
| 2041 | GCTTTACAGG AAATATGTTC CCAATTAGAG CAGGAAGGAA AAATCAGTAG AGTAGGAGGA |
| 2101 | GAAAATGCAT ACAATACCCC AATATTTTGC ATAAAGAAGA AGGACAAATC CCAGTGGAGG |
| 2161 | ATGCTAGTAG ACTTTAGAGA GTTAAATAAG GCAACCCAAG ATTTCTTTGA AGTGCAATTA |
| 2221 | GGGATACCCC ACCCAGCAGG ATTAAGAAAG ATGAGACAGA TAACAGTTTT AGATGTAGGA |
| 2281 | GACGCCTATT ATTCCATACC ATTGGATCCA AATTTTAGGA AATATACTGC TTTTACTATT |
| 2341 | CCCACAGTGA ATAATCAGGG ACCCGGGATT AGGTATCAAT TCAACTGTCT CCCGCAAGGG |
| 2401 | TGGAAAGGAT CTCCTACAAT CTTCCAAAAT ACAGCAGCAT CCATTTTGGA GGAGATAAAA |
| 2461 | AGAAACTTGC CAGCACTAAC CATTGTACAA TACATGGATG ATTTATGGGT AGGTTCTCAA |
| 2521 | GAAAATGAAC ACACCCATGA CAAATTAGTA GAACAGTTAA GAACAAAATT ACAAGCCTGG |
| 2581 | GGCTTAGAAA CCCCAGAAAA GAAGGTGCAA AAAGAACCAC CTTATGAGTG GATGGGATAC |
| 2641 | AAACTTTGGC CTCACAAATG GAACTAAGC AGAATACAAC TGGAGGAAAA AGATGAATGG |
| 2701 | ACTGTCAATG ACATCCAGAA GTTAGTTGGG AAACTAAATT GGGCAGCACA ATTGTATCCA |
| 2761 | GGTCTTAGGA CCAAGAATAT ATGCAAGTTA ATTAGAGGAA AGAAAAATCT GTTAGAGCTA |
| 2821 | GTGACTTGGA CACCTGAGGC AGAAGCTGAA TATGCAGAAA ATGCAGAGAT TCTTAAAACA |
| 2881 | GAACAGGAAG GAACCTATTA CAAACCAGGA ATACCTATTA GGGCAGCAGT ACAGAAATTG |
| 2941 | GAAGGAGGAC AGTGGAGTTA CCAATTCAAA CAAGAAGGAC AAGTCTTGAA AGTAGGAAAA |
| 3001 | TACACCAAGC AAAAGAACAC CCATACAAAT GAACTTCGCA CATTAGCTGG TTTAGTGCAG |
| 3061 | AAGATTTGCA AAGAAGCTCT AGTTATTTGG GGGATATTAC AGTTCTAGA ACTCCCGATA |
| 3121 | GAAAGAGAGG TATGGGAACA ATGGTGGGCG GATTACTGGC AGGTAAGCTG GATTCCCGAA |

-continued

| | Sequences |
|---|---|
| 3181 | TGGGATTTTG TCAGCACCCC ACCTTTGCTC AAACTATGGT ACACATTAAC AAAAGAACCC |
| 3241 | ATACCCAAGG AGGACGTTTA CTATGTAGAT GGAGCATGCA ACAGAAATTC AAAAGAAGGA |
| 3301 | AAAGCAGGAT ACATCTCACA ATACGGAAAA CAGAGAGTAG AAACATTAGA AAACACTACC |
| 3361 | AATCAGCAAG CAGAATTAAC AGCTATAAAA ATGGCTTTGG AAGACAGTGG GCCTAATGTG |
| 3421 | AACATAGTAA CAGACTCTCA ATATGCAATG GAATTTTGA CAGCACAACC CACACAAAGT |
| 3481 | GATTCACCAT TAGTAGAGCA AATTATAGCC TTAATGATAC AAAAGCAACA AATATATTTG |
| 3541 | CAGTGGGTAC CAGCACATAA AGGAATAGGA GGAAATGAGG AGATAGATAA ATTAGTGAGT |
| 3601 | AAAGGCATTA GAAGAGTTTT ATTCTTAGAA AAAATAGAAG AAGCTCAAGA AGAGCATGAA |
| 3661 | AGATATCATA ATAATTGGAA AAACCTAGCA GATACATATG GCTTCCACA AATAGTAGCA |
| 3721 | AAAGAGATAG TGGCCATGTG TCCAAAATGT CAGATAAAGG GAGAACCAGT GCATGGACAA |
| 3781 | GTGGATGCCT CACCTGGAAC ATGGCAGATG GATTGTACTC ATCTAGAAGG AAAAGTAGTC |
| 3841 | ATAGTTGCGG TCCATGTAGC CAGTGGATTC ATAGAAGCAG AAGTCATACC TAGGGAAACA |
| 3901 | GGAAAAGAAA CGGCAAAGTT TCTATTAAAA ATACTGAGTA GATGGCCTAT AACACAGTTA |
| 3961 | CACACAGACA ATGGGCCTAA CTTTACCTCC CAAGAAGTGG CAGCAATATG TTGGTGGGA |
| 4021 | AAAATTGAAC ATACAACAGG TATACCATAT AACCCCCAAT CTCAAGGATC AATAGAAAGC |
| 4081 | ATGAACAAAC AATTAAAAGA GATAATTGGG AAAATAAGAG ATGATTGCCA ATATACAGAG |
| 4141 | ACAGCAGTAC TGATGGCTTG CCATATTCAC AATTTTAAAA GAAAGGGAGG AATAGGGGGA |
| 4201 | CAGACTTCAG CAGAGAGACT AATTAATATA ATAACAACAC AATTAGAAAT ACAACATTTA |
| 4261 | CAAACCAAAA TTCAAAAAAT TTTAAATTTT AGAGTCTACT ACAGAGAAGG GAGAGACCCT |
| 4321 | GTGTGGAAAG GACCAGCACA ATTAATCTGG AAAGGGGAAG GAGCAGTGGT CCTCAAGGAC |
| 4381 | GGAAGTGACC TAAAGGTTGT ACCAAGAAGG AAAGCTAAAA TTATTAAGGA TTATGAACCC |
| 4441 | AAACAAAGAG TGGGTAATGA GGGTGACGTG GAAGGTACCA GGGGATCTGA TAACTAAATG |
| 4501 | GCAGGGAATA GTCAGATATT GGATGAGACA AAGAAATTTG AAATGGAACT ATTATATGCA |
| 4561 | TCAGCTGGCG GCCGCGAATT CACTAGTGAT TCCCGTTTGT GCTAGGGTTC TTAGGCTTCT |
| 4621 | TGGGGGCTGC TGGAACTGCA ATGGGAGCAG CGGCGACAGC CCTGACGGTC CAGTCTCAGC |
| 4681 | ATTTGCTTGC TGGGATACTG CAGCAGCAGA AGAATCTGCT GGCGGCTGTG GAGGCTCAAC |
| 4741 | AGCAGATGTT GAAGCTGACC ATTTGGGGTG TTAAAAACCT CAATGCCCGC GTCACAGCCC |
| 4801 | TTGAGAAGTA CCTAGAGGAT CAGGCACGAC TAAACTCCTG GGGGTGCGCA TGGAAACAAG |
| 4861 | TATGTCATAC CACAGTGGAG TGGCCCTGGA CAAATCGGAC TCCGGATTGG CAAAATATGA |
| 4921 | CTTGGTTGGA GTGGGAAAGA CAAATAGCTG ATTGGAAAG CAACATTACG AGACAATTAG |
| 4981 | TGAAGGCTAG AGAACAAGAG GAAAAGAATC TAGATGCCTA TCAGAAGTTA ACTAGTTGGT |
| 5041 | CAGATTTCTG GTCTTGGTTC GATTTCTCAA AATGGCTTAA CATTTTAAAA ATGGGATTTT |
| 5101 | TAGTAATAGT AGGAATAATA GGGTTAAGAT TACTTTACAC AGTATATGGA TGTATAGTGA |
| 5161 | GGGTTAGGCA GGGATATGTT CCTCTATCTC CACAGATCCA TATCCAATCG AATTCCCGCG |
| 5221 | GCCGCAATTC ACTCCTCAGG TGCAGGCTGC CTATCAGAAG GTGGTGGCTG GTGTGGCCAA |
| 5281 | TGCCCTGGCT CACAAATACC ACTGAGATCT TTTTCCCTCT GCCAAAAATT ATGGGACAT |
| 5341 | CATGAAGCCC CTTGAGCATC TGACTTCTGG CTAATAAAGG AAATTTATTT TCATTGCAAT |
| 5401 | AGTGTGTTGG AATTTTTTGT GTCTCTCACT CGGAAGGACA TATGGGAGGG CAAATCATTT |

-continued

| | Sequences |
|---|---|
| 5461 | AAAACATCAG AATGAGTATT TGGTTTAGAG TTTGGCAACA TATGCCCATA TGCTGGCTGC |
| 5521 | CATGAACAAA GGTTGGCTAT AAAGAGGTCA TCAGTATATG AAACAGCCCC CTGCTGTCCA |
| 5581 | TTCCTTATTC CATAGAAAAG CCTTGACTTG AGGTTAGATT TTTTTTATAT TTTGTTTTGT |
| 5641 | GTTATTTTTT TCTTTAACAT CCCTAAAATT TTCCTTACAT GTTTTACTAG CCAGATTTTT |
| 5701 | CCTCCTCTCC TGACTACTCC CAGTCATAGC TGTCCCTCTT CTCTTATGGA GATCCCTCGA |
| 5761 | CCTGCAGCCC AAGCTTGGCG TAATCATGGT CATAGCTGTT TCCTGTGTGA AATTGTTATC |
| 5821 | CGCTCACAAT TCCACACAAC ATACGAGCCG GAAGCATAAA GTGTAAAGCC TGGGGTGCCT |
| 5881 | AATGAGTGAG CTAACTCACA TTAATTGCGT TGCGCTCACT GCCCGCTTTC CAGTCGGGAA |
| 5941 | ACCTGTCGTG CCAGCGGATC CGCATCTCAA TTAGTCAGCA ACCATAGTCC CGCCCCTAAC |
| 6001 | TCCGCCCATC CCGCCCCTAA CTCCGCCCAG TTCCGCCCAT TCTCCGCCCC ATGGCTGACT |
| 6061 | AATTTTTTTT ATTTATGCAG AGGCCGAGGC CGCCTCGGCC TCTGAGCTAT TCCAGAAGTA |
| 6121 | GTGAGGAGGC TTTTTTGGAG GCCTAGGCTT TTGCAAAAAG CTAACTTGTT TATTGCAGCT |
| 6181 | TATAATGGTT ACAAATAAAG CAATAGCATC ACAAATTTCA CAAATAAAGC ATTTTTTTCA |
| 6241 | CTGCATTCTA GTTGTGGTTT GTCCAAACTC ATCAATGTAT CTTATCATGT CTGTCCGCTT |
| 6301 | CCTCGCTCAC TGACTCGCTG CGCTCGGTCG TTCGGCTGCG GCGAGCGGTA TCAGCTCACT |
| 6361 | CAAAGGCGGT AATACGGTTA TCCACAGAAT CAGGGGATAA CGCAGGAAAG AACATGTGAG |
| 6421 | CAAAAGGCCA GCAAAAGGCC AGGAACCGTA AAAAGGCCGC GTTGCTGGCG TTTTTCCATA |
| 6481 | GGCTCCGCCC CCCTGACGAG CATCACAAAA ATCGACGCTC AAGTCAGAGG TGGCGAAACC |
| 6541 | CGACAGGACT ATAAAGATAC CAGGCGTTTC CCCCTGGAAG CTCCCTCGTG CGCTCTCCTG |
| 6601 | TTCCGACCCT GCCGCTTACC GGATACCTGT CCGCCTTTCT CCCTTCGGGA AGCGTGGCGC |
| 6661 | TTTCTCATAG CTCACGCTGT AGGTATCTCA GTTCGGTGTA GGTCGTTCGC TCCAAGCTGG |
| 6721 | GCTGTGTGCA CGAACCCCCC GTTCAGCCCG ACCGCTGCGC CTTATCCGGT AACTATCGTC |
| 6781 | TTGAGTCCAA CCCGGTAAGA CACGACTTAT CGCCACTGGC AGCAGCCACT GGTAACAGGA |
| 6841 | TTAGCAGAGC GAGGTATGTA GGCGGTGCTA CAGAGTTCTT GAAGTGGTGG CCTAACTACG |
| 6901 | GCTACACTAG AAGAACAGTA TTTGGTATCT GCGCTCTGCT GAAGCCAGTT ACCTTCGGAA |
| 6961 | AAAGAGTTGG TAGCTCTTGA TCCGGCAAAC AAACCACCGC TGGTAGCGGT GGTTTTTTTG |
| 7021 | TTTGCAAGCA GCAGATTACG CGCAGAAAAA AAGGATCTCA AGAAGATCCT TTGATCTTTT |
| 7081 | CTACGGGGTC TGACGCTCAG TGGAACGAAA ACTCACGTTA AGGGATTTTG GTCATGAGAT |
| 7141 | TATCAAAAAG GATCTTCACC TAGATCCTTT TAAATTAAAA ATGAAGTTTT AAATCAATCT |
| 7201 | AAAGTATATA TGAGTAAACT TGGTCTGACA GTTAGAAAAA CTCATCGAGC ATCAAATGAA |
| 7261 | ACTGCAATTT ATTCATATCA GGATTATCAA TACCATATTT TGAAAAAGC CGTTTCTGTA |
| 7321 | ATGAAGGAGA AAACTCACCG AGGCAGTTCC ATAGGATGGC AAGATCCTGG TATCGGTCTG |
| 7381 | CGATTCCGAC TCGTCCAACA TCAATACAAC CTATTAATTT CCCCTCGTCA AAAATAAGGT |
| 7441 | TATCAAGTGA GAAATCACCA TGAGTGACGA CTGAATCCGG TGAGAATGGC AACAGCTTAT |
| 7501 | GCATTTCTTT CCAGACTTGT TCAACAGGCC AGCCATTACG CTCGTCATCA AAATCACTCG |
| 7561 | CATCAACCAA ACCGTTATTC ATTCGTGATT GCGCCTGAGC GAGACGAAAT ACGCGATCGC |
| 7621 | TGTTAAAAGG ACAATTACAA ACAGGAATCG AATGCAACCG GCGCAGGAAC ACTGCCAGCG |
| 7681 | CATCAACAAT ATTTTCACCT GAATCAGGAT ATTCTTCTAA TACCTGGAAT GCTGTTTTTC |

| | Sequences |
|---|---|
| 7741 | CGGGGATCGC AGTGGTGAGT AACCATGCAT CATCAGGAGT ACGGATAAAA TGCTTGATGG |
| 7801 | TCGGAAGAGG CATAAATTCC GTCAGCCAGT TTAGTCTGAC CATCTCATCT GTAACATCAT |
| 7861 | TGGCAACGCT ACCTTTGCCA TGTTTCAGAA ACAACTCTGG CGCATCGGGC TTCCCATACA |
| 7921 | ATCGATAGAT TGTCGCACCT GATTGCCCGA CATTATCGCG AGCCCATTTA TACCCATATA |
| 7981 | AATCAGCATC CATGTTGGAA TTTAATCGCG GCCTAGAGCA AGACGTTTCC CGTTGAATAT |
| 8041 | GGCTCATAAC ACCCCTTGTA TTACTGTTTA TGTAAGCAGA CAGTTTTATT GTTCATGATG |
| 8101 | ATATATTTTT ATCTTGTGCA ATGTAACATC AGAGATTTTG AGACACAACA ATTGTCGACA |
| 8161 | TTGATTATTG ACTAGTTATT AATAGTAATC AATTACGGGG TCATTAGTTC ATAGCCCATA |
| 8221 | TATGGAGTTC CGCGTTACAT AACTTACGGT AAATGGCCCG CCTGGCTGAC CGCCCAACGA |
| 8281 | CCCCCGCCCA TTGACGTCAA TAATGACGTA TGTTCCCATA GTAACGCCAA TAGGGACTTT |
| 8341 | CCATTGACGT CAATGGGTGG AGTATTTACG GTAAACTGCC CACTTGGCAG TACATCAAGT |
| 8401 | GTATCATATG CCAAGTACGC CCCCTATTGA CGTCAATGAC GGTAAATGGC CCGCCTGGCA |
| 8461 | TTATGCCCAG TACATGACCT TATGGGACTT TCCTACTTGG CAGTACATCT ACGTATTAGT |
| 8521 | CATCGCTATT ACCATGGTCG AGGTGAGCCC CACGTTCTGC TTCACTCTCC CCATCTCCCC |
| 8581 | CCCCTCCCCA CCCCCAATTT TGTATTTATT TATTTTTTAA TTATTTTGTG CAGCGATGGG |
| 8641 | GGCGGGGGGG GGGGGGGGGC GCGCGCCAGG CGGGGCGGGG CGGGGCGAGG GGCGGGGCGG |
| 8701 | GGCGAGGCGG AGAGGTGCGG CGGCAGCCAA TCAGAGCGGC GCGCTCCGAA AGTTTCCTTT |
| 8761 | TATGGCGAGG CGGCGGCGGC GGCGGCCCTA TAAAAAGCGA AGCGCGCGGC GGGCGGGAGT |
| 8821 | CGCTGCGCGC TGCCTTCGCC CCGTGCCCCG CTCCGCCGCC GCCTCGCGCC GCCCGCCCCG |
| 8881 | GCTCTGACTG ACCGCGTTAC TCCCACAGGT GAGCGGGCGG GACGGCCCTT CTCCTCCGGG |
| 8941 | CTGTAATTAG CGCTTGGTTT AATGACGGCT TGTTTCTTTT CTGTGGCTGC GTGAAAGCCT |
| 9001 | TGAGGGGCTC CGGGAGGGCC CTTTGTGCGG GGGGAGCGGC TCGGGGGGTG CGTGCGTGTG |
| 9061 | TGTGTGCGTG GGGAGCGCCG CGTGCGGCTC CGCGCTGCCC GGCGGCTGTG AGCGCTGCGG |
| 9121 | GCGCGGCGCG GGGCTTTGTG CGCTCCGCAG TGTGCGCGAG GGGAGCGCGG CCGGGGCGG |
| 9181 | TGCCCCGCGG TGCGGGGGGG GCTGCGAGGG GAACAAAGGC TGCGTGCGGG GTGTGTGCGT |
| 9241 | GGGGGGGTGA GCAGGGGGTG TGGGCGCGTC GGTCGGGCTG CAACCCCCCC TGCACCCCCC |
| 9301 | TCCCCGAGTT GCTGAGCACG GCCCGGCTTC GGGTGCGGGG CTCCGTACGG GGCGTGGCGC |
| 9361 | GGGGCTCGCC GTGCCGGGCG GGGGTGGCG GCAGGTGGGG GTGCCGGGCG GGGCGGGGCC |
| 9421 | GCCTCGGGCC GGGGAGGGCT CGGGGGAGGG GCGCGCGCGGC CCCCGGAGCG CCGGCGGCTG |
| 9481 | TCGAGGCGCG GCGAGCCGCA GCCATTGCCT TTTATGGTAA TCGTGCGAGA GGGCGCAGGG |
| 9541 | ACTTCCTTTG TCCCAAATCT GTGCGGAGCC GAAATCTGGG AGGCGCCGCC GCACCCCCTC |
| 9601 | TAGCGGGCGC GGGGCGAAGC GGTGCGGCGC CGGCAGGAAG GAAATGGGCG GGGAGGGCCT |
| 9661 | TCGTGCGTCG CCGCGCCGCC GTCCCCTTCT CCCTCTCCAG CCTCGGGGCT GTCCGCGGGG |
| 9721 | GGACGGCTGC CTTCGGGGGG GACGGGGCAG GGCGGGGTTC GGCTTCTGGC GTGTGACCGG |
| 9781 | CGGCTCTAGA GCCTCTGCTA ACCATGTTCA TGCCTTCTTC TTTTTCCTAC AGCTCCTGGG |
| 9841 | CAACGTGCTG GTTATTGTGC TGTCTCATCA TTTTGGCAAA GAATT |

SEQ ID NO: 3
| | |
|---|---|
| 1 | TCAATATTGG CCATTAGCCA TATTATTCAT TGGTTATATA GCATAAATCA ATATTGGCTA |
| 61 | TTGGCCATTG CATACGTTGT ATCTATATCA TAATATGTAC ATTTATATTG GCTCATGTCC |

| | -continued |
|---|---|
| | Sequences |
| 121 | AATATGACCG CCATGTTGGC ATTGATTATT GACTAGTTAT TAATAGTAAT CAATTACGGG |
| 181 | GTCATTAGTT CATAGCCCAT ATATGGAGTT CCGCGTTACA TAACTTACGG TAAATGGCCC |
| 241 | GCCTGGCTGA CCGCCCAACG ACCCCCGCCC ATTGACGTCA ATAATGACGT ATGTTCCCAT |
| 301 | AGTAACGCCA ATAGGGACTT TCCATTGACG TCAATGGGTG GAGTATTTAC GGTAAACTGC |
| 361 | CCACTTGGCA GTACATCAAG TGTATCATAT GCCAAGTCCG CCCCCTATTG ACGTCAATGA |
| 421 | CGGTAAATGG CCCGCCTGGC ATTATGCCCA GTACATGACC TTACGGGACT TTCCTACTTG |
| 481 | GCAGTACATC TACGTATTAG TCATCGCTAT TACCATGGTG ATGCGGTTTT GGCAGTACAC |
| 541 | CAATGGGCGT GGATAGCGGT TTGACTCACG GGGATTTCCA AGTCTCCACC CCATTGACGT |
| 601 | CAATGGGAGT TTGTTTTGGC ACCAAAATCA ACGGGACTTT CCAAAATGTC GTAATAACCC |
| 661 | CGCCCCGTTG ACGCAAATGG GCGGTAGGCG TGTACGGTGG GAGGTCTATA TAAGCAGAGC |
| 721 | TCGTTTAGTG AACCGTCAGA TCACTAGAAG CTTTATTGCG GTAGTTTATC ACAGTTAAAT |
| 781 | TGCTAACGCA GTCAGTGCTT CTGACACAAC AGTCTCGAAC TTAAGCTGCA GAAGTTGGTC |
| 841 | GTGAGGCACT GGGCAGGTAA GTATCAAGGT TACAAGACAG GTTTAAGGAG ACCAATAGAA |
| 901 | ACTGGGCTTG TCGAGACAGA GAAGACTCTT GCGTTTCTGA TAGGCACCTA TTGGTCTTAC |
| 961 | TGACATCCAC TTTGCCTTTC TCTCCACAGG TGTCCACTCC CAGTTCAATT ACAGCTCTTA |
| 1021 | AGGCTAGAGT ACTTAATACG ACTCACTATA GGCTAGCCTC GAGAATTCGA TTATGCCCCT |
| 1081 | AGGACCAGAA GAAAGAAGAT TGCTTCGCTT GATTTGGCTC CTTTACAGCA CCAATCCATA |
| 1141 | TCCACCAAGT GGGGAAGGGA CGGCCAGACA ACGCCGACGA GCCAGGAGAA GGTGGAGACA |
| 1201 | ACAGCAGGAT CAAATTAGAG TCTTGGTAGA AAGACTCCAA GAGCAGGTGT ATGCAGTTGA |
| 1261 | CCGCCTGGCT GACGAGGCTC AACACTTGGC TATACAACAG TTGCCTGACC CTCCTCATTC |
| 1321 | AGCTTAGAAT CACTAGTGAA TTCACGCGTG GTACCTCTAG AGTCGACCCG GGCGGCCGCT |
| 1381 | TCGAGCAGAC ATGATAAGAT ACATTGATGA GTTTGGACAA ACCACAACTA GAATGCAGTG |
| 1441 | AAAAAAATGC TTTATTTGTG AAATTTGTGA TGCTATTGCT TTATTTGTAA CCATTATAAG |
| 1501 | CTGCAATAAA CAAGTTAACA ACAACAATTG CATTCATTTT ATGTTTCAGG TTCAGGGGGA |
| 1561 | GATGTGGGAG GTTTTTTAAA GCAAGTAAAA CCTCTACAAA TGTGGTAAAA TCGATAAGGA |
| 1621 | TCCGTCGACC AATTGTTGTG TCTCAAAATC TCTGATGTTA CATTGCACAA GATAAAAATA |
| 1681 | TATCATCATG AACAATAAAA CTGTCTGCTT ACATAAACAG TAATACAAGG GGTGTTATGA |
| 1741 | GCCATATTCA ACGGGAAACG TCTTGCTCTA GGCCGCGATT AAATTCCAAC ATGGATGCTG |
| 1801 | ATTTATATGG GTATAAATGG CTCGCGATA ATGTCGGGCA ATCAGGTGCG ACAATCTATC |
| 1861 | GATTGTATGG GAAGCCCGAT GCGCCAGAGT TGTTTCTGAA ACATGGCAAA GGTAGCGTTG |
| 1921 | CCAATGATGT TACAGATGAG ATGGTCAGAC TAAACTGGCT GACGGAATTT ATGCCTCTTC |
| 1981 | CGACCATCAA GCATTTTATC CGTACTCCTG ATGATGCATG GTTACTCACC ACTGCGATCC |
| 2041 | CCGGAAAAAC AGCATTCCAG GTATTAGAAG AATATCCTGA TTCAGGTGAA AATATTGTTG |
| 2101 | ATGCGCTGGC AGTGTTCCTG CGCCGGTTGC ATTCGATTCC TGTTTGTAAT TGTCCTTTTA |
| 2161 | ACAGCGATCG CGTATTTCGT CTCGCTCAGG CGCAATCACG AATGAATAAC GGTTTGGTTG |
| 2221 | ATGCGAGTGA TTTTGATGAC GAGCGTAATG GCTGGCCTGT GAACAAGTC TGGAAAGAAA |
| 2281 | TGCATAAGCT GTTGCCATTC TCACCGGATT CAGTCGTCAC TCATGGTGAT TTCTCACTTG |
| 2341 | ATAACCTTAT TTTTGACGAG GGGAAATTAA TAGGTTGTAT TGATGTTGGA CGAGTCGGAA |

| | Sequences |
|---|---|
| 2401 | TCGCAGACCG ATACCAGGAT CTTGCCATCC TATGGAACTG CCTCGGTGAG TTTTCTCCTT |
| 2461 | CATTACAGAA ACGGCTTTTT CAAAAATATG GTATTGATAA TCCTGATATG AATAAATTGC |
| 2521 | AGTTTCATTT GATGCTCGAT GAGTTTTTCT AACTGTCAGA CCAAGTTTAC TCATATATAC |
| 2581 | TTTAGATTGA TTTAAAACTT CATTTTTAAT TTAAAAGGAT CTAGGTGAAG ATCCTTTTTG |
| 2641 | ATAATCTCAT GACCAAAATC CCTTAACGTG AGTTTTCGTT CCACTGAGCG TCAGACCCCG |
| 2701 | TAGAAAAGAT CAAAGGATCT TCTTGAGATC CTTTTTTTCT GCGCGTAATC TGCTGCTTGC |
| 2761 | AAACAAAAAA ACCACCGCTA CCAGCGGTGG TTTGTTTGCC GGATCAAGAG CTACCAACTC |
| 2821 | TTTTTCCGAA GGTAACTGGC TTCAGCAGAG CGCAGATACC AAATACTGTT CTTCTAGTGT |
| 2881 | AGCCGTAGTT AGGCCACCAC TTCAAGAACT CTGTAGCACC GCCTACATAC CTCGCTCTGC |
| 2941 | TAATCCTGTT ACCAGTGGCT GCTGCCAGTG GCGATAAGTC GTGTCTTACC GGGTTGGACT |
| 3001 | CAAGACGATA GTTACCGGAT AAGGCGCAGC GGTCGGGCTG AACGGGGGGT TCGTGCACAC |
| 3061 | AGCCCAGCTT GGAGCGAACG ACCTACACCG AACTGAGATA CCTACAGCGT GAGCTATGAG |
| 3121 | AAAGCGCCAC GCTTCCCGAA GGGAGAAAGG CGGACAGGTA TCCGGTAAGC GGCAGGGTCG |
| 3181 | GAACAGGAGA GCGCACGAGG GAGCTTCCAG GGGGAAACGC CTGGTATCTT TATAGTCCTG |
| 3241 | TCGGGTTTCG CCACCTCTGA CTTGAGCGTC GATTTTGTG ATGCTCGTCA GGGGGGCGGA |
| 3301 | GCCTATGGAA AAACGCCAGC AACGCGGCCT TTTTACGGTT CCTGGCCTTT TGCTGGCCTT |
| 3361 | TTGCTCACAT GGCTCGACAG ATCT |

SEQ ID NO: 4

| | |
|---|---|
| 1 | ATTGATTATT GACTAGTTAT TAATAGTAAT CAATTACGGG GTCATTAGTT CATAGCCCAT |
| 61 | ATATGGAGTT CCGCGTTACA TAACTTACGG TAAATGGCCC GCCTGGCTGA CCGCCCAACG |
| 121 | ACCCCCGCCC ATTGACGTCA ATAATGACGT ATGTTCCCAT AGTAACGCCA ATAGGGACTT |
| 181 | TCCATTGACG TCAATGGGTG GAGTATTTAC GGTAAACTGC CCACTTGGCA GTACATCAAG |
| 241 | TGTATCATAT GCCAAGTACG CCCCCTATTG ACGTCAATGA CGGTAAATGG CCCGCCTGGC |
| 301 | ATTATGCCCA GTACATGACC TTATGGGACT TTCCTACTTG GCAGTACATC TACGTATTAG |
| 361 | TCATCGCTAT TACCATGGTC GAGGTGAGCC CCACGTTCTG CTTCACTCTC CCCATCTCCC |
| 421 | CCCCCTCCCC ACCCCCAATT TTGTATTTAT TTATTTTTTA ATTATTTTGT GCAGCGATGG |
| 481 | GGGCGGGGGG GGGGGGGGGG CGCGCGCCAG GCGGGGCGGG GCGGGGCAAG GGGCGGGGCG |
| 541 | GGGCGAGGCG GAAAGGTGCG GCGGCAGCCA ATCAAAGCGG CGCGCTCCGA AAGTTTCCTT |
| 601 | TTATGGCGAG GCGGCGGCGG CGGCGGCCCT ATAAAAAGCG AAGCGCGCGG CGGGCGGGAG |
| 661 | TCGCTGCGCG CTGCCTTCGC CCCGTGCCCC GCTCCGCCGC CGCCTCGCGC CGCCCGCCCC |
| 721 | GGCTCTGACT GACCGCGTTA CTCCCACAGG TGAGCGGGCG GGACGGCCCT TCTCCTCCGG |
| 781 | GCTGTAATTA GCGCTTGGTT TAATGACGGC TTGTTTCTTT TCTGTGGCTG CGTGAAAGCC |
| 841 | TTGAGGGGCT CCGGGAGGGC CCTTTGTGCG GGGGGAGCGG CTCGGGGGGT GCGTGCGTGT |
| 901 | GTGTGTGCGT GGGGAGCGCC GCGTGCGGCT CCGCGCTGCC CGGCGGCTGT GAGCGCTGCG |
| 961 | GGCGCGGCGC GGGGCTTTGT GCGCTCCGCA GTGTGCGCGA GGGGAGCGCG GCCGGGGGCG |
| 1021 | GTGCCCCGCG GTGCGGGGGG GGCTGCGAGG GGAACAAAGG CTGCGTGCGG GGTGTGTGCG |
| 1081 | TGGGGGGGTG AGCAGGGGGT GTGGGCGCGT CGGTCGGGCT GCAACCCCCC CTGCACCCCC |
| 1141 | CTCCCCGAGT TGCTGAGCAC GGCCCGGCTT CGGGTGCGGG GCTCCGTACG GGGCGTGGCG |
| 1201 | CGGGGCTCGC CGTGCCGGGC GGGGGTGGC GGCAGGTGGG GGTGCCGGGC GGGGCGGGGC |

-continued

| | Sequences |
|---|---|
| 1261 | CGCCTCGGGC CGGGGAGGGC TCGGGGAGG GGCGCGGCGG CCCCCGGAGC GCCGGCGGCT |
| 1321 | GTCGAGGCGC GGCGAGCCGC AGCCATTGCC TTTTATGGTA ATCGTGCGAG AGGGCGCAGG |
| 1381 | GACTTCCTTT GTCCCAAATC TGTGCGGAGC CGAAATCTGG GAGGCGCCGC CGCACCCCCT |
| 1441 | CTAGCGGGCG CGGGGCGAAG CGGTGCGGCG CCGGCAGGAA GGAAATGGGC GGGGAGGGCC |
| 1501 | TTCGTGCGTC GCCGCGCCGC CGTCCCCTTC TCCCTCTCCA GCCTCGGGGC TGTCCGCGGG |
| 1561 | GGGACGGCTG CCTTCGGGGG GGACGGGGCA GGGCGGGGTT CGGCTTCTGG CGTGTGACCG |
| 1621 | GCGGCTCTAG AGCCTCTGCT AACCATGTTC ATGCCTTCTT CTTTTTCCTA CAGCTCCTGG |
| 1681 | GCAACGTGCT GGTTATTGTG CTGTCTCATC ATTTTGGCAA AGAATTCGAT TGCCATGGCA |
| 1741 | ACATATATCC AGAGAGTACA GTGCATCTCA ACATCACTAC TGGTTGTTCT CACCACATTG |
| 1801 | GTCTCGTGTC AGATTCCCAG GGATAGGCTC TCTAACATAG GGGTCATAGT CGATGAAGGG |
| 1861 | AAATCACTGA AGATAGCTGG ATCCCACGAA TCGAGGTACA TAGTACTGAG TCTAGTTCCG |
| 1921 | GGGGTAGACT TTGAGAATGG GTGCGGAACA GCCCAGGTTA TCCAGTACAA GAGCCTACTG |
| 1981 | AACAGGCTGT TAATCCCATT GAGGGATGCC TTAGATCTTC AGGAGGCTCT GATAACTGTC |
| 2041 | ACCAATGATA CGACACAAAA TGCCGGTGCT CCCCAGTCGA GATTCTTCGG TGCTGTGATT |
| 2101 | GGTACTATCG CACTTGGAGT GGCGACATCA GCACAAATCA CCGCAGGGAT TGCACTAGCC |
| 2161 | GAAGCGAGGG AGGCCAAAAG AGACATAGCG CTCATCAAAG AATCGATGAC AAAAACACAC |
| 2221 | AAGTCTATAG AACTGCTGCA AAACGCTGTG GGGGAACAAA TTCTTGCTCT AAAGACACTC |
| 2281 | CAGGATTTCG TGAATGATGA GATCAAACCC GCAATAAGCG AATTAGGCTG TGAGACTGCT |
| 2341 | GCCTTAAGAC TGGGTATAAA ATTGACACAG CATTACTCCG AGCTGTTAAC TGCGTTCGGC |
| 2401 | TCGAATTTCG GAACCATCGG AGAGAAGAGC CTCACGCTGC AGGCGCTGTC TTCACTTTAC |
| 2461 | TCTGCTAACA TTACTGAGAT TATGACCACA ATCAGGACAG GCAGTCTAA CATCTATGAT |
| 2521 | GTCATTTATA CAGAACAGAT CAAAGGAACG GTGATAGATG TGGATCTAGA GAGATACATG |
| 2581 | GTCACCCTGT CTGTGAAGAT CCCTATTCTT TCTGAAGTCC CAGGTGTGCT CATACACAAG |
| 2641 | GCATCATCTA TTTCTTACAA CATAGACGGG GAGGAATGGT ATGTGACTGT CCCCAGCCAT |
| 2701 | ATACTCAGTC GTGCTTCTTT CTTAGGGGGT GCAGACATAA CCGATTGTGT TGAGTCCAGA |
| 2761 | TTGACCTATA TATGCCCCAG GGATCCCGCA CAACTGATAC CTGACAGCCA GCAAAAGTGT |
| 2821 | ATCCTGGGGG ACACAACAAG GTGTCCTGTC ACAAAAGTTG TGGACAGCCT TATCCCCAAG |
| 2881 | TTTGCTTTTG TGAATGGGGG CGTTGTTGCT AACTGCATAG CATCCACATG TACCTGCGGG |
| 2941 | ACAGGCCGAA GACCAATCAG TCAGGATCGC TCTAAAGGTG TAGTATTCCT AACCCATGAC |
| 3001 | AACTGTGGTC TTATAGGTGT CAATGGGGTA GAATTGTATG CTAACCGGAG AGGGCACGAT |
| 3061 | GCCACTTGGG GGTCCAGAA CTTGACAGTC GGTCCTGCAA TTGCTATCAG ACCCGTTGAT |
| 3121 | ATTTCTCTCA ACCTTGCTGA TGCTACGAAT TTCTTGCAAG ACTCTAAGGC TGAGCTTGAG |
| 3181 | AAAGCACGGA AAATCCTCTC GGAGGTAGGT AGATGGTACA ACTCAAGAGA GACTGTGATT |
| 3241 | ACGATCATAG TAGTTATGGT CGTAATATTG GTGGTCATTA TAGTGATCAT CATCGTGCTT |
| 3301 | TATAGACTCA GAAGGTGAAA TCACTAGTGA ATTCACTCCT CAGGTGCAGG CTGCCTATCA |
| 3361 | GAAGGTGGTG GCTGGTGTGG CCAATGCCCT GGCTCACAAA TACCACTGAG ATCTTTTTCC |
| 3421 | CTCTGCCAAA AATTATGGGG ACATCATGAA GCCCCTTGAG CATCTGACTT CTGGCTAATA |
| 3481 | AAGGAAATTT ATTTTCATTG CAATAGTGTG TTGGAATTTT TTGTGTCTCT CACTCGGAAG |

-continued

| | Sequences |
|---|---|
| 3541 | GACATATGGG AGGGCAAATC ATTTAAAACA TCAGAATGAG TATTTGGTTT AGAGTTTGGC |
| 3601 | AACATATGCC CATATGCTGG CTGCCATGAA CAAAGGTTGG CTATAAAGAG GTCATCAGTA |
| 3661 | TATGAAACAG CCCCCTGCTG TCCATTCCTT ATTCCATAGA AAAGCCTTGA CTTGAGGTTA |
| 3721 | GATTTTTTTT ATATTTTGTT TTGTGTTATT TTTTTCTTTA ACATCCCTAA AATTTTCCTT |
| 3781 | ACATGTTTTA CTAGCCAGAT TTTTCCTCCT CTCCTGACTA CTCCCAGTCA TAGCTGTCCC |
| 3841 | TCTTCTCTTA TGGAGATCCC TCGACCTGCA GCCCAAGCTT GGCGTAATCA TGGTCATAGC |
| 3901 | TGTTTCCTGT GTGAAATTGT TATCCGCTCA CAATTCCACA CAACATACGA GCCGGAAGCA |
| 3961 | TAAAGTGTAA AGCCTGGGGT GCCTAATGAG TGAGCTAACT CACATTAATT GCGTTGCGCT |
| 4021 | CACTGCCCGC TTTCCAGTCG GGAAACCTGT CGTGCCAGCG GATCCGCATC TCAATTAGTC |
| 4081 | AGCAACCATA GTCCCGCCCC TAACTCCGCC CATCCCGCCC CTAACTCCGC CCAGTTCCGC |
| 4141 | CCATTCTCCG CCCCATGGCT GACTAATTTT TTTTATTTAT GCAGAGGCCG AGGCCGCCTC |
| 4201 | GGCCTCTGAG CTATTCCAGA AGTAGTGAGG AGGCTTTTTT GGAGGCCTAG GCTTTTGCAA |
| 4261 | AAAGCTAACT TGTTTATTGC AGCTTATAAT GGTTACAAAT AAAGCAATAG CATCACAAAT |
| 4321 | TTCACAAATA AAGCATTTTT TTCACTGCAT TCTAGTTGTG GTTTGTCCAA ACTCATCAAT |
| 4381 | GTATCTTATC ATGTCTGTCC GCTTCCTCGC TCACTGACTC GCTGCGCTCG GTCGTTCGGC |
| 4441 | TGCGGCGAGC GGTATCAGCT CACTCAAAGG CGGTAATACG GTTATCCACA GAATCAGGGG |
| 4501 | ATAACGCAGG AAAGAACATG TGAGCAAAAG GCCAGCAAAA GGCCAGGAAC CGTAAAAAGG |
| 4561 | CCGCGTTGCT GGCGTTTTTC CATAGGCTCC GCCCCCCTGA CGAGCATCAC AAAAATCGAC |
| 4621 | GCTCAAGTCA GAGGTGGCGA AACCCGACAG GACTATAAAG ATACCAGGCG TTTCCCCCTG |
| 4681 | GAAGCTCCCT CGTGCGCTCT CCTGTTCCGA CCCTGCCGCT TACCGGATAC CTGTCCGCCT |
| 4741 | TTCTCCCTTC GGGAAGCGTG GCGCTTTCTC ATAGCTCACG CTGTAGGTAT CTCAGTTCGG |
| 4801 | TGTAGGTCGT TCGCTCCAAG CTGGGCTGTG TGCACGAACC CCCCGTTCAG CCCGACCGCT |
| 4861 | GCGCCTTATC CGGTAACTAT CGTCTTGAGT CCAACCCGGT AAGACACGAC TTATCGCCAC |
| 4921 | TGGCAGCAGC CACTGGTAAC AGGATTAGCA GAGCGAGGTA TGTAGGCGGT GCTACAGAGT |
| 4981 | TCTTGAAGTG GTGGCCTAAC TACGGCTACA CTAGAAGAAC AGTATTTGGT ATCTGCGCTC |
| 5041 | TGCTGAAGCC AGTTACCTTC GGAAAAAGAG TTGGTAGCTC TTGATCCGGC AAACAAACCA |
| 5101 | CCGCTGGTAG CGGTGGTTTT TTTGTTTGCA AGCAGCAGAT TACGCGCAGA AAAAAAGGAT |
| 5161 | CTCAAGAAGA TCCTTTGATC TTTTCTACGG GGTCTGACGC TCAGTGGAAC GAAAACTCAC |
| 5221 | GTTAAGGGAT TTTGGTCATG AGATTATCAA AAAGGATCTT CACCTAGATC CTTTTAAATT |
| 5281 | AAAAATGAAG TTTTAAATCA ATCTAAAGTA TATATGAGTA AACTTGGTCT GACAGTTAGA |
| 5341 | AAAACTCATC GAGCATCAAA TGAAACTGCA ATTTATTCAT ATCAGGATTA TCAATACCAT |
| 5401 | ATTTTTGAAA AAGCCGTTTC TGTAATGAAG GAGAAAACTC ACCGAGGCAG TTCCATAGGA |
| 5461 | TGGCAAGATC CTGGTATCGG TCTGCGATTC CGACTCGTCC AACATCAATA CAACCTATTA |
| 5521 | ATTTCCCCTC GTCAAAAATA AGGTTATCAA GTGAGAAATC ACCATGAGTG ACGACTGAAT |
| 5581 | CCGGTGAGAA TGGCAACAGC TTATGCATTT CTTTCCAGAC TTGTTCAACA GGCCAGCCAT |
| 5641 | TACGCTCGTC ATCAAAATCA CTCGCATCAA CCAAACCGTT ATTCATTCGT GATTGCGCCT |
| 5701 | GAGCGAGACG AAATACGCGA TCGCTGTTAA AAGGACAATT ACAAACAGGA ATCGAATGCA |
| 5761 | ACCGGCGCAG GAACACTGCC AGCGCATCAA CAATATTTTC ACCTGAATCA GGATATTCTT |

| | Sequences |
|---|---|
| 5821 | CTAATACCTG GAATGCTGTT TTTCCGGGGA TCGCAGTGGT GAGTAACCAT GCATCATCAG |
| 5881 | GAGTACGGAT AAAATGCTTG ATGGTCGGAA GAGGCATAAA TTCCGTCAGC CAGTTTAGTC |
| 5941 | TGACCATCTC ATCTGTAACA TCATTGGCAA CGCTACCTTT GCCATGTTTC AGAAACAACT |
| 6001 | CTGGCGCATC GGGCTTCCCA TACAATCGAT AGATTGTCGC ACCTGATTGC CCGACATTAT |
| 6061 | CGCGAGCCCA TTTATACCCA TATAAATCAG CATCCATGTT GGAATTTAAT CGCGGCCTAG |
| 6121 | AGCAAGACGT TTCCCGTTGA ATATGGCTCA TAACACCCCT TGTATTACTG TTTATGTAAG |
| 6181 | CAGACAGTTT TATTGTTCAT GATGATATAT TTTTATCTTG TGCAATGTAA CATCAGAGAT |
| 6241 | TTTGAGACAC AACAATTGGT CGAC |
| SEQ ID NO: 5 | |
| 1 | ATTGATTATT GACTAGTTAT TAATAGTAAT CAATTACGGG GTCATTAGTT CATAGCCCAT |
| 61 | ATATGGAGTT CCGCGTTACA TAACTTACGG TAAATGGCCC GCCTGGCTGA CCGCCCAACG |
| 121 | ACCCCCGCCC ATTGACGTCA ATAATGACGT ATGTTCCCAT AGTAACGCCA ATAGGGACTT |
| 181 | TCCATTGACG TCAATGGGTG GAGTATTTAC GGTAAACTGC CCACTTGGCA GTACATCAAG |
| 241 | TGTATCATAT GCCAAGTACG CCCCCTATTG ACGTCAATGA CGGTAAATGG CCCGCCTGGC |
| 301 | ATTATGCCCA GTACATGACC TTATGGGACT TTCCTACTTG GCAGTACATC TACGTATTAG |
| 361 | TCATCGCTAT TACCATGGTC GAGGTGAGCC CCACGTTCTG CTTCACTCTC CCCATCTCCC |
| 421 | CCCCCTCCCC ACCCCCAATT TTGTATTTAT TTATTTTTTA ATTATTTTGT GCAGCGATGG |
| 481 | GGGCGGGGGG GGGGGGGGGG CGCGCGCCAG GCGGGGCGGG GCGGGGCGAG GGGCGGGGCG |
| 541 | GGGCGAGGCG GAAAGGTGCG GCGGCAGCCA ATCAAAGCGG CGCGCTCCGA AAGTTTCCTT |
| 601 | TTATGGCGAG GCGGCGGCGG CGGCGGCCCT ATAAAAAGCG AAGCGCGCGG CGGGCGGGAG |
| 661 | TCGCTGCGCG CTGCCTTCGC CCCGTGCCCC GCTCCGCCGC CGCCTCGCGC CGCCCGCCCC |
| 721 | GGCTCTGACT GACCGCGTTA CTCCCACAGG TGAGCGGGCG GGACGGCCCT TCTCCTCCGG |
| 781 | GCTGTAATTA GCGCTTGGTT TAATGACGGC TTGTTTCTTT TCTGTGGCTG CGTGAAAGCC |
| 841 | TTGAGGGGCT CCGGGAGGGC CCTTTGTGCG GGGGGAGCGG CTCGGGGGGT GCGTGCGTGT |
| 901 | GTGTGTGCGT GGGGAGCGCC GCGTGCGGCT CCGCGCTGCC CGGCGGCTGT GAGCGCTGCG |
| 961 | GGCGCGGCGC GGGGCTTTGT GCGCTCCGCA GTGTGCGCGA GGGGAGCGCG GCCGGGGGCG |
| 1021 | GTGCCCCGCG GTGCGGGGGG GGCTGCGAGG GGAACAAAGG CTGCGTGCGG GGTGTGTGCG |
| 1081 | TGGGGGGGTG AGCAGGGGGT GTGGGCGCGT CGGTCGGGCT GCAACCCCCC CTGCACCCCC |
| 1141 | CTCCCCGAGT TGCTGAGCAC GGCCCGGCTT CGGGTGCGGG GCTCCGTACG GGGCGTGGCG |
| 1201 | CGGGGCTCGC CGTGCCGGGC GGGGGGTGGC GGCAGGTGGG GGTGCCGGGC GGGGCGGGGC |
| 1261 | CGCCTCGGGC CGGGGAGGGC TCGGGGGAGG GGCGCGGCGG CCCCGGAGC GCCGGCGGCT |
| 1321 | GTCGAGGCGC GGCGAGCCGC AGCCATTGCC TTTTATGGTA ATCGTGCGAG AGGGCGCAGG |
| 1381 | GACTTCCTTT GTCCCAAATC TGTGCGGAGC CGAAATCTGG GAGGCGCCGC CGCACCCCCT |
| 1441 | CTAGCGGGCG CGGGGCGAAG CGGTGCGGCG CCGGCAGGAA GGAAATGGGC GGGGAGGGCC |
| 1501 | TTCGTGCGTC GCCGCGCCGC CGTCCCCTTC TCCCTCTCCA GCCTCGGGGC TGTCCGCGGG |
| 1561 | GGGACGGGGC AGGGCGGGGT TCGGCTTCTG GCGTGTGACC GGCGGCTCTA GAGCCTCTGC |
| 1621 | TAACCATGTT CATGCCTTCT TCTTTTTCCT ACAGCTCCTG GCAACGTGC TGGTTATTGT |
| 1681 | GCTGTCTCAT CATTTTGGCA AAGAATTCCT CGAGCATGTG GTCTGAGTTA AAAATCAGGA |
| 1741 | GCAACGACGG AGGTGAAGGA CCAGAGGACG CCAACGACCC CCGGGGAAAG GGGGTGCAAC |

-continued

| | Sequences |
|---|---|
| 1801 | ACATCCATAT CCAGCCATCT CTACCTGTTT ATGGACAGAG GGTTAGGGAT GGTGATAGGG |
| 1861 | GCAAACGTGA CTCGTACTGG TCTACTTCTC CTAGTGGTAG CACCACAAAA CCAGCATCAG |
| 1921 | GTTGGGAGAG GTCAAGTAAA GCCGACACAT GGTTGCTGAT TCTCTCATTC ACCCAGTGGG |
| 1981 | CTTTGTCAAT TGCCACAGTG ATCATCTGTA TCATAATTTC TGCTAGACAA GGGTATAGTA |
| 2041 | TGAAAGAGTA CTCAATGACT GTAGAGGCAT TGAACATGAG CAGCAGGGAG GTGAAAGAGT |
| 2101 | CACTTACCAG TCTAATAAGG CAAGAGGTTA TAGCAAGGGC TGTCAACATT CAGAGCTCTG |
| 2161 | TGCAAACCGG AATCCCAGTC TTGTTGAACA AAAACAGCAG GGATGTCATC CAGATGATTG |
| 2221 | ATAAGTCGTG CAGCAGACAA GAGCTCACTC AGCACTGTGA GAGTACGATC GCAGTCCACC |
| 2281 | ATGCCGATGG AATTGCCCCA CTTGAGCCAC ATAGTTTCTG GAGATGCCCT GTCGGAGAAC |
| 2341 | CGTATCTTAG CTCAGATCCT GAAATCTCAT TGCTGCCTGG TCCGAGCTTG TTATCTGGTT |
| 2401 | CTACAACGAT CTCTGGATGT GTTAGGCTCC CTTCACTCTC AATTGGCGAG GCAATCTATG |
| 2461 | CCTATTCATC AAATCTCATT ACACAAGGTT GTGCTGACAT AGGGAAATCA TATCAGGTCC |
| 2521 | TGCAGCTAGG GTACATATCA CTCAATTCAG ATATGTTCCC TGATCTTAAC CCCGTAGTGT |
| 2581 | CCCACACTTA TGACATCAAC GACAATCGGA ATCATGCTC TGTGGTGGCA ACCGGGACTA |
| 2641 | GGGGTTATCA GCTTTGCTCC ATGCCGACTG TAGACGAAAG AACCGACTAC TCTAGTGATG |
| 2701 | GTATTGAGGA TCTGGTCCTT GATGTCCTGG ATCTCAAAGG GAGAACTAAG TCTCACCGGT |
| 2761 | ATCGCAACAG CGAGGTAGAT CTTGATCACC CGTTCTCTGC ACTATACCCC AGTGTAGGCA |
| 2821 | ACGGCATTGC AACAGAAGGC TCATTGATAT TTCTTGGGTA TGGTGGACTA ACCACCCCTC |
| 2881 | TGCAGGGTGA TACAAAATGT AGGACCCAAG GATGCCAACA GGTGTCGCAA GACACATGCA |
| 2941 | ATGAGGCTCT GAAAATTACA TGGCTAGGAG GGAAACAGGT GGTCAGCGTG ATCATCCAGG |
| 3001 | TCAATGACTA TCTCTCAGAG AGGCCAAAGA TAAGAGTCAC AACCATTCCA ATCACTCAAA |
| 3061 | ACTATCTCGG GGCGGAAGGT AGATTATTAA AATTGGGTGA TCGGGTGTAC ATCTATACAA |
| 3121 | GATCATCAGG CTGGCACTCT CAACTGCAGA TAGGAGTACT TGATGTCAGC CACCCTTTGA |
| 3181 | CTATCAACTG GACACCTCAT GAAGCCTTGT CTAGACCAGG AAATAAAGAG TGCAATTGGT |
| 3241 | ACAATAAGTG TCCGAAGGAA TGCATATCAG GCGTATACAC TGATGCTTAT CCATTGTCCC |
| 3301 | CTGATGCAGC TAACGTCGCT ACCGTCACGC TATATGCCAA TACATCGCGT GTCAACCCAA |
| 3361 | CAATCATGTA TTCTAACACT ACTAACATTA TAAATATGTT AAGGATAAAG GATGTTCAAT |
| 3421 | TAGAGGCTGC ATATACCACG ACATCGTGTA TCACGCATTT TGGTAAAGGC TACTGCTTTC |
| 3481 | ACATCATCGA GATCAATCAG AAGAGCCTGA ATACCTTACA GCCGATGCTC TTTAAGACTA |
| 3541 | GCATCCCTAA ATTATGCAAG GCCGAGTCTT AAGCGGCCGC GCATGCGAAT TCACTCCTCA |
| 3601 | GGTGCAGGCT GCCTATCAGA AGGTGGTGGC TGGTGTGGCC AATGCCCTGG CTCACAAATA |
| 3661 | CCACTGAGAT CTTTTTCCCT CTGCCAAAAA TTATGGGGAC ATCATGAAGC CCCTTGAGCA |
| 3721 | TCTGACTTCT GGCTAATAAA GGAAATTTAT TTTCATTGCA ATAGTGTGTT GGAATTTTTT |
| 3781 | GTGTCTCTCA CTCGGAAGGA CATATGGGAG GGCAAATCAT TTAAAACATC AGAATGAGTA |
| 3841 | TTTGGTTTAG AGTTTGGCAA CATATGCCCA TATGCTGGCT GCCATGAACA AAGGTTGGCT |
| 3901 | ATAAAGAGGT CATCAGTATA TGAAACAGCC CCCTGCTGTC TATTCCTTAT TCCATAGAAA |
| 3961 | AGCCTTGACT TGAGGTTAGA TTTTTTTTAT ATTTTGTTTT GTGTTATTTT TTTCTTTAAC |
| 4021 | ATCCCTAAAA TTTTCCTTAC ATGTTTTACT AGCCAGATTT TTCCTCCTCT CCTGACTACT |

| | Sequences |
|---|---|
| 4081 | CCCAGTCATA GCTGTCCCTC TTCTCTTATG GAGATCCCTC GACCTGCAGC CCAAGCTTGG |
| 4141 | CGTAATCATG GTCATAGCTG TTTCCTGTGT GAAATTGTTA TCCGCTCACA ATTCCACACA |
| 4201 | ACATACGAGC CGGAAGCATA AAGTGTAAAG CCTGGGGTGC CTAATGAGTG AGCTAACTCA |
| 4261 | CATTAATTGC GTTGCGCTCA CTGCCCGCTT TCCAGTCGGG AAACCTGTCG TGCCAGCGGA |
| 4321 | TCCGCATCTC AATTAGTCAG CAACCATAGT CCCGCCCCTA ACTCCGCCCA TCCCGCCCCT |
| 4381 | AACTCCGCCC AGTTCCGCCC ATTCTCCGCC CCATGGCTGA CTAATTTTTT TTATTTATGC |
| 4441 | AGAGGCCGAG GCCGCCTCGG CCTCTGAGCT ATTCCAGAAG TAGTGAGGAG GCTTTTTTGG |
| 4501 | AGGCCTAGGC TTTTGCAAAA AGCTAACTTG TTTATTGCAG CTTATAATGG TTACAAATAA |
| 4561 | AGCAATAGCA TCACAAATTT CACAAATAAA GCATTTTTTT CACTGCATTC TAGTTGTGGT |
| 4621 | TTGTCCAAAC TCATCAATGT ATCTTATCAT GTCTGTCCGC TTCCTCGCTC ACTGACTCGC |
| 4681 | TGCGCTCGGT CGTTCGGCTG CGGCGAGCGG TATCAGCTCA CTCAAAGGCG GTAATACGGT |
| 4741 | TATCCACAGA ATCAGGGGAT AACGCAGGAA AGAACATGTG AGCAAAAGGC CAGCAAAAGG |
| 4801 | CCAGGAACCG TAAAAAGGCC GCGTTGCTGG CGTTTTTCCA TAGGCTCCGC CCCCCTGACG |
| 4861 | AGCATCACAA AAATCGACGC TCAAGTCAGA GGTGGCGAAA CCCGACAGGA CTATAAAGAT |
| 4921 | ACCAGGCGTT TCCCCCTGGA AGCTCCCTCG TGCGCTCTCC TGTTCCGACC CTGCCGCTTA |
| 4981 | CCGGATACCT GTCCGCCTTT CTCCCTTCGG GAAGCGTGGC GCTTTCTCAT AGCTCACGCT |
| 5041 | GTAGGTATCT CAGTTCGGTG TAGGTCGTTC GCTCCAAGCT GGGCTGTGTG CACGAACCCC |
| 5101 | CCGTTCAGCC CGACCGCTGC GCCTTATCCG GTAACTATCG TCTTGAGTCC AACCCGGTAA |
| 5161 | GACACGACTT ATCGCCACTG GCAGCAGCCA CTGGTAACAG GATTAGCAGA GCGAGGTATG |
| 5221 | TAGGCGGTGC TACAGAGTTC TTGAAGTGGT GGCCTAACTA CGGCTACACT AGAAGAACAG |
| 5281 | TATTTGGTAT CTGCGCTCTG CTGAAGCCAG TTACCTTCGG AAAAAGAGTT GGTAGCTCTT |
| 5341 | GATCCGGCAA ACAAACCACC GCTGGTAGCG GTGGTTTTTT TGTTTGCAAG CAGCAGATTA |
| 5401 | CGCGCAGAAA AAAAGGATCT CAAGAAGATC CTTTGATCTT TTCTACGGGG TCTGACGCTC |
| 5461 | AGTGGAACGA AAACTCACGT TAAGGGATTT TGGTCATGAG ATTATCAAAA AGGATCTTCA |
| 5521 | CCTAGATCCT TTTAAATTAA AAATGAAGTT TTAAATCAAT CTAAAGTATA TATGAGTAAA |
| 5581 | CTTGGTCTGA CAGTTAGAAA AACTCATCGA GCATCAAATG AAACTGCAAT TTATTCATAT |
| 5641 | CAGGATTATC AATACCATAT TTTTGAAAAA GCCGTTTCTG TAATGAAGGA GAAAACTCAC |
| 5701 | CGAGGCAGTT CCATAGGATG GCAAGATCCT GGTATCGGTC TGCGATTCCG ACTCGTCCAA |
| 5761 | CATCAATACA ACCTATTAAT TTCCCCTCGT CAAAAATAAG GTTATCAAGT GAGAAATCAC |
| 5821 | CATGAGTGAC GACTGAATCC GGTGAGAATG GCAACAGCTT ATGCATTTCT TTCCAGACTT |
| 5881 | GTTCAACAGG CCAGCCATTA CGCTCGTCAT CAAAATCACT CGCATCAACC AAACCGTTAT |
| 5941 | TCATTCGTGA TTGCGCCTGA GCGAGACGAA ATACGCGATC GCTGTTAAAA GGACAATTAC |
| 6001 | AAACAGGAAT CGAATGCAAC CGGCGCAGGA ACACTGCCAG CGCATCAACA ATATTTTCAC |
| 6061 | CTGAATCAGG ATATTCTTCT AATACCTGGA ATGCTGTTTT TCCGGGGATC GCAGTGGTGA |
| 6121 | GTAACCATGC ATCATCAGGA GTACGGATAA AATGCTTGAT GGTCGGAAGA GGCATAAATT |
| 6181 | CCGTCAGCCA GTTTAGTCTG ACCATCTCAT CTGTAACATC ATTGGCAACG CTACCTTTGC |
| 6241 | CATGTTTCAG AAACAACTCT GGCGCATCGG GCTTCCCATA CAATCGATAG ATTGTCGCAC |
| 6301 | CTGATTGCCC GACATTATCG CGAGCCCATT TATACCCATA TAAATCAGCA TCCATGTTGG |

|  | Sequences |
| --- | --- |
| 6361 | AATTTAATCG CGGCCTAGAG CAAGACGTTT CCCGTTGAAT ATGGCTCATA ACACCCCTTG |
| 6421 | TATTACTGTT TATGTAAGCA GACAGTTTTA TTGTTCATGA TGATATATTT TTATCTTGTG |
| 6481 | CAATGTAACA TCAGAGATTT TGAGACACAA CAATTGGTCG AC |

SEQ ID NO: 6

|  |  |
| --- | --- |
| 1 | AGATCTGTTA CATAACTTAT GGTAAATGGC CTGCCTGGCT GACTGCCCAA TGACCCCTGC |
| 61 | CCAATGATGT CAATAATGAT GTATGTTCCC ATGTAATGCC AATAGGGACT TTCCATTGAT |
| 121 | GTCAATGGGT GGAGTATTTA TGGTAACTGC CCACTTGGCA GTACATCAAG TGTATCATAT |
| 181 | GCCAAGTATG CCCCCTATTG ATGTCAATGA TGGTAAATGG CCTGCCTGGC ATTATGCCCA |
| 241 | GTACATGACC TTATGGGACT TTCCTACTTG GCAGTACATC TATGTATTAG TCATTGCTAT |
| 301 | TACCATGGGA ATTCACTAGT GGAGAAGAGC ATGCTTGAGG GCTGAGTGCC CCTCAGTGGG |
| 361 | CAGAGAGCAC ATGGCCCACA GTCCCTGAGA AGTTGGGGGG AGGGGTGGGC AATTGAACTG |
| 421 | GTGCCTAGAG AAGGTGGGGC TTGGGTAAAC TGGGAAAGTG ATGTGGTGTA CTGGCTCCAC |
| 481 | CTTTTTCCCC AGGGTGGGGG AGAACCATAT ATAAGTGCAG TAGTCTCTGT GAACATTCAA |
| 541 | GCTTCTGCCT TCTCCCTCCT GTGAGTTTGC TAGC |

SEQ ID NO: 7

|  |  |
| --- | --- |
| 1 | GCTAGCCACC ATGCAGAGAA GCCCTCTGGA GAAGGCCTCT GTGGTGAGCA AGCTGTTCTT |
| 61 | CAGCTGGACC AGGCCCATCC TGAGGAAGGG CTACAGGCAG AGACTGGAGC TGTCTGACAT |
| 121 | CTACCAGATC CCCTCTGTGG ACTCTGCTGA CAACCTGTCT GAGAAGCTGG AGAGGGAGTG |
| 181 | GGATAGAGAG CTGGCCAGCA AGAAGAACCC CAAGCTGATC AATGCCCTGA GGAGATGCTT |
| 241 | CTTCTGGAGA TTCATGTTCT ATGGCATCTT CCTGTACCTG GGGGAAGTGA CCAAGGCTGT |
| 301 | GCAGCCTCTG CTGCTGGGCA GAATCATTGC CAGCTATGAC CCTGACAACA AGGAGGAGAG |
| 361 | GAGCATTGCC ATCTACCTGG GCATTGGCCT GTGCCTGCTG TTCATTGTGA GGACCCTGCT |
| 421 | GCTGCACCCT GCCATCTTTG GCCTGCACCA CATTGGCATG CAGATGAGGA TTGCCATGTT |
| 481 | CAGCCTGATC TACAAGAAAA CCCTGAAGCT GTCCAGCAGA GTGCTGGACA AGATCAGCAT |
| 541 | TGGCCAGCTG GTGAGCCTGC TGAGCAACAA CCTGAACAAG TTTGATGAGG GCCTGGCCCT |
| 601 | GGCCCACTTT GTGTGGATTG CCCCTCTGCA GGTGGCCCTG CTGATGGGCC TGATTTGGGA |
| 661 | GCTGCTGCAG GCCTCTGCCT TTTGTGGCCT GGGCTTCCTG ATTGTGCTGG CCCTGTTTCA |
| 721 | GGCTGGCCTG GGCAGGATGA TGATGAAGTA CAGGGACCAG AGGGCAGGCA AGATCAGTGA |
| 781 | GAGGCTGGTG ATCACCTCTG AGATGATTGA GAACATCCAG TCTGTGAAGG CCTACTGTTG |
| 841 | GGAGGAAGCT ATGGAGAAGA TGATTGAAAA CCTGAGGCAG ACAGAGCTGA AGCTGACCAG |
| 901 | GAAGGCTGCC TATGTGAGAT ACTTCAACAG CTCTGCCTTC TTCTTCTCTG GCTTCTTTGT |
| 961 | GGTGTTCCTG TCTGTGCTGC CCTATGCCCT GATCAAGGGG ATCATCCTGA GAAAGATTTT |
| 1021 | CACCACCATC AGCTTCTGCA TTGTGCTGAG GATGGCTGTG ACCAGACAGT TCCCCTGGGC |
| 1081 | TGTGCAGACC TGGTATGACA GCCTGGGGGC CATCAACAAG ATCCAGGACT TCCTGCAGAA |
| 1141 | GCAGGAGTAC AAGACCCTGG AGTACAACCT GACCACCACA GAAGTGGTGA TGGAGAATGT |
| 1201 | GACAGCCTTC TGGGAGGAGG GCTTTGGGGA GCTGTTTGAG AAGGCCAAGC AGAACAACAA |
| 1261 | CAACAGAAAG ACCAGCAATG GGGATGACTC CCTGTTCTTC TCCAACTTCT CCCTGCTGGG |
| 1321 | CACACCTGTG CTGAAGGACA TCAACTTCAA GATTGAGAGG GGGCAGCTGC TGGCTGTGGC |
| 1381 | TGGATCTACA GGGGCTGGCA AGACCAGCCT GCTGATGATG ATCATGGGGG AGCTGGAGCC |

-continued

| | Sequences |
|---|---|
| 1441 | TTCTGAGGGC AAGATCAAGC ACTCTGGCAG GATCAGCTTT TGCAGCCAGT TCAGCTGGAT |
| 1501 | CATGCCTGGC ACCATCAAGG AGAACATCAT CTTTGGAGTG AGCTATGATG AGTACAGATA |
| 1561 | CAGGAGTGTG ATCAAGGCCT GCCAGCTGGA GGAGGACATC AGCAAGTTTG CTGAGAAGGA |
| 1621 | CAACATTGTG CTGGGGGAGG GAGGCATTAC ACTGTCTGGG GGCCAGAGAG CCAGAATCAG |
| 1681 | CCTGGCCAGG GCTGTGTACA AGGATGCTGA CCTGTACCTG CTGGACTCCC CCTTTGGCTA |
| 1741 | CCTGGATGTG CTGACAGAGA AGGAGATTTT TGAGAGCTGT GTGTGCAAGC TGATGGCCAA |
| 1801 | CAAGACCAGA ATCCTGGTGA CCAGCAAGAT GGAGCACCTG AAGAAGGCTG ACAAGATCCT |
| 1861 | GATCCTGCAT GAGGGCAGCA GCTACTTCTA TGGGACCTTC TCTGAGCTGC AGAACCTGCA |
| 1921 | GCCTGACTTC AGCTCTAAGC TGATGGGCTG TGACAGCTTT GACCAGTTCT CTGCTGAGAG |
| 1981 | GAGGAACAGC ATCCTGACAG AGACCCTGCA CAGATTCAGC CTGGAGGGAG ATGCCCCTGT |
| 2041 | GAGCTGGACA GAGACCAAGA AGCAGAGCTT CAAGCAGACA GGGGAGTTTG GGGAGAAGAG |
| 2101 | GAAGAACTCC ATCCTGAACC CCATCAACAG CATCAGGAAG TTCAGCATTG TGCAGAAAAC |
| 2161 | CCCCCTGCAG ATGAATGGCA TTGAGGAAGA TTCTGATGAG CCCCTGGAGA GGAGACTGAG |
| 2221 | CCTGGTGCCT GATTCTGAGC AGGGAGAGGC CATCCTGCCT AGGATCTCTG TGATCAGCAC |
| 2281 | AGGCCCTACA CTGCAGGCCA GAAGGAGGCA GTCTGTGCTG AACCTGATGA CCCACTCTGT |
| 2341 | GAACCAGGGC CAGAACATCC ACAGGAAAAC CACAGCCTCC ACCAGGAAAG TGAGCCTGGC |
| 2401 | CCCTCAGGCC AATCTGACAG AGCTGGACAT CTACAGCAGG AGGCTGTCTC AGGAGACAGG |
| 2461 | CCTGGAGATT TCTGAGGAGA TCAATGAGGA GGACCTGAAA GAGTGCTTCT TTGATGACAT |
| 2521 | GGAGAGCATC CCTGCTGTGA CCACCTGGAA CACCTACCTG AGATACATCA CAGTGCACAA |
| 2581 | GAGCCTGATC TTTGTGCTGA TCTGGTGCCT GGTGATCTTC CTGGCTGAAG TGGCTGCCTC |
| 2641 | TCTGGTGGTG CTGTGGCTGC TGGGAAACAC CCCACTGCAG GACAAGGGCA ACAGCACCCA |
| 2701 | CAGCAGGAAC AACAGCTATG CTGTGATCAT CACCTCCACC TCCAGCTACT ATGTGTTCTA |
| 2761 | CATCTATGTG GGAGTGGCTG ATACCCTGCT GGCTATGGGC TTCTTTAGAG GCCTGCCCCT |
| 2821 | GGTGCACACA CTGATCACAG TGAGCAAGAT CCTCCACCAC AAGATGCTGC ACTCTGTGCT |
| 2881 | GCAGGCTCCT ATGAGCACCC TGAATACCCT GAAGGCTGGG GGCATCCTGA ACAGATTCTC |
| 2941 | CAAGGATATT GCCATCCTGG ATGACCTGCT GCCTCTCACC ATCTTTGACT TCATCCAGCT |
| 3001 | GCTGCTGATT GTGATTGGGG CCATTGCTGT GGTGGCAGTG CTGCAGCCCT ACATCTTTGT |
| 3061 | GGCCACAGTG CCTGTGATTG TGGCCTTCAT CATGCTGAGG GCCTACTTTC TGCAGACCTC |
| 3121 | CCAGCAGCTG AAGCAGCTGG AGTCTGAGGG CAGAAGCCCC ATCTTCACCC ACCTGGTGAC |
| 3181 | AAGCCTGAAG GGCCTGTGGA CCCTGAGAGC CTTTGGCAGG CAGCCCTACT TTGAGACCCT |
| 3241 | GTTCCACAAG GCCCTGAACC TGCACACAGC CAACTGGTTC CTCTACCTGT CCACCCTGAG |
| 3301 | ATGGTTCCAG ATGAGAATTG AGATGATCTT TGTCATCTTC TTCATTGCTG TGACCTTCAT |
| 3361 | CAGCATTCTG ACCACAGGAG AGGGAGAGGG CAGAGTGGGC ATTATCCTGA CCCTGGCCAT |
| 3421 | GAACATCATG AGCACACTGC AGTGGGCAGT GAACAGCAGC ATTGATGTGG ACAGCCTGAT |
| 3481 | GAGGAGTGTG AGCAGAGTGT TCAAGTTCAT TGATATGCCC ACAGAGGGCA AGCCTACCAA |
| 3541 | GAGCACCAAG CCCTACAAGA ATGGCCAGCT GAGCAAAGTG ATGATCATTG AGAACAGCCA |
| 3601 | TGTGAAGAAG GATGATATCT GGCCCAGTGG AGGCCAGATG ACAGTGAAGG ACCTGACAGC |
| 3661 | CAAGTACACA GAGGGGGGCA ATGCTATCCT GGAGAACATC TCCTTCAGCA TCTCCCCTGG |

| | Sequences |
|---|---|
| 3721 | CCAGAGAGTG GGACTGCTGG GAAGAACAGG CTCTGGCAAG TCTACCCTGC TGTCTGCCTT |
| 3781 | CCTGAGGCTG CTGAACACAG AGGGAGAGAT CCAGATTGAT GGAGTGTCCT GGGACAGCAT |
| 3841 | CACACTGCAG CAGTGGAGGA AGGCCTTTGG TGTGATCCCC CAGAAAGTGT TCATCTTCAG |
| 3901 | TGGCACCTTC AGGAAGAACC TGGACCCCTA TGAGCAGTGG TCTGACCAGG AGATTTGGAA |
| 3961 | AGTGGCTGAT GAAGTGGGCC TGAGAAGTGT GATTGAGCAG TTCCCTGGCA AGCTGGACTT |
| 4021 | TGTCCTGGTG GATGGGGGCT GTGTGCTGAG CCATGGCCAC AAGCAGCTGA TGTGCCTGGC |
| 4081 | CAGATCAGTG CTGAGCAAGG CCAAGATCCT GCTGCTGGAT GAGCCTTCTG CCCACCTGGA |
| 4141 | TCCTGTGACC TACCAGATCA TCAGGAGGAC CCTCAAGCAG GCCTTTGCTG ACTGCACAGT |
| 4201 | CATCCTGTGT GAGCACAGGA TTGAGGCCAT GCTGGAGTGC AGCAGTTCC TGGTGATTGA |
| 4261 | GGAGAACAAA GTGAGGCAGT ATGACAGCAT CCAGAAGCTG CTGAATGAGA GGAGCCTGTT |
| 4321 | CAGGCAGGCC ATCAGCCCCT CTGATAGAGT GAAGCTGTTC CCCCACAGGA ACAGCTCCAA |
| 4381 | GTGCAAGAGC AAGCCCCAGA TTGCTGCCCT GAAGGAGGAG ACAGAGGAGG AAGTGCAGGA |
| 4441 | CACCAGGCTG TGAGGGCCC |

SEQ ID NO: 8

| | |
|---|---|
| 1 | GGGCCCAATC AACCTCTGGA TTACAAAATT TGTGAAAGAT TGACTGGTAT TCTTAACTAT |
| 61 | GTTGCTCCTT TTACGCTATG TGGATACGCT GCTTTAATGC CTTTGTATCA TGCTATTGCT |
| 121 | TCCCGTATGG CTTTCATTTT CTCCTCCTTG TATAAATCCT GGTTGCTGTC TCTTTATGAG |
| 181 | GAGTTGTGGC CCGTTGTCAG GCAACGTGGC GTGGTGTGCA CTGTGTTTGC TGACGCAACC |
| 241 | CCCACTGGTT GGGGCATTGC CACCACCTGT CAGCTCCTTT CCGGGACTTT CGCTTTCCCC |
| 301 | CTCCCTATTG CCACGGCGGA ACTCATCGCC GCCTGCCTTG CCCGCTGCTG GACAGGGGCT |
| 361 | CGGCTGTTGG GCACTGACAA TTCCGTGGTG TTGTCGGGGA AATCATCGTC CTTTCCTTGG |
| 421 | CTGCTCGCCT GTGTTGCCAC CTGGATTCTG CGCGGGACGT CCTTCTGCTA CGTCCCTTCG |
| 481 | GCCCTCAATC CAGCGGACCT TCCTTCCCGC GGCCTGCTGC CGGCTCTGCG GCCTCTTCCG |
| 541 | CGTCTTCGCC TTCGCCCTCA GACGAGTCGG ATCTCCCTTT GGGCCGCCTC CCCGCAAGCT |

SEQ ID NO: 9

| | |
|---|---|
| 1 | GGTACCTCAA TATTGGCCAT TAGCCATATT ATTCATTGGT TATATAGCAT AAATCAATAT |
| 61 | TGGCTATTGG CCATTGCATA CGTTGTATCT ATATCATAAT ATGTACATTT ATATTGGCTC |
| 121 | ATGTCCAATA TGACCGCCAT GTTGGCATTG ATTATTGACT AGTTATTAAT AGTAATCAAT |
| 181 | TACGGGGTCA TTAGTTCATA GCCCATATAT GGAGTTCCGC GTTACATAAC TTACGGTAAA |
| 241 | TGGCCCGCCT GGCTGACCGC CCAACGACCC CCGCCCATTG ACGTCAATAA TGACGTATGT |
| 301 | TCCCATAGTA ACGCCAATAG GGACTTTCCA TTGACGTCAA TGGGTGGAGT ATTTACGGTA |
| 361 | AACTGCCCAC TTGGCAGTAC ATCAAGTGTA TCATATGCCA AGTCCGCCCC CTATTGACGT |
| 421 | CAATGACGGT AAATGGCCCG CCTGGCATTA TGCCCAGTAC ATGACCTTAC GGGACTTTCC |
| 481 | TACTTGGCAG TACATCTACG TATTAGTCAT CGCTATTACC ATGGTGATGC GGTTTTGGCA |
| 541 | GTACACCAAT GGGCGTGGAT AGCGGTTTGA CTCACGGGGA TTTCCAAGTC TCCACCCCAT |
| 601 | TGACGTCAAT GGGAGTTTGT TTTGGCACCA AAATCAACGG GACTTTCCAA AATGTCGTAA |
| 661 | CAACTGCGAT CGCCCGCCCC GTTGACGCAA ATGGGCGGTA GGCGTGTACG GTGGGAGGTC |
| 721 | TATATAAGCA GAGCTCGCTG GCTTGTAACT CAGTCTCTTA CTAGGAGACC AGCTTGAGCC |
| 781 | TGGGTGTTCG CTGGTTAGCC TAACCTGGTT GGCCACCAGG GGTAAGGACT CCTTGGCTTA |

|     | Sequences |
| --- | --- |
| 841 | GAAAGCTAAT AAACTTGCCT GCATTAGAGC TTATCTGAGT CAAGTGTCCT CATTGACGCC |
| 901 | TCACTCTCTT GAACGGGAAT CTTCCTTACT GGGTTCTCTC TCTGACCCAG GCGAGAGAAA |
| 961 | CTCCAGCAGT GGCGCCCGAA CAGGGACTTG AGTGAGAGTG TAGGCACGTA CAGCTGAGAA |
| 1021 | GGCGTCGGAC GCGAAGGAAG CGCGGGGTGC GACGCGACCA AGAAGGAGAC TTGGTGAGTA |
| 1081 | GGCTTCTCGA GTGCCGGGAA AAAGCTCGAG CCTAGTTAGA GGACTAGGAG AGGCCGTAGC |
| 1141 | CGTAACTACT CTTGGGCAAG TAGGGCAGGC GGTGGGTACG CAATGGGGGC GGCTACCTCA |
| 1201 | GCACTAAATA GGAGACAATT AGACCAATTT GAGAAAATAC GACTTCGCCC GAACGGAAAG |
| 1261 | AAAAAGTACC AAATTAAACA TTTAATATGG GCAGGCAAGG AGATGGAGCG CTTCGGCCTC |
| 1321 | CATGAGAGGT TGTTGGAGAC AGAGGAGGGG TGTAAAAGAA TCATAGAAGT CCTCTACCCC |
| 1381 | CTAGAACCAA CAGGATCGGA GGGCTTAAAA AGTCTGTTCA ATCTTGTGTG CGTGCTATAT |
| 1441 | TGCTTGCACA AGGAACAGAA AGTGAAAGAC ACAGAGGAAG CAGTAGCAAC AGTAAGACAA |
| 1501 | CACTGCCATC TAGTGGAAAA AGAAAAAAGT GCAACAGAGA CATCTAGTGG ACAAAAGAAA |
| 1561 | AATGACAAGG GAATAGCAGC GCCACCTGGT GGCAGTCAGA ATTTTCCAGC GCAACAACAA |
| 1621 | GGAAATGCCT GGGTACATGT ACCCTTGTCA CCGCGCACCT TAAATGCGTG GGTAAAAGCA |
| 1681 | GTAGAGGAGA AAAAATTTGG AGCAGAAATA GTACCCATTT TTTTGTTTCA AGCCCTATCG |
| 1741 | AATTCCCGTT TGTGCTAGGG TTCTTAGGCT TCTTGGGGGC TGCTGGAACT GCAATGGGAG |
| 1801 | CAGCGGCGAC AGCCCTGACG GTCCAGTCTC AGCATTTGCT TGCTGGGATA CTGCAGCAGC |
| 1861 | AGAAGAATCT GCTGGCGGCT GTGGAGGCTC AACAGCAGAT GTTGAAGCTG ACCATTTGGG |
| 1921 | GTGTTAAAAA CCTCAATGCC CGCGTCACAG CCCTTGAGAA GTACCTAGAG GATCAGGCAC |
| 1981 | GACTAAACTC CTGGGGGTGC GCATGGAAAC AAGTATGTCA TACCACAGTG GAGTGGCCCT |
| 2041 | GGACAAATCG GACTCCGGAT TGGCAAAATA TGACTTGGTT GGAGTGGGAA AGACAAATAG |
| 2101 | CTGATTTGGA AAGCAACATT ACGAGACAAT TAGTGAAGGC TAGAGAACAA GAGGAAAAGA |
| 2161 | ATCTAGATGC CTATCAGAAG TTAACTAGTT GGTCAGATTT CTGGTCTTGG TTCGATTTCT |
| 2221 | CAAAATGGCT TAACATTTTA AAAATGGGAT TTTTAGTAAT AGTAGGAATA ATAGGGTTAA |
| 2281 | GATTACTTTA CACAGTATAT GGATGTATAG TGAGGGTTAG GCAGGGATAT GTTCCTCTAT |
| 2341 | CTCCACAGAT CCATATCCGC GGCAATTTTA AAAGAAAGGG AGGAATAGGG GGACAGACTT |
| 2401 | CAGCAGAGAG ACTAATTAAT ATAATAACAA CACAATTAGA AATACAACAT TTACAAACCA |
| 2461 | AAATTCAAAA AATTTTAAAT TTTAGAGCCG CGGAGATCTG TTACATAACT TATGGTAAAT |
| 2521 | GGCCTGCCTG GCTGACTGCC CAATGACCCC TGCCCAATGA TGTCAATAAT GATGTATGTT |
| 2581 | CCCATGTAAT GCCAATAGGG ACTTTCCATT GATGTCAATG GGTGGAGTAT TTATGGTAAC |
| 2641 | TGCCCACTTG GCAGTACATC AAGTGTATCA TATGCCAAGT ATGCCCCCTA TTGATGTCAA |
| 2701 | TGATGGTAAA TGGCCTGCCT GGCATTATGC CCAGTACATG ACCTTATGGG ACTTTCCTAC |
| 2761 | TTGGCAGTAC ATCTATGTAT TAGTCATTGC TATTACCATG GAATTCACT AGTGGAGAAG |
| 2821 | AGCATGCTTG AGGGCTGAGT GCCCCTCAGT GGGCAGAGAG CACATGGCCC ACAGTCCCTG |
| 2881 | AGAAGTTGGG GGGAGGGGTG GGCAATTGAA CTGGTGCCTA GAGAAGGTGG GGCTTGGGTA |
| 2941 | AACTGGGAAA GTGATGTGGT GTACTGGCTC CACCTTTTTC CCCAGGGTGG GGGAGAACCA |
| 3001 | TATATAAGTG CAGTAGTCTC TGTGAACATT CAAGCTTCTG CCTTCTCCCT CCTGTGAGTT |
| 3061 | TGCTAGCCAC CATGCCCAGC TCTGTGTCCT GGGGCATTCT GCTGCTGGCT GGCCTGTGCT |

-continued

| | Sequences |
|---|---|
| 3121 | GTCTGGTGCC TGTGTCCCTG GCTGAGGACC CTCAGGGGGA TGCTGCCCAG AAAACAGACA |
| 3181 | CCTCCCACCA TGACCAGGAC CACCCCACCT TCAACAAGAT CACCCCCAAC CTGGCAGAGT |
| 3241 | TTGCCTTCAG CCTGTACAGA CAGCTGGCCC ACCAGAGCAA CAGCACCAAC ATCTTTTTCA |
| 3301 | GCCCTGTGTC CATTGCCACA GCCTTTGCCA TGCTGAGCCT GGGCACCAAG GCTGACACCC |
| 3361 | ATGATGAGAT CCTGGAAGGC CTGAACTTCA ACCTGACAGA GATCCCTGAG GCCCAGATCC |
| 3421 | ATGAGGGCTT CCAGGAACTG CTGAGAACCC TGAACCAGCC AGACAGCCAG CTGCAGCTGA |
| 3481 | CAACAGGCAA TGGGCTGTTC CTGTCTGAGG GCCTGAAGCT GGTGGACAAG TTTCTGGAAG |
| 3541 | ATGTGAAGAA GCTGTACCAC TCTGAGGCCT TCACAGTGAA CTTTGGGGAC ACAGAAGAGG |
| 3601 | CCAAGAAACA GATCAATGAC TATGTGGAAA AGGGCACCCA GGGCAAGATT GTGGACCTTG |
| 3661 | TGAAAGAGCT GGACAGGGAC ACTGTGTTTG CCCTTGTGAA CTACATCTTC TTCAAGGGCA |
| 3721 | AGTGGGAGAG GCCCTTTGAA GTGAAGGACA CTGAGGAAGA GGACTTCCAT GTGGACCAAG |
| 3781 | TGACCACAGT GAAGGTGCCA ATGATGAAGA GACTGGGGAT GTTCAATATC CAGCACTGCA |
| 3841 | AGAAACTGAG CAGCTGGGTG CTGCTGATGA AGTACCTGGG CAATGCTACA GCCATATTCT |
| 3901 | TTCTGCCTGA TGAGGGCAAG CTGCAGCACC TGGAAAATGA GCTGACCCAT GACATCATCA |
| 3961 | CCAAATTTCT GGAAAATGAG GACAGAAGAT CTGCCAGCCT GCATCTGCCC AAGCTGAGCA |
| 4021 | TCACAGGCAC ATATGACCTG AAGTCTGTGC TGGGACAGCT GGGAATCACC AAGGTGTTCA |
| 4081 | GCAATGGGGC AGACCTGAGT GGAGTGACAG AGGAAGCCCC TCTGAAGCTG TCCAAGGCTG |
| 4141 | TGCACAAGGC AGTGCTGACC ATTGATGAGA AGGGCACAGA GGCTGCTGGG GCCATGTTTC |
| 4201 | TGGAAGCCAT CCCCATGTCC ATCCCCCCAG AAGTGAAGTT CAACAAGCCC TTTGTGTTCC |
| 4261 | TGATGATTGA GCAGAACACC AAGAGCCCCC TGTTCATGGG CAAGGTTGTG AACCCCACCC |
| 4321 | AGAAATGAGG GCCCAATCAA CCTCTGGATT ACAAAATTTG TGAAAGATTG ACTGGTATTC |
| 4381 | TTAACTATGT TGCTCCTTTT ACGCTATGTG GATACGCTGC TTTAATGCCT TTGTATCATG |
| 4441 | CTATTGCTTC CCGTATGGCT TTCATTTTCT CCTCCTTGTA TAAATCCTGG TTGCTGTCTC |
| 4501 | TTTATGAGGA GTTGTGGCCC GTTGTCAGGC AACGTGGCGT GGTGTGCACT GTGTTTGCTG |
| 4561 | ACGCAACCCC CACTGGTTGG GGCATTGCCA CCACCTGTCA GCTCCTTTCC GGGACTTTCG |
| 4621 | CTTTCCCCCT CCCTATTGCC ACGGCGGAAC TCATCGCCGC CTGCCTTGCC CGCTGCTGGA |
| 4681 | CAGGGGCTCG GCTGTTGGGC ACTGACAATT CCGTGGTGTT GTCGGGAAA TCATCGTCCT |
| 4741 | TTCCTTGGCT GCTCGCCTGT GTTGCCACCT GGATTCTGCG CGGGACGTCC TTCTGCTACG |
| 4801 | TCCCTTCGGC CCTCAATCCA GCGGACCTTC CTTCCCGCGG CCTGCTGCCG GCTCTGCGGC |
| 4861 | CTCTTCCGCG TCTTCGCCTT CGCCCTCAGA CGAGTCGGAT CTCCCTTTGG GCCGCCTCCC |
| 4921 | CGCAAGCTTC GCACTTTTTA AAAGAAAAGG GAGGACTGGA TGGGATTTAT TACTCCGATA |
| 4981 | GGACGCTGGC TTGTAACTCA GTCTCTTACT AGGAGACCAG CTTGAGCCTG GGTGTTCGCT |
| 5041 | GGTTAGCCTA ACCTGGTTGG CCACCAGGGG TAAGGACTCC TTGGCTTAGA AAGCTAATAA |
| 5101 | ACTTGCCTGC ATTAGAGCTC TTACGCGTCC CGGGCTCGAG ATCCGCATCT CAATTAGTCA |
| 5161 | GCAACCATAG TCCCGCCCCT AACTCCGCCC ATCCCGCCCC TAACTCCGCC CAGTTCCGCC |
| 5221 | CATTCTCCGC CCCATGGCTG ACTAATTTTT TTTATTTATG CAGAGGCCGA GGCCGCCTCG |
| 5281 | GCCTCTGAGC TATTCCAGAA GTAGTGAGGA GGCTTTTTTG GAGGCCTAGG CTTTTGCAAA |
| 5341 | AAGCTAACTT GTTTATTGCA GCTTATAATG GTTACAAATA AAGCAATAGC ATCACAAATT |

| | |
|---|---|
| 5401 | TCACAAATAA AGCATTTTTT TCACTGCATT CTAGTTGTGG TTTGTCCAAA CTCATCAATG |
| 5461 | TATCTTATCA TGTCTGTCCG CTTCCTCGCT CACTGACTCG CTGCGCTCGG TCGTTCGGCT |
| 5521 | GCGGCGAGCG GTATCAGCTC ACTCAAAGGC GGTAATACGG TTATCCACAG AATCAGGGGA |
| 5581 | TAACGCAGGA AAGAACATGT GAGCAAAAGG CCAGCAAAAG GCCAGGAACC GTAAAAAGGC |
| 5641 | CGCGTTGCTG GCGTTTTTCC ATAGGCTCCG CCCCCCTGAC GAGCATCACA AAAATCGACG |
| 5701 | CTCAAGTCAG AGGTGGCGAA ACCCGACAGG ACTATAAAGA TACCAGGCGT TTCCCCCTGG |
| 5761 | AAGCTCCCTC GTGCGCTCTC CTGTTCCGAC CCTGCCGCTT ACCGGATACC TGTCCGCCTT |
| 5821 | TCTCCCTTCG GGAAGCGTGG CGCTTTCTCA TAGCTCACGC TGTAGGTATC TCAGTTCGGT |
| 5881 | GTAGGTCGTT CGCTCCAAGC TGGGCTGTGT GCACGAACCC CCCGTTCAGC CCGACCGCTG |
| 5941 | CGCCTTATCC GGTAACTATC GTCTTGAGTC CAACCCGGTA AGACACGACT TATCGCCACT |
| 6001 | GGCAGCAGCC ACTGGTAACA GGATTAGCAG AGCGAGGTAT GTAGGCGGTG CTACAGAGTT |
| 6061 | CTTGAAGTGG TGGCCTAACT ACGGCTACAC TAGAAGAACA GTATTTGGTA TCTGCGCTCT |
| 6121 | GCTGAAGCCA GTTACCTTCG GAAAAAGAGT TGGTAGCTCT TGATCCGGCA AACAAACCAC |
| 6181 | CGCTGGTAGC GGTGGTTTTT TTGTTTGCAA GCAGCAGATT ACGCGCAGAA AAAAAGGATC |
| 6241 | TCAAGAAGAT CCTTTGATCT TTTCTACGGG GTCTGACGCT CAGTGGAACG AAAACTCACG |
| 6301 | TTAAGGGATT TTGGTCATGA GATTATCAAA AAGGATCTTC ACCTAGATCC TTTTAAATTA |
| 6361 | AAAATGAAGT TTTAAATCAA TCTAAAGTAT ATATGAGTAA ACTTGGTCTG ACAGTTAGAA |
| 6421 | AAACTCATCG AGCATCAAAT GAAACTGCAA TTTATTCATA TCAGGATTAT CAATACCATA |
| 6481 | TTTTTGAAAA AGCCGTTTCT GTAATGAAGG AGAAAACTCA CCGAGGCAGT TCCATAGGAT |
| 6541 | GGCAAGATCC TGGTATCGGT CTGCGATTCC GACTCGTCCA ACATCAATAC AACCTATTAA |
| 6601 | TTTCCCCTCG TCAAAAATAA GGTTATCAAG TGAGAAATCA CCATGAGTGA CGACTGAATC |
| 6661 | CGGTGAGAAT GGCAACAGCT TATGCATTTC TTTCCAGACT TGTTCAACAG GCCAGCCATT |
| 6721 | ACGCTCGTCA TCAAAATCAC TCGCATCAAC CAAACCGTTA TTCATTCGTG ATTGCGCCTG |
| 6781 | AGCGAGACGA AATACGCGAT CGCTGTTAAA AGGACAATTA CAAACAGGAA TCGAATGCAA |
| 6841 | CCGGCGCAGG AACACTGCCA GCGCATCAAC AATATTTTCA CCTGAATCAG GATATTCTTC |
| 6901 | TAATACCTGG AATGCTGTTT TTCCGGGGAT CGCAGTGGTG AGTAACCATG CATCATCAGG |
| 6961 | AGTACGGATA AAATGCTTGA TGGTCGGAAG AGGCATAAAT TCCGTCAGCC AGTTTAGTCT |
| 7021 | GACCATCTCA TCTGTAACAT CATTGGCAAC GCTACCTTTG CCATGTTTCA GAAACAACTC |
| 7081 | TGGCGCATCG GGCTTCCCAT ACAATCGATA GATTGTCGCA CCTGATTGCC CGACATTATC |
| 7141 | GCGAGCCCAT TTATACCCAT ATAAATCAGC ATCCATGTTG GAATTTAATC GCGGCCTAGA |
| 7201 | GCAAGACGTT TCCCGTTGAA TATGGCTCAT AACACCCCTT GTATTACTGT TTATGTAAGC |
| 7261 | AGACAGTTTT ATTGTTCATG ATGATATATT TTTATCTTGT GCAATGTAAC ATCAGAGATT |
| 7321 | TTGAGACACA ACAATTGGTC GACGGATCC |

SEQ ID NO: 10

| | |
|---|---|
| 1 | GGTACCTCAA TATTGGCCAT TAGCCATATT ATTCATTGGT TATATAGCAT AAATCAATAT |
| 61 | TGGCTATTGG CCATTGCATA CGTTGTATCT ATATCATAAT ATGTACATTT ATATTGGCTC |
| 121 | ATGTCCAATA TGACCGCCAT GTTGGCATTG ATTATTGACT AGTTATTAAT AGTAATCAAT |
| 181 | TACGGGGTCA TTAGTTCATA GCCCATATAT GGAGTTCCGC GTTACATAAC TTACGGTAAA |
| 241 | TGGCCCGCCT GGCTGACCGC CCAACGACCC CCGCCCATTG ACGTCAATAA TGACGTATGT |

| | Sequences |
|---|---|
| 301 | TCCCATAGTA ACGCCAATAG GGACTTTCCA TTGACGTCAA TGGGTGGAGT ATTTACGGTA |
| 361 | AACTGCCCAC TTGGCAGTAC ATCAAGTGTA TCATATGCCA AGTCCGCCCC CTATTGACGT |
| 421 | CAATGACGGT AAATGGCCCG CCTGGCATTA TGCCCAGTAC ATGACCTTAC GGGACTTTCC |
| 481 | TACTTGGCAG TACATCTACG TATTAGTCAT CGCTATTACC ATGGTGATGC GGTTTTGGCA |
| 541 | GTACACCAAT GGGCGTGGAT AGCGGTTTGA CTCACGGGGA TTTCCAAGTC TCCACCCCAT |
| 601 | TGACGTCAAT GGGAGTTTGT TTTGGCACCA AAATCAACGG GACTTTCCAA AATGTCGTAA |
| 661 | CAACTGCGAT CGCCCGCCCC GTTGACGCAA ATGGGCGGTA GGCGTGTACG GTGGGAGGTC |
| 721 | TATATAAGCA GAGCTCGCTG GCTTGTAACT CAGTCTCTTA CTAGGAGACC AGCTTGAGCC |
| 781 | TGGGTGTTCG CTGGTTAGCC TAACCTGGTT GGCCACCAGG GGTAAGGACT CCTTGGCTTA |
| 841 | GAAAGCTAAT AAACTTGCCT GCATTAGAGC TTATCTGAGT CAAGTGTCCT CATTGACGCC |
| 901 | TCACTCTCTT GAACGGGAAT CTTCCTTACT GGGTTCTCTC TCTGACCCAG GCGAGAGAAA |
| 961 | CTCCAGCAGT GGCGCCCGAA CAGGGACTTG AGTGAGAGTG TAGGCACGTA CAGCTGAGAA |
| 1021 | GGCGTCGGAC GCGAAGGAAG CGCGGGGTGC GACGCGACCA AGAAGGAGAC TTGGTGAGTA |
| 1081 | GGCTTCTCGA GTGCCGGGAA AAAGCTCGAG CCTAGTTAGA GGACTAGGAG AGGCCGTAGC |
| 1141 | CGTAACTACT CTTGGGCAAG TAGGGCAGGC GGTGGGTACG CAATGGGGGC GGCTACCTCA |
| 1201 | GCACTAAATA GGAGACAATT AGACCAATTT GAGAAAATAC GACTTCGCCC GAACGGAAAG |
| 1261 | AAAAAGTACC AAATTAAACA TTTAATATGG GCAGGCAAGG AGATGGAGCG CTTCGGCCTC |
| 1321 | CATGAGAGGT TGTTGGAGAC AGAGGAGGGG TGTAAAAGAA TCATAGAAGT CCTCTACCCC |
| 1381 | CTAGAACCAA CAGGATCGGA GGGCTTAAAA AGTCTGTTCA ATCTTGTGTG CGTGCTATAT |
| 1441 | TGCTTGCACA AGGAACAGAA AGTGAAAGAC ACAGAGGAAG CAGTAGCAAC AGTAAGACAA |
| 1501 | CACTGCCATC TAGTGGAAAA AGAAAAAAGT GCAACAGAGA CATCTAGTGG ACAAAAGAAA |
| 1561 | AATGACAAGG GAATAGCAGC GCCACCTGGT GGCAGTCAGA ATTTTCCAGC GCAACAACAA |
| 1621 | GGAAATGCCT GGGTACATGT ACCCTTGTCA CCGCGCACCT TAAATGCGTG GGTAAAAGCA |
| 1681 | GTAGAGGAGA AAAAATTTGG AGCAGAAATA GTACCCATTT TTTTGTTTCA AGCCCTATCG |
| 1741 | AATTCCCGTT TGTGCTAGGG TTCTTAGGCT TCTTGGGGGC TGCTGGAACT GCAATGGGAG |
| 1801 | CAGCGGCGAC AGCCCTGACG GTCCAGTCTC AGCATTTGCT TGCTGGGATA CTGCAGCAGC |
| 1861 | AGAAGAATCT GCTGGCGGCT GTGGAGGCTC AACAGCAGAT GTTGAAGCTG ACCATTTGGG |
| 1921 | GTGTTAAAAA CCTCAATGCC CGCGTCACAG CCCTTGAGAA GTACCTAGAG GATCAGGCAC |
| 1981 | GACTAAACTC CTGGGGGTGC GCATGGAAAC AAGTATGTCA TACCACAGTG GAGTGGCCCT |
| 2041 | GGACAAATCG GACTCCGGAT TGGCAAAATA TGACTTGGTT GGAGTGGGAA AGACAAATAG |
| 2101 | CTGATTTGGA AAGCAACATT ACGAGACAAT TAGTGAAGGC TAGAGAACAA GAGGAAAAGA |
| 2161 | ATCTAGATGC CTATCAGAAG TTAACTAGTT GGTCAGATTT CTGGTCTTGG TTCGATTTCT |
| 2221 | CAAAATGGCT TAACATTTTA AAAATGGGAT TTTTAGTAAT AGTAGGAATA ATAGGGTTAA |
| 2281 | GATTACTTTA CACAGTATAT GGATGTATAG TGAGGGTTAG GCAGGGATAT GTTCCTCTAT |
| 2341 | CTCCACAGAT CCATATCCGC GGCAATTTTA AAGAAAGGG AGGAATAGGG GGACAGACTT |
| 2401 | CAGCAGAGAG ACTAATTAAT ATAATAACAA CACAATTAGA AATACAACAT TTACAAACCA |
| 2461 | AAATTCAAAA AATTTTAAAT TTTAGAGCCG CGGAGATCTG TTACATAACT TATGGTAAAT |
| 2521 | GGCCTGCCTG GCTGACTGCC CAATGACCCC TGCCCAATGA TGTCAATAAT GATGTATGTT |

| | Sequences |
|---|---|
| 2581 | CCCATGTAAT GCCAATAGGG ACTTTCCATT GATGTCAATG GGTGGAGTAT TTATGGTAAC |
| 2641 | TGCCCACTTG GCAGTACATC AAGTGTATCA TATGCCAAGT ATGCCCCCTA TTGATGTCAA |
| 2701 | TGATGGTAAA TGGCCTGCCT GGCATTATGC CCAGTACATG ACCTTATGGG ACTTTCCTAC |
| 2761 | TTGGCAGTAC ATCTATGTAT TAGTCATTGC TATTACCATG GAATTCACT AGTGGAGAAG |
| 2821 | AGCATGCTTG AGGGCTGAGT GCCCCTCAGT GGGCAGAGAG CACATGGCCC ACAGTCCCTG |
| 2881 | AGAAGTTGGG GGGAGGGGTG GGCAATTGAA CTGGTGCCTA GAGAAGGTGG GGCTTGGGTA |
| 2941 | AACTGGGAAA GTGATGTGGT GTACTGGCTC CACCTTTTTC CCCAGGGTGG GGGAGAACCA |
| 3001 | TATATAAGTG CAGTAGTCTC TGTGAACATT CAAGCTTCTG CCTTCTCCCT CCTGTGAGTT |
| 3061 | TGCTAGCCAC CATGGGAGTG AAGGTGCTGT TGCCCTGAT CTGCATTGCT GTGGCTGAGG |
| 3121 | CCAAGCCCAC AGAGAACAAT GAGGACTTCA ACATTGTGGC TGTGGCCAGC AACTTTGCCA |
| 3181 | CCACAGACCT GGATGCTGAC AGGGGCAAGC TGCCTGGCAA GAAGCTGCCC CTGGAAGTCC |
| 3241 | TGAAAGAGAT GGAAGCCAAT GCCAGGAAGG CTGGCTGCAC AAGAGGCTGT CTGATCTGCC |
| 3301 | TGAGCCACAT CAAGTGCACC CCCAAGATGA AGAAGTTCAT CCCTGGCAGG TGCCACACCT |
| 3361 | ATGAAGGGA CAAAGAGTCT GCCCAGGGGG GAATTGGAGA GGCCATTGTG GACATCCCTG |
| 3421 | AGATCCCTGG CTTCAAGGAC CTGGAACCCA TGGAACAGTT CATTGCCCAG GTGGACCTGT |
| 3481 | GTGTGGACTG CACTACAGGC TGTCTCAAGG GCCTGGCCAA TGTGCAGTGC TCTGACCTGC |
| 3541 | TGAAGAAGTG GCTGCCCCAG AGATGTGCCA CCTTTGCCAG CAAGATCCAG GGCCAGGTGG |
| 3601 | ACAAGATCAA GGGAGCTGGG GGAGATTGAT GAGGGCCCAA TCAACCTCTG GATTACAAAA |
| 3661 | TTTGTGAAAG ATTGACTGGT ATTCTTAACT ATGTTGCTCC TTTTACGCTA TGTGGATACG |
| 3721 | CTGCTTTAAT GCCTTTGTAT CATGCTATTG CTTCCCGTAT GGCTTTCATT TTCTCCTCCT |
| 3781 | TGTATAAATC CTGGTTGCTG TCTCTTTATG AGGAGTTGTG GCCCGTTGTC AGGCAACGTG |
| 3841 | GCGTGGTGTG CACTGTGTTT GCTGACGCAA CCCCCACTGG TTGGGGCATT GCCACCACCT |
| 3901 | GTCAGCTCCT TTCCGGGACT TTCGCTTTCC CCTCCCTAT TGCCACGGCG GAACTCATCG |
| 3961 | CCGCCTGCCT TGCCCGCTGC TGGACAGGGG CTCGGCTGTT GGGCACTGAC AATTCCGTGG |
| 4021 | TGTTGTCGGG GAAATCATCG TCCTTTCCTT GGCTGCTCGC CTGTGTTGCC ACCTGGATTC |
| 4081 | TGCGCGGGAC GTCCTTCTGC TACGTCCCTT CGGCCCTCAA TCCAGCGGAC CTTCCTTCCC |
| 4141 | GCGGCCTGCT GCCGGCTCTG CGGCCTCTTC CGCGTCTTCG CCTTCGCCCT CAGACGAGTC |
| 4201 | GGATCTCCCT TTGGGCCGCC TCCCCGCAAG CTTCGCACTT TTTAAAAGAA AAGGGAGGAC |
| 4261 | TGGATGGGAT TTATTACTCC GATAGGACGC TGGCTTGTAA CTCAGTCTCT TACTAGGAGA |
| 4321 | CCAGCTTGAG CCTGGGTGTT CGCTGGTTAG CCTAACCTGG TTGGCCACCA GGGGTAAGGA |
| 4381 | CTCCTTGGCT TAGAAAGCTA ATAAACTTGC CTGCATTAGA GCTCTTACGC GTCCCGGGCT |
| 4441 | CGAGATCCGC ATCTCAATTA GTCAGCAACC ATAGTCCCGC CCTAACTCC GCCCATCCCG |
| 4501 | CCCCTAACTC CGCCCAGTTC CGCCCATTCT CCGCCCCATG GCTGACTAAT TTTTTTTATT |
| 4561 | TATGCAGAGG CCGAGGCCGC CTCGGCCTCT GAGCTATTCC AGAAGTAGTG AGGAGGCTTT |
| 4621 | TTTGGAGGCC TAGGCTTTTG CAAAAAGCTA ACTTGTTTAT TGCAGCTTAT AATGGTTACA |
| 4681 | AATAAAGCAA TAGCATCACA AATTTCACAA ATAAAGCATT TTTTCACTG CATTCTAGTT |
| 4741 | GTGGTTTGTC CAAACTCATC AATGTATCTT ATCATGTCTG TCCGCTTCCT CGCTCACTGA |
| 4801 | CTCGCTGCGC TCGGTCGTTC GGCTGCGGCG AGCGGTATCA GCTCACTCAA AGGCGGTAAT |

-continued

| | Sequences |
|---|---|
| 4861 | ACGGTTATCC ACAGAATCAG GGGATAACGC AGGAAAGAAC ATGTGAGCAA AAGGCCAGCA |
| 4921 | AAAGGCCAGG AACCGTAAAA AGGCCGCGTT GCTGGCGTTT TTCCATAGGC TCCGCCCCCC |
| 4981 | TGACGAGCAT CACAAAAATC GACGCTCAAG TCAGAGGTGG CGAAACCCGA CAGGACTATA |
| 5041 | AAGATACCAG GCGTTTCCCC CTGGAAGCTC CCTCGTGCGC TCTCCTGTTC CGACCCTGCC |
| 5101 | GCTTACCGGA TACCTGTCCG CCTTTCTCCC TTCGGGAAGC GTGGCGCTTT CTCATAGCTC |
| 5161 | ACGCTGTAGG TATCTCAGTT CGGTGTAGGT CGTTCGCTCC AAGCTGGGCT GTGTGCACGA |
| 5221 | ACCCCCCGTT CAGCCCGACC GCTGCGCCTT ATCCGGTAAC TATCGTCTTG AGTCCAACCC |
| 5281 | GGTAAGACAC GACTTATCGC CACTGGCAGC AGCCACTGGT AACAGGATTA GCAGAGCGAG |
| 5341 | GTATGTAGGC GGTGCTACAG AGTTCTTGAA GTGGTGGCCT AACTACGGCT ACACTAGAAG |
| 5401 | AACAGTATTT GGTATCTGCG CTCTGCTGAA GCCAGTTACC TTCGGAAAAA GAGTTGGTAG |
| 5461 | CTCTTGATCC GGCAAACAAA CCACCGCTGG TAGCGGTGGT TTTTTTGTTT GCAAGCAGCA |
| 5521 | GATTACGCGC AGAAAAAAAG GATCTCAAGA AGATCCTTTG ATCTTTTCTA CGGGGTCTGA |
| 5581 | CGCTCAGTGG AACGAAAACT CACGTTAAGG GATTTTGGTC ATGAGATTAT CAAAAAGGAT |
| 5641 | CTTCACCTAG ATCCTTTTAA ATTAAAAATG AAGTTTTAAA TCAATCTAAA GTATATATGA |
| 5701 | GTAAACTTGG TCTGACAGTT AGAAAAACTC ATCGAGCATC AAATGAAACT GCAATTTATT |
| 5761 | CATATCAGGA TTATCAATAC CATATTTTTG AAAAAGCCGT TTCTGTAATG AAGGAGAAAA |
| 5821 | CTCACCGAGG CAGTTCCATA GGATGGCAAG ATCCTGGTAT CGGTCTGCGA TTCCGACTCG |
| 5881 | TCCAACATCA ATACAACCTA TTAATTTCCC CTCGTCAAAA ATAAGGTTAT CAAGTGAGAA |
| 5941 | ATCACCATGA GTGACGACTG AATCCGGTGA GAATGGCAAC AGCTTATGCA TTTCTTTCCA |
| 6001 | GACTTGTTCA ACAGGCCAGC CATTACGCTC GTCATCAAAA TCACTCGCAT CAACCAAACC |
| 6061 | GTTATTCATT CGTGATTGCG CCTGAGCGAG ACGAAATACG CGATCGCTGT TAAAAGGACA |
| 6121 | ATTACAAACA GGAATCGAAT GCAACCGGCG CAGGAACACT GCCAGCGCAT CAACAATATT |
| 6181 | TTCACCTGAA TCAGGATATT CTTCTAATAC CTGGAATGCT GTTTTTCCGG GGATCGCAGT |
| 6241 | GGTGAGTAAC CATGCATCAT CAGGAGTACG GATAAAATGC TTGATGGTCG GAAGAGGCAT |
| 6301 | AAATTCCGTC AGCCAGTTTA GTCTGACCAT CTCATCTGTA ACATCATTGG CAACGCTACC |
| 6361 | TTTGCCATGT TTCAGAAACA ACTCTGGCGC ATCGGGCTTC CCATACAATC GATAGATTGT |
| 6421 | CGCACCTGAT TGCCCGACAT TATCGCGAGC CCATTTATAC CCATATAAAT CAGCATCCAT |
| 6481 | GTTGGAATTT AATCGCGGCC TAGAGCAAGA CGTTTCCCGT TGAATATGGC TCATAACACC |
| 6541 | CCTTGTATTA CTGTTTATGT AAGCAGACAG TTTTATTGTT CATGATGATA TATTTTTATC |
| 6601 | TTGTGCAATG TAACATCAGA GATTTTGAGA CACAACAATT GGTCGACGGA TCC |

SEQ ID NO: 11

| | |
|---|---|
| 1 | GGTACCTCAA TATTGGCCAT TAGCCATATT ATTCATTGGT TATATAGCAT AAATCAATAT |
| 61 | TGGCTATTGG CCATTGCATA CGTTGTATCT ATATCATAAT ATGTACATTT ATATTGGCTC |
| 121 | ATGTCCAATA TGACCGCCAT GTTGGCATTG ATTATTGACT AGTTATTAAT AGTAATCAAT |
| 181 | TACGGGGTCA TTAGTTCATA GCCCATATAT GGAGTTCCGC GTTACATAAC TTACGGTAAA |
| 241 | TGGCCCGCCT GGCTGACCGC CCAACGACCC CCGCCCATTG ACGTCAATAA TGACGTATGT |
| 301 | TCCCATAGTA ACGCCAATAG GGACTTTCCA TTGACGTCAA TGGGTGGAGT ATTTACGGTA |
| 361 | AACTGCCCAC TTGGCAGTAC ATCAAGTGTA TCATATGCCA AGTCCGCCCC CTATTGACGT |
| 421 | CAATGACGGT AAATGGCCCG CCTGGCATTA TGCCCAGTAC ATGACCTTAC GGGACTTTCC |

-continued

| | Sequences |
|---|---|
| 481 | TACTTGGCAG TACATCTACG TATTAGTCAT CGCTATTACC ATGGTGATGC GGTTTTGGCA |
| 541 | GTACACCAAT GGGCGTGGAT AGCGGTTTGA CTCACGGGGA TTTCCAAGTC TCCACCCCAT |
| 601 | TGACGTCAAT GGGAGTTTGT TTTGGCACCA AAATCAACGG GACTTTCCAA AATGTCGTAA |
| 661 | CAACTGCGAT CGCCCGCCCC GTTGACGCAA ATGGGCGGTA GGCGTGTACG GTGGGAGGTC |
| 721 | TATATAAGCA GAGCTCGCTG GCTTGTAACT CAGTCTCTTA CTAGGAGACC AGCTTGAGCC |
| 781 | TGGGTGTTCG CTGGTTAGCC TAACCTGGTT GGCCACCAGG GGTAAGGACT CCTTGGCTTA |
| 841 | GAAAGCTAAT AAACTTGCCT GCATTAGAGC TTATCTGAGT CAAGTGTCCT CATTGACGCC |
| 901 | TCACTCTCTT GAACGGGAAT CTTCCTTACT GGGTTCTCTC TCTGACCCAG GCGAGAGAAA |
| 961 | CTCCAGCAGT GGCGCCCGAA CAGGGACTTG AGTGAGAGTG TAGGCACGTA CAGCTGAGAA |
| 1021 | GGCGTCGGAC GCGAAGGAAG CGCGGGGTGC GACGCGACCA AGAAGGAGAC TTGGTGAGTA |
| 1081 | GGCTTCTCGA GTGCCGGGAA AAAGCTCGAG CCTAGTTAGA GGACTAGGAG AGGCCGTAGC |
| 1141 | CGTAACTACT CTGGGCAAGT AGGGCAGGCG GTGGGTACGC AATGGGGGCG GCTACCTCAG |
| 1201 | CACTAAATAG GAGACAATTA GACCAATTTG AGAAAATACG ACTTCGCCCG AACGGAAAGA |
| 1261 | AAAAGTACCA AATTAAACAT TTAATATGGG CAGGCAAGGA GATGGAGCGC TTCGGCCTCC |
| 1321 | ATGAGAGGTT GTTGGAGACA GAGGAGGGGT GTAAAAGAAT CATAGAAGTC CTCTACCCCC |
| 1381 | TAGAACCAAC AGGATCGGAG GGCTTAAAAA GTCTGTTCAA TCTTGTGTGC GTGCTATATT |
| 1441 | GCTTGCACAA GGAACAGAAA GTGAAAGACA CAGAGGAAGC AGTAGCAACA GTAAGACAAC |
| 1501 | ACTGCCATCT AGTGGAAAAA GAAAAAAGTG CAACAGAGAC ATCTAGTGGA CAAAAGAAAA |
| 1561 | ATGACAAGGG AATAGCAGCG CCACCTGGTG GCAGTCAGAA TTTTCCAGCG CAACAACAAG |
| 1621 | GAAATGCCTG GGTACATGTA CCCTTGTCAC CGCGCACCTT AAATGCGTGG GTAAAAGCAG |
| 1681 | TAGAGGAGAA AAAATTTGGA GCAGAAATAG TACCCATGTT TCAAGCCCTA TCGAATTCCC |
| 1741 | GTTTGTGCTA GGGTTCTTAG GCTTCTTGGG GGCTGCTGGA ACTGCAATGG GAGCAGCGGC |
| 1801 | GACAGCCCTG ACGGTCCAGT CTCAGCATTT GCTTGCTGGG ATACTGCAGC AGCAGAAGAA |
| 1861 | TCTGCTGGCG GCTGTGGAGG CTCAACAGCA GATGTTGAAG CTGACCATTT GGGGTGTTAA |
| 1921 | AAACCTCAAT GCCCGCGTCA CAGCCCTTGA GAAGTACCTA GAGGATCAGG CACGACTAAA |
| 1981 | CTCCTGGGGG TGCGCATGGA ACAAGTATG TCATACCACA GTGGAGTGGC CCTGGACAAA |
| 2041 | TCGGACTCCG GATTGGCAAA ATATGACTTG GTTGGAGTGG GAAAGACAAA TAGCTGATTT |
| 2101 | GGAAAGCAAC ATTACGAGAC AATTAGTGAA GGCTAGAGAA CAAGAGGAAA AGAATCTAGA |
| 2161 | TGCCTATCAG AAGTTAACTA GTTGGTCAGA TTTCTGGTCT TGGTTCGATT TCTCAAAATG |
| 2221 | GCTTAACATT TTAAAAATGG GATTTTTAGT AATAGTAGGA ATAATAGGGT TAAGATTACT |
| 2281 | TTACACAGTA TATGGATGTA TAGTGAGGGT TAGGCAGGGA TATGTTCCTC TATCTCCACA |
| 2341 | GATCCATATC CGCGGCAATT TTAAAAGAAA GGGAGGAATA GGGGACAGA CTTCAGCAGA |
| 2401 | GAGACTAATT AATATAATAA CAACACAATT AGAAATACAA CATTTACAAA CCAAAATTCA |
| 2461 | AAAAATTTTA AATTTTAGAG CCGCGGAGAT CTCAATATTG GCCATTAGCC ATATTATTCA |
| 2521 | TTGGTTATAT AGCATAAATC AATATTGGCT ATTGGCCATT GCATACGTTG TATCTATATC |
| 2581 | ATAATATGTA CATTTATATT GGCTCATGTC CAATATGACC GCCATGTTGG CATTGATTAT |
| 2641 | TGACTAGTTA TTAATAGTAA TCAATTACGG GGTCATTAGT TCATAGCCCA TATATGGAGT |
| 2701 | TCCGCGTTAC ATAACTTACG GTAAATGGCC CGCCTGGCTG ACCGCCCAAC GACCCCCGCC |

| | Sequences |
|---|---|
| 2761 | CATTGACGTC AATAATGACG TATGTTCCCA TAGTAACGCC AATAGGGACT TTCCATTGAC |
| 2821 | GTCAATGGGT GGAGTATTTA CGGTAAACTG CCCACTTGGC AGTACATCAA GTGTATCATA |
| 2881 | TGCCAAGTCC GCCCCCTATT GACGTCAATG ACGGTAAATG CCCGCCTGG CATTATGCCC |
| 2941 | AGTACATGAC CTTACGGGAC TTTCCTACTT GGCAGTACAT CTACGTATTA GTCATCGCTA |
| 3001 | TTACCATGGT GATGCGGTTT TGGCAGTACA CCAATGGGCG TGGATAGCGG TTTGACTCAC |
| 3061 | GGGGATTTCC AAGTCTCCAC CCCATTGACG TCAATGGGAG TTTGTTTTGG CACCAAAATC |
| 3121 | AACGGGACTT TCCAAAATGT CGTAATAACC CCGCCCCGTT GACGCAAATG GGCGGTAGGC |
| 3181 | GTGTACGGTG GGAGGTCTAT ATAAGCAGAG CTCGTTTAGT GAACCGTCAG ATCACTAGAA |
| 3241 | GCTTTATTGC GGTAGTTTAT CACAGTTAAA TTGCTAACGC AGTCAGTGCT TCTGACACAA |
| 3301 | CAGTCTCGAA CTTAAGCTGC AGAAGTTGGT CGTGAGGCAC TGGGCAGGCT AGCCACCAAT |
| 3361 | GCAGATTGAG CTGAGCACCT GCTTCTTCCT GTGCCTGCTG AGGTTCTGCT TCTCTGCCAC |
| 3421 | CAGGAGATAC TACCTGGGGG CTGTGGAGCT GAGCTGGGAC TACATGCAGT CTGACCTGGG |
| 3481 | GGAGCTGCCT GTGGATGCCA GGTTCCCCCC CAGAGTGCCC AAGAGCTTCC CCTTCAACAC |
| 3541 | CTCTGTGGTG TACAAGAAGA CCCTGTTTGT GGAGTTCACT GACCACCTGT TCAACATTGC |
| 3601 | CAAGCCCAGG CCCCCCTGGA TGGGCCTGCT GGGCCCCACC ATCCAGGCTG AGGTGTATGA |
| 3661 | CACTGTGGTG ATCACCCTGA AGAACATGGC CAGCCACCCT GTGAGCCTGC ATGCTGTGGG |
| 3721 | GGTGAGCTAC TGGAAGGCCT CTGAGGGGGC TGAGTATGAT GACCAGACCA GCCAGAGGGA |
| 3781 | GAAGGAGGAT GACAAGGTGT TCCCTGGGGG CAGCCACACC TATGTGTGGC AGGTGCTGAA |
| 3841 | GGAGAATGGC CCCATGGCCT CTGACCCCCT GTGCCTGACC TACAGCTACC TGAGCCATGT |
| 3901 | GGACCTGGTG AAGGACCTGA ACTCTGGCCT GATTGGGGCC CTGCTGGTGT GCAGGGAGGG |
| 3961 | CAGCCTGGCC AAGGAGAAGA CCCAGACCCT GCACAAGTTC ATCCTGCTGT TTGCTGTGTT |
| 4021 | TGATGAGGGC AAGAGCTGGA CTCTGAAAC CAAGAACAGC CTGATGCAGG ACAGGGATGC |
| 4081 | TGCCTCTGCC AGGGCCTGGC CCAAGATGCA CACTGTGAAT GGCTATGTGA ACAGGAGCCT |
| 4141 | GCCTGGCCTG ATTGGCTGCC ACAGGAAGTC TGTGTACTGG CATGTGATTG GCATGGGCAC |
| 4201 | CACCCCTGAG GTGCACAGCA TCTTCCTGGA GGGCCACACC TTCCTGGTCA GGAACCACAG |
| 4261 | GCAGGCCAGC CTGGAGATCA GCCCCATCAC CTTCCTGACT GCCCAGACCC TGCTGATGGA |
| 4321 | CCTGGGCCAG TTCCTGCTGT TCTGCCACAT CAGCAGCCAC CAGCATGATG GCATGGAGGC |
| 4381 | CTATGTGAAG GTGGACAGCT GCCCTGAGGA GCCCCAGCTG AGGATGAAGA ACAATGAGGA |
| 4441 | GGCTGAGGAC TATGATGATG ACCTGACTGA CTCTGAGATG GATGTGGTGA GGTTTGATGA |
| 4501 | TGACAACAGC CCCAGCTTCA TCCAGATCAG GTCTGTGGCC AAGAAGCACC CCAAGACCTG |
| 4561 | GGTGCACTAC ATTGCTGCTG AGGAGGAGGA CTGGGACTAT GCCCCCCTGG TGCTGGCCCC |
| 4621 | TGATGACAGG AGCTACAAGA GCCAGTACCT GAACAATGGC CCCCAGAGGA TTGGCAGGAA |
| 4681 | GTACAAGAAG GTCAGGTTCA TGGCCTACAC TGATGAAACC TTCAAGACCA GGGAGGCCAT |
| 4741 | CCAGCATGAG TCTGGCATCC TGGGCCCCCT GCTGTATGGG GAGGTGGGGG ACACCCTGCT |
| 4801 | GATCATCTTC AAGAACCAGG CCAGCAGGCC CTACAACATC TACCCCCATG GCATCACTGA |
| 4861 | TGTGAGGCCC CTGTACAGCA GGAGGCTGCC CAAGGGGGTG AAGCACCTGA AGGACTTCCC |
| 4921 | CATCCTGCCT GGGGAGATCT TCAAGTACAA GTGGACTGTG ACTGTGGAGG ATGGCCCCAC |
| 4981 | CAAGTCTGAC CCCAGGTGCC TGACCAGATA CTACAGCAGC TTTGTGAACA TGGAGAGGGA |

-continued

| | Sequences |
|---|---|
| 5041 | CCTGGCCTCT GGCCTGATTG GCCCCCTGCT GATCTGCTAC AAGGAGTCTG TGGACCAGAG |
| 5101 | GGGCAACCAG ATCATGTCTG ACAAGAGGAA TGTGATCCTG TTCTCTGTGT TTGATGAGAA |
| 5161 | CAGGAGCTGG TACCTGACTG AGAACATCCA GAGGTTCCTG CCCAACCCTG CTGGGGTGCA |
| 5221 | GCTGGAGGAC CCTGAGTTCC AGGCCAGCAA CATCATGCAC AGCATCAATG GCTATGTGTT |
| 5281 | TGACAGCCTG CAGCTGTCTG TGTGCCTGCA TGAGGTGGCC TACTGGTACA TCCTGAGCAT |
| 5341 | TGGGGCCCAG ACTGACTTCC TGTCTGTGTT CTTCTCTGGC TACACCTTCA AGCACAAGAT |
| 5401 | GGTGTATGAG GACACCCTGA CCCTGTTCCC CTTCTCTGGG GAGACTGTGT TCATGAGCAT |
| 5461 | GGAGAACCCT GGCCTGTGGA TTCTGGGCTG CCACAACTCT GACTTCAGGA ACAGGGGCAT |
| 5521 | GACTGCCCTG CTGAAAGTCT CCAGCTGTGA CAAGAACACT GGGGACTACT ATGAGGACAG |
| 5581 | CTATGAGGAC ATCTCTGCCT ACCTGCTGAG CAAGAACAAT GCCATTGAGC CCAGGAGCTT |
| 5641 | CAGCCAGAAT GCCACTAATG TGTCTAACAA CAGCAACACC AGCAATGACA GCAATGTGTC |
| 5701 | TCCCCCAGTG CTGAAGAGGC ACCAGAGGGA GATCACCAGG ACCACCCTGC AGTCTGACCA |
| 5761 | GGAGGAGATT GACTATGATG ACACCATCTC TGTGGAGATG AAGAAGGAGG ACTTTGACAT |
| 5821 | CTACGACGAG GACGAGAACC AGAGCCCCAG GAGCTTCCAG AAGAAGACCA GGCACTACTT |
| 5881 | CATTGCTGCT GTGGAGAGGC TGTGGGACTA TGGCATGAGC AGCAGCCCCC ATGTGCTGAG |
| 5941 | GAACAGGGCC CAGTCTGGCT CTGTGCCCCA GTTCAAGAAG GTGGTGTTCC AGGAGTTCAC |
| 6001 | TGATGGCAGC TTCACCCAGC CCTGTACAG AGGGGAGCTG AATGAGCACC TGGGCCTGCT |
| 6061 | GGGCCCCTAC ATCAGGGCTG AGGTGGAGGA CAACATCATG GTGACCTTCA GGAACCAGGC |
| 6121 | CAGCAGGCCC TACAGCTTCT ACAGCAGCCT GATCAGCTAT GAGGAGGACC AGAGGCAGGG |
| 6181 | GGCTGAGCCC AGGAAGAACT TTGTGAAGCC CAATGAAACC AAGACCTACT TCTGGAAGGT |
| 6241 | GCAGCACCAC ATGGCCCCCA CCAAGGATGA GTTTGACTGC AAGGCCTGGG CCTACTTCTC |
| 6301 | TGATGTGGAC CTGGAGAAGG ATGTGCACTC TGGCCTGATT GGCCCCCTGC TGGTGTGCCA |
| 6361 | CACCAACACC CTGAACCCTG CCCATGGCAG GCAGGTGACT GTGCAGGAGT TTGCCCTGTT |
| 6421 | CTTCACCATC TTTGATGAAA CCAAGAGCTG GTACTTCACT GAGAACATGG AGAGGAACTG |
| 6481 | CAGGGCCCCC TGCAACATCC AGATGGAGGA CCCCACCTTC AAGGAGAACT ACAGGTTCCA |
| 6541 | TGCCATCAAT GGCTACATCA TGGACACCCT GCCTGGCCTG GTGATGGCCC AGGACCAGAG |
| 6601 | GATCAGGTGG TACCTGCTGA GCATGGGCAG CAATGAGAAC ATCCACAGCA TCCACTTCTC |
| 6661 | TGGCCATGTG TTCACTGTGA GGAAGAAGGA GGAGTACAAG ATGGCCCTGT ACAACCTGTA |
| 6721 | CCCTGGGGTG TTTGAGACTG TGGAGATGCT GCCCAGCAAG GCTGGCATCT GGAGGGTGGA |
| 6781 | GTGCCTGATT GGGGAGCACC TGCATGCTGG CATGAGCACC CTGTTCCTGG TGTACAGCAA |
| 6841 | CAAGTGCCAG ACCCCCCTGG GCATGGCCTC TGGCCACATC AGGGACTTCC AGATCACTGC |
| 6901 | CTCTGGCCAG TATGGCCAGT GGGCCCCCAA GCTGGCCAGG CTGCACTACT CTGGCAGCAT |
| 6961 | CAATGCCTGG AGCACCAAGG AGCCCTTCAG CTGGATCAAG GTGGACCTGC TGGCCCCCAT |
| 7021 | GATCATCCAT GGCATCAAGA CCCAGGGGGC CAGGCAGAAG TTCAGCAGCC TGTACATCAG |
| 7081 | CCAGTTCATC ATCATGTACA GCCTGGATGG CAAGAAGTGG CAGACCTACA GGGGCAACAG |
| 7141 | CACTGGCACC CTGATGGTGT TCTTTGGCAA TGTGGACAGC TCTGGCATCA AGCACAACAT |
| 7201 | CTTCAACCCC CCATCATTG CCAGATACAT CAGGCTGCAC CCCACCCACT ACAGCATCAG |
| 7261 | GAGCACCCTG AGGATGGAGC TGATGGGCTG TGACCTGAAC AGCTGCAGCA TGCCCCTGGG |

| | Sequences |
|---|---|
| 7321 | CATGGAGAGC AAGGCCATCT CTGATGCCCA GATCACTGCC AGCAGCTACT TCACCAACAT |
| 7381 | GTTTGCCACC TGGAGCCCCA GCAAGGCCAG GCTGCACCTG CAGGGCAGGA GCAATGCCTG |
| 7441 | GAGGCCCCAG GTCAACAACC CCAAGGAGTG GCTGCAGGTG GACTTCCAGA AGACCATGAA |
| 7501 | GGTGACTGGG GTGACCACCC AGGGGGTGAA GAGCCTGCTG ACCAGCATGT ATGTGAAGGA |
| 7561 | GTTCCTGATC AGCAGCAGCC AGGATGGCCA CCAGTGGACC CTGTTCTTCC AGAATGGCAA |
| 7621 | GGTGAAGGTG TTCCAGGGCA ACCAGGACAG CTTCACCCCT GTGGTGAACA GCCTGGACCC |
| 7681 | CCCCCTGCTG ACCAGATACC TGAGGATTCA CCCCCAGAGC TGGGTGCACC AGATTGCCCT |
| 7741 | GAGGATGGAG GTGCTGGGCT GTGAGGCCCA GGACCTGTAC TGAGCGGCCG CGGGCCCAAT |
| 7801 | CAACCTCTGG ATTACAAAAT TTGTGAAAGA TTGACTGGTA TTCTTAACTA TGTTGCTCCT |
| 7861 | TTTACGCTAT GTGGATACGC TGCTTTAATG CCTTTGTATC ATGCTATTGC TTCCCGTATG |
| 7921 | GCTTTCATTT TCTCCTCCTT GTATAAATCC TGGTTGCTGT CTCTTTATGA GGAGTTGTGG |
| 7981 | CCCGTTGTCA GGCAACGTGG CGTGGTGTGC ACTGTGTTTG CTGACGCAAC CCCCACTGGT |
| 8041 | TGGGGCATTG CCACCACCTG TCAGCTCCTT TCCGGGACTT TCGCTTTCCC CCTCCCTATT |
| 8101 | GCCACGGCGG AACTCATCGC CGCCTGCCTT GCCCGCTGCT GGACAGGGGC TCGGCTGTTG |
| 8161 | GGCACTGACA ATTCCGTGGT GTTGTCGGGG AAATCATCGT CCTTTCCTTG GCTGCTCGCC |
| 8221 | TGTGTTGCCA CCTGGATTCT GCGCGGGACG TCCTTCTGCT ACGTCCCTTC GGCCCTCAAT |
| 8281 | CCAGCGGACC TTCCTTCCCG CGGCCTGCTG CCGGCTCTGC GGCCTCTTCC GCGTCTTCGC |
| 8341 | CTTCGCCCTC AGACGAGTCG GATCTCCCTT TGGGCCGCCT CCCCGCAAGC TTCGCACTTT |
| 8401 | TTAAAAGAAA AGGGAGGACT GGATGGGATT TATTACTCCG ATAGGACGCT GGCTTGTAAC |
| 8461 | TCAGTCTCTT ACTAGGAGAC CAGCTTGAGC CTGGGTGTTC GCTGGTTAGC CTAACCTGGT |
| 8521 | TGGCCACCAG GGGTAAGGAC TCCTTGGCTT AGAAAGCTAA TAAACTTGCC TGCATTAGAG |
| 8581 | CTCTTACGCG TCCCGGGCTC GAGATCCGCA TCTCAATTAG TCAGCAACCA TAGTCCCGCC |
| 8641 | CCTAACTCCG CCCATCCCGC CCCTAACTCC GCCCAGTTCC GCCCATTCTC CGCCCCATGG |
| 8701 | CTGACTAATT TTTTTTATTT ATGCAGAGGC CGAGGCCGCC TCGGCCTCTG AGCTATTCCA |
| 8761 | GAAGTAGTGA GGAGGCTTTT TTGGAGGCCT AGGCTTTTGC AAAAAGCTAA CTTGTTTATT |
| 8821 | GCAGCTTATA ATGGTTACAA ATAAAGCAAT AGCATCACAA ATTTCACAAA TAAAGCATTT |
| 8881 | TTTTCACTGC ATTCTAGTTG TGGTTTGTCC AAACTCATCA ATGTATCTTA TCATGTCTGT |
| 8941 | CCGCTTCCTC GCTCACTGAC TCGCTGCGCT CGGTCGTTCG GCTGCGGCGA GCGGTATCAG |
| 9001 | CTCACTCAAA GGCGGTAATA CGGTTATCCA CAGAATCAGG GGATAACGCA GGAAAGAACA |
| 9061 | TGTGAGCAAA AGGCCAGCAA AAGGCCAGGA ACCGTAAAAA GGCCGCGTTG CTGGCGTTTT |
| 9121 | TCCATAGGCT CCGCCCCCCT GACGAGCATC ACAAAAATCG ACGCTCAAGT CAGAGGTGGC |
| 9181 | GAAACCCGAC AGGACTATAA AGATACCAGG CGTTTCCCCC TGGAAGCTCC CTCGTGCGCT |
| 9241 | CTCCTGTTCC GACCCTGCCG CTTACCGGAT ACCTGTCCGC CTTTCTCCCT TCGGGAAGCG |
| 9301 | TGGCGCTTTC TCATAGCTCA CGCTGTAGGT ATCTCAGTTC GGTGTAGGTC GTTCGCTCCA |
| 9361 | AGCTGGGCTG TGTGCACGAA CCCCCCGTTC AGCCCGACCG CTGCGCCTTA TCCGGTAACT |
| 9421 | ATCGTCTTGA GTCCAACCCG GTAAGACACG ACTTATCGCC ACTGGCAGCA GCCACTGGTA |
| 9481 | ACAGGATTAG CAGAGCGAGG TATGTAGGCG GTGCTACAGA GTTCTTGAAG TGGTGGCCTA |
| 9541 | ACTACGGCTA CACTAGAAGA ACAGTATTTG GTATCTGCGC TCTGCTGAAG CCAGTTACCT |

| | Sequences |
|---|---|
| 9601 | TCGGAAAAAG AGTTGGTAGC TCTTGATCCG GCAAACAAAC CACCGCTGGT AGCGGTGGTT |
| 9661 | TTTTTGTTTG CAAGCAGCAG ATTACGCGCA GAAAAAAGG ATCTCAAGAA GATCCTTTGA |
| 9721 | TCTTTTCTAC GGGGTCTGAC GCTCAGTGGA ACGAAAACTC ACGTTAAGGG ATTTTGGTCA |
| 9781 | TGAGATTATC AAAAAGGATC TTCACCTAGA TCCTTTTAAA TTAAAAATGA AGTTTTAAAT |
| 9841 | CAATCTAAAG TATATATGAG TAAACTTGGT CTGACAGTTA GAAAAACTCA TCGAGCATCA |
| 9901 | AATGAAACTG CAATTTATTC ATATCAGGAT TATCAATACC ATATTTTTGA AAAAGCCGTT |
| 9961 | TCTGTAATGA AGGAGAAAAC TCACCGAGGC AGTTCCATAG GATGGCAAGA TCCTGGTATC |
| 10021 | GGTCTGCGAT TCCGACTCGT CCAACATCAA TACAACCTAT TAATTTCCCC TCGTCAAAAA |
| 10081 | TAAGGTTATC AAGTGAGAAA TCACCATGAG TGACGACTGA ATCCGGTGAG AATGGCAACA |
| 10141 | GCTTATGCAT TTCTTTCCAG ACTTGTTCAA CAGGCCAGCC ATTACGCTCG TCATCAAAAT |
| 10201 | CACTCGCATC AACCAAACCG TTATTCATTC GTGATTGCGC CTGAGCGAGA CGAAATACGC |
| 10261 | GATCGCTGTT AAAAGGACAA TTACAAACAG GAATCGAATG CAACCGGCGC AGGAACACTG |
| 10321 | CCAGCGCATC AACAATATTT TCACCTGAAT CAGGATATTC TTCTAATACC TGGAATGCTG |
| 10381 | TTTTTCCGGG GATCGCAGTG GTGAGTAACC ATGCATCATC AGGAGTACGG ATAAAATGCT |
| 10441 | TGATGGTCGG AAGAGGCATA AATTCCGTCA GCCAGTTTAG TCTGACCATC TCATCTGTAA |
| 10501 | CATCATTGGC AACGCTACCT TTGCCATGTT TCAGAAACAA CTCTGGCGCA TCGGGCTTCC |
| 10561 | CATACAATCG ATAGATTGTC GCACCTGATT GCCCGACATT ATCGCGAGCC CATTTATACC |
| 10621 | CATATAAATC AGCATCCATG TTGGAATTTA ATCGCGGCCT AGAGCAAGAC GTTTCCCGTT |
| 10681 | GAATATGGCT CATAACACCC CTTGTATTAC TGTTTATGTA AGCAGACAGT TTTATTGTTC |
| 10741 | ATGATGATAT ATTTTTATCT TGTGCAATGT AACATCAGAG ATTTTGAGAC ACAACAATTG |
| 10801 | GTCGACGGAT CC |
| SEQ ID NO: 12 | |
| 1 | GGTACCTCAA TATTGGCCAT TAGCCATATT ATTCATTGGT TATATAGCAT AAATCAATAT |
| 61 | TGGCTATTGG CCATTGCATA CGTTGTATCT ATATCATAAT ATGTACATTT ATATTGGCTC |
| 121 | ATGTCCAATA TGACCGCCAT GTTGGCATTG ATTATTGACT AGTTATTAAT AGTAATCAAT |
| 181 | TACGGGGTCA TTAGTTCATA GCCCATATAT GGAGTTCCGC GTTACATAAC TTACGGTAAA |
| 241 | TGGCCCGCCT GGCTGACCGC CCAACGACCC CCGCCCATTG ACGTCAATAA TGACGTATGT |
| 301 | TCCCATAGTA ACGCCAATAG GGACTTTCCA TTGACGTCAA TGGGTGGAGT ATTTACGGTA |
| 361 | AACTGCCCAC TTGGCAGTAC ATCAAGTGTA TCATATGCCA AGTCCGCCCC CTATTGACGT |
| 421 | CAATGACGGT AAATGGCCCG CCTGGCATTA TGCCCAGTAC ATGACCTTAC GGGACTTTCC |
| 481 | TACTTGGCAG TACATCTACG TATTAGTCAT CGCTATTACC ATGGTGATGC GGTTTTGGCA |
| 541 | GTACACCAAT GGGCGTGGAT AGCGGTTTGA CTCACGGGGA TTTCCAAGTC TCCACCCCAT |
| 601 | TGACGTCAAT GGGAGTTTGT TTTGGCACCA AAATCAACGG GACTTTCCAA AATGTCGTAA |
| 661 | CAACTGCGAT CGCCCGCCCC GTTGACGCAA ATGGGCGGTA GGCGTGTACG GTGGGAGGTC |
| 721 | TATATAAGCA GAGCTCGCTG GCTTGTAACT CAGTCTCTTA CTAGGAGACC AGCTTGAGCC |
| 781 | TGGGTGTTCG CTGGTTAGCC TAACCTGGTT GGCCACCAGG GGTAAGGACT CCTTGGCTTA |
| 841 | GAAAGCTAAT AAACTTGCCT GCATTAGAGC TTATCTGAGT CAAGTGTCCT CATTGACGCC |
| 901 | TCACTCTCTT GAACGGGAAT CTTCCTTACT GGGTTCTCTC TCTGACCCAG GCGAGAGAAA |
| 961 | CTCCAGCAGT GGCGCCCGAA CAGGGACTTG AGTGAGAGTG TAGGCACGTA CAGCTGAGAA |

|      | Sequences |
|------|-----------|
| 1021 | GGCGTCGGAC GCGAAGGAAG CGCGGGGTGC GACGCGACCA AGAAGGAGAC TTGGTGAGTA |
| 1081 | GGCTTCTCGA GTGCCGGGAA AAAGCTCGAG CCTAGTTAGA GGACTAGGAG AGGCCGTAGC |
| 1141 | CGTAACTACT CTGGGCAAGT AGGGCAGGCG GTGGGTACGC AATGGGGGCG GCTACCTCAG |
| 1201 | CACTAAATAG GAGACAATTA GACCAATTTG AGAAAATACG ACTTCGCCCG AACGGAAAGA |
| 1261 | AAAAGTACCA AATTAAACAT TTAATATGGG CAGGCAAGGA GATGGAGCGC TTCGGCCTCC |
| 1321 | ATGAGAGGTT GTTGGAGACA GAGGAGGGGT GTAAAAGAAT CATAGAAGTC CTCTACCCCC |
| 1381 | TAGAACCAAC AGGATCGGAG GGCTTAAAAA GTCTGTTCAA TCTTGTGTGC GTGCTATATT |
| 1441 | GCTTGCACAA GGAACAGAAA GTGAAAGACA CAGAGGAAGC AGTAGCAACA GTAAGACAAC |
| 1501 | ACTGCCATCT AGTGGAAAAA GAAAAAGTG CAACAGAGAC ATCTAGTGGA CAAAAGAAAA |
| 1561 | ATGACAAGGG AATAGCAGCG CCACCTGGTG GCAGTCAGAA TTTTCCAGCG CAACAACAAG |
| 1621 | GAAATGCCTG GGTACATGTA CCCTTGTCAC CGCGCACCTT AAATGCGTGG GTAAAAGCAG |
| 1681 | TAGAGGAGAA AAAATTTGGA GCAGAAATAG TACCCATGTT TCAAGCCCTA TCGAATTCCC |
| 1741 | GTTTGTGCTA GGGTTCTTAG GCTTCTTGGG GGCTGCTGGA ACTGCAATGG GAGCAGCGGC |
| 1801 | GACAGCCCTG ACGGTCCAGT CTCAGCATTT GCTTGCTGGG ATACTGCAGC AGCAGAAGAA |
| 1861 | TCTGCTGGCG GCTGTGGAGG CTCAACAGCA GATGTTGAAG CTGACCATTT GGGGTGTTAA |
| 1921 | AAACCTCAAT GCCCGCGTCA CAGCCCTTGA GAAGTACCTA GAGGATCAGG CACGACTAAA |
| 1981 | CTCCTGGGGG TGCGCATGGA AACAAGTATG TCATACCACA GTGGAGTGGC CCTGGACAAA |
| 2041 | TCGGACTCCG GATTGGCAAA ATATGACTTG GTTGGAGTGG GAAAGACAAA TAGCTGATTT |
| 2101 | GGAAAGCAAC ATTACGAGAC AATTAGTGAA GGCTAGAGAA CAAGAGGAAA AGAATCTAGA |
| 2161 | TGCCTATCAG AAGTTAACTA GTTGGTCAGA TTTTCTGGTCT TGGTTCGATT TCTCAAAATG |
| 2221 | GCTTAACATT TTAAAAATGG GATTTTTAGT AATAGTAGGA ATAATAGGGT TAAGATTACT |
| 2281 | TTACACAGTA TATGGATGTA TAGTGAGGGT TAGGCAGGGA TATGTTCCTC TATCTCCACA |
| 2341 | GATCCATATC CGCGGCAATT TTAAAAGAAA GGGAGGAATA GGGGACAGA CTTCAGCAGA |
| 2401 | GAGACTAATT AATATAATAA CAACACAATT AGAAATACAA CATTTACAAA CCAAAATTCA |
| 2461 | AAAAATTTTA AATTTTAGAG CCGCGGAGAT CTGTTACATA ACTTATGGTA AATGGCCTGC |
| 2521 | CTGGCTGACT GCCCAATGAC CCCTGCCCAA TGATGTCAAT AATGATGTAT GTTCCCATGT |
| 2581 | AATGCCAATA GGGACTTTCC ATTGATGTCA ATGGGTGGAG TATTTATGGT AACTGCCCAC |
| 2641 | TTGGCAGTAC ATCAAGTGTA TCATATGCCA AGTATGCCCC CTATTGATGT CAATGATGGT |
| 2701 | AAATGGCCTG CCTGGCATTA TGCCCAGTAC ATGACCTTAT GGACTTTCC TACTTGGCAG |
| 2761 | TACATCTATG TATTAGTCAT TGCTATTACC ATGGGAATTC ACTAGTGGAG AAGAGCATGC |
| 2821 | TTGAGGGCTG AGTGCCCCTC AGTGGGCAGA GAGCACATGG CCCACAGTCC CTGAGAAGTT |
| 2881 | GGGGGGAGGG GTGGGCAATT GAACTGGTGC CTAGAGAAGG TGGGGCTTGG GTAAACTGGG |
| 2941 | AAAGTGATGT GGTGTACTGG CTCCACCTTT TTCCCCAGGG TGGGGAGAA CCATATATAA |
| 3001 | GTGCAGTAGT CTCTGTGAAC ATTCAAGCTT CTGCCTTCTC CCTCCTGTGA GTTTGCTAGC |
| 3061 | CACCAATGCA GATTGAGCTG AGCACCTGCT TCTTCCTGTG CCTGCTGAGG TTCTGCTTCT |
| 3121 | CTGCCACCAG GAGATACTAC CTGGGGGCTG TGGAGCTGAG CTGGGACTAC ATGCAGTCTG |
| 3181 | ACCTGGGGGA GCTGCCTGTG GATGCCAGGT TCCCCCCCAG AGTGCCCAAG AGCTTCCCCT |
| 3241 | TCAACACCTC TGTGGTGTAC AAGAAGACCC TGTTTGTGGA GTTCACTGAC CACCTGTTCA |

| | Sequences |
|---|---|
| 3301 | ACATTGCCAA GCCCAGGCCC CCCTGGATGG GCCTGCTGGG CCCCACCATC CAGGCTGAGG |
| 3361 | TGTATGACAC TGTGGTGATC ACCCTGAAGA ACATGGCCAG CCACCCTGTG AGCCTGCATG |
| 3421 | CTGTGGGGGT GAGCTACTGG AAGGCCTCTG AGGGGCTGA GTATGATGAC CAGACCAGCC |
| 3481 | AGAGGGAGAA GGAGGATGAC AAGGTGTTCC CTGGGGGCAG CCACACCTAT GTGTGGCAGG |
| 3541 | TGCTGAAGGA GAATGGCCCC ATGGCCTCTG ACCCCCTGTG CCTGACCTAC AGCTACCTGA |
| 3601 | GCCATGTGGA CCTGGTGAAG GACCTGAACT CTGGCCTGAT TGGGGCCCTG CTGGTGTGCA |
| 3661 | GGGAGGGCAG CCTGGCCAAG GAGAAGACCC AGACCCTGCA CAAGTTCATC CTGCTGTTTG |
| 3721 | CTGTGTTTGA TGAGGGCAAG AGCTGGCACT CTGAAACCAA GAACAGCCTG ATGCAGGACA |
| 3781 | GGGATGCTGC CTCTGCCAGG GCCTGGCCCA GATGCACAC TGTGAATGGC TATGTGAACA |
| 3841 | GGAGCCTGCC TGGCCTGATT GGCTGCCACA GGAAGTCTGT GTACTGGCAT GTGATTGGCA |
| 3901 | TGGGCACCAC CCCTGAGGTG CACAGCATCT TCCTGGAGGG CCACACCTTC CTGGTCAGGA |
| 3961 | ACCACAGGCA GGCCAGCCTG GAGATCAGCC CCATCACCTT CCTGACTGCC CAGACCCTGC |
| 4021 | TGATGGACCT GGGCCAGTTC CTGCTGTTCT GCCACATCAG CAGCCACCAG CATGATGGCA |
| 4081 | TGGAGGCCTA TGTGAAGGTG GACAGCTGCC CTGAGGAGCC CCAGCTGAGG ATGAAGAACA |
| 4141 | ATGAGGAGGC TGAGGACTAT GATGATGACC TGACTGACTC TGAGATGGAT GTGGTGAGGT |
| 4201 | TTGATGATGA CAACAGCCCC AGCTTCATCC AGATCAGGTC TGTGGCCAAG AAGCACCCCA |
| 4261 | AGACCTGGGT GCACTACATT GCTGCTGAGG AGGAGGACTG GGACTATGCC CCCCTGGTGC |
| 4321 | TGGCCCCTGA TGACAGGAGC TACAAGAGCC AGTACCTGAA CAATGGCCCC CAGAGGATTG |
| 4381 | GCAGGAAGTA CAAGAAGGTC AGGTTCATGG CCTACACTGA TGAAACCTTC AAGACCAGGG |
| 4441 | AGGCCATCCA GCATGAGTCT GGCATCCTGG GCCCCCTGCT GTATGGGGAG GTGGGGGACA |
| 4501 | CCCTGCTGAT CATCTTCAAG AACCAGGCCA GCAGGCCCTA CAACATCTAC CCCCATGGCA |
| 4561 | TCACTGATGT GAGGCCCCTG TACAGCAGGA GGCTGCCCAA GGGGGTGAAG CACCTGAAGG |
| 4621 | ACTTCCCCAT CCTGCCTGGG GAGATCTTCA AGTACAAGTG GACTGTGACT GTGGAGGATG |
| 4681 | GCCCCACCAA GTCTGACCCC AGGTGCCTGA CCAGATACTA CAGCAGCTTT GTGAACATGG |
| 4741 | AGAGGGACCT GGCCTCTGGC CTGATTGGCC CCCTGCTGAT CTGCTACAAG GAGTCTGTGG |
| 4801 | ACCAGAGGGG CAACCAGATC ATGTCTGACA AGAGGAATGT GATCCTGTTC TCTGTGTTTG |
| 4861 | ATGAGAACAG GAGCTGGTAC CTGACTGAGA ACATCCAGAG GTTCCTGCCC AACCCTGCTG |
| 4921 | GGGTGCAGCT GGAGGACCCT GAGTTCCAGG CCAGCAACAT CATGCACAGC ATCAATGGCT |
| 4981 | ATGTGTTTGA CAGCCTGCAG CTGTCTGTGT GCCTGCATGA GGTGGCCTAC TGGTACATCC |
| 5041 | TGAGCATTGG GGCCCAGACT GACTTCCTGT CTGTGTTCTT CTCTGGCTAC ACCTTCAAGC |
| 5101 | ACAAGATGGT GTATGAGGAC ACCCTGACCC TGTTCCCCTT CTCTGGGGAG ACTGTGTTCA |
| 5161 | TGAGCATGGA GAACCCTGGC CTGTGGATTC TGGGCTGCCA CAACTCTGAC TTCAGGAACA |
| 5221 | GGGGCATGAC TGCCCTGCTG AAAGTCTCCA GCTGTGACAA GAACACTGGG GACTACTATG |
| 5281 | AGGACAGCTA TGAGGACATC TCTGCCTACC TGCTGAGCAA GAACAATGCC ATTGAGCCCA |
| 5341 | GGAGCTTCAG CCAGAATGCC ACTAATGTGT CTAACAACAG CAACACCAGC AATGACAGCA |
| 5401 | ATGTGTCTCC CCCAGTGCTG AAGAGGCACC AGAGGGAGAT CACCAGGACC ACCCTGCAGT |
| 5461 | CTGACCAGGA GGAGATTGAC TATGATGACA CCATCTCTGT GGAGATGAAG AAGGAGGACT |
| 5521 | TTGACATCTA CGACGAGGAC GAGAACCAGA GCCCCAGGAG CTTCCAGAAG AAGACCAGGC |

-continued

| | Sequences |
|---|---|
| 5581 | ACTACTTCAT TGCTGCTGTG GAGAGGCTGT GGGACTATGG CATGAGCAGC AGCCCCCATG |
| 5641 | TGCTGAGGAA CAGGGCCCAG TCTGGCTCTG TGCCCCAGTT CAAGAAGGTG GTGTTCCAGG |
| 5701 | AGTTCACTGA TGGCAGCTTC ACCCAGCCCC TGTACAGAGG GGAGCTGAAT GAGCACCTGG |
| 5761 | GCCTGCTGGG CCCCTACATC AGGGCTGAGG TGGAGGACAA CATCATGGTG ACCTTCAGGA |
| 5821 | ACCAGGCCAG CAGGCCCTAC AGCTTCTACA GCAGCCTGAT CAGCTATGAG GAGGACCAGA |
| 5881 | GGCAGGGGGC TGAGCCCAGG AAGAACTTTG TGAAGCCCAA TGAAACCAAG ACCTACTTCT |
| 5941 | GGAAGGTGCA GCACCACATG GCCCCCACCA AGGATGAGTT TGACTGCAAG GCCTGGGCCT |
| 6001 | ACTTCTCTGA TGTGGACCTG GAGAAGGATG TGCACTCTGG CCTGATTGGC CCCCTGCTGG |
| 6061 | TGTGCCACAC CAACACCCTG AACCCTGCCC ATGGCAGGCA GGTGACTGTG CAGGAGTTTG |
| 6121 | CCCTGTTCTT CACCATCTTT GATGAAACCA AGAGCTGGTA CTTCACTGAG AACATGGAGA |
| 6181 | GGAACTGCAG GGCCCCCTGC AACATCCAGA TGGAGGACCC CACCTTCAAG GAGAACTACA |
| 6241 | GGTTCCATGC CATCAATGGC TACATCATGG ACACCCTGCC TGGCCTGGTG ATGGCCCAGG |
| 6301 | ACCAGAGGAT CAGGTGGTAC CTGCTGAGCA TGGGCAGCAA TGAGAACATC CACAGCATCC |
| 6361 | ACTTCTCTGG CCATGTGTTC ACTGTGAGGA AGAAGGAGGA GTACAAGATG GCCCTGTACA |
| 6421 | ACCTGTACCC TGGGGTGTTT GAGACTGTGG AGATGCTGCC CAGCAAGGCT GGCATCTGGA |
| 6481 | GGGTGGAGTG CCTGATTGGG GAGCACCTGC ATGCTGGCAT GAGCACCCTG TTCCTGGTGT |
| 6541 | ACAGCAACAA GTGCCAGACC CCCCTGGGCA TGGCCTCTGG CCACATCAGG GACTTCCAGA |
| 6601 | TCACTGCCTC TGGCCAGTAT GGCCAGTGGG CCCCCAAGCT GGCCAGGCTG CACTACTCTG |
| 6661 | GCAGCATCAA TGCCTGGAGC ACCAAGGAGC CCTTCAGCTG GATCAAGGTG GACCTGCTGG |
| 6721 | CCCCCATGAT CATCCATGGC ATCAAGACCC AGGGGGCCAG GCAGAAGTTC AGCAGCCTGT |
| 6781 | ACATCAGCCA GTTCATCATC ATGTACAGCC TGGATGGCAA GAAGTGGCAG ACCTACAGGG |
| 6841 | GCAACAGCAC TGGCACCCTG ATGGTGTTCT TTGGCAATGT GGACAGCTCT GGCATCAAGC |
| 6901 | ACAACATCTT CAACCCCCCC ATCATTGCCA GATACATCAG GCTGCACCCC ACCCACTACA |
| 6961 | GCATCAGGAG CACCCTGAGG ATGGAGCTGA TGGGCTGTGA CCTGAACAGC TGCAGCATGC |
| 7021 | CCCTGGGCAT GGAGAGCAAG GCCATCTCTG ATGCCCAGAT CACTGCCAGC AGCTACTTCA |
| 7081 | CCAACATGTT TGCCACCTGG AGCCCCAGCA AGGCCAGGCT GCACCTGCAG GGCAGGAGCA |
| 7141 | ATGCCTGGAG GCCCCAGGTC AACAACCCCA AGGAGTGGCT GCAGGTGGAC TTCCAGAAGA |
| 7201 | CCATGAAGGT GACTGGGGTG ACCACCCAGG GGGTGAAGAG CCTGCTGACC AGCATGTATG |
| 7261 | TGAAGGAGTT CCTGATCAGC AGCAGCCAGG ATGGCCACCA GTGGACCCTG TTCTTCCAGA |
| 7321 | ATGGCAAGGT GAAGGTGTTC CAGGGCAACC AGGACAGCTT CACCCCTGTG GTGAACAGCC |
| 7381 | TGGACCCCCC CCTGCTGACC AGATACCTGA GGATTCACCC CCAGAGCTGG GTGCACCAGA |
| 7441 | TTGCCCTGAG GATGGAGGTG CTGGGCTGTG AGGCCCAGGA CCTGTACTGA GCGGCCGCGG |
| 7501 | GCCCAATCAA CCTCTGGATT ACAAAATTTG TGAAAGATTG ACTGGTATTC TTAACTATGT |
| 7561 | TGCTCCTTTT ACGCTATGTG GATACGCTGC TTTAATGCCT TTGTATCATG CTATTGCTTC |
| 7621 | CCGTATGGCT TTCATTTTCT CCTCCTTGTA TAAATCCTGG TTGCTGTCTC TTTATGAGGA |
| 7681 | GTTGTGGCCC GTTGTCAGGC AACGTGGCGT GGTGTGCACT GTGTTTGCTG ACGCAACCCC |
| 7741 | CACTGGTTGG GGCATTGCCA CCACCTGTCA GCTCCTTTCC GGGACTTTCG CTTTCCCCCT |
| 7801 | CCCTATTGCC ACGGCGGAAC TCATCGCCGC CTGCCTTGCC CGCTGCTGGA CAGGGGCTCG |

-continued

| | Sequences |
|---|---|
| 7861 | GCTGTTGGGC ACTGACAATT CCGTGGTGTT GTCGGGGAAA TCATCGTCCT TTCCTTGGCT |
| 7921 | GCTCGCCTGT GTTGCCACCT GGATTCTGCG CGGGACGTCC TTCTGCTACG TCCCTTCGGC |
| 7981 | CCTCAATCCA GCGGACCTTC CTTCCCGCGG CCTGCTGCCG GCTCTGCGGC CTCTTCCGCG |
| 8041 | TCTTCGCCTT CGCCCTCAGA CGAGTCGGAT CTCCCTTTGG GCCGCCTCCC CGCAAGCTTC |
| 8101 | GCACTTTTTA AAAGAAAAGG GAGGACTGGA TGGGATTTAT TACTCCGATA GGACGCTGGC |
| 8161 | TTGTAACTCA GTCTCTTACT AGGAGACCAG CTTGAGCCTG GGTGTTCGCT GGTTAGCCTA |
| 8221 | ACCTGGTTGG CCACCAGGGG TAAGGACTCC TTGGCTTAGA AAGCTAATAA ACTTGCCTGC |
| 8281 | ATTAGAGCTC TTACGCGTCC CGGGCTCGAG ATCCGCATCT CAATTAGTCA GCAACCATAG |
| 8341 | TCCCGCCCCT AACTCCGCCC ATCCCGCCCC TAACTCCGCC CAGTTCCGCC CATTCTCCGC |
| 8401 | CCCATGGCTG ACTAATTTTT TTTATTTATG CAGAGGCCGA GGCCGCCTCG GCCTCTGAGC |
| 8461 | TATTCCAGAA GTAGTGAGGA GGCTTTTTTG GAGGCCTAGG CTTTTGCAAA AAGCTAACTT |
| 8521 | GTTTATTGCA GCTTATAATG GTTACAAATA AAGCAATAGC ATCACAAATT TCACAAATAA |
| 8581 | AGCATTTTTT TCACTGCATT CTAGTTGTGG TTTGTCCAAA CTCATCAATG TATCTTATCA |
| 8641 | TGTCTGTCCG CTTCCTCGCT CACTGACTCG CTGCGCTCGG TCGTTCGGCT GCGGCGAGCG |
| 8701 | GTATCAGCTC ACTCAAAGGC GGTAATACGG TTATCCACAG AATCAGGGGA TAACGCAGGA |
| 8761 | AAGAACATGT GAGCAAAAGG CCAGCAAAAG GCCAGGAACC GTAAAAAGGC CGCGTTGCTG |
| 8821 | GCGTTTTTCC ATAGGCTCCG CCCCCCTGAC GAGCATCACA AAAATCGACG CTCAAGTCAG |
| 8881 | AGGTGGCGAA ACCCGACAGG ACTATAAAGA TACCAGGCGT TTCCCCCTGG AAGCTCCCTC |
| 8941 | GTGCGCTCTC CTGTTCCGAC CCTGCCGCTT ACCGGATACC TGTCCGCCTT TCTCCCTTCG |
| 9001 | GGAAGCGTGG CGCTTTCTCA TAGCTCACGC TGTAGGTATC TCAGTTCGGT GTAGGTCGTT |
| 9061 | CGCTCCAAGC TGGGCTGTGT GCACGAACCC CCCGTTCAGC CCGACCGCTG CGCCTTATCC |
| 9121 | GGTAACTATC GTCTTGAGTC CAACCCGGTA AGACACGACT TATCGCCACT GGCAGCAGCC |
| 9181 | ACTGGTAACA GGATTAGCAG AGCGAGGTAT GTAGGCGGTG CTACAGAGTT CTTGAAGTGG |
| 9241 | TGGCCTAACT ACGGCTACAC TAGAAGAACA GTATTTGGTA TCTGCGCTCT GCTGAAGCCA |
| 9301 | GTTACCTTCG GAAAAAGAGT TGGTAGCTCT TGATCCGGCA AACAAACCAC CGCTGGTAGC |
| 9361 | GGTGGTTTTT TTGTTTGCAA GCAGCAGATT ACGCGCAGAA AAAAAGGATC TCAAGAAGAT |
| 9421 | CCTTTGATCT TTTCTACGGG GTCTGACGCT CAGTGGAACG AAAACTCACG TTAAGGGATT |
| 9481 | TTGGTCATGA GATTATCAAA AAGGATCTTC ACCTAGATCC TTTTAAATTA AAAATGAAGT |
| 9541 | TTTAAATCAA TCTAAAGTAT ATATGAGTAA ACTTGGTCTG ACAGTTAGAA AAACTCATCG |
| 9601 | AGCATCAAAT GAAACTGCAA TTTATTCATA TCAGGATTAT CAATACCATA TTTTTGAAAA |
| 9661 | AGCCGTTTCT GTAATGAAGG AGAAAACTCA CCGAGGCAGT TCCATAGGAT GGCAAGATCC |
| 9721 | TGGTATCGGT CTGCGATTCC GACTCGTCCA ACATCAATAC AACCTATTAA TTTCCCCTCG |
| 9781 | TCAAAAATAA GGTTATCAAG TGAGAAATCA CCATGAGTGA CGACTGAATC CGGTGAGAAT |
| 9841 | GGCAACAGCT TATGCATTTC TTTCCAGACT TGTTCAACAG GCCAGCCATT ACGCTCGTCA |
| 9901 | TCAAAATCAC TCGCATCAAC CAAACCGTTA TTCATTCGTG ATTGCGCCTG AGCGAGACGA |
| 9961 | AATACGCGAT CGCTGTTAAA AGGACAATTA CAAACAGGAA TCGAATGCAA CCGGCGCAGG |
| 10021 | AACACTGCCA GCGCATCAAC AATATTTTCA CCTGAATCAG GATATTCTTC TAATACCTGG |
| 10081 | AATGCTGTTT TTCCGGGGAT CGCAGTGGTG AGTAACCATG CATCATCAGG AGTACGGATA |

```
   10141   AAATGCTTGA TGGTCGGAAG AGGCATAAAT TCCGTCAGCC AGTTTAGTCT
           GACCATCTCA
   10201   TCTGTAACAT CATTGGCAAC GCTACCTTTG CCATGTTTCA GAAACAACTC
           TGGCGCATCG
   10261   GGCTTCCCAT ACAATCGATA GATTGTCGCA CCTGATTGCC CGACATTATC
           GCGAGCCCAT
   10321   TTATACCCAT ATAAATCAGC ATCCATGTTG GAATTTAATC GCGGCCTAGA
           GCAAGACGTT
   10381   TCCCGTTGAA TATGGCTCAT AACACCCCTT GTATTACTGT TTATGTAAGC
           AGACAGTTTT
   10441   ATTGTTCATG ATGATATATT TTTATCTTGT GCAATGTAAC ATCAGAGATT
           TTGAGACACA
   10501   ACAATTGGTC GACGGATCC

SEQ ID NO: 13
      1   GGTACCTCAA TATTGGCCAT TAGCCATATT ATTCATTGGT TATATAGCAT
          AAATCAATAT
     61   TGGCTATTGG CCATTGCATA CGTTGTATCT ATATCATAAT ATGTACATTT
          ATATTGGCTC
    121   ATGTCCAATA TGACCGCCAT GTTGGCATTG ATTATTGACT AGTTATTAAT
          AGTAATCAAT
    181   TACGGGGTCA TTAGTTCATA GCCCATATAT GGAGTTCCGC GTTACATAAC
          TTACGGTAAA
    241   TGGCCCGCCT GGCTGACCGC CCAACGACCC CCGCCCATTG ACGTCAATAA
          TGACGTATGT
    301   TCCCATAGTA ACGCCAATAG GGACTTTCCA TTGACGTCAA TGGGTGGAGT
          ATTTACGGTA
    361   AACTGCCCAC TTGGCAGTAC ATCAAGTGTA TCATATGCCA AGTCCGCCCC
          CTATTGACGT
    421   CAATGACGGT AAATGGCCCG CCTGGCATTA TGCCCAGTAC ATGACCTTAC
          GGGACTTTCC
    481   TACTTGGCAG TACATCTACG TATTAGTCAT CGCTATTACC ATGGTGATGC
          GGTTTTGGCA
    541   GTACACCAAT GGGCGTGGAT AGCGGTTTGA CTCACGGGGA TTTCCAAGTC
          TCCACCCCAT
    601   TGACGTCAAT GGGAGTTTGT TTTGGCACCA AAATCAACGG GACTTTCCAA
          AATGTCGTAA
    661   CAACTGCGAT CGCCCGCCCC GTTGACGCAA ATGGGCGGTA GGCGTGTACG
          GTGGGAGGTC
    721   TATATAAGCA GAGCTCGCTG GCTTGTAACT CAGTCTCTTA CTAGGAGACC
          AGCTTGAGCC
    781   TGGGTGTTCG CTGGTTAGCC TAACCTGGTT GGCCACCAGG GGTAAGGACT
          CCTTGGCTTA
    841   GAAAGCTAAT AAACTTGCCT GCATTAGAGC TTATCTGAGT CAAGTGTCCT
          CATTGACGCC
    901   TCACTCTCTT GAACGGGAAT CTTCCTTACT GGGTTCTCTC TCTGACCCAG
          GCGAGAGAAA
    961   CTCCAGCAGT GGCGCCCGAA CAGGGACTTG AGTGAGAGTG TAGGCACGTA
          CAGCTGAGAA
   1021   GGCGTCGGAC GCGAAGGAAG CGCGGGGTGC GACGCGACCA AGAAGGAGAC
          TTGGTGAGTA
   1081   GGCTTCTCGA GTGCCGGGAA AAAGCTCGAG CCTAGTTAGA GGACTAGGAG
          AGGCCGTAGC
   1141   CGTAACTACT CTGGGCAAGT AGGGCAGGCG GTGGGTACGC AATGGGGGCG
          GCTACCTCAG
   1201   CACTAAATAG GAGACAATTA GACCAATTTG AGAAAATACG ACTTCGCCCG
          AACGGAAAGA
   1261   AAAAGTACCA AATTAAACAT TTAATATGGG CAGGCAAGGA GATGGAGCGC
          TTCGGCCTCC
   1321   ATGAGAGGTT GTTGGAGACA GAGGAGGGGT GTAAAGAAT CATAGAAGTC
          CTCTACCCCC
   1381   TAGAACCAAC AGGATCGGAG GGCTTAAAAA GTCTGTTCAA TCTTGTGTGC
          GTGCTATATT
   1441   GCTTGCACAA GGAACAGAAA GTGAAAGACA CAGAGGAAGC AGTAGCAACA
          GTAAGACAAC
   1501   ACTGCCATCT AGTGGAAAAA GAAAAAAGTG CAACAGAGAC ATCTAGTGGA
          CAAAAGAAAA
   1561   ATGACAAGGG AATAGCAGCG CCACCTGGTG GCAGTCAGAA TTTTCCAGCG
          CAACAACAAG
   1621   GAAATGCCTG GGTACATGTA CCCTTGTCAC CGCGCACCTT AAATGCGTGG
          GTAAAAGCAG
   1681   TAGAGGAGAA AAAATTTGGA GCAGAAATAG TACCCATGTT CAAGCCCTA
          TCGAATTCCC
   1741   GTTTGTGCTA GGGTTCTTAG CTTCTTGGG GGCTGCTGGA ACTGCAATGG
          GAGCAGCGGC
   1801   GACAGCCCTG ACGGTCCAGT CTCAGCATTT GCTTGCTGGG ATACTGCAGC
          AGCAGAAGAA
```

| | Sequences |
|---|---|
| 1861 | TCTGCTGGCG GCTGTGGAGG CTCAACAGCA GATGTTGAAG CTGACCATTT GGGGTGTTAA |
| 1921 | AAACCTCAAT GCCCGCGTCA CAGCCCTTGA GAAGTACCTA GAGGATCAGG CACGACTAAA |
| 1981 | CTCCTGGGGG TGCGCATGGA AACAAGTATG TCATACCACA GTGGAGTGGC CCTGGACAAA |
| 2041 | TCGGACTCCG GATTGGCAAA ATATGACTTG GTTGGAGTGG GAAAGACAAA TAGCTGATTT |
| 2101 | GGAAAGCAAC ATTACGAGAC AATTAGTGAA GGCTAGAGAA CAAGAGGAAA AGAATCTAGA |
| 2161 | TGCCTATCAG AAGTTAACTA GTTGGTCAGA TTTCTGGTCT TGGTTCGATT TCTCAAAATG |
| 2221 | GCTTAACATT TTAAAAATGG GATTTTTAGT AATAGTAGGA ATAATAGGGT TAAGATTACT |
| 2281 | TTACACAGTA TATGGATGTA TAGTGAGGGT TAGGCAGGGA TATGTTCCTC TATCTCCACA |
| 2341 | GATCCATATC CGCGGCAATT TTAAAAGAAA GGGAGGAATA GGGGACAGA CTTCAGCAGA |
| 2401 | GAGACTAATT AATATAATAA CAACACAATT AGAAATACAA CATTTACAAA CCAAAATTCA |
| 2461 | AAAAATTTTA AATTTTAGAG CCGCGGAGAT CTCAATATTG GCCATTAGCC ATATTATTCA |
| 2521 | TTGGTTATAT AGCATAAATC AATATTGGCT ATTGGCCATT GCATACGTTG TATCTATATC |
| 2581 | ATAATATGTA CATTTATATT GGCTCATGTC CAATATGACC GCCATGTTGG CATTGATTAT |
| 2641 | TGACTAGTTA TTAATAGTAA TCAATTACGG GGTCATTAGT TCATAGCCCA TATATGGAGT |
| 2701 | TCCGCGTTAC ATAACTTACG GTAAATGGCC CGCCTGGCTG ACCGCCCAAC GACCCCCGCC |
| 2761 | CATTGACGTC AATAATGACG TATGTTCCCA TAGTAACGCC AATAGGGACT TTCCATTGAC |
| 2821 | GTCAATGGGT GGAGTATTTA CGGTAAACTG CCCACTTGGC AGTACATCAA GTGTATCATA |
| 2881 | TGCCAAGTCC GCCCCCTATT GACGTCAATG ACGGTAAATG GCCCGCCTGG CATTATGCCC |
| 2941 | AGTACATGAC CTTACGGGAC TTTCCTACTT GGCAGTACAT CTACGTATTA GTCATCGCTA |
| 3001 | TTACCATGGT GATGCGGTTT TGGCAGTACA CCAATGGGCG TGGATAGCGG TTTGACTCAC |
| 3061 | GGGGATTTCC AAGTCTCCAC CCCATTGACG TCAATGGGAG TTTGTTTTGG CACCAAAATC |
| 3121 | AACGGGACTT TCCAAAATGT CGTAATAACC CCGCCCCGTT GACGCAAATG GGCGGTAGGC |
| 3181 | GTGTACGGTG GGAGGTCTAT ATAAGCAGAG CTCGTTTAGT GAACCGTCAG ATCACTAGAA |
| 3241 | GCTTTATTGC GGTAGTTTAT CACAGTTAAA TTGCTAACGC AGTCAGTGCT TCTGACACAA |
| 3301 | CAGTCTCGAA CTTAAGCTGC AGAAGTTGGT CGTGAGGCAC TGGGCAGGCT AGCCACCAAT |
| 3361 | GCAGATTGAG CTGAGCACCT GCTTCTTCCT GTGCCTGCTG AGGTTCTGCT TCTCTGCCAC |
| 3421 | CAGGAGATAC TACCTGGGGG CTGTGGAGCT GAGCTGGGAC TACATGCAGT CTGACCTGGG |
| 3481 | GGAGCTGCCT GTGGATGCCA GGTTCCCCCC CAGAGTGCCC AAGAGCTTCC CCTTCAACAC |
| 3541 | CTCTGTGGTG TACAAGAAGA CCCTGTTTGT GGAGTTCACT GACCACCTGT TCAACATTGC |
| 3601 | CAAGCCCAGG CCCCCCTGGA TGGGCCTGCT GGGCCCCACC ATCCAGGCTG AGGTGTATGA |
| 3661 | CACTGTGGTG ATCACCCTGA AGAACATGGC CAGCCACCCT GTGAGCCTGC ATGCTGTGGG |
| 3721 | GGTGAGCTAC TGGAAGGCCT CTGAGGGGGC TGAGTATGAT GACCAGACCA GCCAGAGGGA |
| 3781 | GAAGGAGGAT GACAAGGTGT TCCCTGGGGG CAGCCACACC TATGTGTGGC AGGTGCTGAA |
| 3841 | GGAGAATGGC CCCATGGCCT CTGACCCCCT GTGCCTGACC TACAGCTACC TGAGCCATGT |
| 3901 | GGACCTGGTG AAGGACCTGA ACTCTGGCCT GATTGGGGCC CTGCTGGTGT GCAGGGAGGG |
| 3961 | CAGCCTGGCC AAGGAGAAGA CCCAGACCCT GCACAAGTTC ATCCTGCTGT TTGCTGTGTT |
| 4021 | TGATGAGGGC AAGAGCTGGC ACTCTGAAAC CAAGAACAGC CTGATGCAGG ACAGGGATGC |
| 4081 | TGCCTCTGCC AGGGCCTGGC CCAAGATGCA CACTGTGAAT GGCTATGTGA ACAGGAGCCT |

| | Sequences |
|---|---|
| 4141 | GCCTGGCCTG ATTGGCTGCC ACAGGAAGTC TGTGTACTGG CATGTGATTG GCATGGGCAC |
| 4201 | CACCCCTGAG GTGCACAGCA TCTTCCTGGA GGGCCACACC TTCCTGGTCA GGAACCACAG |
| 4261 | GCAGGCCAGC CTGGAGATCA GCCCCATCAC CTTCCTGACT GCCCAGACCC TGCTGATGGA |
| 4321 | CCTGGGCCAG TTCCTGCTGT TCTGCCACAT CAGCAGCCAC CAGCATGATG GCATGGAGGC |
| 4381 | CTATGTGAAG GTGGACAGCT GCCCTGAGGA GCCCCAGCTG AGGATGAAGA ACAATGAGGA |
| 4441 | GGCTGAGGAC TATGATGATG ACCTGACTGA CTCTGAGATG GATGTGGTGA GGTTTGATGA |
| 4501 | TGACAACAGC CCCAGCTTCA TCCAGATCAG GTCTGTGGCC AAGAAGCACC CCAAGACCTG |
| 4561 | GGTGCACTAC ATTGCTGCTG AGGAGGAGGA CTGGGACTAT GCCCCCCTGG TGCTGGCCCC |
| 4621 | TGATGACAGG AGCTACAAGA GCCAGTACCT GAACAATGGC CCCCAGAGGA TTGGCAGGAA |
| 4681 | GTACAAGAAG GTCAGGTTCA TGGCCTACAC TGATGAAACC TTCAAGACCA GGGAGGCCAT |
| 4741 | CCAGCATGAG TCTGGCATCC TGGGCCCCCT GCTGTATGGG GAGGTGGGGG ACACCCTGCT |
| 4801 | GATCATCTTC AAGAACCAGG CCAGCAGGCC CTACAACATC TACCCCCATG GCATCACTGA |
| 4861 | TGTGAGGCCC CTGTACAGCA GGAGGCTGCC CAAGGGGGTG AAGCACCTGA AGGACTTCCC |
| 4921 | CATCCTGCCT GGGGAGATCT TCAAGTACAA GTGGACTGTG ACTGTGGAGG ATGGCCCCAC |
| 4981 | CAAGTCTGAC CCCAGGTGCC TGACCAGATA CTACAGCAGC TTTGTGAACA TGGAGAGGGA |
| 5041 | CCTGGCCTCT GGCCTGATTG GCCCCCTGCT GATCTGCTAC AAGGAGTCTG TGGACCAGAG |
| 5101 | GGGCAACCAG ATCATGTCTG ACAAGAGGAA TGTGATCCTG TTCTCTGTGT TTGATGAGAA |
| 5161 | CAGGAGCTGG TACCTGACTG AGAACATCCA GAGGTTCCTG CCCAACCCTG CTGGGGTGCA |
| 5221 | GCTGGAGGAC CCTGAGTTCC AGGCCAGCAA CATCATGCAC AGCATCAATG GCTATGTGTT |
| 5281 | TGACAGCCTG CAGCTGTCTG TGTGCCTGCA TGAGGTGGCC TACTGGTACA TCCTGAGCAT |
| 5341 | TGGGGCCCAG ACTGACTTCC TGTCTGTGTT CTTCTCTGGC TACACCTTCA AGCACAAGAT |
| 5401 | GGTGTATGAG GACACCCTGA CCCTGTTCCC CTTCTCTGGG GAGACTGTGT TCATGAGCAT |
| 5461 | GGAGAACCCT GGCCTGTGGA TTCTGGGCTG CCACAACTCT GACTTCAGGA ACAGGGGCAT |
| 5521 | GACTGCCCTG CTGAAAGTCT CCAGCTGTGA CAAGAACACT GGGGACTACT ATGAGGACAG |
| 5581 | CTATGAGGAC ATCTCTGCCT ACCTGCTGAG CAAGAACAAT GCCATTGAGC CCAGGAGCTT |
| 5641 | CAGCCAGAAC AGCAGGCACC CCAGCACCAG GCAGAAGCAG TTCAATGCCA CCACCATCCC |
| 5701 | TGAGAATGAC ATAGAGAAGA CAGACCCATG GTTTGCCCAC CGGACCCCCA TGCCCAAGAT |
| 5761 | CCAGAATGTG AGCAGCTCTG ACCTGCTGAT GCTGCTGAGG CAGAGCCCCA CCCCCCATGG |
| 5821 | CCTGAGCCTG TCTGACCTGC AGGAGGCCAA GTATGAAACC TTCTCTGATG ACCCCAGCCC |
| 5881 | TGGGGCCATT GACAGCAACA ACAGCCTGTC TGAGATGACC CACTTCAGGC CCCAGCTGCA |
| 5941 | CCACTCTGGG GACATGGTGT TCACCCCTGA GTCTGGCCTG CAGCTGAGGC TGAATGAGAA |
| 6001 | GCTGGGCACC ACTGCTGCCA CTGAGCTGAA GAAGCTGGAC TTCAAAGTCT CCAGCACCAG |
| 6061 | CAACAACCTG ATCAGCACCA TCCCCTCTGA CAACCTGGCT GCTGGCACTG ACAACACCAG |
| 6121 | CAGCCTGGGC CCCCCAGCA TGCCTGTGCA CTATGACAGC CAGCTGGACA CCACCCTGTT |
| 6181 | TGGCAAGAAG AGCAGCCCCC TGACTGAGTC TGGGGGCCCC CTGAGCCTGT CTGAGGAGAA |
| 6241 | CAATGACAGC AAGCTGCTGG AGTCTGGCCT GATGAACAGC CAGGAGAGCA GCTGGGGCAA |
| 6301 | GAATGTGAGC AGCAGGGAGA TCACCAGGAC CACCCTGCAG TCTGACCAGG AGGAGATTGA |
| 6361 | CTATGATGAC ACCATCTCTG TGGAGATGAA GAAGGAGGAC TTTGACATCT ACGACGAGGA |

| | Sequences |
|---|---|
| 6421 | CGAGAACCAG AGCCCCAGGA GCTTCCAGAA GAAGACCAGG CACTACTTCA TTGCTGCTGT |
| 6481 | GGAGAGGCTG TGGGACTATG GCATGAGCAG CAGCCCCCAT GTGCTGAGGA ACAGGGCCCA |
| 6541 | GTCTGGCTCT GTGCCCCAGT TCAAGAAGGT GGTGTTCCAG GAGTTCACTG ATGGCAGCTT |
| 6601 | CACCCAGCCC CTGTACAGAG GGGAGCTGAA TGAGCACCTG GGCCTGCTGG GCCCCTACAT |
| 6661 | CAGGGCTGAG GTGGAGGACA ACATCATGGT GACCTTCAGG AACCAGGCCA GCAGGCCCTA |
| 6721 | CAGCTTCTAC AGCAGCCTGA TCAGCTATGA GGAGGACCAG AGGCAGGGGG CTGAGCCCAG |
| 6781 | GAAGAACTTT GTGAAGCCCA ATGAAACCAA GACCTACTTC TGGAAGGTGC AGCACCACAT |
| 6841 | GGCCCCCACC AAGGATGAGT TTGACTGCAA GGCCTGGGCC TACTTCTCTG ATGTGGACCT |
| 6901 | GGAGAAGGAT GTGCACTCTG GCCTGATTGG CCCCCTGCTG GTGTGCCACA CCAACACCCT |
| 6961 | GAACCCTGCC CATGGCAGGC AGGTGACTGT GCAGGAGTTT GCCCTGTTCT TCACCATCTT |
| 7021 | TGATGAAACC AAGAGCTGGT ACTTCACTGA GAACATGGAG AGGAACTGCA GGGCCCCCTG |
| 7081 | CAACATCCAG ATGGAGGACC CCACCTTCAA GGAGAACTAC AGGTTCCATG CCATCAATGG |
| 7141 | CTACATCATG GACACCCTGC CTGGCCTGGT GATGGCCCAG GACCAGAGGA TCAGGTGGTA |
| 7201 | CCTGCTGAGC ATGGGCAGCA ATGAGAACAT CCACAGCATC CACTTCTCTG GCCATGTGTT |
| 7261 | CACTGTGAGG AAGAAGGAGG AGTACAAGAT GGCCCTGTAC AACCTGTACC CTGGGGTGTT |
| 7321 | TGAGACTGTG GAGATGCTGC CCAGCAAGGC TGGCATCTGG AGGGTGGAGT GCCTGATTGG |
| 7381 | GGAGCACCTG CATGCTGGCA TGAGCACCCT GTTCCTGGTG TACAGCAACA AGTGCCAGAC |
| 7441 | CCCCCTGGGC ATGGCCTCTG GCCACATCAG GGACTTCCAG ATCACTGCCT CTGGCCAGTA |
| 7501 | TGGCCAGTGG GCCCCCAAGC TGGCCAGGCT GCACTACTCT GGCAGCATCA ATGCCTGGAG |
| 7561 | CACCAAGGAG CCCTTCAGCT GGATCAAGGT GGACCTGCTG GCCCCCATGA TCATCCATGG |
| 7621 | CATCAAGACC CAGGGGGCCA GGCAGAAGTT CAGCAGCCTG TACATCAGCC AGTTCATCAT |
| 7681 | CATGTACAGC CTGGATGGCA AGAAGTGGCA GACCTACAGG GGCAACAGCA CTGGCACCCT |
| 7741 | GATGGTGTTC TTTGGCAATG TGGACAGCTC TGGCATCAAG CACAACATCT TCAACCCCCC |
| 7801 | CATCATTGCC AGATACATCA GGCTGCACCC CACCCACTAC AGCATCAGGA GCACCCTGAG |
| 7861 | GATGGAGCTG ATGGGCTGTG ACCTGAACAG CTGCAGCATG CCCCTGGGCA TGGAGAGCAA |
| 7921 | GGCCATCTCT GATGCCCAGA TCACTGCCAG CAGCTACTTC ACCAACATGT TTGCCACCTG |
| 7981 | GAGCCCCAGC AAGGCCAGGC TGCACCTGCA GGGCAGGAGC AATGCCTGGA GGCCCCAGGT |
| 8041 | CAACAACCCC AAGGAGTGGC TGCAGGTGGA CTTCCAGAAG ACCATGAAGG TGACTGGGGT |
| 8101 | GACCACCCAG GGGGTGAAGA GCCTGCTGAC CAGCATGTAT GTGAAGGAGT TCCTGATCAG |
| 8161 | CAGCAGCCAG GATGGCCACC AGTGGACCCT GTTCTTCCAG AATGGCAAGG TGAAGGTGTT |
| 8221 | CCAGGGCAAC CAGGACAGCT TCACCCCTGT GGTGAACAGC CTGGACCCCC CCCTGCTGAC |
| 8281 | CAGATACCTG AGGATTCACC CCAGAGCTGG GGTGCACCAG ATTGCCCTGA GGATGGAGGT |
| 8341 | GCTGGGCTGT GAGGCCCAGG ACCTGTACTG AGCGGCCGCG GGCCCAATCA ACCTCTGGAT |
| 8401 | TACAAAATTT GTGAAAGATT GACTGGTATT CTTAACTATG TTGCTCCTTT TACGCTATGT |
| 8461 | GGATACGCTG CTTTAATGCC TTTGTATCAT GCTATTGCTT CCCGTATGGC TTTCATTTTC |
| 8521 | TCCTCCTTGT ATAAATCCTG GTTGCTGTCT CTTTATGAGG AGTTGTGGCC CGTTGTCAGG |
| 8581 | CAACGTGGCG TGGTGTGCAC TGTGTTTGCT GACGCAACCC CCACTGGTTG GGGCATTGCC |
| 8641 | ACCACCTGTC AGCTCCTTTC CGGGACTTTC GCTTTCCCCC TCCCTATTGC CACGGCGGAA |

| | Sequences |
|---|---|
| 8701 | CTCATCGCCG CCTGCCTTGC CCGCTGCTGG ACAGGGGCTC GGCTGTTGGG CACTGACAAT |
| 8761 | TCCGTGGTGT TGTCGGGGAA ATCATCGTCC TTTCCTTGGC TGCTCGCCTG TGTTGCCACC |
| 8821 | TGGATTCTGC GCGGGACGTC CTTCTGCTAC GTCCCTTCGG CCCTCAATCC AGCGGACCTT |
| 8881 | CCTTCCCGCG GCCTGCTGCC GGCTCTGCGG CCTCTTCCGC GTCTTCGCCT TCGCCCTCAG |
| 8941 | ACGAGTCGGA TCTCCCTTTG GGCCGCCTCC CCGCAAGCTT CGCACTTTTT AAAAGAAAAG |
| 9001 | GGAGGACTGG ATGGGATTTA TTACTCCGAT AGGACGCTGG CTTGTAACTC AGTCTCTTAC |
| 9061 | TAGGAGACCA GCTTGAGCCT GGGTGTTCGC TGGTTAGCCT AACCTGGTTG GCCACCAGGG |
| 9121 | GTAAGGACTC CTTGGCTTAG AAAGCTAATA AACTTGCCTG CATTAGAGCT CTTACGCGTC |
| 9181 | CCGGGCTCGA GATCCGCATC TCAATTAGTC AGCAACCATA GTCCCGCCCC TAACTCCGCC |
| 9241 | CATCCCGCCC CTAACTCCGC CCAGTTCCGC CCATTCTCCG CCCCATGGCT GACTAATTTT |
| 9301 | TTTTATTTAT GCAGAGGCCG AGGCCGCCTC GGCCTCTGAG CTATTCCAGA AGTAGTGAGG |
| 9361 | AGGCTTTTTT GGAGGCCTAG GCTTTTGCAA AAAGCTAACT TGTTTATTGC AGCTTATAAT |
| 9421 | GGTTACAAAT AAAGCAATAG CATCACAAAT TTCACAAATA AAGCATTTTT TTCACTGCAT |
| 9481 | TCTAGTTGTG GTTTGTCCAA ACTCATCAAT GTATCTTATC ATGTCTGTCC GCTTCCTCGC |
| 9541 | TCACTGACTC GCTGCGCTCG GTCGTTCGGC TGCGGCGAGC GGTATCAGCT CACTCAAAGG |
| 9601 | CGGTAATACG GTTATCCACA GAATCAGGGG ATAACGCAGG AAAGAACATG TGAGCAAAAG |
| 9661 | GCCAGCAAAA GGCCAGGAAC CGTAAAAAGG CCGCGTTGCT GGCGTTTTTC CATAGGCTCC |
| 9721 | GCCCCCCTGA CGAGCATCAC AAAAATCGAC GCTCAAGTCA GAGGTGGCGA AACCCGACAG |
| 9781 | GACTATAAAG ATACCAGGCG TTTCCCCCTG GAAGCTCCCT CGTGCGCTCT CCTGTTCCGA |
| 9841 | CCCTGCCGCT TACCGGATAC CTGTCCGCCT TTCTCCCTTC GGGAAGCGTG GCGCTTTCTC |
| 9901 | ATAGCTCACG CTGTAGGTAT CTCAGTTCGG TGTAGGTCGT TCGCTCCAAG CTGGGCTGTG |
| 9961 | TGCACGAACC CCCCGTTCAG CCCGACCGCT GCGCCTTATC CGGTAACTAT CGTCTTGAGT |
| 10021 | CCAACCCGGT AAGACACGAC TTATCGCCAC TGGCAGCAGC CACTGGTAAC AGGATTAGCA |
| 10081 | GAGCGAGGTA TGTAGGCGGT GCTACAGAGT TCTTGAAGTG GTGGCCTAAC TACGGCTACA |
| 10141 | CTAGAAGAAC AGTATTTGGT ATCTGCGCTC TGCTGAAGCC AGTTACCTTC GGAAAAAGAG |
| 10201 | TTGGTAGCTC TTGATCCGGC AAACAAACCA CCGCTGGTAG CGGTGGTTTT TTTGTTTGCA |
| 10261 | AGCAGCAGAT TACGCGCAGA AAAAAAGGAT CTCAAGAAGA TCCTTTGATC TTTTCTACGG |
| 10321 | GGTCTGACGC TCAGTGGAAC GAAAACTCAC GTTAAGGGAT TTTGGTCATG AGATTATCAA |
| 10381 | AAAGGATCTT CACCTAGATC CTTTTAAATT AAAAATGAAG TTTTAAATCA ATCTAAAGTA |
| 10441 | TATATGAGTA AACTTGGTCT GACAGTTAGA AAAACTCATC GAGCATCAAA TGAAACTGCA |
| 10501 | ATTTATTCAT ATCAGGATTA TCAATACCAT ATTTTTGAAA AGCCGTTTC TGTAATGAAG |
| 10561 | GAGAAAACTC ACCGAGGCAG TTCCATAGGA TGGCAAGATC CTGGTATCGG TCTGCGATTC |
| 10621 | CGACTCGTCC AACATCAATA CAACCTATTA ATTTCCCCTC GTCAAAAATA AGGTTATCAA |
| 10681 | GTGAGAAATC ACCATGAGTG ACGACTGAAT CCGGTGAGAA TGGCAACAGC TTATGCATTT |
| 10741 | CTTTCCAGAC TTGTTCAACA GGCCAGCCAT TACGCTCGTC ATCAAAATCA CTCGCATCAA |
| 10801 | CCAAACCGTT ATTCATTCGT GATTGCGCCT GAGCGAGACG AAATACGCGA TCGCTGTTAA |
| 10861 | AAGGACAATT ACAAACAGGA ATCGAATGCA ACCGGCGCAG AACACTGCC AGCGCATCAA |
| 10921 | CAATATTTTC ACCTGAATCA GGATATTCTT CTAATACCTG GAATGCTGTT TTTCCGGGGA |

| | Sequences |
|---|---|
| 10981 | TCGCAGTGGT GAGTAACCAT GCATCATCAG GAGTACGGAT AAAATGCTTG ATGGTCGGAA |
| 11041 | GAGGCATAAA TTCCGTCAGC CAGTTTAGTC TGACCATCTC ATCTGTAACA TCATTGGCAA |
| 11101 | CGCTACCTTT GCCATGTTTC AGAAACAACT CTGGCGCATC GGGCTTCCCA TACAATCGAT |
| 11161 | AGATTGTCGC ACCTGATTGC CCGACATTAT CGCGAGCCCA TTTATACCCA TATAAATCAG |
| 11221 | CATCCATGTT GGAATTTAAT CGCGGCCTAG AGCAAGACGT TTCCCGTTGA ATATGGCTCA |
| 11281 | TAACACCCCT TGTATTACTG TTTATGTAAG CAGACAGTTT TATTGTTCAT GATGATATAT |
| 11341 | TTTTATCTTG TGCAATGTAA CATCAGAGAT TTTGAGACAC AACAATTGGT CGACGGATCC |

SEQ ID NO: 14

| | |
|---|---|
| 1 | GGTACCTCAA TATTGGCCAT TAGCCATATT ATTCATTGGT TATATAGCAT AAATCAATAT |
| 61 | TGGCTATTGG CCATTGCATA CGTTGTATCT ATATCATAAT ATGTACATTT ATATTGGCTC |
| 121 | ATGTCCAATA TGACCGCCAT GTTGGCATTG ATTATTGACT AGTTATTAAT AGTAATCAAT |
| 181 | TACGGGGTCA TTAGTTCATA GCCCATATAT GGAGTTCCGC GTTACATAAC TTACGGTAAA |
| 241 | TGGCCCGCCT GGCTGACCGC CCAACGACCC CCGCCCATTG ACGTCAATAA TGACGTATGT |
| 301 | TCCCATAGTA ACGCCAATAG GGACTTTCCA TTGACGTCAA TGGGTGGAGT ATTTACGGTA |
| 361 | AACTGCCCAC TTGGCAGTAC ATCAAGTGTA TCATATGCCA AGTCCGCCCC CTATTGACGT |
| 421 | CAATGACGGT AAATGGCCCG CCTGGCATTA TGCCCAGTAC ATGACCTTAC GGGACTTTCC |
| 481 | TACTTGGCAG TACATCTACG TATTAGTCAT CGCTATTACC ATGGTGATGC GGTTTTGGCA |
| 541 | GTACACCAAT GGGCGTGGAT AGCGGTTTGA CTCACGGGGA TTTCCAAGTC TCCACCCCAT |
| 601 | TGACGTCAAT GGGAGTTTGT TTTGGCACCA AAATCAACGG GACTTTCCAA AATGTCGTAA |
| 661 | CAACTGCGAT CGCCCGCCCC GTTGACGCAA ATGGGCGGTA GGCGTGTACG GTGGGAGGTC |
| 721 | TATATAAGCA GAGCTCGCTG GCTTGTAACT CAGTCTCTTA CTAGGAGACC AGCTTGAGCC |
| 781 | TGGGTGTTCG CTGGTTAGCC TAACCTGGTT GGCCACCAGG GGTAAGGACT CCTTGGCTTA |
| 841 | GAAAGCTAAT AAACTTGCCT GCATTAGAGC TTATCTGAGT CAAGTGTCCT CATTGACGCC |
| 901 | TCACTCTCTT GAACGGGAAT CTTCCTTACT GGGTTCTCTC TCTGACCCAG GCGAGAGAAA |
| 961 | CTCCAGCAGT GGCGCCCGAA CAGGGACTTG AGTGAGAGTG TAGGCACGTA CAGCTGAGAA |
| 1021 | GGCGTCGGAC GCGAAGGAAG CGCGGGGTGC GACGCGACCA AGAAGGAGAC TTGGTGAGTA |
| 1081 | GGCTTCTCGA GTGCCGGGAA AAAGCTCGAG CCTAGTTAGA GGACTAGGAG AGGCCGTAGC |
| 1141 | CGTAACTACT CTTGGGCAAG TAGGGCAGGC GGTGGGTACG CAATGGGGGC GGCTACCTCA |
| 1201 | GCACTAAATA GGAGACAATT AGACCAATTT GAGAAAATAC GACTTCGCCC GAACGGAAAG |
| 1261 | AAAAAGTACC AAATTAAACA TTTAATATGG GCAGGCAAGG AGATGGAGCG CTTCGGCCTC |
| 1321 | CATGAGAGGT TGTTGGAGAC AGAGGAGGGG TGTAAAAGAA TCATAGAAGT CCTCTACCCC |
| 1381 | CTAGAACCAA CAGGATCGGA GGGCTTAAAA AGTCTGTTCA ATCTTGTGTG CGTGCTATAT |
| 1441 | TGCTTGCACA AGGAACAGAA AGTGAAAGAC ACAGAGGAAG CAGTAGCAAC AGTAAGACAA |
| 1501 | CACTGCCATC TAGTGGAAAA AGAAAAAAGT GCAACAGAGA CATCTAGTGG ACAAAAGAAA |
| 1561 | AATGACAAGG GAATAGCAGC GCCACCTGGT GGCAGTCAGA ATTTTCCAGC GCAACAACAA |
| 1621 | GGAAATGCCT GGGTACATGT ACCCTTGTCA CCGCGCACCT TAAATGCGTG GGTAAAAGCA |
| 1681 | GTAGAGGAGA AAAAATTTGG AGCAGAAATA GTACCCATGT TTCAAGCCCT ATCGAATTCC |
| 1741 | CGTTTGTGCT AGGGTTCTTA GGCTTCTTGG GGGCTGCTGG AACTGCAATG GGAGCAGCGG |

| | Sequences |
|---|---|
| 1801 | CGACAGCCCT GACGGTCCAG TCTCAGCATT TGCTTGCTGG GATACTGCAG CAGCAGAAGA |
| 1861 | ATCTGCTGGC GGCTGTGGAG GCTCAACAGC AGATGTTGAA GCTGACCATT TGGGGTGTTA |
| 1921 | AAAACCTCAA TGCCCGCGTC ACAGCCCTTG AGAAGTACCT AGAGGATCAG GCACGACTAA |
| 1981 | ACTCCTGGGG GTGCGCATGG AAACAAGTAT GTCATACCAC AGTGGAGTGG CCCTGGACAA |
| 2041 | ATCGGACTCC GGATTGGCAA AATATGACTT GGTTGGAGTG GGAAAGACAA ATAGCTGATT |
| 2101 | TGGAAAGCAA CATTACGAGA CAATTAGTGA AGGCTAGAGA ACAAGAGGAA AAGAATCTAG |
| 2161 | ATGCCTATCA GAAGTTAACT AGTTGGTCAG ATTTCTGGTC TTGGTTCGAT TTCTCAAAAT |
| 2221 | GGCTTAACAT TTTAAAAATG GGATTTTTAG TAATAGTAGG AATAATAGGG TTAAGATTAC |
| 2281 | TTTACACAGT ATATGGATGT ATAGTGAGGG TTAGGCAGGG ATATGTTCCT CTATCTCCAC |
| 2341 | AGATCCATAT CCGCGGCAAT TTTAAAAGAA AGGGAGGAAT AGGGGACAG ACTTCAGCAG |
| 2401 | AGAGACTAAT TAATATAATA ACAACACAAT TAGAAATACA ACATTTACAA ACCAAAATTC |
| 2461 | AAAAAATTTT AAATTTTAGA GCCGCGGAGA TCTGTTACAT AACTTATGGT AAATGGCCTG |
| 2521 | CCTGGCTGAC TGCCCAATGA CCCCTGCCCA ATGATGTCAA TAATGATGTA TGTTCCCATG |
| 2581 | TAATGCCAAT AGGGACTTTC CATTGATGTC AATGGGTGGA GTATTTATGG TAACTGCCCA |
| 2641 | CTTGGCAGTA CATCAAGTGT ATCATATGCC AAGTATGCCC CCTATTGATG TCAATGATGG |
| 2701 | TAAATGGCCT GCCTGGCATT ATGCCCAGTA CATGACCTTA TGGGACTTTC CTACTTGGCA |
| 2761 | GTACATCTAT GTATTAGTCA TTGCTATTAC CATGGGAATT CACTAGTGGA GAAGAGCATG |
| 2821 | CTTGAGGGCT GAGTGCCCCT CAGTGGGCAG AGAGCACATG GCCCACAGTC CCTGAGAAGT |
| 2881 | TGGGGGGAGG GGTGGGCAAT TGAACTGGTG CCTAGAGAAG GTGGGGCTTG GGTAAACTGG |
| 2941 | GAAAGTGATG TGGTGTACTG GCTCCACCTT TTTCCCCAGG GTGGGGGAGA ACCATATATA |
| 3001 | AGTGCAGTAG TCTCTGTGAA CATTCAAGCT TCTGCCTTCT CCCTCCTGTG AGTTTGCTAG |
| 3061 | CCACCAATGC AGATTGAGCT GAGCACCTGC TTCTTCCTGT GCCTGCTGAG GTTCTGCTTC |
| 3121 | TCTGCCACCA GGAGATACTA CCTGGGGGCT GTGGAGCTGA GCTGGGACTA CATGCAGTCT |
| 3181 | GACCTGGGGG AGCTGCCTGT GGATGCCAGG TTCCCCCCCA GAGTGCCCAA GAGCTTCCCC |
| 3241 | TTCAACACCT CTGTGGTGTA CAAGAAGACC CTGTTTGTGG AGTTCACTGA CCACCTGTTC |
| 3301 | AACATTGCCA AGCCCAGGCC CCCCTGGATG GGCCTGCTGG GCCCCACCAT CCAGGCTGAG |
| 3361 | GTGTATGACA CTGTGGTGAT CACCCTGAAG AACATGGCCA GCCACCCTGT GAGCCTGCAT |
| 3421 | GCTGTGGGGG TGAGCTACTG GAAGGCCTCT GAGGGGGCTG AGTATGATGA CCAGACCAGC |
| 3481 | CAGAGGGAGA AGGAGGATGA CAAGGTGTTC CCTGGGGGCA GCCACACCTA TGTGTGGCAG |
| 3541 | GTGCTGAAGG AGAATGGCCC CATGGCCTCT GACCCCCTGT GCCTGACCTA CAGCTACCTG |
| 3601 | AGCCATGTGG ACCTGGTGAA GGACCTGAAC TCTGGCCTGA TTGGGGCCCT GCTGGTGTGC |
| 3661 | AGGGAGGGCA GCCTGGCCAA GGAGAAGACC CAGACCCTGC ACAAGTTCAT CCTGCTGTTT |
| 3721 | GCTGTGTTTG ATGAGGGCAA GAGCTGGCAC TCTGAAACCA AGAACAGCCT GATGCAGGAC |
| 3781 | AGGGATGCTG CCTCTGCCAG GGCCTGGCCC AAGATGCACA CTGTGAATGG CTATGTGAAC |
| 3841 | AGGAGCCTGC CTGGCCTGAT TGGCTGCCAC AGGAAGTCTG TGTACTGGCA TGTGATTGGC |
| 3901 | ATGGGCACCA CCCCTGAGGT GCACAGCATC TTCCTGGAGG GCCACACCTT CCTGGTCAGG |
| 3961 | AACCACAGGC AGGCCAGCCT GGAGATCAGC CCCATCACCT TCCTGACTGC CCAGACCCTG |
| 4021 | CTGATGGACC TGGGCCAGTT CCTGCTGTTC TGCCACATCA GCAGCCACCA GCATGATGGC |

-continued

| | Sequences |
|---|---|
| 4081 | ATGGAGGCCT ATGTGAAGGT GGACAGCTGC CCTGAGGAGC CCCAGCTGAG GATGAAGAAC |
| 4141 | AATGAGGAGG CTGAGGACTA TGATGATGAC CTGACTGACT CTGAGATGGA TGTGGTGAGG |
| 4201 | TTTGATGATG ACAACAGCCC CAGCTTCATC CAGATCAGGT CTGTGGCCAA GAAGCACCCC |
| 4261 | AAGACCTGGG TGCACTACAT TGCTGCTGAG GAGGAGGACT GGGACTATGC CCCCCTGGTG |
| 4321 | CTGGCCCCTG ATGACAGGAG CTACAAGAGC CAGTACCTGA ACAATGGCCC CCAGAGGATT |
| 4381 | GGCAGGAAGT ACAAGAAGGT CAGGTTCATG GCCTACACTG ATGAAACCTT CAAGACCAGG |
| 4441 | GAGGCCATCC AGCATGAGTC TGGCATCCTG GCCCCCTGC TGTATGGGGA GGTGGGGGAC |
| 4501 | ACCCTGCTGA TCATCTTCAA GAACCAGGCC AGCAGGCCCT ACAACATCTA CCCCCATGGC |
| 4561 | ATCACTGATG TGAGGCCCCT GTACAGCAGG AGGCTGCCCA AGGGGGTGAA GCACCTGAAG |
| 4621 | GACTTCCCCA TCCTGCCTGG GGAGATCTTC AAGTACAAGT GGACTGTGAC TGTGGAGGAT |
| 4681 | GGCCCCACCA AGTCTGACCC CAGGTGCCTG ACCAGATACT ACAGCAGCTT TGTGAACATG |
| 4741 | GAGAGGGACC TGGCCTCTGG CCTGATTGGC CCCCTGCTGA TCTGCTACAA GGAGTCTGTG |
| 4801 | GACCAGAGGG GCAACCAGAT CATGTCTGAC AAGAGGAATG TGATCCTGTT CTCTGTGTTT |
| 4861 | GATGAGAACA GGAGCTGGTA CCTGACTGAG AACATCCAGA GGTTCCTGCC CAACCCTGCT |
| 4921 | GGGGTGCAGC TGGAGGACCC TGAGTTCCAG GCCAGCAACA TCATGCACAG CATCAATGGC |
| 4981 | TATGTGTTTG ACAGCCTGCA GCTGTCTGTG TGCCTGCATG AGGTGGCCTA CTGGTACATC |
| 5041 | CTGAGCATTG GGGCCCAGAC TGACTTCCTG TCTGTGTTCT TCTCTGGCTA CACCTTCAAG |
| 5101 | CACAAGATGG TGTATGAGGA CACCCTGACC CTGTTCCCCT TCTCTGGGGA GACTGTGTTC |
| 5161 | ATGAGCATGG AGAACCCTGG CCTGTGGATT CTGGGCTGCC ACAACTCTGA CTTCAGGAAC |
| 5221 | AGGGGCATGA CTGCCCTGCT GAAAGTCTCC AGCTGTGACA AGAACACTGG GGACTACTAT |
| 5281 | GAGGACAGCT ATGAGGACAT CTCTGCCTAC CTGCTGAGCA AGAACAATGC CATTGAGCCC |
| 5341 | AGGAGCTTCA GCCAGAACAG CAGGCACCCC AGCACCAGGC AGAAGCAGTT CAATGCCACC |
| 5401 | ACCATCCCTG AGAATGACAT AGAGAAGACA GACCCATGGT TTGCCCACCG GACCCCCATG |
| 5461 | CCCAAGATCC AGAATGTGAG CAGCTCTGAC CTGCTGATGC TGCTGAGGCA GAGCCCCACC |
| 5521 | CCCCATGGCC TGAGCCTGTC TGACCTGCAG GAGGCCAAGT ATGAAACCTT CTCTGATGAC |
| 5581 | CCCAGCCCTG GGGCCATTGA CAGCAACAAC AGCCTGTCTG AGATGACCCA CTTCAGGCCC |
| 5641 | CAGCTGCACC ACTCTGGGGA CATGGTGTTC ACCCCTGAGT CTGGCCTGCA GCTGAGGCTG |
| 5701 | AATGAGAAGC TGGGCACCAC TGCTGCCACT GAGCTGAAGA AGCTGGACTT CAAAGTCTCC |
| 5761 | AGCACCAGCA ACAACCTGAT CAGCACCATC CCCTCTGACA ACCTGGCTGC TGGCACTGAC |
| 5821 | AACACCAGCA GCCTGGGCCC CCCCAGCATG CCTGTGCACT ATGACAGCCA GCTGGACACC |
| 5881 | ACCCTGTTTG GCAAGAAGAG CAGCCCCCTG ACTGAGTCTG GGGCCCCCT GAGCCTGTCT |
| 5941 | GAGGAGAACA TGACAGCAA GCTGCTGGA TCTGGCCTGA TGACAGCCA GGAGAGCAGC |
| 6001 | TGGGGCAAGA ATGTGAGCAG CAGGGAGATC ACCAGGACCA CCCTGCAGTC TGACCAGGAG |
| 6061 | GAGATTGACT ATGATGACAC CATCTCTGTG GAGATGAAGA AGGAGGACTT TGACATCTAC |
| 6121 | GACGAGGACG AGAACCAGAG CCCCAGGAGC TTCCAGAAGA AGACCAGGCA CTACTTCATT |
| 6181 | GCTGCTGTGG AGAGGCTGTG GGACTATGGC ATGAGCAGCA GCCCCCATGT GCTGAGGAAC |
| 6241 | AGGGCCCAGT CTGGCTCTGT GCCCCAGTTC AAGAAGGTGG TGTTCCAGGA GTTCACTGAT |
| 6301 | GGCAGCTTCA CCCAGCCCCT GTACAGAGGG GAGCTGAATG AGCACCTGGG CCTGCTGGGC |

-continued

| | Sequences |
|---|---|
| 6361 | CCCTACATCA GGGCTGAGGT GGAGGACAAC ATCATGGTGA CCTTCAGGAA CCAGGCCAGC |
| 6421 | AGGCCCTACA GCTTCTACAG CAGCCTGATC AGCTATGAGG AGGACCAGAG GCAGGGGCT |
| 6481 | GAGCCCAGGA AGAACTTTGT GAAGCCCAAT GAAACCAAGA CCTACTTCTG GAAGGTGCAG |
| 6541 | CACCACATGG CCCCCACCAA GGATGAGTTT GACTGCAAGG CCTGGGCCTA CTTCTCTGAT |
| 6601 | GTGGACCTGG AGAAGGATGT GCACTCTGGC CTGATTGGCC CCCTGCTGGT GTGCCACACC |
| 6661 | AACACCCTGA ACCCTGCCCA TGGCAGGCAG GTGACTGTGC AGGAGTTTGC CCTGTTCTTC |
| 6721 | ACCATCTTTG ATGAAACCAA GAGCTGGTAC TTCACTGAGA ACATGGAGAG GAACTGCAGG |
| 6781 | GCCCCCTGCA ACATCCAGAT GGAGGACCCC ACCTTCAAGG AGAACTACAG GTTCCATGCC |
| 6841 | ATCAATGGCT ACATCATGGA CACCCTGCCT GGCCTGGTGA TGGCCCAGGA CCAGAGGATC |
| 6901 | AGGTGGTACC TGCTGAGCAT GGGCAGCAAT GAGAACATCC ACAGCATCCA CTTCTCTGGC |
| 6961 | CATGTGTTCA CTGTGAGGAA GAAGGAGGAG TACAAGATGG CCCTGTACAA CCTGTACCCT |
| 7021 | GGGGTGTTTG AGACTGTGGA GATGCTGCCC AGCAAGGCTG GCATCTGGAG GGTGGAGTGC |
| 7081 | CTGATTGGGG AGCACCTGCA TGCTGGCATG AGCACCCGTT CCTGGTGTA CAGCAACAAG |
| 7141 | TGCCAGACCC CCCTGGGCAT GGCCTCTGGC CACATCAGGG ACTTCCAGAT CACTGCCTCT |
| 7201 | GGCCAGTATG GCCAGTGGGC CCCCAAGCTG GCCAGGCTGC ACTACTCTGG CAGCATCAAT |
| 7261 | GCCTGGAGCA CCAAGGAGCC CTTCAGCTGG ATCAAGGTGG ACCTGCTGGC CCCCATGATC |
| 7321 | ATCCATGGCA TCAAGACCCA GGGGGCCAGG CAGAAGTTCA GCAGCCTGTA CATCAGCCAG |
| 7381 | TTCATCATCA TGTACAGCCT GGATGGCAAG AAGTGGCAGA CCTACAGGGG CAACAGCACT |
| 7441 | GGCACCCTGA TGGTGTTCTT TGGCAATGTG GACAGCTCTG GCATCAAGCA CAACATCTTC |
| 7501 | AACCCCCCCA TCATTGCCAG ATACATCAGG CTGCACCCCA CCCACTACAG CATCAGGAGC |
| 7561 | ACCCTGAGGA TGGAGCTGAT GGGCTGTGAC CTGAACAGCT GCAGCATGCC CCTGGGCATG |
| 7621 | GAGAGCAAGG CCATCTCTGA TGCCCAGATC ACTGCCAGCA GCTACTTCAC CAACATGTTT |
| 7681 | GCCACCTGGA GCCCCAGCAA GGCCAGGCTG CACCTGCAGG GCAGGAGCAA TGCCTGGAGG |
| 7741 | CCCCAGGTCA ACAACCCCAA GGAGTGGCTG CAGGTGGACT TCCAGAAGAC CATGAAGGTG |
| 7801 | ACTGGGGTGA CCACCCAGGG GGTGAAGAGC CTGCTGACCA GCATGTATGT GAAGGAGTTC |
| 7861 | CTGATCAGCA GCAGCCAGGA TGGCCACCAG TGGACCCTGT TCTTCCAGAA TGGCAAGGTG |
| 7921 | AAGGTGTTCC AGGGCAACCA GGACAGCTTC ACCCCTGTGG TGAACAGCCT GGACCCCCCC |
| 7981 | CTGCTGACCA GATACCTGAG GATTCACCCC CAGAGCTGGG TGCACCAGAT TGCCCTGAGG |
| 8041 | ATGGAGGTGC TGGGCTGTGA GGCCCAGGAC CTGTACTGAG CGGCCGCGGG CCCAATCAAC |
| 8101 | CTCTGGATTA CAAAATTTGT GAAAGATTGA CTGGTATTCT TAACTATGTT GCTCCTTTTA |
| 8161 | CGCTATGTGG ATACGCTGCT TTAATGCCTT TGTATCATGC TATTGCTTCC CGTATGGCTT |
| 8221 | TCATTTTCTC CTCCTTGTAT AAATCCTGGT TGCTGTCTCT TTATGAGGAG TTGTGGCCCG |
| 8281 | TTGTCAGGCA ACGTGGCGTG GTGTGCACTG TGTTTGCTGA CGCAACCCCC ACTGGTTGGG |
| 8341 | GCATTGCCAC CACCTGTCAG CTCCTTTCCG GGACTTTCGC TTTCCCCCTC CCTATTGCCA |
| 8401 | CGGCGGAACT CATCGCCGCC TGCCTTGCCC GCTGCTGGAC AGGGGCTCGG CTGTTGGGCA |
| 8461 | CTGACAATTC CGTGGTGTTG TCGGGAAAT CATCGTCCTT TCCTTGGCTG CTCGCCTGTG |
| 8521 | TTGCCACCTG GATTCTGCGC GGGACGTCCT TCTGCTACGT CCCTTCGGCC CTCAATCCAG |
| 8581 | CGGACCTTCC TTCCCGCGGC CTGCTGCCGG CTCTGCGGCC TCTTCCGCGT CTTCGCCTTC |

| | Sequences |
|---|---|
| 8641 | GCCCTCAGAC GAGTCGGATC TCCCTTTGGG CCGCCTCCCC GCAAGCTTCG CACTTTTTAA |
| 8701 | AAGAAAAGGG AGGACTGGAT GGGATTTATT ACTCCGATAG GACGCTGGCT TGTAACTCAG |
| 8761 | TCTCTTACTA GGAGACCAGC TTGAGCCTGG GTGTTCGCTG GTTAGCCTAA CCTGGTTGGC |
| 8821 | CACCAGGGGT AAGGACTCCT TGGCTTAGAA AGCTAATAAA CTTGCCTGCA TTAGAGCTCT |
| 8881 | TACGCGTCCC GGGCTCGAGA TCCGCATCTC AATTAGTCAG CAACCATAGT CCCGCCCCTA |
| 8941 | ACTCCGCCCA TCCCGCCCCT AACTCCGCCC AGTTCCGCCC ATTCTCCGCC CCATGGCTGA |
| 9001 | CTAATTTTTT TTATTTATGC AGAGGCCGAG GCCGCCTCGG CCTCTGAGCT ATTCCAGAAG |
| 9061 | TAGTGAGGAG GCTTTTTTGG AGGCCTAGGC TTTTGCAAAA AGCTAACTTG TTTATTGCAG |
| 9121 | CTTATAATGG TTACAAATAA AGCAATAGCA TCACAAATTT CACAAATAAA GCATTTTTTT |
| 9181 | CACTGCATTC TAGTTGTGGT TTGTCCAAAC TCATCAATGT ATCTTATCAT GTCTGTCCGC |
| 9241 | TTCCTCGCTC ACTGACTCGC TGCGCTCGGT CGTTCGGCTG CGGCGAGCGG TATCAGCTCA |
| 9301 | CTCAAAGGCG GTAATACGGT TATCCACAGA ATCAGGGGAT AACGCAGGAA AGAACATGTG |
| 9361 | AGCAAAAGGC CAGCAAAAGG CCAGGAACCG TAAAAAGGCC GCGTTGCTGG CGTTTTTCCA |
| 9421 | TAGGCTCCGC CCCCCTGACG AGCATCACAA AAATCGACGC TCAAGTCAGA GGTGGCGAAA |
| 9481 | CCCGACAGGA CTATAAAGAT ACCAGGCGTT TCCCCCTGGA AGCTCCCTCG TGCGCTCTCC |
| 9541 | TGTTCCGACC CTGCCGCTTA CCGGATACCT GTCCGCCTTT CTCCCTTCGG GAAGCGTGGC |
| 9601 | GCTTTCTCAT AGCTCACGCT GTAGGTATCT CAGTTCGGTG TAGGTCGTTC GCTCCAAGCT |
| 9661 | GGGCTGTGTG CACGAACCCC CCGTTCAGCC CGACCGCTGC GCCTTATCCG GTAACTATCG |
| 9721 | TCTTGAGTCC AACCCGGTAA GACACGACTT ATCGCCACTG GCAGCAGCCA CTGGTAACAG |
| 9781 | GATTAGCAGA GCGAGGTATG TAGGCGGTGC TACAGAGTTC TTGAAGTGGT GGCCTAACTA |
| 9841 | CGGCTACACT AGAAGAACAG TATTTGGTAT CTGCGCTCTG CTGAAGCCAG TTACCTTCGG |
| 9901 | AAAAAGAGTT GGTAGCTCTT GATCCGGCAA ACAAACCACC GCTGGTAGCG GTGGTTTTTT |
| 9961 | TGTTTGCAAG CAGCAGATTA CGCGCAGAAA AAAAGGATCT CAAGAAGATC CTTTGATCTT |
| 10021 | TTCTACGGGG TCTGACGCTC AGTGGAACGA AAACTCACGT TAAGGGATTT TGGTCATGAG |
| 10081 | ATTATCAAAA AGGATCTTCA CCTAGATCCT TTTAAATTAA AAATGAAGTT TTAAATCAAT |
| 10141 | CTAAAGTATA TATGAGTAAA CTTGGTCTGA CAGTTAGAAA AACTCATCGA GCATCAAATG |
| 10201 | AAACTGCAAT TTATTCATAT CAGGATTATC AATACCATAT TTTTGAAAAA GCCGTTTCTG |
| 10261 | TAATGAAGGA GAAAACTCAC CGAGGCAGTT CCATAGGATG CAAGATCCT GGTATCGGTC |
| 10321 | TGCGATTCCG ACTCGTCCAA CATCAATACA ACCTATTAAT TTCCCCTCGT CAAAAATAAG |
| 10381 | GTTATCAAGT GAGAAATCAC CATGAGTGAC GACTGAATCC GGTGAGAATG GCAACAGCTT |
| 10441 | ATGCATTTCT TTCCAGACTT GTTCAACAGG CCAGCCATTA CGCTCGTCAT CAAAATCACT |
| 10501 | CGCATCAACC AAACCGTTAT TCATTCGTGA TTGCGCCTGA GCGAGACGAA ATACGCGATC |
| 10561 | GCTGTTAAAA GGACAATTAC AAACAGGAAT CGAATGCAAC CGGCGCAGGA ACACTGCCAG |
| 10621 | CGCATCAACA ATATTTTCAC CTGAATCAGG ATATTCTTCT AATACCTGGA ATGCTGTTTT |
| 10681 | TCCGGGGATC GCAGTGGTGA GTAACCATGC ATCATCAGGA GTACGGATAA AATGCTTGAT |
| 10741 | GGTCGGAAGA GGCATAAATT CCGTCAGCCA GTTTAGTCTG ACCATCTCAT CTGTAACATC |
| 10801 | ATTGGCAACG CTACCTTTGC CATGTTTCAG AAACAACTCT GGCGCATCGG GCTTCCCATA |
| 10861 | CAATCGATAG ATTGTCGCAC CTGATTGCCC GACATTATCG CGAGCCCATT TATACCCATA |

| | Sequences |
|---|---|
| 10921 | TAAATCAGCA TCCATGTTGG AATTTAATCG CGGCCTAGAG CAAGACGTTT CCCGTTGAAT |
| 10981 | ATGGCTCATA ACACCCCTTG TATTACTGTT TATGTAAGCA GACAGTTTTA TTGTTCATGA |
| 11041 | TGATATATTT TTATCTTGTG CAATGTAACA TCAGAGATTT TGAGACACAA CAATTGGTCG |
| 11101 | ACGGATCC |

SEQ ID NO: 15
ATGCCCAGCTCTGTGTCCTGGGGCATTCTGCTGCTGGCTGGCCTGTGCTGTCTGGTGCCTGTGTCCCTGG
CTGAGGACCCTCAGGGGATGCTGCCCAGAAAACAGACACCTCCCACCATGACCAGGACCACCCCCACCTT
CAACAAGATCACCCCCAACCTGGCAGAGTTTGCCTTCAGCCTGTACAGACAGCTGGCCCACCAGAGCAAC
AGCACCAACATCTTTTTCAGCCCTGTGTCCATTGCCACAGCCTTTGCCATGCTGAGCCTGGGCACCAAGG
CTGACACCCATGATGAGATCCTGGAAGGCCTGAACTTCAACCTGACAGAGATCCCTGAGGCCCAGATCCA
TGAGGGCTTCCAGGAACTGCTGAGAACCCTGAACCAGCCAGACAGCCAGCTGCAGCTGACAACAGGCAAT
GGGCTGTTCCTGTCTGAGGGCCTGAAGCTGGTGGACAAGTTTCTGGAAGATGTGAAGAAGCTGTACCACT
CTGAGGCCTTCACAGTGAACTTTGGGGACACAGAAGAGGCCAAGAAACAGATCAATGACTATGTGGAAAA
GGGCACCCAGGGCAAGATTGTGGACCTTGTGAAAGAGCTGGACAGGGACACTGTGTTTGCCCTTGTGAAC
TACATCTTCTTCAAGGGCAAGTGGGAGAGGCCCTTTGAAGTGAAGGACACTGAGGAAGAGGACTTCCATG
TGGACCAAGTGACCACAGTGAAGGTGCCAATGATGAAGAGACTGGGGATGTTCAATATCCAGCACTGCAA
GAAACTGAGCAGCTGGGTGCTGCTGATGAAGTACCTGGGCAATGCTACAGCCATATTCTTTCTGCCTGAT
GAGGGCAAGCTGCAGCACCTGGAAAATGAGCTGACCCATGACATCATCACCAAATTTCTGGAAAATGAGG
ACAGAAGATCTGCCAGCCTGCATCTGCCCAAGCTGAGCATCACAGGCACATATGACCTGAAGTCTGTGCT
GGGACAGCTGGGAATCACCAAGGTGTTCAGCAATGAGGGACACCTGAGTGGAGTGACAGAGGAAGCCCCT
CTGAAGCTGTCCAAGGCTGTGCACAAGGCAGTGCTGACCATTGATGAGAAGGGCACAGAGGCTGCTGGGG
CCATGTTTCTGGAAGCCATCCCCATGTCCATCCCCCAGAAGTGAAGTTCAACAAGCCCTTTGTGTTCCT
GATGATTGAGCAGAACACCAAGAGCCCCCTGTTCATGGGCAAGGTTGTGAACCCCACCCAGAAATGA

SEQ ID NO: 16
ATGCAGATTGAGCTGAGCACCTGCTTCTTCCTGTGCCTGCTGAGGTTCTGCTTCTCTGCCACCAGGAGAT
ACTACCTGGGGGCTGTGGAGCTGAGCTGGGACTACATGCAGTCTGACCTGGGGGAGCTGCCTGTGGATGC
CAGGTTCCCCCCCAGAGTGCCCAAGAGCTTCCCCTTCAACACCTCTGTGGTGTACAAGAAGACCCTGTTT
GTGGAGTTCACTGACCACCTGTTCAACATTGCCAAGCCCAGGCCCCCCTGGATGGGCCTGCTGGGCCCCA
CCATCCAGGCTGAGGTGTATGACACTGTGGTGATCACCCTGAAGAACATGGCCAGCCACCCTGTGAGCCT
GCATGCTGTGGGGGTGAGCTACTGGAAGGCCTCTGAGGGGGCTGAGTATGATGACCAGACCAGCCAGAGG
GAGAAGGAGGATGACAAGGTGTTCCCTGGGGGCAGCCACACCTATGTGTGGCAGGTGCTGAAGGAGAATG
GCCCCATGGCCTCTGACCCCCTGTGCCTGACCTACAGCTACCTGAGCCATGTGGACCTGGTGAAGGACCT
GAACTCTGGCCTGATTGGGGCCCTGCTGGTGTGCAGGGAGGGCAGCCTGGCCAAGGAGAAGACCCAGACC
CTGCACAAGTTCATCCTGCTGTTTGCTGTGTTTGATGAGGGCAAGAGCTGGCACTCTGAAACCAAGAACA
GCCTGATGCAGGACAGGGATGCTGCCTCTGCCAGGGCCTGGCCCAAGATGCACACTGTGAATGGCTATGT
GAACAGGAGCCTGCCTGGCCTGATTGGCTGCCACAGGAAGTCTGTGTACTGGCATGTGATTGGCATGGGC
ACCACCCCTGAGGTGCACAGCATCTTCCTGGAGGGCCACACCTTCCTGGTCAGGAACCACAGGCAGGCCA
GCCTGGAGATCAGCCCCATCACCTTCCTGACTGCCCAGACCCTGCTGATGGACCTGGGCCAGTTCCTGCT
GTTCTGCCACATCAGCAGCCACCAGCATGATGGCATGGAGGCCTATGTGAAGGTGGACAGCTGCCCTGAG
GAGCCCCAGCTGAGGATGAAGAACAATGAGGAGGCTGAGGACTATGATGACCTGACTGACTCTGAGA
TGGATGTGGTGAGGTTTGATGATGACAACAGCCCCAGCTTCATCCAGATCAGGTCTGTGGCCAAGAAGCA
CCCCAAGACCTGGGTGCACTACATTGCTGCTGAGGAGGAGGACTGGGACTATGCCCCCCTGGTGCTGGCC
CCTGATGACAGGAGCTACAAGAGCCAGTACCTGAACAATGGCCCCCAGAGGATTGGCAGGAAGTACAAGA
AGGTCAGGTTCATGGCCTACACTGATGAAACCTTCAAGACCAGGGAAGCCATCCAGCATGAGTCTGGCAT
CCTGGGCCCCCTGCTGTATGGGGAGGTGGGGGACACCCTGCTGATCATCTTCAAGAACCAGGCCAGCAGG
CCCTACAACATCTACCCCCATGGCATCACTGATGTGAGGCCCCTGTACAGCAGGAGGCTGCCCAAGGGGG
TGAAGCACCTGAAGGACTTCCCCATCCTGCCTGGGGAGATCTTCAAGTACAAGTGGACTGTGACTGTGGA
GGATGGCCCCACCAAGTCTGACCCCAGGTGCCTGACCAGATACTACAGCAGCTTTGTGAACATGGAGAGG
GACCTGGCCTCTGGCCTGATTGGCCCCCTGCTGATCTGCTACAAGGAGTCTGTGGACCAGAGGGGCAACC
AGATCATGTCTGACAAGAGGAATGTGATCCTGTTCTCTGTGTTTGATGAGAACAGGAGCTGGTACCTGAC
TGAGAACATCCAGAGGTTCCTGCCCAACCCTGCTGGGGTGCAGCTGGAGGACCCTGAGTTCCAGGCCAGC
AACATCATGCACAGCATCAATGGCTATGTGTTTGACAGCCTGCAGCTGTCTGTGTGCCTGCATGAGGTGG
CCTACTGGTACATCCTGAGCATTGGGGCCCAGACTGACTTCCTGTCTGTGTTCTTCTCTGGCTACACCTT
CAAGCACAAGATGGTGTATGAGGACACCCTGACCCTGTTCCCCTTCTCTGGGGAGACTGTGTTCATGAGC
ATGGAGAACCCTGGCCTGTGGATTCTGGGCTGCCACAACTCTGACTTCAGGAACAGGGGCATGACTGCCC
TGCTGAAAGTCTCCAGCTGTGACAAGAACACTGGGGACTACTATGAGGACAGCTATGAGGACATCTCTGC
CTACCTGCTGAGCAAGAACAATGCCATTGAGCCCAGGAGCTTCAGCCAGAACAGCAGGCACCCCAGCACC
AGGCAGAAGCAGTTCAATGCCACCACCATCCCTGAGAATGACATAGAGAAGACAGACCCATGGTTTGCCC
ACCGGACCCCCATGCCCAAGATCCAGAATGTGAGCAGCTCTGACCTGCTGATGCTGCTGAGGCAGAGCCC
CACCCCCCATGGCCTGAGCCTGTCTGACCTGCAGGAGGCCAAGTATGAAACCTTCTCTGATGACCCCAGC
CCTGGGGCCATTGACAGCAACAACAGCCTGTCTGAGATGACCCACTTCAGGCCCCAGCTGCACCACTCTG
GGGACATGGTGTTCACCCCTGAGTCTGGCCTGCAGCTGAGGCTGAATGAGAAGCTGGGCACCACTGCTGC
CACTGAGCTGAAGAAGCTGGACTTCAAAGTCTCCAGCACCAGCAACAACCTGATCAGCACCATCCCCTCT
GACAACCTGGCTGCTGGCACTGACAACACCAGCAGCCTGGGCCCCCCCAGCATGCCTGTGCACTATGACA
GCCAGCTGGACACCACCCTGTTTGGCAAGAAGAGCAGCCCCTGACTGAGTCTGGGGCCCCCTGAGCCT
GTCTGAGGAGAACAATGACAGCAAGCTGCTGGAGTCTGGCCTGATGAACAGCCAGGAGAGCTCTGGGGC
AAGAATGTGAGCAGCAGGGAGATCACCAGGACCACCCTGCAGTCTGACCAGGAGGAGATTGACTATGATG
ACACCATCTCTGTGGAGATGAAGAAGGAGGACTTTGACATCTACGACGAGGACGAGAACCAGAGCCCCAG
GAGCTTCCAGAAGAAGACCAGGCACTACTTCATTGCTGCTGTGGAGAGGCTGTGGGACTATGGCATGAGC
AGCAGCCCCCATGTGCTGAGGAACAGGGCCCAGTCTGGCTCTGTGCCCCAGTTCAAGAAGGTGGTGTTCC
AGGAGTTCACTGATGGCAGCTTCACCCAGCCCCTGTACAGAGGGGAGCTGAATGAGCACCTGGGCCTGCT
GGGCCCCTACATCAGGGCTGAGGTGGAGGACAACATCATGGTGACCTTCAGGAACCAGGCCAGCAGGCCC

```
TACAGCTTCTACAGCAGCCTGATCAGCTATGAGGAGGACCAGAGGCAGGGGCTGAGCCCAGGAAGAACT
TTGTGAAGCCCAATGAAACCAAGACCTACTTCTGGAAGGTGCAGCACCACATGGCCCCCACCAAGGATGA
GTTTGACTGCAAGGCCTGGGCCTACTTCTCTGATGTGGACCTGGAGAAGGATGTGCACTCTGGCCTGATT
GGCCCCCTGCTGGTGTGCCACACCAACACCCTGAACCCTGCCCATGGCAGGCAGGTGACTGTGCAGGAGT
TTGCCCTGTTCTTCACCATCTTTGATGAAACCAAGAGCTGGTACTTCACTGAGAACATGGAGAGGAACTG
CAGGGCCCCCTGCAACATCCAGATGGAGGACCCCACCTTCAAGGAGAACTACAGGTTCCATGCCATCAAT
GGCTACATCATGGACACCCTGCCTGGCCTGGTGATGGCCCAGGACCAGAGGATCAGGTGGTACCTGCTGA
GCATGGGCAGCAATGAGAACATCCACAGCATCCACTTCTCTGGCCATGTGTTCACTGTGAGGAAGAAGGA
GGAGTACAAGATGGCCCTGTACAACCTGTACCCTGGGGTGTTTGAGACTGTGGAGATGCTGCCCAGCAAG
GCTGGCATCTGGAGGGTGGAGTGCCTGATTGGGGAGCACCTGCATGCTGGCATGAGCACCCTGTTCCTGG
TGTACAGCAACAAGTGCCAGACCCCCCTGGGCATGGCCTCTGGCCACATCAGGGACTTCCAGATCACTGC
CTCTGGCCAGTATGGCCAGTGGGCCCCCAAGCTGGCCAGGCTGCACTACTCTGGCAGCATCAATGCCTGG
AGCACCAAGGAGCCCTTCAGCTGGATCAAGGTGGACCTGCTGGCCCCCATGATCATCCATGGCATCAAGA
CCCAGGGGGCCAGGCAGAAGTTCAGCAGCCTGTACATCAGCCAGTTCATCATCATGTACAGCCTGGATGG
CAAGAAGTGGCAGACCTACAGGGGCAACAGCACTGGCACCCTGATGGTGTTCTTTGGCAATGTGGACAGC
TCTGGCATCAAGCACAACATCTTCAACCCCCCCATCATTGCCAGATACATCAGGCTGCACCCCACCCACT
ACAGCATCAGGAGCACCCTGAGGATGGAGCTGATGGGCTGTGACCTGAACAGCTGCAGCATGCCCCTGGG
CATGGAGAGCAAGGCCATCTCTGATGCCCAGATCACTGCCAGCAGCTACTTCACCAACATGTTTGCCACC
TGGAGCCCCAGCAAGGCCAGGCTGCACCTGCAGGGCAGGAGCAATGCCTGGAGGCCCCAGGTCAACAACC
CCAAGGAGTGGGCTGCAGGTGGACTTCAGAAGACCATGAAGGTGACTGGGGTGACCACCCAGGGGGTGAA
GAGCCTGCTGACCAGCATGTATGTGAAGGAGTTCCTGATCAGCAGCAGCCAGGATGGCCACCAGTGGACC
CTGTTCTTCCAGAATGGCAAGGTGAAGGTGTTCCAGGGCAACCAGGACAGCTTCACCCCTGTGGTGAACA
GCCTGGACCCCCCCCTGCTGACCAGATACCTGAGGATTCACCCCAGAGCTGGGTGCACCAGATTGCCCT
GAGGATGGAGGTGCTGGGCTGTGAGGCCCAGGACCTGTACTGA

SEQ ID NO: 17
CCGCGGAGATCTCAATATTGGCCATTAGCCATATTATTCATTGGTTATATAGCATAAATCAATATTGGCT
ATTGGCCATTGCATACGTTGTATCTATATCATAATATGTACATTTATATTGGCTCATGTCCAATATGACC
GCCATGTTGGCATTGATTATTGACTAGTTATTAATAGTAATCAATTACGGGGTCATTAGTTCATAGCCCA
TATATGGAGTTCCGCGTTACATAACTTACGGTAAATGGCCCGCCTGGCTGACCGCCCAACGACCCCCGCC
CATTGACGTCAATAATGACGTATGTTCCCATAGTAACGCCAATAGGGACTTTCCATTGACGTCAATGGGT
GGAGTATTTACGGTAAACTGCCCACTTGGCAGTACATCAAGTGTATCATATGCCAAGTCCGCCCCCTATT
GACGTCAATGACGGTAAATGGCCCGCCTGGCATTATGCCCAGTACATGACCTTACGGGACTTTCCTACTT
GGCAGTACATCTACGTATTAGTCATCGCTATTACCATGGTGATGCGGTTTTGGCAGTACACCAATGGGCG
TGGATAGCGGTTTGACTCACGGGGATTTCCAAGTCTCCACCCCATTGACGTCAATGGGAGTTTGTTTTGG
CACCAAAATCAACGGGACTTTCCAAAATGTCGTAATAACCCCGCCCCGTTGACGCAAATGGGCGGTAGGC
GTGTACGGTGGGAGGTCTATATAAGCAGAGCTCGTTTAGTGAACCGTCAGATCACTAGAAGCTTTATTGC
GGTAGTTTATCACAGTTAAATTGCTAACGCAGTCAGTGCTTCTGACACAACAGTCTCGAACTTAAGCTGC
AGAAGTTGGTCGTGAGGCACTGGGCAGGCTAGC

SEQ ID NO: 18
TCGAGATGTGGTCTGAGTTAAAAATCAGGAGCAACGACGGAGGTGAAGGACCAGACGCCAACGACCC

SEQ ID NO: 19
CCGGGGGTCGTTGGCGTCTGGTCCTTCACCTCCGTCGTTGCTCCTGATTTTTAACTCAGACCACATC

SEQ ID NO: 20
CCGGGGAAAGGGGGTGCAACACATCCATATCCAGCCATCTCTACCTGTTTATGGACA

SEQ ID NO: 21
ACCCTCTGTCCATAAACAGGTAGAGATGGCTGGATATGGATGTGTTGCACCCCTTTCC

SEQ ID NO: 22
GGGTTAGGTGGTTGCTGATTCTCTCATTCACCCAGTGGG

SEQ ID NO: 23
GATCCCCACTGGGTGAATGAGAGAATCAGCAACCACCTA

SEQ ID NO: 24
GAGACTCGAGATGTGGTCTGAGTTAAAAATCAGG

SEQ ID NO: 25
AGAGGTAGACCAGTACGAGTCACGTTTGCCCCTATCACCATCCCTAACCCTCTGTCATAAAC

SEQ ID NO: 26
TACGGGTCGAGACACAGGACCCCGTAAGACGACGACCGACCGGACACGACAGACCACGGACACAGGGACC
GACTCCTGGGAGTCCCCCTACGACGGGTCTTTTGTCTGTGGAGGGTGGTACTGGTCCTGGTGGGGTGGAA
GTTGTTCTAGTGGGGGTTGGACCGTCTCAAACGGAAGTCGGACATGTCTGTCGACCGGGTGGTCTCGTTG
TCGTGGTTGTAGAAAAAGTCGGACACAGGTAACGGTGTCGGAAACGGTACGACTCGGACCCGTGGTTCC
GACTGTGGGTACTACTCTAGGACCTTCCGGACTTGAAGTTGGACTGTCTCTAGGGACTCCGGGTCTAGGT
ACTCCCGAAGGTCCTTGACGACTCTTGGGACTTGGTCGGTCGTGGTCGACTGTTGTCGTTA
CCCGACAAGGACAGACTCCCGGACTTCGACCACCTGTTCAAAGACCTTCTACACTTCTTCGACATGGTGA
GACTCCGGAAGTGTCACTTGAAACCCCTGTGTCTTCTCCGGTTCTTTGTCTAGTTACTGATACACCTTTT
CCCGTGGGTCCGTTCTAACACCTGGAACACTTTCTCGACCTGTCCCTGTGACACAAACGGGAACACTTG
ATGTAGAAGAAGTTCCCGTTCACCCTCTCCGGGAAACTTCACTTCCTGTGACTCCTTCTCCTGAAGGTAC
ACCTGGTTCACTGGTGTCACTTCCACGGTTACTACTTCTCTGACCCCTACAAGTTATAGGTCGTGACGTT
CTTTGACTCGTCGACCCACGACGACTACTTCATGGACCCGTTACGATGTCGGTATAAGAAAGACGGACTA
```

CTCCCGTTCGACGTCGTGGACCTTTTACTCGACTGGGTACTGTAGTAGTGGTTTAAAGACCTTTTACTCC
TGTCTTCTAGACGGTCGGACGTAGACGGGTTCGACTCGTAGTGTCCGTGTATACTGGACTTCAGACACGA
CCCTGTCGACCCTTAGTGGTTCCACAAGTCGTTACCCCGTCTGGACTCACCTCACTGTCTCCTTCGGGGA
GACTTCGACAGGTTCCGACACGTGTTCCGTCACGACTGGTAACTACTCTTCCCGTGTCTCCGACGACCCC
GGTACAAAGACCTTCGGTAGGGGTACAGGTAGGGGGGTCTTCACTTCAAGTTGTTCGGGAAACACAAGGA
CTACTAACTCGTCTTGTGGTTCTCGGGGGACAAGTACCCGTTCCAACACTTGGGGTGGGTCTTTACT

SEQ ID NO: 27
AEDPQGDAAQKTDTSHHDQDHPTFAEDPQGDAAQKTDTSHHDQDHPTFNKITPNLAEFAFSLYRQLAHQSN
STNIFFSPVSIATAFAMLSLGTKADTHDEILEGLNFNLTEIPEAQIHEGFQELLRTLNQPDSQLQLTTGNG
LPLSEGLKLVDKFLEDVKKLYHSEAFTVNFGDTEEAKKQINDYVEKGTQGKIVDLVKELDRDTVFALVNYI
FFKGKWERPFEVKDTEEEDPHVDQVTTVKVPMMKRLGMFNIQHCKKLSSWVLLMKYLGNATAIFFLPDEGK
LQHLENELTHDIITKFLENEDRRSASLHLPKLSITGTYDLKSVLGQLGITKVFSNGADLSGVTEEAPLKLS
KAVHKAVLTIDEKGTEAAGAMFLEAIPMSIPPEVKFNKPFVFLMIEQNTKSPLFMGKVVNPTQK

SEQ ID NO: 28
TACGTCTAACTCGACTCGTGGACGAAGAAGGACACGGACGACTCCAAGACGAAGAGACGGTGGTCCTCTA
TGATGGACCCCCGACACCTCGACTCGACCCTGATGTACGTCAGACTGGACCCCCTCGACGGACACCTACG
GTCCAAGGGGGGGTCTCACGGGTTCTCGAAGGGGAAGTTGTGGAGACACCACATGTTCTTCTGGGACAAA
CACCTCAAGTGACTGGTGGACAAGTTGTAACGGTTCGGGTCCGGGGGGACCTACCCGGACGACCCGGGGT
GGTAGGTCCGACTCCACATACTGTGACACCACTAGTGGGACTTCTTGTACCGGTCGGTGGGACACTCGGA
CGTACGACACCCCCACTCGATGACCTTCCGGAGACTCCCCCGACTCATACTACTGGTCTGGTCGGTCTCC
CTCTTCCTCCTACTGTTCCACAAGGGACCCCCGTCGGTGTGGATACACACCGTCCACGACTTCCTCTTAC
CGGGGTACCGGAGACTGGGGGACACGGACTGGATGTCGATGGACTCGGTACACCTGGACGACTTCCTGGA
CTTGAGACCGGACTAACCCCGGGACGACCACACGTCCCTCCCGTCGGACCGGTTCCTCTTCGGGTCTGG
GACGTGTTCAAGTAGGACGACAAACGACACAAACTACTCCCGTTCTCGACCGTGAGACTTTGGTTCTTGT
CGGACTACGTCCTGTCCCTACGACGGAGACGGTCCCGGACCGGGTTCTACGTGTGACACTTACCGATACA
CTTGTCCTCGGACGGACCGGACTAACCGACGGTGTCCTTCAGACACATGACCGTACACTAACCGTACCCG
TGGTGGGGACTCCACGTGTCGTAGAAGGACCTCCCGGTGTGAAGGACCAGTCCTTGGTGTCCGTCCGGT
CGGACCTCTAGTCGGGGTAGTGGAAGGACTGACGGGTCTGGGACGACTACCTGGACCCGGTCAAGGACGA
CAAGACGGTGTAGTCGTCGGTGGTCGTACTACCGTACCTCCGGATACACTTCCACCTGTCGACGGGACTC
CTCGGGGTCGACTCCTACTTCTTGTTACTCCTCCGACTCCTGATACTACTACTGGACTGACTGAGACTCT
ACCTACACCACTCCAAACTACTACTGTTGTCGGGGTCGAAGTAGGTCTAGTCCAGACACCGGTTCTTCGT
GGGGTTCTGGACCCACGTGATGTAACGACGACTCCTCCTCCTGACCCTGATACGGGGGGACCACGACCGG
GGACTACTGTCCTCGATGTTCTCGGTCATGGACTTGTTACCGGGGGTCTCCTAACCGTCCTTCATGTTCT
TCCAGTCCAAGTACCGGATGTGACTACTTTGGAAGTTCTGGTCCTCCGGTAGGTCGTACTCAGACCGTA
GGACCCGGGGGACGACATACCCCTCCACCCCCTGTGGGACGACTAGTAGAAGTTCTTGGTCCGGTCGTCC
GGGATGTTGTAGATGGGGGTACCGTAGTGACTACACTCCGGGGACATGTCGTCCTCCGACGGGTTCCCCC
ACTTCGTGGACTTCCTGAAGGGGTAGGACGGACCCCTCTAGAAGTTCATGTTCACCTGACACTGACACCT
CCTACCGGGGTGGTTCAGACTGGGGTCCACGGACTGGTCTATGATGTCGTCGAAACACTTGTACCTCTCC
CTGGACCGGAGACCGGACTAACCGGGGGACGACTAGACGATGTTCCTCAGACACCCTGGTCTCCCCGTTGG
TCTAGTACAGACTGTTCTCCTTACACTAGGACAAGAGACACAAACTACTCTTGTCCTCGACCATGGACTG
ACTCTTGTAGGCTCCAAGGACGGGTTGGGACGACCCCACGTCGACCTCCTGGGACTCAAGGTCCGGTCG
TTGTAGTACGTGTCGTAGTTACCGATACACAAACTGTCGGACGTCGACAGACACACGGACGTACTCCACC
GGATGACCATGTAGGACTCGTAACCCCGGGTCTGACTGAAGGACCAGACACAAGAAGAGACCGATGTGGAA
GTTCGTGTTCTACCACATACTCCTGTGGGACTGGGACAAGGGGAAGAGACCCCTCTGACACAAGTACTCG
TACCTCTTGGGACCGGACACCTAAGACCCGACGGTGTTGAGACTGAAGTCCTTGTCCCCGTACTGACGGG
ACGACTTTCAGAGGTCGACACTGTTCTTGTGACCCCTGATGATACTCCTGTCGATACTCCTGTAGAGACG
GATGGACGACTCGTTCTTGTTACGGTAACTCGGGTCCTCGAAGTCGGTCTTGTCGTCCGTGGGGTCGTGG
TCCGTCTTCGTCAAGTTACGGTGGTGGTAGGGACTCTTACTGTATCTCTTCGTCTGGGTACCAAACGGG
TGGCCTGGGGGTACGGGTTCTAGGTCTTACACTCGTCGAGACTGACGACTACGACGACTCCGTCTCGGG
GTGGGGGGTACCGGACTCGGACAGACTGGACGTCCTCCGGTTCATACTTTGGAAGAGACTACTGGGGTCG
GGACCCCGGTAACTGTCGTTGTTGTCGGACAGACTCTACTGGGTGAAGTCCGGGGTCGACGTGGTGAGAC
CCCTGTACCACAAGTGGGGACTCAGACCGGACGTCGACTCCGACTTACTCTTCGACCCGTGGTGACGACG
GTGACTGACTTCTTCGACCTGAAGTTTCAGAGGTCGTGGTCGTTGTTGGACTAGTCGTGGTAGGGGAGA
CTGTTGGACCGACGACCGTGACTGTTGTGGTCGTCGGACCCGGGGGGGTCGTACGGACACGTGATACTGT
CGGTCGACCTGTGGTGGGACAAACCGTTCTTCTCGTCGGGGGACTGACTTGTCGGTCCTCTCGTCGACCCCG
TTCTTACACTCGTCGTCCCTCAGTGGTCCTGGTGGGACGTCAGACTGGTCCTCCTCTAACTGATACTAC
TGTGGTAGAGACACCTCTACTTCTTCCTCCTGAAACTGTAGATGCTGCTCCTGCTCTTGGTCTCGGGGTC
CTCGAAGGTCTTCTTCTGGTCCGTGATGAAGTAACGACGACACCTCTCCGACACCCTGATACCGTACTCG
TCGTCGGGGGTACACGACTCCTTGTCCCGGGTCAGACCGAGACACGGGGTCAAGTTCTTCCACCACAAGG
TCCTCAAGTGACTACCGTCGAAGTGGGTCGGGGACATGTCTCCCCTCGACTTACTCGTGGACCCGGACGA
CCCGGGGATGTAGTCCCGACTCCACCTCCTGTTGTAGTACCACTGGAAGTCCTTGGTCCGGTCGTCCGGG
ATGTCGAAGATGTCGTCGGACTAGTCGATACTCCTCCTGGTCTCCGTCCCCCGACTCGGGTCCTTCTTGA
AACACTTCGGGTTACTTTGGTTCTGGATGAAGACCTTCCACGTCGTGATTACCGCGGGGTTGTTCCTACT
CAAACTGACGTTCCGGACCCGGATGAAGAGACTACACCTGGACCTCTTCCTACACGTGAGACCGGACTAA
CCGGGGGACGACCACACGGTGTGGTTGTGGGACTTGGGACGGGTACCGTCCGTCCACTGACACGTCCTCA
AACGGGACAAGAAGTGGTAGAAACTACTTTGGTTCTCGACCATGAAGTGACTCTTGTACCTCTCCTTGAC
GTCCCGGGGACGTTGTAGGTCTACCTCCTGGGGTGGAAGTTCCTCTTGATGTCCAAGGTACGGTAGTTA
CCGATGTAGTACCTGTGGGACGGACCGGACCACTACCGGGTCCTGGTCTCCACCATGGACGACT
CGTACCCGTCGTTACTCTTGTAGGTGTCGTAGGTGAAGAGACCGGTACACAAGTGACACTCCTTCTTCCT
CCTCATGTTCTACCGGGACATGTTGGACATGGGACCCCACAAACTCTGACACCTCTACGACGGGTCGTTC
CGACCGTAGACCTCCCACCTCACGGACTAACCCCTCGTGGACGTACGACCGTACTCGTGGGACAAGGACC
ACATGTCGTTGTTCACGGTCTGGGGGACCCGTACCGGAGACCGGTGTAGTCCCTGAAGGTCTAGTGACG
GAGACCGGTCATACCGGTCACCCGGGGGTTCGACCGGTCCGACGTGATGAGACCGTCGTAGTTACGGACC
TCGTGGTTCCTCGGGAAGTCGACCTAGTTCCACCTGGACGACCGGGGGTACTAGTAGGTACCGTAGTTCT

-continued

| Sequences |
|---|
| GGGTCCCCCGGTCCGTCTTCAAGTCGTCGGACATGTAGTCGGTCAAGTAGTAGTACATGTCGGACCTACC |
| GTTCTTCACCGTCTGGATGTCCCCGTTGTCGTGACCGTGGGACTACCACAAGAAACCGTTACACCTGTCG |
| AGACCGTAGTTCGTGTTGTAGAAGTTGGGGGGGTAGTAACGGTCTATGTAGTCCGACGTGGGGTGGGTGA |
| TGTCGTAGTCCTCGTGGGACTCCTACCTCGACTACCCGACACTGGACTTGTCGACGTCGTACGGGGACCC |
| GTACCTCTCGTTCCGGTAGAGACTACGGGTCTAGTGACGGTCGTCGATGAAGTGGTTGTACAAACGGTGG |
| ACCTCGGGGTCGTTCCGGTCCGACGTGGACGTCCCGTCCTCGTTACGGACCTCCGGGGTCCAGTTGTTGG |
| GGTTCCTCACCGACGTCCACCTGAAGGTCTTCTGGTACTTCCACTGACCCCACTGGTGGGTCCCCCACTT |
| CTCGGACGACTGGTCGTACATACACTTCCTCAAGGACTAGTCGTCGTCGGTCCTACCGGTGGTCACCTGG |
| GACAAGAAGGTCTTACCGTTCCACTTCCACAAGGTCCCGTTGGTCCTGTCGAAGTGGGGACACCACTTGT |
| CGGACCTGGGGGGGGACGACTGGTCTATGGACTCCTAAGTGGGGGTCTCGACCCACGTGGTCTAACGGGA |
| CTCCTACCTCCACGACCCGACACTCCGGGTCCTGGACATGACT |

SEQ ID NO: 29
MQIELSTCFFLCLLRFCFSATRRYYLGAVELSWDYMQSDLGELPVDARFPPRVPKSFPFNTSVVYKKTLFV
EFTDHLFNIAKPRPPWMGLLGPTIQAEVYDTVVITLKNMASHPVSLHAVGVSYWKASEGAEYDDQTSQREK
EDDKVFPGGSHTYVWQVLKENGPMASDPLCLTYSYLSHVDLVKDLNSGLIGALLVCREGSLAKEKTQTLHK
FILLFAVFDEGKSWHSETKNSLMQDRDAASARAWPKMHTVNGYVNRSLPGLIGCHRKSVYWHVIGMGTTPE
VHSIFLEGHTFLVRNHRQASLEISPITFLTAQTLLMDLGQFLLFCHISSHQHDGMEAYVKVDSCPEEPQLR
MKNNEEAEDYDDDLTDSEMDVVRFDDDNSPSFIQIRSVAKKHPKTWVHYIAAEEEDWDYAPLVLAPDDRSY
KSQYLNNGPQRIGRKYKKVRFMAYTDETFKTREAIQHESGILGPLLYGEVGDTLLIIFKNQASRPYNIYPH
GITDVRPLYSRRLPKGVKHLKDFPILPGEIFKYKWTVTVEDGPTKSDPRCLTRYYSSFVNMERDLASGLIG
PLLICYKESVDQRGNQIMSDKRNVILFSVFDENRSWYLTENIQRFLPNPAGVQLEDPEFQASNIMHSINGY
VFDSLQLSVCLHEVAYWYILSIGAQTDFLSVFFSGYTFKHKMVYEDTLTLFPFSGETVFMSMENPGLWILG
CHNSDFRNRGMTALLKVSSCDKNTGDYYEDSYEDISAYLLSKNNAIEPRSFSQNSRHPSTRQKQFNATTIP
ENDIEKTDPWFAHRTPMPKIQNVSSSDLLMLLRQSPTPHGLSLSDLQEAKYETFSDDPSPGAIDSNNSLSE
MTHFRPQLHHSGDMVFTPESGLQLRLNEKLGTTAATELKKLDFKVSSTSNNLISTIPSDNLAAGTDNTSSL
GPPSMPVHYDSQLDTTLFGKKSSPLTESGGPLSLSEENNDSKLLESGLMNSQESSWGKNVSSREITRTTLQ
SDQEEIDYDDTISVEMKKEDFDIYDEDENQSPRSFQKKTRHYFIAAVERLWDYGMSSSPHVLRNRAQSGSV
PQFKKVVFQEFTDGSFTQPLYRGELNEHLGLLGPYIRAEVEDNIMVTFRNQASRPYSFYSSLISYEEDQRQ
GAEPRKNFVKPNETKTYFWKVQHHMAPTKDEFDCKAWAYFSDVDLEKDVHSGLIGPLLVCHTNTLNPAHGR
QVTVQEFALFFTIFDETKSWYFTENMERNCRAPCNIQMEDPTFKENYRFHAINGYIMDTLPGLVMAQDQRI
RWYLLSMGSNENIHSIHFSGHVFTVRKKEEYKMALYNLYPGVFETVEMLPSKAGIWRVECLIGEHLHAGMS
TLFLVYSNKCQTPLGMASGHIRDFQITASGQYGQWAPKLARLHYSGSINAWSTKEPFSWIKVDLLAPMIIH
GIKTQGARQKFSSLYISQFIIMYSLDGKKWQTYRGNSTGTLMVFFGNVDSSGIKHNIFNPPIIARYIRLHP
THYSIRSTLRMELMGCDLNSCSMPLGMESKAISDAQITASSYFTNMFATWSPSKARLHLQGRSNAWRPQVN
NPKEWLQVDFQKTMKVTGVTTQGVKSLLTSMYVKEFLISSSQDGHQWTLFFQNGKVKVFQGNQDSFTPVVN
SLDPPLLTRYLRIHPQSWVHQIALRMEVLGCEAQDLY

SEQ ID NO: 30
ATGCAGATTGAGCTGAGCACCTGCTTCTTCCTGTGCCTGCTGAGGTTCTGCTTCTCTGCCACCAGGAGAT
ACTACCTGGGGGCTGTGGAGCTGAGCTGGGACTACATGCAGTCTGACCTGGGGGAGCTGCCTGTGGATGC
CAGGTTCCCCCCCAGAGTGCCCAAGAGCTTCCCCTTCAACACCTCTGTGGTGTACAAGAAGACCCTGTTT
GTGGAGTTCACTGACCACCTGTTCAACATTGCCAAGCCCAGGCCCCCCTGGATGGGCCTGCTGGGCCCCA
CCATCCAGGCTGAGGTGTATGACACTGTGGTGATCACCCTGAAGAACATGGCCAGCCACCCTGTGAGCCT
GCATGCTGTGGGGGTGAGCTACTGGAAGGCCTCTGAGGGGGCTGAGTATGATGACCAGACCAGCCAGGAG
GAGAAGGAGGATGACAAGGTGTTCCCTGGGGGCAGCCACACCTATGTGTGGCAGGTGCTGAAGGAGAATG
GCCCCATGGCCTCTGACCCCCTGTGCCTGACCTACAGCTACCTGAGCCATGTGGACCTGGTGAAGGACCT
GAACTCTGGCCTGATTGGGGCCCTGCTGGTGTGCAGGGAGGGCAGCCTGGCCAAGGAGAAGACCCAGACC
CTGCACAAGTTCATCCTGCTGTTTGCTGTGTTTGATGAGGGCAAGAGCTGGCACTCTGAAACCAAGAACA
GCCTGATGCAGGACAGGGATGCTGCCTCTGCCAGGGCCTGGCCCAAGATGCACACTGTGAATGGCTATGT
GAACAGGAGCCTGCCTGGCCTGATTGGCTGCCACAGGAAGTCTGTGTACTGGCATGTGATTGGCATGGGC
ACCACCCCTGAGGTGCACAGCATCTTCCTGGAGGGCCACACCTTCCTGGTCAGGAACCACAGGCAGGCCA
GCCTGGAGATCAGCCCCATCACCTTCCTGACTGCCCAGACCCTGCTGATGGACCTGGGCCAGTTCCTGCT
GTTCTGCCACATCAGCAGCCACCAGCATGATGGCATGGAGGCCTATGTGAAGGTGGACAGCTGCCCTGAG
GAGCCCCAGCTGAGGATGAAGAACAATGAGGAGGCTGAGGACTATGATGATGACCTGACTGACTCTGAGA
TGGATGTGGTGAGGTTTGATGATGACAACAGCCCCAGCTTCATCCAGATCAGGTCTGTGGCCAAGAAGCA
CCCCAAGACCTGGGTGCACTACATTGCTGCTGAGGAGGAGGACTGGGATTATGCCCCCCTGGTGCTGGCC
CCTGATGACAGGAGCTACAAGAGCCAGTACCTGAACAATGGCCCCCAGAGGATTGGCAGGAAGTACAAGA
AGGTCAGGTTCATGGCCTACACTGATGAAACCTTCAAGACCAGGGAGGCCATCCAGCATGAGTCTGGCAT
CCTGGGCCCCCTGCTGTATGGGGAGGTGGGGGACACCCTGCTGATCATCTTCAAGAACCAGGCCAGCAGG
CCCTACAACATCTACCCCCATGGCATCACTGATGTGAGGCCCCTGTACAGCAGGAGGCTGCCCAAGGGGG
TGAAGCACCTGAAGGACTTCCCCATCCTGCCTGGGGAGATCTTCAAGTACAAGTGGACTGTGACTGTGGA
GGATGGCCCCACCAAGTCTGACCCCAGGTGCCTGACCAGATACTACAGCAGCTTTGTGAACATGGAGAGG
GACCTGGCCTCTGGCCTGATTGGCCCCTGCTGATCTGCTACAAGGAGTCTGTGGACCAGAGGGGCAACC
AGATCATGTCTGACAAGAGGAATGTGATCCTGTTCTCTGTGTTTGATGAGAACAGGAGCTGGTACCTGAC
TGAGAACATCCAGAGGTTCCTGCCCAACCCTGCTGGGGTGCAGCTGGAGGACCCTGAGTTCCAGGCCAGC
AACATCATGCACAGCATCAATGGCTATGTGTTTGACAGCCTGCAGCTGTCTGTGTGCCTGCATGAGGTGG
CCTACTGGTACATCCTGAGCATTGGGGCCCAGACTGACTTCCTGTCTGTGTTCTTCTCTGGCTACACCTT
CAAGCACAAGATGGTGTATGAGGACACCCTGACCCTGTTCCCCTTCTCTGGGGAGACTGTGTTCATGAGC
ATGGAGAACCCTGGCCTGTGGATTCTGGGCTGCCACAACTCTGACTTCAGGAACAGGGGCATGACTGCCC
TGCTGAAAGTCTCCAGCTGTGACAAGAACACTGGGGACTACTATGAGGACAGCTATGAGGACATCTCTGC
CTACCTGCTGAGCAAGAACAATGCCATTGAGCCCAGGAGCTTCAGCCAGAATGCCACTAATGTGTCTAAC
AACAGCAACACCAGCAATGACAGCAATGTGTCTCCCCCAGTGCTGAAGAGGCACCAGAGGGAGATCACCA
GGACCACCCTGCAGTCTGACCAGGAGGAGATTGACTATGATGACACCATCTCTGTGGAGATGAAGAAGGA
GGACTTTGACATCTACGACGAGGACGAGAACCAGAGCCCCAGGAGCTTCCAGAAGAAGACCAGGCACTAC
TTCATTGCTGCTGTGGAGAGGCTGTGGGACTATGGCATGAGCAGCAGCCCCCATGTGCTGAGGAACAGGG
CCCAGTCTGGCTCTGTGCCCCAGTTCAAGAAGGTGGTGTTCCAGGAGTTCACTGATGGCAGCTTCACCCA

| Sequences |
|---|
| GCCCCTGTACAGAGGGGAGCTGAATGAGCACCTGGGCCTGCTGGGCCCCTACATCAGGGCTGAGGTGGAG
GACAACATCATGGTGACCTTCAGGAACCAGGCCAGCAGGCCCTACAGCTTCTACAGCAGCCTGATCAGCT
ATGAGGAGGACCAGAGGCAGGGGGCTGAGCCCAGGAAGAACTTTGTGAAGCCCAATGAAACCAAGACCTA
CTTCTGGAAGGTGCAGCACCACATGGCCCCCACCAAGGATGAGTTTGACTGCAAGGCCTGGGCCTACTTC
TCTGATGTGGACCTGGAGAAGGATGTGCACTCTGGCCTGATTGGCCCCCTGCTGGTGTGCCACACCAACA
CCCTGAACCCTGCCCATGGCAGGCAGGTGACTGTGCAGGAGTTTGCCCTGTTCTTCACCATCTTTGATGA
AACCAAGAGCTGGTACTTCACTGAGAACATGGAGAGGAACTGCAGGGCCCCCTGCAACATCCAGATGGAG
GACCCCACCTTCAAGGAGAACTACAGGTTCCATGCCATCAATGGCTACATCATGGACACCCTGCCTGGCC
TGGTGATGGCCCAGGACCAGAGGATCAGGTGGTACCTGCTGAGCATGGGCAGCAATGAGAACATCCACAG
CATCCACTTCTCTGGCCATGTGTTCACTGTGAGGAAGAAGGAGGAGTACAAGATGGCCCTGTACAACCTG
TACCCTGGGGTGTTTGAGACTGTGGAGATGCTGCCCAGCAAGGCTGGCATCTGGAGGGTGGAGTGCCTGA
TTGGGGAGCACCTGCATGCTGGCATGAGCACCCTGTTCCTGGTGTACAGCAACAAGTGCCAGACCCCCCT
GGGCATGGCCTCTGGCCACATCAGGGACTTCCAGATCACTGCCTCTGGCCAGTATGGCCAGTGGGCCCCC
AAGCTGGCCAGGCTGCACTACTCTGGCAGCATCAATGCCTGGAGCACCAAGGAGCCCTTCAGCTGGATCA
AGGTGGACCTGCTGGCCCCCATGATCATCCATGGCATCAAGACCCAGGGGGCCAGGCAGAAGTTCAGCAG
CCTGTACATCAGCCAGTTCATCATCATGTACAGCCTGGATGGCAAGAAGTGGCAGACCTACAGGGGCAAC
AGCACTGGCACCCTGATGGTGTTCTTTGGCAATGTGGACAGCTCTGGCATCAAGCACAACATCTTCAACC
CCCCCATCATTGCCAGATACATCAGGCTGCACCCCACCCACTACAGCATCAGGAGCACCCTGAGGATGGA
GCTGATGGGCTGTGACCTGAACAGCTGCAGCATGCCCCTGGGCATGGAGAGCAAGGCCATCTCTGATGCC
CAGATCACTGCCAGCAGCTACTTCACCAACATGTTTGCCACCTGGAGCCCCTCCAAGGCCAGGCTGCACC
TGCAGGGCAGGAGCAATGCCTGGAGGCCCCAGGTCAACAACCCCAAGGAGTGGCTGCAGGTGGACTTCCA
GAAGACCATGAAGGTGACTGGGGTGACCACCCAGGGGGTGAAGAGCCTGCTGACCAGCATGTATGTGAAG
GAGTTCCTGATCAGCAGCAGCCAGGATGGCCACCAGTGGACCCTGTTCTTCCAGAATGGCAAGGTGAAGG
TGTTCCAGGGCAACCAGGACAGCTTCACCCCTGTGGTGAACAGCCTGGACCCCCCCCTGCTGACCAGATA
CCTGAGGATTCACCCCCAGAGCTGGGTGCACCAGATTGCCCTGAGGATGGAGGTGCTGGGCTGTGAGGCC
CAGGACCTGTACTGA |

SEQ ID NO: 31
TACGTCTAACTCGACTCGTGGACGAAGAAGGACACGGACGACTCCAAGACGAAGAGACGGTGGTCCTCTA
TGATGGACCCCCGACACCTCGACTCGACCCTGATGTACGTCAGACTGGACCCCCTCGACGGACACCTACG
GTCCAAGGGGGGGTCTCACGGGTTCTCGAAGGGGAAGTTGTGGAGACACCACATGTTCTTCTGGGACAAA
CACCTCAAGTGACTGGTGGACAAGTTGTAACGGTTCGGGTCCGGGGGGACCTACCCGGACGACCCGGGGT
GGTAGGTCCGACTCCACATACTGTGACACCACTAGTGGGACTTCTTGTACCGGTCGGTGGGACACTCGGA
CGTACGACACCCCCACTCGATGACCTTCCGGAGACTCCCCCGACTCATACTACTGGTCTGGTCGGTCTCC
CTCTTCCTCCTACTGTTCCACAAGGGACCCCCGTCGGTGTGGATACACACCGTCCACGACTTCCTCTTAC
CGGGGTACCGGAGACTGGGGGACACGGACTGGATGTCGATGGAGTCGGGTACACCTGGACCACTTCCTGGA
CTTGAGACCGGACTAACCCCGGGACGACCACACGTCCCTCCCGTCGGACCGGTTCCTCCTTCTGGGTCTGG
GACGTGTTCAAGTAGGACGACAAACGACACAAACTACTCCCGTTCTCGACCGTGAGACTTTGGTTCTTGT
CGGACTACGTCCTGTCCCTACGACGGAGACGGTCCCGGACCGGGTTCTACGTGTGACACTTACCGATACA
CTTGTCCTCGGACGGACCGGACTAACCGACGGTGTCCTTCAGACACATGACCGTACACTAACCGTACCCG
TGGTGGGGACTCCACGTGTCGTAGAAGGACCTCCCGGTGTGGAAGGACCAGTCCTTGGTGTCCGTCCGGT
CGGACCTCTAGTCGGGGTAGTGGAAGGACTGACGGGTCTGGGACGACTACCTGGACCCGGTCAAGGACGA
CAAGACGGTGTAGTCGTCGGTGGTCGTACTACCGTACCTCCGGATACACTTCCACCTGTCGACGGGACTC
CTCGGGGTCGACTCCTACTTCTTGTTACTCCTCCGACTCCTGATACTACTACTGGACTGACTGAGACTCT
ACCTACACCACTCCAAACTACTACTGTTGTCGGGGTCGAAGTAGGTCTAGTCCAGACACCGGTTCTTCGT
GGGGTTCTGGACCCACGTGATGTAACGACGACTCCTCCTCCTGACCCTGATACGGGGGGACCACGACCGG
GGACTACTGTCCTCGATGTTCTCGGTCATGGACTTGTTACCGGGGGTCTCCTAACCGTCCTTCATGTTCT
TCCAGTCCAAGTACCGGATGTGACTACTTTGGAAGTTCTGGTCCCTCCGGTAGGTCGTACTCAGACCGTA
GGACCCGGGGGACGACATACCCCTCCACCCCCTGTGGGACGGGTAGGTAGAAGTTCTTGGTCCGGTCGTCC
GGGATGTTGTAGATGGGGGTACCGTAGTGACTACACTCCGGGGACATGTCGTCCTCCGACGGGTTCCCCC
ACTTCGTGGACTTCCTGAAGGGGTAGGACGGACCCCCTCTAGAAGTTCATGTTCACCTGACACTGACACCT
CCTACCGGGGTGGTTCAGACTGGGGTCCACGGACTGGTCTATGATGTCGTCGAAACACTTGTACCTCTCC
CTGGACCGGAGACCGGACTAACCGGGGACGGACTAGACGATGTTCCTCAGACACCTGGTCTCCCCGTTGG
TCTAGTACAGACTGTTCTCCTTACACTAGGACAAGAGACACAAACTACTCTTGTCCTCGACCATGGACTG
ACTCTTGTAGGTCTCCAAGGACGGGTTGGGACGACCCCACGTCGACCTCCTGGGACTCAAGGTCCGGTCG
TTGTAGTACGTGTCGTAGTTACCGATACACAAACTGTCGGACGTCGACAGACACACGGACGTACTCCACC
GGATGACCATGTAGGACTCGTAACCCCGGGTCTGACTGAAGGACAGACACAAGAAGACCGATGTGGAA
GTTCGTGTTCTACCACATACTCCTGTGGGACTGGGACAAGGGGAAGAGACCCCTCTGACACAAGTACTCG
TACCTCTTGGGACCGGACACCTAAGACCCGACGGTGTTGAGACTGAAGTCCTTGTCCCCGTACTGACGGG
ACGACTTTCAGAGGTCGACACTGTTCTTGTGACCCCTGATGATACTCCTGTCGATACTCCTGTAGAGACG
GATGGACGACTCGTTCTTGTTACGGTAACTCGGGTCCTCGAAGTCGGTCTTACGGTGATTACACAGATTG
TTGTCGTTGTGGTCGTTACTGTCGTTACACAGAGGGGGTCACGACTTCTCCGTGGTCTCCCTCTAGTGGT
CCTGGTGGGACGTCAGACTGGTCCTCCTCTAACTGATACTACTGTGGTAGAGACACCTCTACTTCTTCCT
CCTGAAACTGTAGATGCTGCTCCTGCTCTTGGTCTCGGGGTCCTCGAAGGTCTTCTTCTGGTCCGTGATG
AAGTAACGACGACACCTCTCCGACACCCTGATACCGTACTCGTCGTCGGGGGTACACGACTCCTTGTCCC
GGGTCAGACCGAGACAGGGGTCAAGTTCTTCCACCACAAGGTCCTCAAGTGACTACCGTCGAAGTGGGT
CGGGGACATGTCTCCCCTCGACTTACTCGTGGACCCGGACGACCCGGGGATGTAGTCCCGACTCCACCTC
CTGTTGTAGTACCACTGGAAGTCCTTGGTCCGGTCGTCCGGGATGTCGAAGATGTCGTCGGACTAGTCGA
TACTCCTCCTGGTCTCCGTCCCCCGACTCGGGTCCTTCTTGAAACACTTCGGGTTACTTTGGTTCTGGAT
GAAGACCTTCCACGTCGTGGTGTACCGGGGGTGGTTCCTACTCAAACTGACGTTCCGGACCCGGATGAAG
AGACTACACCTGGACCTCTTCCTACACGTGAGACCGGACTAACCGGGGACCACAACACCGTGGTTGT
GGGACTTGGGACGGGTACCGTCCGTCCACTGACACGTCCTCAAACGGGACAAGAAGTGGTAGAAACTACT
TTGGTTCTCGACCATGAAGTGACTCTTGTACCTCTCCTTGACGTCCCGGGGACGTTGTAGGTCTACCTC
CTGGGGTGGAAGTTCCTCTTGATGTCCAAGGTACGGTAGTTACCGATGTAGTACCTGTGGGACGGACCGG
ACCACTACCGGGTCCTGGTCTCCTAGTCCACCATGGACGACTCGTACCCGTCGTTACTCTTGTAGGTGTC
GTAGGTGAAGAGACCGGTACACAAGTGACACTCCTTCTTCCTCCTCATGTTCTACCGGGACATGTTGGAC
ATGGGACCCCACAAACTCTGACACCTCTACGACGGGTCGTTCCGACCGTAGACCTCCCACCTCACGGACT

-continued

Sequences

AACCCCTCGTGGACGTACGACCGTACTCGTGGGACAAGGACCACATGTCGTTGTTCACGGTCTGGGGGGA
CCCGTACCGGAGACCGGTGTAGTCCCTGAAGGTCTAGTGACGGAGACCGGTCATACCGGTCACCCGGGGG
TTCGACCGGTCCGACGTGATGAGACCGTCGTAGTTACGGACCGTCGGTTCCTCGGGAAGTCGACCTAGT
TCCACCTGGACGACCGGGGGTACTAGTAGGTACCGTAGTTCTGGGTCCCCCGGTCCGTCTTCAAGTCGTC
GGACATGTAGTCGGTCAAGTAGTAGTACATGTCGGACCTACCGTTCTTCACCGTCTGGATGTCCCCGTTG
TCGTGACCGTGGGACTACCACAAGAAACCGTTACACCTGTCGAGACCGTAGTTCGTGTTGTAGAAGTTGG
GGGGGTAGTAACGGTCTATGTAGTCCGACGTGGGGTGGGTGGTTGCTGTAGTCCTCGTGGGACTCCTACCT
CGACTACCCGACACTGGACTTGTCGACGTCGTACGGGGACCCGTACCTCTCGTTCCGGTAGAGACTACGG
GTCTAGTGACGGTCGTCGATGAAGTGGTTGTACAAACGGTGGACCTCGGGGTCGTTCCGGTCCGACGTGG
ACGTCCCGTCCTCGTTACGGACCTCCGGGGTCCAGTTGTTGGGGTTCCTCACCGACGTCCACCTGAAGGT
CTTCTGGTACTTCCACTGACCCCACTGGTGGGTCCCCCACTTCTCGGACGACTGGTCGTACATACACTTC
CTCAAGGACTAGTCGTCGTCGGTCCTACCGGTGGTCACCTGGGACAAGAAGGTCTTACCGTTCCACTTCC
ACAAGGTCCCGTTGGTCCTGTCGAAGTGGGGACACCCACTTGTCGGACCTGGGGGGGGACGACTGGTCTAT
GGACTCCTAAGTGGGGGTCTCGACCCACGTGGTCTAACGGGACTCCTACCTCCACGACCCGACACTCCGG
GTCCTGGACATGACT

SEQ ID NO: 32
MQIELSTCFFLCLLRFCFSATRRYYLGAVELSWDYMQSDLGELPVDARFPPRVPKSFPFNTSVVYKKTLF
VEFTDHLFNIAKPRPPWMGLLGPTIQAEVYDTVVITLKNMASHPVSLHAVGVSYWKASEGAEYDDQTSQR
EKEDDKVFPGGSHTYVWQVLKENGPMASDPLCLTYSYLSHVDLVKDLNSGLIGALLVCREGSLAKEKTQT
LHKFILLFAVFDEGKSWHSETKNSLMQDRDAASARAWPKMHTVNGYVNRSLPGLIGCHRKSVYWHVIGMG
TTPEVHSIFLEGHTFLVRNHRQASLEISPITFLTAQTLLMDLGQFLLFCHISSHQHDGMEAYVKVDSCPE
EPQLRMKNNEEAEDYDDDLTDSEMDVVRFDDDNSPSFIQIRSVAKKHPKTWVHYIAAEEEDWDYAPLVLA
PDDRSYKSQYLNNGPQRIGRKYKKVRFMAYTDETFKTREAIQHESGILGPLLYGEVGDTLLIIFKNQASR
PYNIYPHGITDVRPLYSRRLPKGVKHLKDFPILPGEIFKYKWTVTVEDGPTKSDPRCLTRYYSSFVNMER
DLASGLIGPLLICYKESVDQRGNQIMSDKRNVILFSVFDENRSWYLTENIQRFLPNPAGVQLEDPEFQAS
NIMHSINGYVFDSLQLSVCLHEVAYWYILSIGAQTDFLSVFFSGYTFKHKMVYEDTLTLFPPFSGETVFMS
MENPGLWILGCHNSDFRNRGMTALLKVSSCDKNTGDYYEDSYEDISAYLLSKNNAIEPRSFSQNATNVSN
NSNTSNDSNVSPPVLKRHQREITRTTLQSDQEEIDYDDTISVEMKKEDFDIYDEDENQSPRSFQKKTRHY
FIAAVERLWDYGMSSSPHVLRNRAQSGSVPQFKKVVFQEFTDGSFTQPLYRGELNEHLGLLGPYIRAEVE
DNIMVTFRNQASRPYSFYSSLISYEEDQRQGAEPRKNFVKPNETKTYFWKVQHHMAPTKDEFDCKAWAYF
SDVDLEKDVHSGLIGPLLVCHTNTLNPAHGRQVTVQEFALFFITDETKSWYFTENMERNCRAPCNIQME
DPTFKENYRPHAINGYIMDTLPGLVMAQDQRIRWYLLSMGSNENIHSIHFSGHVFTVRKKEEYKMALYNL
YPGVFETVEMLPSKAGIWRVECLIGEHLHAGMSTLFLVYSNKCQTPLGMASGHIRDFQITASGQYGQWAP
KLARLHYSGSINAWSTKEPFSWIKVDLLAPMIIHGIKTQGARQKFSSLYISQFIIMYSLDGKKWQTYRGN
STGTLMVFFGNVDSSGIKHNIFNPPIIARYIRLHPTHYSIRSTLRMELMGCDLNSCSMPLGMESKAISDA
QITASSYFTNMFATWSPSKARLHLQGRSNAWRPQVNNPKEWLQVDFQKTMKVTGVTTQGVKSLLTSMYVK
EFLISSSQDGHQWTLFFQNGKVKVFQGNQDSFTPVVNSLDPPLLTRYLRIHPQSWVHQIALRMEVLGCEA
QDLY

SEQ ID NO: 33
GGCGCCTCTAGAGTTATAACCGGTAATCGGTATAATAAGTAACCAATATATCGTATTTAGTTATAACCGA
TAACCGGTAACGTATGCAACATAGATATAGTATTATACATGTAAATATAACCGAGTACAGGTTATACTGG
CGGTACAACCGTAACTAATAACTGATCAATAATTATCATTAGTTAATGCCCCAGTAATCAAGTATCGGGT
ATATACCTCAAGGCGCAATGTATTGAATGCCATTTACCGGGCGGACTGGCGGGTTGCTGGGGGCGG
GTAACTGCAGTTATTACTGCATACAAGGGTATCATTGCGGTTATCCCTGAAAGGTAACTGCAGTTACCCA
CCTCATAAATGCCATTTGACGGGTGAACCGTCATGTAGTTCACATAGTATACGGTTCAGGCGGGGGATAA
CTGCAGTTACTGCCATTTACCGGGCGGACCGTAATACGGGTCATGTACTGGAATGCCCTGAAAGGATGAA
CCGTCATGTAGATGCATAATCAGTAGCGATAATGGTACCACTACGCCAAAACCGTCATGGTTACCCGC
ACCTATCGCCAAACTGAGTGCCCCTAAAGGTTCAGAGGTGGGGTAACTGCAGTTACCCTCAAACAAAACC
GTGGTTTTAGTTGCCCTGAAAGGTTTTACAGCATTATTGGGGCGGGCAACTGCGTTTACCCGCCATCCG
CACATGCCACCCTCCAGATATATTCGTCTCGAGCAAATCACTTGGCAGTCTAGTGATCTTCGAAATAACG
CCATCAAATAGTGTCAATTTAACGATTGCGTCAGTCACGAAGACTGTGTTGTCAGAGCTTGAATTCGACG
TCTTCAACCAGCACTCCGTGACCCGTCCGATCG

The invention claimed is:

1. A lentiviral vector pseudotyped with hemagglutinin-neuraminidase (HN) and fusion (F) proteins from a respiratory paramyxovirus, wherein said lentiviral vector comprises a hybrid human CMV enhancer/EF1a (hCEF) promoter and a transgene, and wherein the lentiviral vector lacks an intron positioned between said promoter and said transgene.

2. The lentiviral vector according to claim 1, wherein the lentiviral vector is selected from the group consisting of a Human immunodeficiency virus (HIV) vector, a Simian immunodeficiency virus (SIV) vector, a Feline immunodeficiency virus (FIV) vector, an Equine infectious anaemia virus (EIAV) vector, and a Visna/maedi virus vector.

3. The lentiviral vector according to claim 1, wherein lentiviral vector is a SIV vector.

4. The lentiviral vector according claim 1, wherein the respiratory paramyxovirus is a Sendai virus.

5. The lentiviral vector according to claim 1, wherein the transgene:
(a) encodes a secreted therapeutic protein selected from Alpha-1 Antitrypsin (A1 AT), Surfactant Protein B (SFTPB), Factor VII, Factor VIII, Factor IX, Factor X, Factor XI, von Willebrand Factor or Granulocyte-Macrophage Colony-Stimulating Factor (GM-CSF)
(b) encodes a monoclonal antibody against an infectious agent; or
(c) is selected from the group consisting of CFTR, DNAH5, DNAH11, DNAI1, and DNAI2.

6. A method of treating a disease, the method comprising administering a lentiviral vector of claim 1 to a subject.

7. The method according to claim 6, wherein the disease is a lung disease selected from: cystic fibrosis (CF); Primary Ciliary Dyskinesia (PCD); Surfactant Protein B (SP-B) deficiency; Alpha 1-antitrypsin Deficiency (A1AD); Pulmonary Alveolar Proteinosis (PAP); and Chronic obstructive pulmonary disease (COPD).

8. The method according to claim 6, wherein the transgene is Factor VIII and the disease is Haemophilia.

9. A host cell comprising the vector according to claim 1.

10. A composition comprising a vector according to claim 1, and a pharmaceutically-acceptable carrier.

11. The lentiviral vector according to claim 1, wherein the transgene encodes cystic fibrosis transmembrane conductance regulator (CFTR).

12. The lentiviral vector according to claim 1, wherein the transgene encodes A1AT.

13. The lentiviral vector according to claim 1, wherein the transgene encodes Factor VIII.

* * * * *